US006762024B2

(12) United States Patent
Maertens et al.

(10) Patent No.: US 6,762,024 B2
(45) Date of Patent: Jul. 13, 2004

(54) SEQUENCES OF HEPATITIS C VIRUS GENOTYPES AND THEIR USE AS THERAPEUTIC AND DIAGNOSTIC AGENTS

(75) Inventors: Geert Maertens, Bruges (BE); Lieven Stuyver, Lede (BE)

(73) Assignee: Innogenetics, S.A., Ghent (BE)

( * ) Notice: Subject to any disclaimer, the term of this patent is extended or adjusted under 35 U.S.C. 154(b) by 4 days.

(21) Appl. No.: 09/878,281

(22) PCT Filed: Apr. 27, 1994

(86) PCT No.: PCT/EP94/01323

§ 371 (c)(1),
(2), (4) Date: Jan. 11, 1995

(87) PCT Pub. No.: WO94/25601

PCT Pub. Date: Nov. 10, 1994

(65) Prior Publication Data

US 2003/0032005 A1 Feb. 13, 2003

Related U.S. Application Data

(63) Continuation of application No. 08/362,455, filed on Jan. 11, 1995.

(30) Foreign Application Priority Data

Apr. 27, 1993 (EP) .............................................. 93401099
Aug. 5, 1993 (EP) .............................................. 93402019

(51) Int. Cl.⁷ .................................................. C12Q 1/68

(52) U.S. Cl. ............................ 435/6; 435/5; 435/320.1; 536/23.1; 536/23.7

(58) Field of Search ............................. 435/5, 6, 320.1; 536/23.1, 23.7; 702/20

(56) References Cited

U.S. PATENT DOCUMENTS

| 5,372,928 A | 12/1994 | Miyamura ...................... 435/5 |
| 5,514,539 A | 5/1996 | Bukh ............................. 435/5 |
| 5,846,704 A | 12/1998 | Maertens ....................... 435/5 |
| 5,882,852 A | 3/1999 | Bukh et al. ..................... 435/5 |
| 6,548,244 B2 | 4/2003 | Maertens et al. ............... 435/5 |

FOREIGN PATENT DOCUMENTS

| EP | 0419182 | | 3/1991 |
| EP | 0463848 A2 | | 1/1992 |
| EP | 0 532 167 | * | 3/1993 |
| GB | 2239245 | | 6/1991 |
| JP | 6-319563 | | 11/1994 |
| WO | 92/19743 | | 11/1992 |
| WO | WO 93 00365 | | 1/1993 |
| WO | 93/06126 | | 4/1993 |
| WO | 93/10239 | | 5/1993 |
| WO | WO 94 25601 | | 1/1995 |
| WO | 95 01442 | * | 1/1995 |

OTHER PUBLICATIONS

S. Mori et al., "A new type of hepatitis C in patients in Thailand", Biochemical and Biophysical Research Communications, vol. 183, No. 1, 1992, pp. 334–342.

T.A. Cha et al., "At least five related but distinct genotypes of hepatitis C virus exist", Proc. National Acad. Sci., USA, vol. 89, pp. 7144–7148, Aug., 1992.

A. Weiner et al., "Variable and hypervariable regions are found in the regions of HCV corresponding to the flavivirus envelope and NS1 proteins", Virology, 180, (1991) pp. 842–848.

K. Chayama et al., "Genotypic subtyping of hepatitis C virus", Journal of Gastronenterology and Hepatology, vol. 8, (1993) pp. 150–156.

L. Stuyver et al., "Typing of hepatitis C virus isolates and characterization of new subtypes using a line probe assay", Journal of General Virology, vol. 74, 1993, pp. 1093–1102.

P. Simmonds et al., Mapping of serotype–specific immunodominant epitopes in the NS4 region of hepatitis C virus, Journal of Clinical Microbiology, vol. 31, 1993, pp. 1493–1503.

Majzoub et al., "Vasopressin and Oxytocin mRNA Regulation in the Rat Assessed by Hybridization with Synthetic Oligonucleotides", J. Biol. Chem. 258: 14061 (1983).

Chan et al, "Analysis of a new hepatitis C type and its phylogenetic relationship to existing variants' cited in the application", J. Gen. Virol., vol. 73, 1992, pp. 1131–1141.

Liu et al, "Genomic typing of hepatitis C viruses present in China", GENE, vol. 114, No. 2, pp. 245–250 (1992).

Stuyver et al, "Classification of hepatitis C viruses based on phylogenetic analysis of the envelope 1 and nonstructural 5B regions and identification of five additional subtypes", Proceedings of the National Academy of Sciences of USA, vol. 91, No. 21, pp. 10134–10138 (1994).

(List continued on next page.)

Primary Examiner—James Martinell
(74) Attorney, Agent, or Firm—Nixon & Vanderhye P.C.

(57) ABSTRACT

The present invention relates to a polynucleic acid composition comprising or consisting of at least one polynucleic acid containing 8 or more contiguous nucleotides corresponding to a nucleotide sequence from the region spanning positions 417 to 957 of the Core/E1 region of HCV type 3; and/or the region spanning positions 4664 to 4730 of the NS3 region of HCV type 3; and/or the region spanning positions 4892 to 5292 of the NS3/4 region of HCV type 3; and/or the region spanning positions 8 023 to 8 235 of the NS5 region of the BR36 subgroup of HCV type 3a; and/or the coding region of HCV type 4a starting at nucleotide 379 in the core region; and/or the coding region of HCV type 4; and/or the coding region of HCV type 5, with said nucleotide numbering being with respect to the numbering of HCV nucleic acids as shown in Table 1, and with said polynucleic acids containing at least one nucleotide difference with known HCV type 1, and/or HCV type 2 genomes in the above-indicated regions, or the complement thereof.

8 Claims, 111 Drawing Sheets

OTHER PUBLICATIONS

Van Doorn et al, "Analysis of hepatitis C virus genotypes by a line probe assay and correlation with antibody profiles", Journal of Hepatology, vol. 21, No. 1, pp. 122–129 (1994).

Bukh et al, "At least 12 genotypes of hepatitis C virus predicated by sequence analysis of the putative E1 gene of isolates collected worldwide", Proceedings of the National Academy of Sciences of USA, vol. 90, pp. 8234–8238 (1993).

Bukh et al, "Sequence analysis of the core gene of the 14 hepatitis C virus genotypes", Proceedings of the National Academy of Sciences of USA, vol. 91, pp. 8239–8424 (1994).

Driesel et al, "Hepatitis C virus (HCV) genotype distribution in german isolates: studies on the sequence variability in the E2 and NS5 region", Archives of Virology, vol. 139, No. 3/04, pp. 379–388.

Tokita et al, "Hepatitis C virus variants from vietnam are classifiable into the seventh, eighth and ninth major genetic groups", Proceedings of the National Academy of Sciences of USA, vol. 91, No. 23, pp. 11022–11026 (1994).

Stuyver et al, "Hepatisis C virus genotyping by means of 5'–UR/core line probe assays and molecular analysis of untypeable samples", Virus Research, vol. 38, No. 2–3, pp. 137–157 (1995).

Qu et al, Journal General Virology, vol. 75, No. 5, pp. 1063–1070 (1994).

Kato et al, "Molecular Cloning of the Human Hepatitis C Virus Genome Form Japanese Patients with Non–A Non–B Hepatitis", Proc. Natl. Acad. Sci. USA, vol. 87, 1990, pp. 9254–9258, XP000168621.

Database Genban 'Online! Accession No. X78863, May 20, 1994, Van Doorn et al: "Sequence Analysis of Hepatitis C Virus Genotypes 1 to 5", XP002017147 * abstract * and J. Gen. Virol., vol. 76, 1994, pp. 1871–1876.

Database Genban 'Online! Accession No. D26387, Feb. 4, 1994, Hotta et al: Subtype Analysis of Hepatitis C Virus in Indonesia XP002017146 * abstract * and J. Clin. Microbiol., vol. 32, 1994, pp. 3049–3051.

Biochem. Biophys. Res. Commun., vol. 170, No. 3, 1990, pp. 1021–1025, XPOO2017145 N. Enomoto et al: "There are Two Major Types of Hepatitis C Virus in Japan".

George et al, in Mcromolecular Sequencing and Synthesis, Selected Methods and Applications, Schlesinger (ed.), 1988, Alan R. Liss, Inc., New York, pp. 127–149.

Chen et al, Virology, 188: 102 (1992).

Wallace et al, Methods Enzymol. 152: 432 (1987).

Bukh et al, Proc. Natl. Acad. Sci. USA 89: 4942 (1992).

Innis et al, PCR Protocols: A Guide to Methods and Applications, 1990, Innis et al (ed.), Academic Press, New York, pp. 3–11.

* cited by examiner

Figure 1

```
            7932                                                                    7981
            CTCCACAGTCACTGAGAGGCGACATCCGTACGGAGGAGGCAATCTACCAAT
HCV-1   1a  ---------------------AT-----T----AT--T-------------
HCV-J   1b  ---A--G--------------AT-----T----AT--T-------------
BE90    1b  ---A-----------C-----A------T----T---T-------------
2TY4    1c  ---A-----------------A------------------A----------
4TY4    1c  ------------------------GTT-----------------A-T----
HC-J6   2a  ---A--C--------A----------A-G--T-------T-C--A--T-GGG
HC-J8   2a  ---A--C-----G-----G------AA-A--A--A--AT-C--A--T--GG
NE91    2b  ---A--C-----G-----------AA-A--A--A--AT-C--A--T---G
EB12    2b  ---A--C-----G----T------AA-A--A--A--AT-C--A--T--GG
ARG6    2b                                              -A--T--GG
ARG8    2b                                              ---T-TG-
I10     2c                                              ----G---
T983    2c                                              ---T-TG-
NE92    2c                                              ----GG
CHR20   2d  ---A--G-----G--------G-----A--A--T-------T-C--A----TTG
CHR21   3a  ---T--T-----ACAG-----------A-GGT-----A-----AG--A---G-
CHR22   3a  ---G--T-----ACAG-----------A-GGT-----A-----AG--A---
T1      3a  ---A--T-----ACAG-----------A-GGT-----A-----AG--A---
T7      3a  ---A--T-----ACAG-----------A-GGT-----A-----AG--A---
NE93    3a  ---A--T-----ACAG-----------A-GGT-----A-----AG--A---
NZL13   3a  ---G--T-----ACAG-----------A-GGT-----A-----AG--A---
EB1     3a  ---A--T-----ACAG-----------A-GGT-----A-----AG--A---
EB2     3a                                                    ---A--T
EB3     3a                                                    ---A-----
EB7     3a                                                    ---A-----
T9      3a                                                    ---A--T
T10     3b  ---T--T-----ACAT--------A-G---------A-----AG--A----
BE98    3b  ---T--T-----ACAG-------A-G--A-------------AG--A----
        3c                                                                      GG
```

Figure 1 - Continued 1

```
                              7932                                                    7981
GB48       4c     ----T--A--C---A-AG-------A-GGTC-------AGG----T--G-
GB116      4c     ----T--A--C---A-AG-------A-GGTC-------AGG-A--T--G-
GB215      4c     ----T--A--C---A-AA-------A-GGTC-------AGG-A--T--G-
GB358      4c     ----T--A--C---A-AG-------A-GGTC-------AGG-A--T--G-
GB809      4c     ----T--A--C---A-AG------AAGGTC----A--A-A-G--T--G-
CAM600     4e     ----T--G------A----------A-GGTC---A--A-A-G--T--G-
CAMG22     4e     ----T--G------A----------A-GGTC---A--A-A-G-----G-
GB549      4f     -------G------A-A--------A-GGTC-------A-AGG-----G-
GB438      4g     ---G--G--C---A--G--T-----A-G--C-------A-AG------G-
CAR4/1205  4h     ---G--G--C---A--G-------TA-GGTC-------A-AG--T--G-
CAR1/501   4i     -C---C--G--N------G-----N--A-GGTC-------A-AGG--T--G-
EG-13      4j     ---G--T--GN-C-------G------A-G--A-----GA-AGG--T--G-
EG-19      4k     -----------------------------------G-----G----T--G-
           4k     -----------------------------------G-----G----T--G-
BE95       5a     ---G--C--T--C--ACAT-----AATG---C--A-----T-C--T----
BE96       5a     ---A--C--C--C--ACAT-----ATTG--T--A------T-C--A----
CHR18      5a     ---G--C--T--C--ACAT-----AATG--T--A------T-T--T----
CHR19      5a     ---G--C--T--C--ACAT-----AATG--T--A------T-C--T----
```

Figure 1 - Continued 2

| | | SEQ ID | 7982 ... 8031 |
|---|---|---|---|
| | | | GTTGTGACCTCGACCCCCCAAGCCCGGTGGCCATCAAGTCCCTCACCGAG |
| HCV-1 | 1a | | |
| HCV-J | 1b | | ---T-G-C-----G-------A-GCA--------A-G---G-----A--- |
| BE90 | 1b | 213 | ---T-G-C-----G-G----A-ACA--------A------G-----A--- |
| 2TY4 | 1c | | ------GC----G-C-----A------T-------------------T--- |
| 4TY4 | 1c | | ------GC----G-C-----A------CT----------AAAT---T--- |
| HC-J6 | 2a | | C-----TC-T-GCC-GAGG-G----A-ACT-----AC-C--A--G--T--- |
| HC-J8 | 2a | | C-----TCT--GCCT-AAG------A-AACT-T--AC-C--C--G---T--- |
| NE91 | 2b | | C-----TC---GCC--AAG-G----A-AACT-T--AC-C--C--G------- |
| EB12 | 2b | 215 | C-----TC---GCCT-AAG-G----A-AACT-T--AC-C--C--G------- |
| ARG6 | 2c | | CC----TCA--GCCTGAGG-G----T--AACT---AC-C--A--G--T--- |
| ARG8 | 2c | | CC----TCA--GCC-GAGG-G----T--AACT-T--AC-C--A--G--T--- |
| I10 | 2c | | CC----CTCA--GCC-GAGG-G---T----AACT----AC-C--A--G--T--- |
| T983 | 2c | | C-----TCA--GCCT-AGG-G----T--GACT-T--AC-C--AT-G--T--- |
| NE92 | 2d | 145 | C-----CTCTT-ACC-GAG--G----A--GACT-----AC-C--A--G--T--- |
| CHR20 | 3a | | -C----A-----T--A--GG-G----A-GAAA--TG----TCC-------G--- |
| CHR21 | 3a | | -C----A-----T--A--GG-G----A-GAAA--TG----TCC-------G--- |
| CHR22 | 3a | | -C----A-----T--A--GG-G----A-GAAA--TG----TCC-------G--- |
| T1 | 3a | | -C----A-----T--A--GG-G----A-GAGA--TG----TCC-------G--- |
| T7 | 3a | | -C----A-----T--A--GG-G----A-GAAA--TG----TCC-------G--- |
| NE93 | 3a | 217 | -C----A-T---T--G--GG-G----A-GAAA--TG----TCC-------G---A |
| NZL13 | 3a | | -C----CA----T--A--GG-G----A-GAAA--TG----TCC-------G--- |
| EB1 | 3a | | -C----A-----T--A--GG-G----A-GAAA--TG----TCC-------G---A |
| EB2 | 3a | | -C----A-----T--A--GG-G----A-GAAA--TG----TCC-------G--- |
| EB3 | 3a | | -C----A-----T--A--GG-G----A-GAAA--TG----TCC-------G---A |
| EB7 | 3a | | -C----A-----T--A--GG-G----A-AAAA--TG----TCC-------G--- |
| BR33 | 3a | 9,11 | -------------T--G--AG-G---T--GAA-----G------G--- |
| BR34 | 3a | 1,3 | -----------------------------------------------G--A |
| BR36 | 3a | 5,7 | -----------------------------------GCG-T-----A--- |
| T9 | 3b | | -C----------T--G--AG-G---T--GAA-----G------GCG-T-----A--- |

Figure 1 - Continued 3

| | SEQ ID | 7982 | | | | | | | | | | | | | | | | 8031 |
|---|---|---|---|---|---|---|---|---|---|---|---|---|---|---|---|---|---|---|
| T10 | 3b | -C- | --- | --- | -T- | -G- | -AG | -G- | --T | -GAA | --- | -G- | --- | GCG | -T- | --- | -A- | --- |
| BE98 | 3c | CC- | --- | --- | -A- | -GGA | -G- | -G- | --T | -GAG | -TG | -A- | -CT | --A | --- | -G- | --- | --- |
| GB48 | 4c | --- | --- | --- | --- | -G- | --- | -G- | --- | --- | -AA | -A- | --T | -CCG | --- | --- | -A- | -A- |
| GB116 | 4c | --- | --- | --- | --- | -G- | --- | -G- | --- | --- | AGA | -A- | --T | -CCG | --- | --- | -A- | -A- |
| GB215 | 4c | --- | --- | --- | --- | -G- | --- | -G- | --- | --- | -AA | -TA | --T | -CCG | --- | --- | -A- | -A- |
| GB358 | 4c | --- | --- | --- | --- | -G- | --- | -G- | --- | --- | -AA | -A- | --T | -CTG | --- | --- | -A- | -A- |
| GB809 | 4e | --- | --- | --- | --- | -G- | --- | -G- | --- | --- | -AA | -TA | --- | AGCCG | --- | --- | -G- | --- |
| CAM600 | 4e | --- | -T- | --- | --- | -G- | --- | -G- | --- | --- | -AA | -TA | -A- | -CCG | --- | --- | -G- | --- |
| CAMG22 | 4f | --- | --- | --- | --- | -G- | -TG | -A- | --- | --- | -AA | -TA | -ATCTG | --- | --- | --- | -T- | -A- |
| GB549 | 4g | -C- | -C- | --- | --- | -G- | --- | -G- | --- | --- | -AA | -TG | -ATCCG | --- | --- | --- | -G- | -A- |
| GB438 | 4h | -C- | --- | --- | --- | -G- | --- | -G- | -A- | --- | -AA | -TG | -ATCCG | -T- | --- | --- | -A- | -A- |
| CAR4/1205 | 4i | -C- | --A | -T- | -G- | -GN | -G- | -T- | -N- | --- | -AA | -T- | --- | -CG | --- | --- | -A- | --- |
| CAR1/501 | 4j | --- | -C- | --- | -G- | --A | -GG | --- | --- | --- | -AA | -TA | --- | -CCG | --- | --- | -T- | --- |
| EG-13 | 4k | --- | -A- | --- | --- | -G- | --- | -G- | --- | --T | -AA | --T | --T | -CTG | --- | --- | -A- | -A- |
| EG-19 | 4k | --- | AGT | --- | -G- | --G | -T- | -G- | -G- | --T | -AA | --T | -T- | -CTG | --- | --- | -G- | -A- |
| BE95 | 5a | CA- | --- | -T- | -GC | -G- | --- | -G- | -A- | --- | -CA | -A- | -ACG | --- | -A- | --- | -C- | -A- |
| BE96 | 5a | CA- | --- | -TCGC | -G- | --- | -G- | -C- | -A- | --- | -CA | -A- | -ACG | --- | -A- | --- | -C- | -A- |
| CHR18 | 5a | CA- | -TGT | -T- | -GC | -G- | --- | -TG | -G- | -T- | --- | -A- | -ACG | --- | -A- | --- | -C- | -A- |
| CHR19 | 5a | CA- | -TGT | -T- | -GC | -G- | --- | -TG | -G- | --- | -C- | -A- | -ACG | --- | -A- | --- | -C- | -A- |

Figure 1 - Continued 4

| | 8032 | | | | | | | | | 8081 |
|---|---|---|---|---|---|---|---|---|---|---|
| HCV-1 | 1a | AGGCTTTATGTTGGGGGCCCTCTTACCAATTCAAGGGGGAGAACTGCGG |
| HCV-J | 1b | C------------C-----T--C--G--T------G-A----C------- |
| BE90 | 1b | C-----------A-C-----T--C--G--T------A----C-----T-- |
| 2TY4 | 1c | --AT-G--C--C--A---G--C--G-----------A----T--A----- |
| 4TY4 | 1c | --AT-G--C--C--C-----T--G--CT-G--T-------AA--C----- |
| HC-J6 | 2a | --A-----C--G--A---G--CA-GTT---CAGC-A---CC---C----- |
| HC-J8 | 2b | --A-----C--A--A---G--CA-G--A--CAGC-AA--C-ATC------ |
| NE91 | 2b | --A-----C--C--A---G--CA-G--A--CAGC-AA--C-ATC------ |
| EB12 | 2b | --A-----C--C--A---G--CA-G--TA--CAGC-AA--C-ATC----- |
| ARG6 | 2c | --A-----G--C--A---G--CA-G--A--CAGC-AA--C-ATC------ |
| ARG8 | 2c | --------G--C--A---G--CA-G--A--CAGC-AA--CC-ATC----- |
| I10 | 2c | --A-----A--C--A---G--CA-G--A--CAGC-A---C-ATC------ |
| T983 | 2c | --A-----A--C--A---G--CA-G--A--CAGC-AA--C-TC------- |
| NE92 | 2d | --A-----A--C--G--A---G--CA-GCTA--CAGC-AA--C-A-C--- |
| CHR20 | 3a | C-------------CTGC------A-GTT---CAGC-A----CCC-G--T- |
| CHR21 | 3a | C-------------CTGC------A-GTT---AGC-A----CCC-G--T- |
| CHR22 | 3a | C-------------CTGC------A-GTT---CAGC-A----CCC-G--T- |
| T1 | 3a | C-------------CTGC------A-GTT---CAGC-A----CCC-G--T- |
| T7 | 3a | C-------------CTGC---A--A-GTA---CAGC-A----TCC-G--T- |
| NE93 | 3a | C-------------CTGC---A----A-GTTT--CAGC-A----CCC-G--T- |
| NZL13 | 3a | C-------------CTGC--------A-GTT---CAGC-A----CCC-G--T- |
| EB1 | 3a | C-------------CTGC--------CA-GTT---CAGC-A----CCC-G--T |
| EB2 | 3a | C-------------CTGC--------CA-GTT---CAGC-AA---CCC-G-- |
| EB3 | 3a | C-------------CTGC--------CA-GTT---CAGC-AA---CCC-G-- |
| EB7 | 3a | C-------------CTGC--------A-GTT---CAGC-A----CCC-A--T- |
| BR33 | 3a | C-------------CTGC--------A-GTT---CAGC-A----TCC-G--T- |
| BR34 | 3a | C-------------CTGC--------A-GTT---CAGC-A----CCC-G--T- |
| BR36 | 3a | C-------------CTGC--------A-GTTT--CAGC-AA---CCC-G--- |
| T9 | 3b | C----G--CA-C--A--T--CA-GTA---CAGT-A- |

Figure 1 - Continued 5

| | | | | | | | | | |
|---|---|---|---|---|---|---|---|---|---|
| T10 | 3b | C----- | -G--- | -CA- | -C-- | -A-- | -T-- | -CA- | -GTA--- | -CAGT- | -A--- | --CTCC- | -G--- | --- |
| BE98 | 3c | C----- | ----- | -CTG- | ---- | -T-- | -T-- | -A- | -GTT--- | -CAGC- | -A--- | --AC- | -AC--- | --- |
| GB48 | 4c | --A-- | -C-- | -C-- | -G-- | -C-- | -T-- | -CA- | -GCAT- | -CAGC- | -A--- | --- | -A--- | --CCTG--- | --- |
| GB116 | 4c | --A-- | -C-- | -C-- | -G-- | -C-- | -T-- | -CA- | -GCAT- | -CAGC- | ---- | --- | -A--- | --CCTG--- | --- |
| GB215 | 4c | --A-- | -C-- | -C-- | -G-- | -C-- | -T-- | -CA- | -GCAT- | --AGC- | -AA-- | --- | -A--- | --CCTG--- | --- |
| GB358 | 4c | --A-- | -C-- | -C-- | -G-- | -C-- | -T-- | -CA- | -GCAT- | -CAGC- | -A--- | --- | -A--- | --CCTG--- | -T-- |
| GB809 | 4e | --A-- | -C-- | -C-- | -G-- | -C-- | --- | -CA- | -GCAT- | -CAGC- | -A--- | --- | -A--- | --CCTT--- | -T-- |
| CAM600 | 4e | --A-- | -C-- | -C-- | ---- | -C-- | --- | -A- | -GTA--- | --AGC- | -A--- | --- | -A--- | --CCTT--- | --- |
| CAMG22 | 4f | --A-- | -C-- | -C-- | -G-- | -C-- | -T-- | -CA- | -GCA--- | -CAGC- | --- | --- | -A--- | --CCTA--- | --- |
| GB549 | 4g | --A-- | -C-- | -C-- | -G-- | -C-- | -T-- | -CA- | -GTA--- | -C-- | -C- | -A--- | --- | --CCTA--- | --- |
| GB438 | 4h | --A-- | -C-- | -CAAG | -C-- | ---- | --- | -CA- | -GTAT- | -CAGC- | -A--- | --- | --- | --CCTA--- | --- |
| CAR4/1205 | 4i | --A-- | -C-- | -C-- | -G-- | -C-- | --- | -A- | -GCA--- | -CAGC- | -A--- | --- | -A--- | --CCTG--- | -T-- |
| CAR1/501 | 4j | --A-- | -C-- | ---- | -G-- | -C-- | -A-- | -CA- | -GTT--- | -CAGC- | -A--- | --- | -A--- | --CCTG--- | --- |
| EG-13 | 4k | --A-- | -C-- | -C-- | -G-- | -C-- | --- | -CA- | -GCA--- | -CAGC- | -A--- | --- | -A--- | --CCTT--- | -T-- |
| EG-19 | 4k | --A-- | -C-- | -C-- | -G-- | -C-- | --- | -CA- | -GCA--- | --AGC- | -A--- | --- | -A--- | --CCTT--- | -T-- |
| BE95 | 5a | C-C-- | -C-- | -CTG- | ---- | -A-- | --- | -CA- | -GTA--- | -CAGC- | -A--- | --- | -C- | -AC- | -G--- | -T-- |
| BE96 | 5a | C-CT- | -G-- | -TCTG | ---- | -A-- | --- | -CA- | -GTAT- | -CAGC- | -A--- | --- | -C- | -AC- | -A--- | -T-- |
| CHR18 | 5a | C-C-- | -G-- | -CTG- | ---- | -A-- | --- | -CA- | -GTAT- | -CAGC- | -A--- | --- | -C- | -AC- | -A--- | -T-- |
| CHR19 | 5a | C-C-- | -G-- | -CTG- | ---- | -A-- | --- | -CA- | -GTAT- | -CAGC- | -A--- | --- | -C- | -AC- | -A--- | -T-- |

|  | | 8082 | | | | | | | | 8131 |
|---|---|---|---|---|---|---|---|---|---|---|
| T10 | 3b | ---- | -C-C | ---- | -C-- | ---- | -CT- | -C-T | -C-- | -TC- | -C-- | T- |
| BE98 | 3c | T--C | -C-C | ---- | -T-T | -T--G- | -G-- | -AC- | -C-- | -TC- | -C-- | G- |
| GB48 | 4c | G--- | ---A | -T-- | ---A | ---- | -CTAC | -C-- | -C-- | -TC- | -G-- | -- |
| GB116 | 4c | G--- | ---A | ---- | ---T | ---- | -CTAC | -C-- | -C-- | -TC- | -G-- | -- |
| GB215 | 4c | G--- | ---A | ---- | ---A | ---- | -CTAC | -C-- | -C-- | -TC- | -G-- | -- |
| GB358 | 4c | G--- | ---A | ---- | ---A | ---- | -CTAC | -C-- | -C-- | -TC- | -G-- | -- |
| GB809 | 4e | G--- | -T-A | ---- | ---- | ---- | -TAC- | -C-- | -C-- | -TC- | -G-- | -- |
| CAM600 | 4e | G--- | ---- | ---- | ---A | ---- | -TAT- | -C-- | -C-- | -TC- | -G-- | -- |
| CAMG22 | 4f | G--C | -T-A | ---- | ---- | ---- | -TAC- | -C-- | -A-- | -TC- | -G-- | -- |
| GB549 | 4g | GC-A | --G- | ---- | ---A | -G-- | -CTAC | -C-- | -C-- | -TC- | -G-- | -- |
| GB438 | 4h | GCT- | --G- | ---- | ---A | -G-- | -TAC- | -C-- | -A-- | -TC- | -G-- | -- |
| CAR4/1205 | 4i | -ATC | -T-A | ---- | ---- | ---- | -TTAC | -C-- | -G-- | -TC- | -A-- | -- |
| CAR1/501 | 4j | AC-A | --C- | ---- | ---A | ---- | -GT-C | -C-- | -C-- | -TC- | -G-- | -- |
| EG-13 | 4k | G--- | --G- | -A-T | -G-A | -A-- | -CT-T | -G-- | -C-- | -TC- | -A-- | -- |
| EG-19 | 4k | G--- | --G- | -A-- | -G-A | -A-- | -CTAT | -G-- | -C-- | -TC- | -A-- | -- |
| BE95 | 5a | T--- | ---A | ---- | ---C | ---- | -TT-C | -C-- | -C-- | -TATG | -C-- | -- |
| BE96 | 5a | T--- | ---- | ---- | ---C | ---- | -CT-C | -C-- | -C-- | -TATG | -C-- | -- |
| CHR18 | 5a | T--C | -T-A | ---- | ---C | ---- | -CT-C | -C-- | -C-- | -TATG | -C-- | -- |
| CHR19 | 5a | T--C | -T-A | ---- | ---C | ---- | -CT-C | -C-- | -C-- | -TATG | -C-- | -- |

Figure 1 - Continued 8

|  | 8132 |  |  |  |  | 8181 |
|---|---|---|---|---|---|---|
|  | CCCTCACTTGCTACATCAAGGCCCCGGGCAGCCTGTCGAGCCGCAGGGCTC |
| HCV-1 | ---------------------------------------------------- |
| HCV-J | -----A---T---T-G----------ACT--G---------T---AA---- |
| BE90 | ---------T---T-G----------TCT------------T---GAA--- |
| 2TY4 | ---T-----A---C-A----------TA----------------------- |
| 4TY4 | ---T-----C----------------TA----------------------- |
| HC-J6 | --A------A------TG-G--A---TTA-G------AAG--T-----A-A |
| HC-J8 | --A-G----A---T------------A--T--G----AAG--T-----A-- |
| NE91 | --A-G----A---T------------A--TT-G----AA---------A-- |
| EB12 | --A-G----A---T------------A--TT-G----CAA--T---G-A-- |
| ARG6 | --A------G------G-G--A-TAAA-G-A---AAC-----G---CA-T |
| ARG8 | -A-------G------G-G--A----A--G-G----AAC-----G---CA-T |
| I10 | -A-------G------G-G--A----A--G-G----AAC-----G---CA-T |
| T983 | -G-------G------G-G--A----AA---G----CAAC----TG--CA-T |
| NE92 | --A--T---G---T----------A-AA---------AAG--T-G--CA-A |
| C1IR20 | --A------G---T----------TA-A--G----T-CGAAG------C-- |
| CHR21 | -AA------G---T----------TA-A--G----TGCGAAG--------- |
| CHR22 | -AA------G---T------A---TA-A--G----TGCCGA--------C- |
| T1 | -AA------G---T----------ACA---G----TGCGAAG-------C- |
| T7 | -GA------G---T----------ACA---G----TGCAA-G-------C- |
| NE93 | -AA------G---T----------ACAA--G----GCGAAG--------C- |
| N2L13 | -AA------G---T----------ACA---G----TGC-AAG---AAC--- |
| EB1 | -AA------G---T--------A-TACA--G----CGAG---------C-- |
| EB2 | -AA------G---T----------ACA---G----CGAG---------C-- |
| EB3 | -AA------G---T----------ACA---G----CAAG---------C-- |
| EB7 | -AA------G--------------ACA---G----CAA----------C-- |
| BR33 | -AA------G--------------ACA---G--TGCAAA---------C-- |
| BR34 | -AA------G------------A-ACA---G--TGCAA-G--------C-- |
| BR36 | -AA------G--------------ACA---G--GCAAA----------C-- |
| T9 | -AA-A----C---T----------ACT----A-CA-G--T--G--T---- |

Figure 1 - Continued 9

```
                  8132                                    8181
T10       3b     -AA-A--C--T-----------ACT--G---A-CA-G---T--G---
BE98      3c     -AA----C--T--------A--AAA-----TACCAA---T--C--AA-T

GB48      4c     -A--G--G-----C-----A--TCA--C--TATCAA---G--G-----G
GB116     4c     -A--G--G-----TC----A--TCA--C--TATCA----G--G-----G
GB215     4c     -A--G--G-----TC----A--TCA--C--ATCA-G--GT--------G
GB358     4c     -A--G--G-----C-----A--TCA--C--TATCA----G--G-----G
GB809     4c     -A--G--G-----C--T--A--TCA-----ATCA-G--T--G-----A
CAM600    4e     -AA-G--G-----C--T--A--TCA-----ATCA-G--T--G-----G
G22       4e     -A--G--G-----C--T-----TCA-----ATCA-G-----T--C--A
GB549     4f     -T--G--G-----T-C------ACA--G--ACCAA-------T--G
GB438     4g     -TG-A--G--T--TC----A--GTT--G--TAC-A-G-----T-----G
CAR4/1205 4h     -GG-G--A-----C--T--A--ACA--G--ACCA-G--T--------G
CAR1/501  4i     -G--G--------C-----A--ACA--G--ACCA-G-----G--CT-C
EG-13     4j     -A--G--G-----C--T--A--ACA--T--TAC-A-----A--C--CT-
EG-19     4k     -G--G--------C--T--A--AC----TAC-A-----C--CT-
BE95      4k     -G--G--------C--A--A--ACA--C--TAT-A-----G-----G
BE96      5a     -G--G--------C--------TAT-A-G--G--G--?
CHR18     5a     -A--G--------------TTTA--CT-------A----------A
CHR19     5a     -A--G--------------TTTA--CT-------A--A-------T
          5a     -A--G--------T-----TTTA--CT-------A-----------
          5a     -A--G--------------TTCA--C--------A----------T-
```

Figure 1 - Continued 10

```
         8182                                              8231
         CAGGACTGCACCATGCTCGTGTGTGGCGACGACTTAGTCGTTATCTGTGA
HCV-1    --------------------------------------------------
HCV-J    ------------------G-------AAC--A-----C--T---------
BE90     ------------------G--------------C--G--T----------
2TY4     --G-----------------------------------------------
4TY4     --------------------------------------------------
HC-J6    ATT-CGCC---A------G--A--C-----T-----G--T-----CA---
HC-J8    GT-----CCTGTT---T-G--------A-------------C-------CA---
NE91     GT-----CC-GT------G--------A-------------C-------CA---
EB12     GT-----CC-GTT.------------------------------------
ARG6     GTT--C-CC----------------------------------------
ARG8     GTT-CTCC---------------------------------------------
I10      GTT-CTCC------------------------------------------
T983     GTT-CTCC------------------------------------------
NE92     GTT-CT-C------------------------------------------
CHR20    ATT-C-CC---G------G-------C-----------TC---T--C---CA---
CHR21    -G-A---CCGGA-T-T---C-----A--T--TC-G----GG-GGC---
CHR22    -G-AC--CCGGA-T-T---C-----A--T--TC-G----GG-GGC---
T1       -G-A---CCGGA-T-T---T-----C-----A--T--TC-G----T--GG-GGC---
T7       -G-A---CCGGA-T-T---T-----C-----A--T--TC-G----T--GG-GGC---
NE93     -G-A---CCGGA-T-T---T-----C-----A--T--TC-G----T--GG-GGC---
N2L13    -G-A---CCGGA-T-T---T-----C-----A--T--TC-G----AG-GGC---
EB1      -G-A---CCGGA-T-T---T-----C-----A--T--TC-G----GG-GGC---
EB2      -G-A---CCGGA-T-T---T-----C-----A--T--TC-G----GG-GGC---
EB3      -G-A---CCGGA----------------C-----A--T--TC-G----GG-GGC---
EB7      -G-A---TCCGGA----------------C-----A--T---G---GG-GGC---
BR33     -G-A---CCGGA-T-T---C-----A--T--T--G----T---GG-GGC---
BR34     -G-A---CCGGA-T-T---C-----A--T--TC-G----GG-GGC---
BR36     -G-AG--CCGGA-T-T---T-----C-----A--T--TC-G-------G-A-C---
T9       A-A----CCAT-TT--C---T--C----A-----T--G------
```

HCV-1 1a
HCV-J 1b
BE90 1b
2TY4 1c
4TY4 1c
HC-J6 2a
HC-J8 2b
NE91 2b
EB12 2b
ARG6 2c
ARG8 2c
I10 2c
T983 2c
NE92 2c
CHR20 2d
CHR21 3a
CHR22 3a
T1 3a
T7 3a
NE93 3a
N2L13 3a
EB1 3a
EB2 3a
EB3 3a
EB7 3a
BR33 3a
BR34 3a
BR36 3a
T9 3b

Figure 1 - Continued 11

```
                 8182                                                                                    8231
T10         3b   A-A----CCAT--T-C--T--C--C--A------T--G--G---G-G-C---
BE98        3c   A-AA-TCCAT-AT-C--T--C--A------T------G------G--TGC---

GB48        4c   AGA-----------------T-G--C----------T----C-G--T---GC---
GB116       4c   AGA-----------------T-G--C----------T----C-G--C--TGC---
GB215       4c   AGA--------T--------T-G--C-A--------T----C-G--C--TGCC--
GB358       4c   AGA-----------------T-G--C----------T----C-G--C--TGCC--
GB809       4e   A----T--------------G----T--C-------T---------C---GC---
CAM600      4e   A----T--------------G----T--C-------T---------G---GCC---
G22         4f   A-------------------G----T----------T---------G---GC---
GB549       4g   A-A-GT-----G--------G----T--A-------A---------GCC---
GB438       4h   A-A----T------------G----A--C-T-----T------C------TGCC---
CAR4/1205   4i   A----T--------------G----C--C-N-----T----C-G--T--C--TGC---
CAR1/501    4j   A-A----T------------G----C--C-------T-------------T--CC---
EG-13       4k   AGA------T----------------------------------------
EG-19       4k   A-A----A--T------------------------------------------
BE95        5a   -G---------GC--C---G----------------T------TC-T--G-CC---C---
BE96        5a   -G------A--GC--C---G----------------T------TCAT--G-CC---C---
CHR18       5a   -----------GC--C---G----------------T--T---TC-T--G-CC---T---C---
CHR19       5a   -----------GC--C---G----------------T-TTAC-T-TTAC--G--CC---T---C---
```

Figure 1 - Continued 12

```
       8232                                      8271
       AAGCGCGGGGGGTCCAGGAGGACGCGGCGAGCCTGAGAGCC
HCV-1
HCV-J  G--T----AAC-------T-----GC---AC-------
BE90   ---------AAC---A--------------AC---T---
HC-J6  G------CA---AC-G--------A-CG--A--------
HC-J8  G------CAA--TAA-G-------A-CGA-A-------T
NE91   G------CA---TAA-G-------A-CGA-A-------T
NE92   G------CA---TAA-G-------A-CGA-A--------
NE92   G------TCA---AC-G-------A-CG--A---AC---
CHR20  G--T-AT----C---G-C---TAGA--AGC---------
CHR21  G--T-AT----C---G-C---TAGAA-AGC---C-----
CHR22  G--T-AT----C---A-T---TAGA--AGC---G-----
T1     G----AT----C---G-T---TAGA--AGC---------
T7     G--T-AT----C---G-C---TAGA--AGC---------
NE93   G--T-AT----C---G-C---TAG-A--GC---------
NZL13  G--T-AT----C---G-T---TAGA--AGC---------
BR33   G--T-T----------------------------------
BR34   G--T-T----------------------------------
BR36   G--T-T----------------------------------
T9     ----TGC--C---G--------AGA--AGCT---C----
T10    ----TGC--C---G--------AGA--AGCT---C----
BE98   G--T--A---G-T---------AGA---------------
```

Figure 1 - Continued 13

```
                    8232                                      8271
GB48        4c   G----AT---C---AG-------------AAACGACC---CG-----
GB116       4c   -----AT---C---AG-------------AAACGAGC---CG-----
GB215       4c   G----AT---C---AG-------------AAACGAGC---CG---T-
GB358       4c   G----AT---C---TG-------------AAACGAGC---CG-----
GB809       4e   G----GT---C---TG-------------AA-CGAGC---CG---T-
CAM600      4e   -----GT---C---G--------------AA-CGAGC---CG---T-
G22         4f   -----AT---T---G-A------------CGCCGAGC---CG---T-
GB549       4g   G----GC---C---AG----------T--AAGAGC-----CC-----
GB438       4h   -----GT---C---GG-------------CCGAGC-----CC-----
CAR4/1205   4i   G----ATT--CA--AG-C-----------AA-CAAGC---CC--NA-T
CAR1/501    4j   G----C----T---GG-------------TC-CANA-C--NNC--C-N
BE95        5a   G----CA---ACA-C--------------T-AA--A-----------
BE96        5a   G----CA---ACA-C--------------T-AA--A-----------
CHR18       5a   G----CA---ACG-C--------------TAAA--------------
CHR19       5a   G----CAA--ACG-C--------------T-AA--T---------T-
```

Figure 2

```
                      2645                                              2694
          SEQ ID      STVTESDIRTEEAIYQCCDLDPQARVAIKSLTERLYVGGPLTNSRGENCG
HCV-1  1a
HCV-J  1b             ----N--------S-------A-E--Q-R-------------------K-Q--
BE90   1b    214      ----N----V---S-------A-E--Q---------------I-----K-Q--
2TY4   1c             -------------------------N-------------------------K-----
4TY4   1c             -----------------H-D---A---N-----------------K-----

HC-J6  2a             ------------R-----S--RA-S-PEE-HT--H-----------MF---K-QT--
HC-J8  2b             ------------R-----S--A-S-PQE--TV--H------------M---K-QS--
NE91   2b    216      ------------R-----S--A-S-PQE--TV--H-----------MI---K-QS--
EB12   2b             ------------------A-S-PQE--TV--H------------M---K-QS--
ARG8   2c             ------------------S-S-PEE--T---H------------M---K-QS--
I10    2c             -----------------LS-S-PEE--T---H------------M---K-QS--
T983   2c             ------------------A-S-PQE--T---H------------M---K-QS--
NE92   2d    146      ------------R-----S--LA-S-PE---T---H-----------ML---K-QT--

CHR20  3a             ----Q----V---E-------N-E-E--KV-S------------C---MF--K-AQ--
CHR21  3a             ----Q----V---E-------N-E-E--KV-S------------C---MF--K-AQ--
CHR22  3a             ----Q----V---E-------N-E-E--KV-S------------C---MF--K-AQ--
T1     3a             ----Q----V---E-------N-E-E--RV-S------------C---MF--K-AQ--
T7     3a             ----Q----V---E-------N-E-E--KV-S------------C---MY--K-VQ--
NE93   3a    218      ----Q----V---E-------N-E-E--KV-S------------C---MF--K-AQ--
NZL13  3a             N----Q----V---E------N-E-E--KV-S------------C---MF--K-AQ--
EB1    3a             ---------------------N-E-E--KV-S------------C---MF--K-AQ--
EB2    3a             ---------------------N-E-E--KV-S------------C---MF--K-AQ--
EB3    3a             ---------------------N-E-E--KV-S------------C---MF--K-AQ--
EB7    3a             ---------------------N-E-E--KV-S------------C---MF--K-AQ--
BR33   3a    10,12                                                C---MF--K-AQ--
BR34   3a    2,4                                                 C---MF--K-AQ--
BR36   3a    6,8                                                 C---MF--K-AQ--
T9     3b             --------H----E-------E---K--SA--------------I---MY--K-LQ--
T10    3b             ----Q--------E-------E-E--K--SA--------------I---MY--K-LQ--
BE98   3c    150                        A---KDE--RV-T-------------C---MF--K-QH--
```

Figure 2 - Continued 1

| | | | 2645 | 2694 |
|---|---|---|---|---|
| EG13 | 4a | | V----N-E-E--K--TA------------ | -MH---K-DL-- |
| EG19 | 4a | | V----S-ELE--KV-TA------------ | -MH---K-DL-- |
| GB48 | 4c | 107 | ----K---V--EV------E-E--K--TA------------ | -MH---K-DL-- |
| GB116 | 4c | 109 | ----K---V--EV------E-E--R--TA------------ | -MH-----DL-- |
| GB215 | 4c | 111 | ----K---V--EV------E-E--KV-TA------------ | -MH---K-DL-- |
| GB358 | 4c | 113 | ----K---V--EV------E-E--K--TA------------ | -MH---K-DL-- |
| GB809 | 4c | 117 | ----K---V--EV------E-E--KV-AA------------ | -MH---K-DL-- |
| CAM600 | 4e | 202 | ----R--KV--EV------E-E--KV-TA------------ | -MH---K-DL-- |
| CAMG22 | 4e | 204 | ----R---V--EV------E-ET-KV-SA------------ | -MY---K-DL-- |
| GB549 | 4f | 115 | ----R---V--EV------E-E--KV-SA------------ | -MH-----DL-- |
| GB438 | 4g | 208 | ----R---V--E-------E-E--KV-SA----K------- | -MY---K-DL-- |
| CAR4/1205 | 4h | 210 | ----R-X-V--EV------N-EXDX-KV-NA---------- | -MI---K-DL-- |
| CAR1/501 | 4i | 212 | P---R-X-V--EV------N-EXDX-KV-NA---------- | -MI---K-DL-- |
| | 4j | | ---X-R------GEV-----E-E--KV-TA----------- | -MF---K-DL-- |
| BE95 | 5a | 160 | ----H---M---S-----S----Q-E--A--R---Q----C----MY--K-QQ-- |
| BE96 | 5a | 162 | --A-H---L---S-----S--SQ-D--A--R---Q--FC----MY--K-QQ-- |
| CHR18 | 5a | | ----H---M---S-----SLY-Q-E----R---Q----C----MY--K-QQ-- |
| CHR19 | 5a | | ----H---M---S-----SLY-Q-E--A--R---Q----C----MY--K-QQ-- |

Figure 2 - Continued 2

```
              2695                                              2744
         YRRCRASGVLTTSCGNTLTCYIKARAACRAAGLQDCTMLVCGDDLVVICE
HCV-1  1a ------------------------------------------------- 
HCV-J  1b ------------------L--T---K-------N-------------
BB90   1b ------------------L--S---K---------------------
2TY4   1c ------------------L------R---------------------
4TY4   1c ---------------------L-------------------------
HC-J6  2a ------------M---I---V--L--K----IIAP------------S-
HC-J8  2b ------F-----M-------V--L--K---IV-PV------------S-
NE91   2b ------F-----M-------V--L--K---IV-PV------------S-
EB12   2b ------F-----M-------V--L--K---IV-PV-----------
ARG8   2c ------------M-------V--L--K---IV-PV-----------
I10    2c ---A--------M-------V-----N---IVAP-----------
T983   2c ------------M-------V-----N---IVAP-----------
NE92   2c ---V--------M-------V--K--N-V-IVAS-----------
NZL13  2d ------F-----M---I---V--Q--K---IIAP------------S-
CHR20  3a ---------P--F---I---------SK----RNPDF----------VA-
CHR21  3a ---------P--F---I---------AK----RTPDF----------VA-
CHR22  3a ---------P--F---I---------AE----RNPDF----------VA-
T1     3a ---------P--F---I------T--AK----RNPDF----------VA-
T7     3a ---------P--F---I------T--A-----RNPDF----------VA-
NE93   3a ---------P--F---I------TT-AK----RNPDF----------VA-
NZL13  3a ---------P--F---I------T--AK--N-RNPDF----------VA-
EB1    3a ---------P--F---I------T--E-----RNPD-----------
EB2    3a ---------P--F---I------T--E-----RNPD-----------
EB3    3a ---------P--F---I------T--K-----RNPDF----------
EB7    3a ---------P--F---I------T--K-----RNPD-----------
BR33   3a ---------P--F---I------T--AK----RNPDF----------VA-
BR34   3a ---------P--F---I------T--A-----RNPDF----------VA-
BR36   3a ---------P--F---I------T--AK----RSPDF----------VA-
T9     3b ---------P--F---I------T--S-----K-PSF----------VS-
T10    3b ---------P--F---I------T--S-----K-PSF----------VS-
BE98   3c ---------P--F---I------K--TK----IKNPSF---------A-
```

Figure 2 - Continued 3

```
                 2695                                              2744
GB48       4c    -------Y---F-------L--S--IK---R---------------A-
GB116      4c    -------Y---F-------L--S--I----R---------------A-
GB215      4c    -------Y---F-------L--S--I---------------Y----A-
GB358      4c    -------Y---F-------L--S--I-S-R----------------A-
GB809      4c    -------Y---F---M---L--S--I----K---------------A-
CAM600     4e    -------Y---F-------L--S--I----K---------------A-
CAMG22     4e    -------Y---F-----FL--T--TK---K----------------A-
GB549      4f    Q------Y---F---V---L--V--T---KG-S----------------
GB438      4g    L------Y---F---V---L--T--T---K----------------A-
CAR4/1205  4h    I------Y---F-------L--T--T---K----------------A-
CAR1/501   4i    Q------F---F-------L--T--T---K----------------S-
EG13       4j    -------F---F-------L--T--I---R-------------------
EG19       4k    -------Y---F-------L--T--I-----K-S---------------
                 4k
BE95       5a    -------F---M---M---L--S---R-R----L---------A----
BE96       5a    -------F---M---M---L--S--T--R-Y-L--------H-A----
CHR18      5a    -------F---M---M---L--S-----K----L---------A----
CHR19      5a    -------F---M---M---S--------K----L-------VT--A--
```

Figure 2 - Continued 4

|       |     | 2745 SAGVQEDAASLRA | 2757 |
|-------|-----|--------------------|------|
| HCV-1 | 1a  | SAGVQEDAASLRA      |      |
| HCV-J | 1b  | ---T----A---       |      |
| BE90  | 1b  | ---T-------V       |      |
| HC-J6 | 2a  | -Q-TE--ERN---      |      |
| HC-J8 | 2b  | -Q-NE--ERN---      |      |
| NE91  | 2b  | -Q-NE--ERN---      |      |
| NE92  | 2d  | -Q-TE--ERN---      |      |
| CHR20 | 3a  | -D---D---R--A--    |      |
| CHR21 | 3a  | -D---D---RTA--     |      |
| CHR22 | 3a  | -D---N---R-A-G-    |      |
| T1    | 3a  | -D---D---R--A--    |      |
| T7    | 3a  | -D---D---R--A--    |      |
| NE93  | 3a  | -D---D---RTA--     |      |
| NZL13 | 3a  | -D---D---R--A--    |      |
| BR33  | 3a  | -                  |      |
| BR34  | 3a  | -                  |      |
| BR36  | 3a  | -                  |      |
| T9    | 3b  | -C--E--R--A--      |      |
| T10   | 3b  | -C--E--R--A--      |      |
| BE98  | 3c  | ---ID--R-          |      |

Figure 2 - Continued 5

|  |  | 2745 | 2757 |
|---|---|---|---|
| GB48 | 4c | -D--E---KRP-G- |  |
| GB116 | 4c | -D--E---KRA-G- |  |
| GB215 | 4c | -D--E---KRA-GV |  |
| GB358 | 4c | -D--E---KRA-G- |  |
| GB809 | 4e | -G--E---KRA-G- |  |
| CAM600 | 4e | -G--E---KRA-G- |  |
| G22 | 4f | -D--E---KRA-G- |  |
| GB549 | 4g | -G--E---RA--- |  |
| GB438 | 4h | -G--E---RA--- |  |
| CAR4/1205 | 4i | -I-ID--KQA--T |  |
| CAR1/501 | 4j | ----E---PXTX-P |  |
| BE95 | 5a | -Q--TH--E---- |  |
| BE96 | 5a | -Q--TH--E-N--- |  |
| CHR18 | 5a | -Q--TH--K---- |  |
| CHR19 | 5a | -Q--TH--E-C---V |  |

Figure 3

|  |  | SEQ ID | 1 ATGAGCACGAATCCTAAACCTCAAAAAAACAAACGTAACACCAACCG |
|---|---|---|---|
| HCV-1 | 1a | | |
| HCV-J | 1b | | ------------A-----------------G-----C---------- |
| HC-J6 | 2a | | ------------A-----------------G---T-C--A-A----- |
| HC-J8 | 2b | | ------------A-----------------G-----C--A-A--A-- |
| NE92 | 2d | 143 | ------------A-----------------G-----C--A-A--T-- |
| EB1 | 3a | | ---------ACT------------------G-----C--A-A----T |
| NZL1 | 3a | | ---------ACT------------------G-----C--A-A----T |
| HCV-TR | 3b | | ---------ACT------------------G-----C--A-A--ACT |
| BE98 | 3c | 147 | ---------ACT------A-----------G-C---C--A-A-----S |
| GB358 | 4c | 191 | -------------------------------G-----C---------- |
| GB809 | 4e | 163 | --------------------T----------G-----C---------- |
| CAM600 | 4e | 165 | -------------------------------G-----C---------- |
| GB724 | 4? | 193 | -------------------------------G-----C---------- |
| EG-29 | 4? | | -------------------------------G-----C---------- |
| BE95 | 5a | 151 | -------------------------------G-----C--A-A----- |

|  |  | 51 TCGCCCACAGGACGTCAAGTTCCCGGGTGGCGGTCAGATCGTTGGTGGAG |
|---|---|---|
| HCV-1 | 1a | |
| HCV-J | 1b | C--------------------T----C------------------C--- |
| HC-J6 | 2a | ------------A-------T-----C------------------C--- |
| HC-J8 | 2b | -------------------T------C---------------------- |
| NE92 | 2d | -------------------T------C--------C-T-C-------- |
| EB1 | 3a | --------------------------------------A--------- |
| NZL1 | 3a | --------------------------------------A--------- |
| HCV-TR | 3b | ------------A-------T-----------A--C--A--------- |
| BE98 | 3c | C--G---------------T------C--------C-T-C-------- |
| GB358 | 4c | C------CAT----------T-----C--------C-T-C-----C--- |
| GB809 | 4e | C------CAT----------T-----C--------C-T-C-----C--- |
| CAM600 | 4e | C------TAT-------A--T-----C------A-C-T-C-----C--- |
| GB724 | 4? | C------TAT----------T-----C--------C-T-A-----C--- |
| EG-29 | 4? | C------CAT----------T-----C--------C-T-C-----C--- |
| BE95 | 5a | -----------------------------------C-T-------C--- |

Figure 3 – Continued 1

```
        101
        TTTACTTGTTGCCGCGCAGGGGCCCTAGATTGGGTGTGCGCGACGAGA
HCV-1   1a  ------------------------------C--G--------T--G
HCV-J   1b  --C---------------------------C--G--------A--G
HC-J6   2a  -A----------------------------C--G--------A--G
HC-J8   2b  ---------C--------------------CC-G-----------G
NE92    2d  -A----------------------------AC----------T--G
EB1     3a  -A--G-------------------------AC----------C-T
NZL1    3a  -A--G-------------------------AC----------C-T
HCV-TR  3b  -A--TG--C--------T------------AC-------AGTAC-T
BE98    3c  ----G--C-A--A-----------------CCAG---T--AGT-C-C
GB358   4c  ------------------------------C--G--------T--G
GB809   4e  ---------------------------------G--------TC-G
CAM600  4e  ------------------------------C--G--------TC-G
GB724   4?  ------------------------------CC-G--------TC-G
EG-29   4?  ---------------------------------GA-------TC-G
BE95    5a  ---------------------------------GA-------TC-G

151
        AAGACTTCCGAGCGGTCGCAACCTCGAGGTAGACGTCAGCCTATCCCCAA
HCV-1   1a  --------------------------------------------------
HCV-J   1b  --------G--------C--G--A--T--A--G--C-----A--------
HC-J6   2a  --------T-----A--C--G--G--T--AC-----G--C--------T
HC-J8   2b  -A------T-----A--C--G--A--T--G--G--C--------C---G
NE92    2d  -A------T--A-----A--G--A--G--G--C-----C--------
EB1     3a  -A------T--A--------A--G-----AC--A-----A--------
NZL1    3a  -A------T--A--------A--G-----AC--A-----A--------
HCV-TR  3b  -A--------------G-------G-----CAAACAG---C-T-----
BE98    3c  --------G--------------------------CA---G--C--A--C
GB358   4c  --------G-----------------------T--G--G--C--A----T
GB809   4e  --------G-----------------------T--G--G--C--A----G
CAM600  4e  --------G-----------------------T--G--G--C--A----
GB724   4?  --------G-----------------------T--C--G--C--A----
EG-29   4?  --------G--A--------------------T--G-----C--A----A--
BE95    5a  --------G--A--------------C--T--AC-G--------T----
```

Figure 3 - Continued 2

```
        201
        GGCTCGTCGGCCCGAGGGCAGGACCTGGGCTCAGCCCGGGTACCCTTGGC
HCV-1   --------------------------------------------------
HCV-J   ----C-------------T----------------------------G--
HC-J6   --A---G--CT--ACT----AAT------GAA-A--A--A---------
HC-J8   A-A---G--CT--ACC----A-T------GAA----A--A--T------
NE92    A-A---G--C---ACT----A-T------GAA-A--A--A---------
EB1     ---G-----AG--A------T------------------C---------
NZL1    ---G-----AG--A---C--T----------------------------
HCV-TR  ----CTC--G-------C--T----------------------------
BE98    ---G--C--AA---------T----------------------------
GB358   --A---AT-T---A------T----------------------A-----
GB809   ---G--C--AT---------AT--------G--T---------------
CAM600  ---G--C--AA---------AT--------G------------------
GB724   ---G-----T----------T---------G--AG--------C-----
EG-29   ---G-----AT------A--T--------A--A--A--T--A-------
BE95    ---G--C--A---AC--C--T--------G-----A-------------

251
        CCCTCTATGGCAATGAGGGCTGCGGGTGGGCGGATGGCTCCTGTCTCCC
HCV-1   --------------------------------------------------
HCV-J   ---A--C--G-------A------A---------------------C--A
HC-J6   ---G--C--A--C----ACT----C---A---------------T-C--A
HC-J8   ---G--C--G-------T------C---T--------A--G----C---G
NE92    ---G--C--G-------CT---------C---A--G----------C--T
EB1     ---------T---C---T--C-------A--G----------C--T
NZL1    ---------T---C---T--C-------A--G----------C--T
HCV-TR  ---------C--G--A----------T-A--G----------C--T
BE98    ---A-----G-------T----T-------A--G-----T-----C--T
GB358   ---T--T--C--T-----T----T------A--G-----T-----C--T
GB809   ---G--C--A-------------T------A--G----------C--T
CAM600  ---T--C-----------------T-----A--G----------C--T
GB724   ---T--C--T-------------T------A--G----------C--T
EG-29   ---T--T--T-------------------A-----G---G-C--C--T
BE95    ---T--C--C-------CT----------A-----G---G-C--C--T
```

Figure 3 - Continued 3

|        | 301                                                |
|--------|----------------------------------------------------|
| HCV-1  | CGTGGCTCTCGGCCTAGCTGGGGCCCCACAGACCCCCGGCGTAGGTCGCG |
| HCV-J  | ------------------T------------------------------- |
| HC-J6  | --A--T--C--T---CTCT---------AT--------A---------C-- |
| HC-J8  | --C--G-----T----CT----------------------A----A--A-- |
| NE92   | --A--G-----C---GTCA---------C----------AC-------A-- |
| EB1    | --C-----C--T---ATCT--------A--T--------A--------C-- |
| 3a     | --C-----C--T---ATC---------A-AT--------A--------C-- |
| NZL1   | --C-----C--T---ATC----------A-AT-------G--------C-- |
| HCV-TR | ----T---C-----T------------A-AT------------A---C-- |
| BE98   | --C-----C---GTCG-----------A-AT---------C---A----- |
| GB809  | --C--G-----GTCT-----------T-AT--T------G-------C-- |
| CAM600 | --C--N-----N-GTCT----------AT--T------N-G--A----C-- |
| CAM600 | --C-----ATCT--------------A-AT--T------G--A------- |
| GB724  | --C-----ATCT--------------A-AT----------G--A------- |
| BE95   | --A--------AT--------------AT-----------A-AA------ |

|        | 351                                                |
|--------|----------------------------------------------------|
| HCV-1  | CAATTTGGGTAAGGTCATCGATACCCTTACGTGCGGCTTCGCCGACCTCA |
| HCV-J  | T------------------------------------T------------ |
| HC-J6  | ---CG-----------------------A------T--T----------- |
| HC-J8  | --------C-GA---------A-------------T--T-T--------- |
| NE92   | ---C-------------------------------T--T----------- |
| EB1    | ------------A-----------C----G-------------------- |
| 3a     | ------------A-----------A-------A----------------- |
| NZL1   | ---C--T-----------------A-----T--A---------------- |
| HCV-TR | ---CC-------------------A-A-----T--A-------------- |
| GB809  | ---C--------------------A-A------------------A----- |
| CAM600 | ---C--------------------G------------------------- |
| GB724  | ------------------------A------------------------- |
| BE95   | T---------------------------------------------T--- |

Figure 3 - Continued 4

```
        401
HCV-1   TGGGGTACATACCGCTCGTCGGCGCCCCTCTTGGAGGCGCTGCCAGGGCC
HCV-J   ------------------T-----------C--A--G-----------
HC-J6   -------C---TG----A----------G--C--C-----TC----A--T
HC-J8   -------C---TG----T----------G--C--C-----TC----A--T
NE92    -------C---TG----T----------GG----------TC----A--T
NE92    -------C---TG---------------AG----T--T-TC----A--T
NZL1    -------C-----------------T--G--A--------TC----A--
HCV-TR  -------T-------------------G-G--G-------TC----A--
GB809   ----A--C-----T--A----------CG-G--T------TC----A--
CAM600  ----A--C-----T--A----------CG-G--T------TC----
GB724   ----A--C-----------G-------CG-C--G------TC----
BE95    ----T--C--------A---G------CA----G------TC----A--T

451
HCV-1   CTGGCCGCATGGCCGTCCGGGTTCTGGAAGACGGCGTGAACTATGCAACAG
HCV-J   ----A------------------G-------------------------
HC-J6   --C-------GA-A--C------G-------G--T--T-----------
HC-J8   --C---A--C-T--TA--C----G-------GA-A--T---C-------
NE92    --C-------GA-A---------G-------GA-A--------------
NE92    --C-------GA-----C-T---G-------GA-A--T-TC--------
NZL1    --C---T---GA--CA--T-GG---------A-----C-----------
HCV-TR  --C---T---GA--CA--T-GG---------A-----C-----------
GB809   ----A--C--TA--C-G------G-------GA-C--T--C--------
CAM600  ----A--C--TA--C-G--------------GA-C--T-----------
GB724   -------A---C-G-----------------GA-T-----N-G------
BE95    --C-A--C--T---GA---C-T-G-------G--A--------------
```

Figure 4

| Name | Subtype | SEQ ID NO |
|---|---|---|
| HCV-1 | 1a | |
| HCVEC1 | 1a | |
| HCVHCT18 | 1a | |
| HCVHCT23 | 1a | |
| HCVHCT27 | 1a | |
| HCVTH | 1a | |
| HCV-J | 1b | |
| HC-J6 | 2a | |
| HC-J8 | 2b | |
| NE92 | 2d | 143 |
| HD10 | 3a | 13, 15, 17 |
| BR33 | 3a | 23, 25, 27 |
| BR36 | 3a | 19, 21 |
| NZL15 | 3a | |
| HCV-TR | 3b | |
| GB809_4 | 4a | 189 |
| GB116 | 4c | 183 |
| GB215 | 4c | 185 |
| GB358 | 4c | 118, 187 |
| GB809_2 | 4c | 122, 169 |
| CAM600 | 4e | 167 |
| CAMG22 | 4f | 171 |
| CAMG27 | 4f | 173 |
| GB549 | 4g | 120, 175 |
| GB438 | 4h | 177 |
| CAR4/1205 | 4i | 179 |

Reference sequence (positions 379–428):

`ACGTGCGGCTTCGCCGACCTCATGGGTACATACCGCTCGTCGGCGCCCCC`

Figure 4 - Continued 1

```
CAR4/901  4?   181  G----------------T-----A-----C-----A---------
BE95      5a   143  ----A-----------T-----------C-----A------G---
BE100     5a   195  ----A--------G--------------C-----A------G---
```

Figure 4 : Continued 2

```
                     429                                                          478
                     TCTTGGAGGGCGCTGCCAGGGCCCTGGCGCATGGCGTCCGGGTTCTGGAAG
HCV-1         1a     --------------------------------------------------
HCVEC1        1a     --------------------------------------------------
HCVHCT18      1a     ------------------CG------------C-----------------
HCVHCT23      1a     ------------G-----------------------------T-------
HCVHCT27      1a     ------------G-------------------------------------
HCVTH         1a     ------------------------------A-------------------
HCV-J         1b     C--A--G-----------------------A----T------------G-

HC-J6         2a     G--C--C-----TC-----A--T--C--------GA-A---C-------G-
HC-J8         2b     GG----------TC-----A--T-----------GA----C-------G-
NE92          2d     AG---T--T---TC-----A--T--C--------GA-A------------

HD10          3a     -G-A--------TC-----A--A-----T-----GA----CC--T-----G-
BR33          3a     CG-A--------TC-----A--A-----T-----GA----CC--T---G-
BR36          3a     CG-A--------TC-----A--A-----T-----GA----CC--T-----G-
NZL15         3a     -G-A--------TC-----A--A-----T-----GA----CC--T-----G-
HCV-TR        3b     -G-G--G-----TC-----A--A-----C-----GA----CC--T-----G-
GB809_4       4a     CG-----G----TC-----A--------C--T--GA----CA--T-GG--G-
GB116         4c     CG---------TC----------------A-AA--C--T--TA--C-G-----G-
GB215         4c     CG-G--------TC---------A------AA---T--TA--C-G-----G-
GB358         4c     CG-G--T-----TC-----A----------A----T--TA--C-G-----G-
GB809_2       4c     CG-G--T-----TC---------A------A----T--TA--C-G-----G-
CAM600        4e     CG-G--T-----TC-----A--C--T--------A---TA--C-G-----G-
CAM22         4e     CG-G--T-----TC-----------------------A---C-G-----G-
CAMG27        4f     -G----T-----TC--------------T----------C-G-----G-
GB549         4g     -G-G--T-----TC---------------T---------A---C-CCG-----G-

GB438         4h     AG--A-------TC-------A---T-------------A---C-G-------
CAR4/1205     4i     CG--G-------TC-------AR-T--------------A---C------
```

Figure 4 : Continued 3

```
CAR4/901  4?   CG-G--T----TC-----A---------C--T--TA---C-G----G-
BE95      5a   CG----G----TC--A----T-C--A--C--T--GA----C--T--G-
BE100     5a   CG----G----TC--A----T-C--A-----T--GA-----T--G-
```

Figure 4 : Continued 4

```
                  479                                                        528
HCV-1       1a    ACGGCGTGAACTATGCAACAGGGAACCTTCCTGGTTGCTCTTTCTCTATC
HCVEC1      1a    --------------------------------------------------
HCVHCT18    1a    --------------------------------------------------
HCVHCT23    1a    ------------------------------------C---T---------
HCVHCT27    1a    --------------------------------------------------
HCVTH       1a    -----------------T---G--C-----------------C-------
HCV-J       1b    --------------------------------------------------

HC-J6       2a    ---G--T--T-T--------------T-A--C----C---T---------
HC-J8       2b    ---GA-A--T--C-------------TT-A--C----C---T---------
NE92        2d    ---GA-A-----------------T-T-G--C----C---T---------

HD10        3a    ---GA-A--T-TC-------------TT-G--C----C---T---------
BR33        3a    ---GA-A---TC--------------TT-G--C----C---T---------
BR36        3a    ---GA-A--T-TC-------------TT-G--C----C---T---------
NZL15       3a    ---GA-A--T-TC-------------T-G--C----C---T---------
HCV-TR      3b    ---A-------------------------T------C---T-------T

GB809_4     4a    ---GA-T-------G-----------T--------C---T---------T
GB116       4c    ---TA-T--T----------------T--------C-----T--------
GB215       4c    ---A-C--T-----------------T--------C---T----T-----
GB358       4c    ---GA-C--T----G-----------T--------C---T---------
GB809_2     4e    ---GA-C----C--------------T--------C---T---------
CAM600      4e    ---GA-C--T----------------T--------C---T---------

CAMG22      4f    ---GA-T-------------------T-----C---T---------
CAMG27      4f    ---GA-A-------------------------C---T---------
GB549       4g    ---GA-T-------------------T-----C---T---------
GB438       4h    ---GA-C--T-C--------------------C---T---------
```

Figure 4 - Continued 5

```
CAR4/1205  4i  ---GA-C--T----------T-----------------
CAR4/901   4?  ---GA-T--C----------T-----------------
BE95       5a  ---G--A----C------TT-A--C-------------
BE100      5a  ---G-----T----------T--G--------------
```

Figure 4 : Continued 6

```
              529                                              578
HCV-1    1a   TTCCTTCTGGCCCCTGCTCTCTTGCTTGACTGTGCCCGCTTCGGCCTACCA
HCVEC1   1a   --------------T-----------------------------------
HCVHCT18 1a   ------------------------------------------A-------
HCVHCT23 1a   ----------A--------C----------------------A----C--
HCVHCT27 1a   ------------------C-------------------------------
HCVTH    1a   -------------T----C---------A---------------A-----
HCVJ     1a   ------------------C-------------TC----------------
HCV-J    1b   ---CT-A--TT----G----CA-C--A-------C--T---G--

HC-J6    2a   ---T-G---------G--C---A-C--CACC--G-TC---C--TGC-G--
HC-J8    2b   --TT-G--T--T---G--T--T-G----A---TG---T--AGTGG-----
S83      2c   -------------------------A---G-C--A-----------GTGG-
NE92     2d   ---T-AT-------A-----TA-C-----------G-TC--C-G--TG--

HD10     3a   -----T--T---T---T-------A-TCCAT--A--AG-TAGTCTAG-
BR33     3a   -----T--T---T---T-------A-TCCAT--A--AG-T-GTCTAG-
BR36     3a   -----T--T---T---T-------A-T-CAT--A--AG-TAGTCTAG-
NZL15    3a   -----T--T---T---T-------A-T-CAT--A--AG-CAGTCTAG-
HCV-TR   3b   ----C--C--T--CT------C---------TGC-----G--T-G--TAG-
```

Figure 4 - Continued 7

```
              529                                                                   578
GB809_4       ----------C------A--T--T--G--C-C------C--A--G--A--TG-G--
Z4                                                                      G-G-----
Z1                                                                      GTG-----
GB116         -C-------CT------A--T--T--G----C-----T--A-C--A----GT-A-
GB215         -A-------CT------A--T--T--G----C-----T--A-C----AT------
GB358         ---------CT------A--T--T--G----C-----T--A-C--A----GT-A-
Z6                                                                     GTTA-----
Z7                                                                     GT-A-----
DK13                                                                   ---A-----
GB809_2       ---------CT------A--T--T--G----C-C---T------G------G-GTTA-
CAM600        ---------CT------G--C--T--G----C-C---T--A-A-------GTTA-
G22           ---------------A--T--T--G----C-----C------C------TGTG-
G27           ---------------A--T--T--G----C-----C------A----TGTG-
GB549         ---------------A--T--T--G----------C--G-C------GC-G--
GB438         -----A---A-----TA--T--T--GC-C-A---C--A-G--T--TC-G--
CAR4/1205     -C-----CT--TA--T--T--G----C-----T--C--A---AT---
CAR4/901      -N-------------A--T--T--G----C-----C--G--C------TC-G--

BE95          --TA-----T--T--T------G--TC---C--T--G-C--T--AGTT-C
BE100         --A------T--A--T------G------C--C--G--C--T--AGTT-C
SA4                                                         GTT-C
```

Figure 4 - Continued 8

```
                   579                                                           628
HCV-1       1a     AGTGCGCAACTCCACGGGGGCTTTACCACGTCACCAATGATTGCCCTAACT
HCVEC1      1a     -------------------------------T--------------------
HCVHCT18    1a     -------------------------------T-----------C--------
HCVHCT23    1a     -------------------------------T--------------------
HCVHCT27    1a     ---A---------------------T--CA-T--------------------
HCVTH       1a     -------------------------------T----------------T---
HCV-J       1b     G-----------GTGT-C---A-A-----T----G---C------T-C----

HC-J6       2a     ----AAG----AT--GTACCGGC---ATG--G------C---C---A-C--TG
HC-J8       2b     ---CA-G----ATT-GTTCTAGC---T---C---T-------T-A---T-A--A
S83         2c     G--CAAGG---A--GGC-ACTCC---ATGCCG------C-----------T-C---
NE92        2d     G--CAAG----A--GCA-CTC-----ATG--A------C------AG---A

HD10        3a     GTG----G----A-GT-T---C--C--TGT-C-T----C--C--TT-C--TA
BR33        3a     GTG----G----TA-GT-T---C--C--TGT-C-T----C--C--TT-C--TA
BR36        3a     GTG----G----TA-GT-T---C--C--TGT-C-T----C--C--TT-C--TA
NZL15       3a     GTG----G----TA-GT-T---C--C---GT-C-T----C--C--TT-C--TA
HCV-TR      3b     GTACACG----A-GT-T---C--A--TGTGC-T----C--C----T-----TG
```

Figure 4 - Continued 9

|  |  | 579 |  |  |  |  |  |  | 628 |
|---|---|---|---|---|---|---|---|---|---|
| GB809_4 | 4a | CTAC | -G- | -TG- | -TT- | ---- | -CA- | -C- | -T- | --A- | ---- | ---- | -C- | -T- | -G- | -T- |
| Z4 | 4a | CTAC | -G- | -TG- | -TT- | ---- | -CA- | -C- | -T- | --A- | ---- | ---- | ---- | ---- | -T- | -G- | -T- |
| Z1 | 4b | CTAC | -G- | -TG- | -TT- | ---- | -CG- | -C- | -T- | --T- | ---- | ---- | ---- | ---- | ---- | ---- | --A |
| GB116 | 4c | CTAT | ---- | --G- | -T- | ---- | -CG- | -C- | -T- | -TA- | ---- | ---- | -C- | ---- | -G- | -T- |
| GB215 | 4c | CTAT | ---- | -TG- | -T- | ---- | -CG- | -C- | ---- | ---- | ---- | ---- | -C- | ---- | -G- | ---- |
| GB358 | 4c | CTAT | ---- | -TG- | -T- | ---- | -CA- | -C- | -T- | --A- | ---- | ---- | -C- | ---- | -G- | ---- |
| Z6 | 4c | CTAT | ---- | -TG- | -T- | ---- | -CG- | -C- | -T- | ---- | ---- | -C- | -C- | ---- | -G- | ---- |
| Z7 | 4c | CTAT | ---- | -TG- | -T- | ---- | -CG- | -C- | -T- | --A- | ---- | -C- | -C- | ---- | -G- | ---- |
| DK13 | 4d | CTAT | -A- | -AG- | -T- | ---- | -TG- | -C- | ---- | --T- | ---- | -C- | -C- | ---- | -G- | ---- |
| GB809_2 | 4e | CTAT | ---- | -TG- | -TT- | ---- | -CG- | ---- | ---- | --T- | ---- | ---- | -C- | ---- | -G- | -TG |
| CAM600 | 4e | CTAT | ---- | -TG- | -TT- | ---- | -CA- | -C- | -T- | --A- | ---- | ---- | -C- | ---- | -G- | -TG |
| G22 | 4f | TTAT | -A- | --A- | -T- | ---- | -CA- | -C- | ---- | --C- | ---- | ---- | -C- | ---- | ---- | ---- |
| G27 | 4f | TTAT | -A- | --A- | -T- | ---- | -CA- | -C- | -T- | --A- | -T- | ---- | -C- | ---- | -G- | ---- |
| GB549 | 4g | CTAC | -G- | -AT- | -T- | ---- | -CA- | ---- | -T- | ---- | ---- | ---- | ---- | ---- | -G- | ---- |
| GB438 | 4h | CTAC | -G- | -TG- | -AT- | ---- | -CA- | -C- | ---- | ---- | -T- | ---- | -C- | -C- | -G- | ---- |
| CAR4/1205 | 4i | CTAT | ---- | -TG- | -TT- | --ACGG | ---- | ---- | -TT- | -TA- | ---- | ---- | ---- | ---- | -G- | ---- |
| CAR4/901 | 4? | CTAC | -G- | -TGT- | -T- | ---- | -CA- | -C- | ---- | ---- | ---- | ---- | ---- | ---- | -G- | -T- |
| BE95 | 5a | CTAC | -A- | -TG- | -T- | ---- | ---- | ---- | ---- | --A- | -T- | -T- | ---- | ---- | ---- | --A- |
| BE100 | 5a | CTAC | -A- | -TG- | -T- | -T- | --A- | -C- | -T- | -T- | ---- | ---- | ---- | ---- | ---- | --A- |
| SA4 | 5a | CTAC | -A- | --G- | -T- | -T- | --G- | ---- | ---- | -T- | ---- | ---- | ---- | ---- | ---- | --A- |

Figure 4 - Continued 10

| | | 629 | | | | | | | | 678 |
|---|---|---|---|---|---|---|---|---|---|---|
| HCV-1 | 1a | CGAGTATTGT | GTACGAGGGC | CGATGCCATC | CTGCACACTC | CGGGGTGC | | | | |
| HCVEC1 | 1a | ---C------ | ---------- | ---------- | ---------- | -------T | | | | |
| HCVHCT18 | 1a | ---------- | ----A----A | -----C---- | ---------- | -------T | | | | |
| HCVHCT23 | 1a | ---------- | ---------- | ---------- | ------G--- | -------T | | | | |
| HCVHCT27 | 1a | ---------- | ------A--- | -CA----A-- | -----T---- | -------T | | | | |
| HCVTH | 1a | ---------- | ---------- | ----T----- | ------G--- | -------T | | | | |
| HCV-J | 1b | -A-------- | T-------T- | ---A--G--C | ATG--A---- | ----C--- | | | | |
| HC-J6 | 2a | AT--C----- | ACC-GGC-AC | TCCAG-C--- | TG----C--- | -GTC-C-- | | | | |
| HC-J8 | 2b | AC--C----- | CACC-GGC-- | CTCA-T--C- | AG--T--C-- | TCT---A- | | | | |
| S83 | 2c | -T------T- | GGC--CTT-A | A-GA--AG-G | --T--T---- | T--T---A | | | | |
| NE92 | 2d | GT--C---C- | -C-GGC--CT | CAGG------ | TG-T--T--- | GTC-C--T | | | | |
| HD10 | 3a | GC-------- | ------T--- | --C-AT--C- | TT--T----- | -A--C--C | | | | |
| BR33 | 3a | GT-------- | ------T--- | --C-AT--C- | TT--T----- | -G-G-C--C | | | | |
| BR36 | 3a | GC-------- | ---------- | --C-AT--C- | TT--T----- | -A--C--C | | | | |
| NZL15 | 3a | GC-------- | ------T--- | --C-AT---T | ---T------ | -A--C--C | | | | |
| HCV-TR | 3b | G---C----- | ---------- | --C-AA---- | TG---T---- | TTA--C--A | | | | |

```
           679                                                              728
HCV-1      GTCCCTTGCGTTCGTGAGGGCAACGCCCTCGAGGTGTTGGGTGGCGATGAC
HCVEC1     1a  ----------AC----------T-------------------------
HCVHCT18   1a  ----------AC----------T-------------------G------
HCVHCT23   1a  ------------AT----T---A--------------------G------
HCVHCT27   1a  -----------C-------T------AA-----------------C--G-AG-
HCVTH      1a  -----------C-------T-----------------------------
HCV-J      1b  --G---C-----C--G---A-T--TTT---CC-T--C------A-----C-C--

HC-J6      2a  ------G----AGAAA-T---G--TA-A----TC----C----A-AC--G-CT-
HC-J8      2b  ---A---T-AGAA---TAATGG-A--T-CAT---C----A-ACAAG-A--
S83        2c  ------T-AG---ACC-C----T---TC-A--------C--G-TG-
NE92       2d  ------T-AGGAGA-------ATA---CC-C------A-AC--G-TT-

HD10       3a  --A-----T-----AG---C---T---TA-A----TGC---C---ACCC-AG---
BR33       3a  --A-----T---C-AG---C-------TA-G---T-CA---C---ACCC-AG-A--
BR36       3a  A-A-----T---C-AG---C-------TA-A---C-C----C---ACCC-AG---
NZL15      3a  ---A-----T---C-AG---C-------TA-A---T-C---C---ACCC-AG---
HCV-TR     3b  --G---C-----CACAACC-----CAA--ATCA---C---ACAA--G-CT-
```

Figure 4 - Continued 13

| | | 679 | | | | | 728 |
|---|---|---|---|---|---|---|---|
| GB809_4 | 4a | --A--C----- | --GA-G-CC--G-- | ---TG- | TC-T--C-- | --AC--C--G-A-- |
| Z4 | 4a | --A--C--T-- | -GATGACT--G-- | --A-A- | --C-T--C-- | --AC--C--G--- |
| Z1 | 4b | -----C--T-- | --G--GAC--AG-- | --TA-T- | --TC-C--C-- | ---C-CT------ |
| GB116 | 4c | T-A--C----- | --GA-G-TT--G-- | -TCAG- | -AC-C--C-- | ------CC--T-- |
| GB215 | 4c | T-A--C--T-- | --GA-G-TT--G-- | -TCAG- | -AC-T----- | ------CC-CT-- |
| GB358 | 4c | T-A--C----- | --GA-G-TT--G-- | -TCAG- | -AC-C--C-- | ------CC--C-- |
| Z6 | 4c | T-G--C--T-- | --GA-G-TT--G-- | -TCAG- | -AC-C--C-- | ------CC--T-- |
| Z7 | 4c | --A--C--T-- | --GA-G------G- | --CAG- | -AC-C--C-- | ------CC--T-- |
| DK13 | 4d | --T-------- | --GA-G--A--G-- | -AAG- | -T-CA--C-- | ---T-TC--C--- |
| GB809_2 | 4e | --A--C--T-- | -GAAGACC--G-- | --CAG- | ---C------ | ------CC--C-- |
| CAM600 | 4e | --A--C--T-- | --GA-GACT--G-- | --CAG- | ---C------ | ------CC--C-- |
| G22 | 4f | ---------T- | --AA-AACT--G-- | --CAG- | --TC--C-- | ---A---CT---- |
| G27 | 4f | ---------C- | --GA-AACT--G-- | --CAG- | -AC-A--C-- | --A-A---CT--- |
| GB549 | 4g | --G------- | --GA-AACC--G-- | --A--- | ---C--C-- | ---TC-TT--A-- |
| GB438 | 4h | --G--C--T-- | --AA-AACT--G-- | -T-T-- | --C-T--C-- | --A-TC-TT--A- |
| CAR4/1205 | 4i | A-A--C--T-- | -GAAGACC---G- | -TCAG- | ---C------ | ------TC-C--- |
| CAR4/901 | 4? | A-A--C----- | --GA-GACC--G-- | ---TT- | --C-C--C-- | ---AT-TC----- |
| BE95 | 5a | --G------T- | --CATGACA--T- | -T-TGAGT- | --A--C-- | --CCAA--T--- |
| BE100 | 5a | --G------T- | --CA-GA-A-AT- | -T-TGAGT- | -----C-- | --CCAA--T--- |
| SA4 | 5a | --G------T- | --CA-GC-A-AT- | -T-T-AGT-A- | --C-- | --CCAA--C--- |

Figure 4 - Continued 14

```
              729                                                           778
HCV-1      CCCTACGGTGGCCACCAGGGATGGCAAACTCCCCGGACGCAGCTTCGAC
HCVEC1     ---C--------------------C--------A-A-------------
HCVHCT18   ---C-----------------------------A-A-------------
HCVHCT23   ---C------------A--------C-------A-A-------------
HCVHCT27   ---C--A---------------------A---------------------
HCVTH      ---C---------------------C-------A-A-------------
HCV-J      T--C----C-C--GG------C---A-CA----A-C----ACAA-A----

HC-J6      A--G-AT------GTGCA-C-GCC-GGCGC--T-A---CA-GGCT-A--GA
HC-J8      A--C-AC------TGTG-AAC-CC--GGTGCG-T-A-TCGTAGC--G---A
S83        ---C-ATC-C----TA--TC-ACCTGGCGCT-T-A-T-A-GGC--G---G
NE92       G--C-ATA-A---TGTG--CC-ACCTGGTGCG-TTA-C-A-GGC--G--GA

HD10       A------A-----AGT----T-C-T-GG-GCAA--A-CG-TTC-A-A--CA
BR33       A------A-----AGT----T-C-T-GGGGCAA--A-CG-TTC-A-A--CA
BR36       A------A-----AGT--A-T-C-T-GG-GCAA--A-CG-TTC-A-A--CA
NZL15      A------A-----AGT----T-C-T-GG-GCAA-TA-TG-TTC-A-A--CA
HCV-TR     AA-G---------GTT---ACCCTTGGCG-GA--A-CG--TC-A-C---A
```

Figure 4 - Continued 15

```
              729                                                        778
GB809_4  4a   A-------------TG--GTATCCATGG-CGCT--GCTCGA-TCCT-C---G-
Z4       4a   G-----A-------TGT-GCAC-CCCGGGCGCT--GCTTGA-TC-T-C---G-
Z1       4b   ----T-------G-GCCCT--CC----CGCA--GTTAGA-TCCA-G---CA
GB116    4c   T---C-------C-GCCTT-C-TTGGTGCT--GCTAGAATCC---C---GA
GB215    4c   T---C--------GG-GCCTT-CAT-GGTGCT--A-TTGAATCCT-C---GA
GB358    4c   T---C--------GG-GCCTT-CAT-GGCGCT--GCTTGAATCC--C---GA
Z6       4c   T---C--------GGTGTCTT--AT-GGTGCT--GCTGACTCC--C---GA
Z7       4c   T---C--------GG-GCCTT--AT-GGTGCA--GCTTGAATCCA-C---GA
DK13     4d   ----C--------TG-GCAAC--CTG--TGCT--GCTTGA-TCTT-GA---
GB809_2  4e   T---C---A----GT-GCCTT-C-T-GGTGCT--GCTCGA--CCT-G---G-
CAM600   4e   T---C---A--A-GT-GCCAT-C-C-GGTGCT--GCTTGA--CCT-G---G-
G22      4f   ----C--------G-GCCAT-CCTTGGCGCT--ACTCGA-TCCA-G---G-
G27      4f   -------T-----G-GCCAC-CATTGGCGCT--ACTTGA-TCCA-G-----
GB549    4g   A---C---T----TG--CCCT---TTGGCGCG--GCTCGAATCCA-G---G-
GB438    4h   A---C---T--A--GT-CCCT-CCT-GGGGCT--ACTT---TCTG-A---G-
CAR4/1205 4i  ----C-------GG--CCAC-CCTACGTGCT--GCTTT--TCCT-A---GG
CAR4/901 4?   A-------T-----TG-TCCCT-CCT-GGGGCT--GCTT--TC---A---G-

BE95     5a   ----AC--T-AG--CC-AGCCT-GG-GCAGT-A--G-T-CT----GA
BE100    5a   ---C--T-AG--CC-AGCTT-GG-GCAGT-A--G-T-CC----GA
SA4      5a   ---C--T--T-AG--CC-A--CT-GG-GCGGT-A--G-T-CT----GA
```

Figure 4 - Continued 16

```
              779                                                 828
              GTCACATCGATCTGCTTGTCGGGAGCGCCACCCTCTGTTCGGCCCTCTAC
HCV-1    1a   --------------------------------------------------
HCVEC1   1a   ----------------------------------C--------------T
HCVHCT18 1a   ----------------------------------C---------------
HCVHCT23 1a   ----------------------------------C--------------T
HCVHCT27 1a   -------------------T--------T-----C---------------
HCVTH    1a   ---------------------------------------------T---T
HCV-J    1b   -C-----G-------T-----C---T---GCG--TG-T------C--TA-G

HC-J6    2a   CG-----T---CA--G---GAT-TC--------G------C---C--T--T
HC-J8    2b   CA-----G---CA--A-C--AAT-GCA---T--GGC----C---T-G--T
S83      2c   CA---------A-CA-C--GAT-TCT---T--GG------------T--T
NE92     2d   CG-----T---ACCA-CA-T-CATC----T--GT-T----C---T----G

HD10     3a   -G--TG-A---CA--T-G--G--CGCG-----GA-G----C--T--T---
BR33     3a   ----TG-G---C---T-A--A--CGCG-----GA-G----C--T-G--T-
BR36     3a   ---TG-G---C--AT-A--G--CGCG-----GA-G----C--T-G--T-
NZL15    3a   ---TG-G---C--AT-A--A--CGCG-----GA-G----C--T-G--T-
HCV-TR   3b   CC--TG-G---A-----G--A--CGCACGACAA--G-----------G--G
```

Figure 4 - Continued 17

| | | 779 | | | | | | | | 828 |
|---|---|---|---|---|---|---|---|---|---|---|
| GB809_4 | 4a | -G--TG-G | --C--AA-G | --A--TGCG | ---- | --G-G | ---- | ---- | T-T | ---- | -T |
| Z4 | 4a | -A--TG-G | --CT-AA-G | --A--CGCG | ---- | TT-G | ---- | ---- | T-T | ---- | -T |
| Z1 | 4b | -G--TG-A | --C----- | --G--TGCG | ---- | TA-G | ---- | --C- | --T | ---- | -- |
| GB116 | 4c | -G--TG-G | --C---- | --A-G--A | --T- | TG-G | ---- | --C- | --T | -T-- | -- |
| GB215 | 4c | ---- | -A--G-G | --CA--A-G | --G--CGCT | --T- | TG-G | ---- | --C- | --T | ---- | -- |
| GB358 | 4c | ---- | -A--G-G | --CA--A-G | --G--CGCT | --T- | TG-G | ---- | --C- | --T | ---- | -- |
| Z6 | 4c | ---- | --TG-G | --C--A-G | --A--TGC | --T- | TGCG | ---- | --C- | --T | -T-- | -- |
| Z7 | 4c | -A--TG-G | --C--A-G | --G--CGC | --T- | TG-A | ---- | --C- | --T | ---- | -- |
| DK13 | 4d | -A--TG-G | --C--A-G | --A--CGCT | --T- | AG-G | ---- | --C- | --T | ---- | -- |
| GB809_2 | 4e | ---- | --G-G | --A-G--G | --CG | ---- | T | ---- | C | ---- | -- |
| CAM600 | 4e | ---- | -C--TG-G | --C--A-G | --A--TGCT | ---- | -G-G | ---- | --C- | ---- | -- |
| G22 | 4f | ---- | --TG-G | --C--A-G | --A--TGCT | ---- | -A-G | ---- | --C- | ---- | -- |
| G27 | 4f | ---- | --G-G | --T--A-G | --G--C-CT | --T- | AT-G | ---- | --C- | A-A | ---- | -G |
| GB549 | 4g | ---- | --TG-G | --CT-AA-G | --A--C-CT | ---- | AT-G | ---- | --C- | --A | ---- | -- |
| GB438 | 4h | -G--G-G | --C--A-G | --G--TGC | ---- | -G-- | ---- | --C- | ---- | ---- | -G |
| CAR4/1205 | 4i | AG--TG-G | --C--A-G | --G--GCG | ---- | T-A | ---- | --C- | --T | ---- | -- |
| CAR4/901 | 4? | CG--TG-G | --C--AA-G | --G--GC | ---- | GGCA | ---- | --C- | --C | -TT-T | -- |
| | | -G--TG-G | --T--A-G | --G--TGCA | ---- | ---T | ---- | --C- | --T | ---- | -- |
| BE95 | 5a | -AGC-G-T | --CTAC--A | -CG--AG-G | --TG | ---- | ---- | --C- | ---- | C--GT-A | -- |
| BE100 | 5a | -AGC-G-T | --TACT-G | --AG-G | --TG | ---- | ---- | --C- | ---- | C--GT-A | -- |
| SA4 | 5a | -GGC-G-T | --CTACT-A | -CG--AG-G | --TG | ---- | ---- | --C- | ---- | C---A--A | -- |

Figure 4 - Continued 18

```
              829                                                878
HCV-1    1a   GTGGGGGACCTATGCGGGTCTCTGTCTTTCTTGTCGGCCAACTGTTCACCTT
HCVEC1   1a   ------------G---------------------C----------T-----
HCVHCT18 1a   ----------T-G---------------------------------T----
HCVHCT23 1a   -------------------T---CA---------------------T----
HCVHCT27 1a   ----------T-G---------------------------------T----
HCVTH    1a   -------------------G---CA---------------------T----
HCV-J    1b   ---T-------T--C-------A--C--T-----C---TC---G-------

HC-J6    2a   ----------C-----TGGG--GA-G------CA-C---GA-----TTG--
HC-J8    2b   ----A---TG-G-----G-C--GA-GA--C-ATCG--GGCT---TGG--
S83      2c   ----------G-T------CG-GC-GA-G-C--CT--GG-CG--GT-G--
NE92     2d   A-A--A------G--T---CG-G--GA-GT-G-CTTCT---G-C---T-A

HD10     3a   ------T---TA-G--T-----G-C---C---C--A---GCC----G--
BR33     3a   ------T---TA-G--T-----G-C---C---G--A---GCC----G--
BR36     3a   ------T---A-G--T------G-----C---G--A---GCC----G--
NZL15    3a   ------T---TA-G--T-----G---------C--A---GCC----G--
HCV-TR   3b   --C-----GCT-T----G----G---------G--A---GC--------
```

Figure 4 - Continued 19

|  |  | 829 |  |  |  |  |  |  |  |  | 878 |
|---|---|---|---|---|---|---|---|---|---|---|---|
| GB809_4 | 4a | --T--A-- | ---- | ---- | --C-- | -T-- | -AGG- | -CT-- | C---- | A---- | -G-- | -GA-- | ---- | ---- |
| Z4 | 4a | --T---- | ---- | ---- | --C-- | ---- | -AGG- | ---- | C---- | ------ | -G-- | -GA-- | ---- | ---- |
| Z1 | 4b | A-T--A-- | -T-- | -G-- | ---- | -T-- | -AGGC | ---- | C---- | -GA-- | -G-- | -GA-- | --A- | --T- |
| GB116 | 4c | A-C---- | ---- | -G-- | ---- | ---- | -TGGC | -A-- | -T-G- | ------ | -G-- | -T-- | --GA | -- |
| GB215 | 4c | A-T---- | -T-- | -G-- | -T-G- | -T-- | -TGGC | -A-- | -CT-G | ------ | -T-- | -T-- | --GA | --TT-T-- |
| GB358 | 4c | A-C--A-- | ---- | -G-- | ---- | ---- | -TGGC | -A-- | -T-G- | ------ | -T-- | -T-- | --GA | --TT-T-- |
| Z6 | 4c | ---- | -T-- | -A-- | -T-- | ---- | -TGG- | -CA- | -CT-G | ------ | -T-- | -T-- | --GA | ---T-- |
| Z7 | 4c | A-T---- | -T-- | -G-- | ---- | ---- | -TGG- | -CA- | -T-G- | ------ | -T-- | -T-- | --GA | ---- |
| DK13 | 4d | A-C--A-- | ---- | -G-G- | -T-- | ---- | -GG-- | ---- | -CT-G | ------ | -T-- | ---- | ---- | --TT-T-- |
| GB809_2 | 4e | --C---- | -C-- | ---- | -G-- | ---- | -TGGCT | -A-- | -CT-G | --A-- | ---- | ---- | -A-- | ---- |
| CAM600 | 4e | A-C---- | -C-- | -T-G- | ---- | ---- | -TGGCT | -A-- | -CT-G | ------ | -G-- | ---- | -A-- | ---- |
| G22 | 4f | --T---- | ---- | ---- | -G-- | ---- | -GGCA | -A-- | -C--- | -A-CG | ---- | ---- | --GA | ---- |
| G27 | 4f | A-T--A-- | -T-- | -G-- | ---- | ---- | -AGGCA | -A-- | -A--- | -A--- | -G-- | ---- | --GA | --A-- |
| GB549 | 4g | A-C--A-- | ---- | -T-- | -G-- | ---- | -AGG- | ---- | C---- | -G--- | ---- | -G-- | --GA | ---- |
| GB438 | 4h | A-C--A-- | ---- | -AT- | ---- | ---- | -AGG- | ---- | -CT-G | -CA-- | -G-- | -CA- | --GA | --G---GT-- |
| CAR4/1205 | 4i | A-T--A-- | -T-- | -G-- | ---- | ---- | -GG-- | ---- | -T--- | -G--- | ---- | -CG- | ---- | --TA- |
| CAR4/901 | 4? | --C--A-- | ---- | ---- | --C-- | -T-- | -AGG- | ---- | C---- | -A--- | -G-- | -A-- | --GA | -- |
| BE95 | 5a | --A--A-- | -GCG | -T-- | -G-AC | -A-- | -CT-G | --A-- | ---- | ---- | -A-- | ---- | ---A |
| BE100 | 5a | --T--A-- | -GCG | -T-- | -G-AC | -A-- | -T-G- | -A-- | ---- | ---- | -A-- | ---- | ---A |
| SA4 | 5a | --C---- | -GCG | ---- | -G-A- | -G-- | -T-G- | -A-- | ---- | ---- | -A-- | ---- | ---A |

Figure 4 - Continued 20

```
              879                                                928
HCV-1         CTCTCCCAGGCGCCACTGGACGACGCAAGGTTGCAATTGCTCTATCTATC
HCVEC1    1a  --------------------------------------------------
HCVHCT18  1a  --------------------------------------------------
HCVHCT23  1a  ----------------------------G-AC-----C--T---------
HCVHCT27  1a  ---C------------------------------A---C-----------
HCVTH     1a  --------------------------A---------------------C-
HCV-J     1b  ---A--TC-C---GT-TGA------GTA----A---------A-------

HC-J6     2a  ---G--ACA--A--------TTTGT-----AC-------C----------
HC-J8     2b  A--A--ACAA--------AACTTC--C------AG----C---T----C-
S83       2c  G--G--ACAA--A---TAC-TTGTC--G-AA------C--T--C--A--C-
NE92      2d  ---G---CA--AT--TAA-TTTGTC--G-AC------C--T--C--A--C-

HD10      3a  -AGA---TC-T-----TCAA---GTC--GACC--T--C-----AC-G--C-
BR33      3a  -AGA---C-C------TCAA---GTC--GACC--T--C-----GC-G--C-
BR36      3a  -AGA---TC-T-----TCAA---GTC--GACC--T--C-----GC-G--C-
NZL15     3a  -AGA---TC-A-----TCAA---GTC--GACC--T--C-----GC-G--C-
HCV-TR    3b  -AGA---TC-C-------AC---CGT--GACG------C-----G--A--C-
```

Figure 4 - Continued 21

```
           879                                               928
GB809_4    -CAG---GC-T-------------------C------G--A---T-----C-------A
4a         TCGG---GC-T-------------------C------G-AG--------T--C-----CA
Z1         -CGG---GC-C---G---------------C---C--G--A--------------C----
GB116      -CGA---GC-A-------------------C------G--A--------T--C-----CG
GB215      -CAG---GC-A-----------------T-C--T---G-AC--------T--C-----CG
GB358      -CGG---AC-A-----------------T-T------G-AC--------T--C-----CG
Z6         -CAG---GC-----------------------T----G-AC--------T--C-----CG
Z7         -CAG---GC-A-----------------T--------G-AC--------T--C-----CG
DK13       -CAA---TC-C--------------------------G-AC--------T--C-----G
GB809_2    -CAA---GC-A---T-----------------C----G--AC---T---T--C-----CA
CAM600     -CAA---GC-A-------------------C--C---G-AC--------T--C-----CG
G22        -CGG-----C-C---T----T----------------G-AC--------T--C--C--CA
G27        -AGG-----C-C--TG-----------------C---G-AG--------T--C------
GB549      -CGG---GC-C----------T--------C--C---G-AG--------T--C-----G
GB438      -CAA-----C----------T-----T----------G--A--------T--C-----G
CAR4/1205  -CGG---AC-CATT---TGAA---------C--T---G-AC--------C--C-----CT
CAR4/901   -CAG---GC-C-------------------C--T---G-AC-----C------T----CG

BE95       TAGG--TC-C-AG---GCT---GT---GAAC--------C--T--C--T-----CA
BE100      TAGG--TC-C-AG--TGCT---GT---G-AC--------C--T--C-------CA
SA4        TAGG--TC-C-AG--ACT---GT----AC----------------T-------CA
```

Figure 4 - Continued 22

```
              929                         957
HCV-1    1a   CCGGCCATATAACGGGTCACCGCATGGCA
HCVHCT18 1a   -----------C-----G-----------
HCVHCT23 1a   -----------C-----------------
HCVHCT27 1a   ----------------A------------
HCVTH    1a   -----------------------------
HCV-J    1b   --------CG--T-A------------T

HC-J6    2a   -T--TACC--C--T--A----------G
HC-J8    2b   AA--T--C--C--C--T----------T
S83      2c   -G----GC--T-----A----------T
NE92     2d   -A-----C--T--A--T--G-------G

HD10     3a   -A-----C-TT-A--A--------A--T
BR33     3a   -A-----C-TT-A--A--T-----A--T
BR36     3a   -A-----C-TT-A--A--T-----A--T
NZL15    3a   -A-----C-TT-A--A--T-----A--T
HCV-TR   3b   -A-----G-TT-A--A--T-----T--G
```

Figure 4 - Continued 23

| | | 929 | | | | | | | 957 |
|---|---|---|---|---|---|---|---|---|---|
| GB809_4  | 4a | -T----- | -C--- | C---- | C---- | A-G-- | --- | -G |
| Z4       | 4a | -T----- | -C--- | C---- | C---- | A-G-- | --- | -G |
| Z1       | 4b | -T--T-CG | -CT--- | --- | C---- | A-G-- | --- | -C |
| GB116    | 4c | -G--G-CG | -T--- | --- | C---- | A-G-- | --- | -- |
| GB215    | 4c | -G--G-CG | -T--- | T--- | C---- | G-A-- | --- | -- |
| GB358    | 4c | -G--G-C- | ---- | --- | C---- | A-G-- | --- | -- |
| Z6       | 4c | -A--G--- | ---- | --- | C---- | A-G-- | --- | -- |
| Z7       | 4c | -G--G-CG | -T--- | A--- | C---- | A-G-- | --- | -- |
| DK13     | 4d | -A--A--- | -C--- | A--- | A---- | A-A-- | --- | -- |
| GB809_2  | 4e | -A--G--- | -T--- | --- | C---- | T-G-- | --- | -T |
| CAM600   | 4e | -G--G--- | -C--- | --- | ---- | T-G-- | --- | -- |
| G22      | 4f | -G----- | -C--- | --- | ---- | TA-A- | --- | -G |
| G27      | 4f | -A----- | -C--- | --- | ---- | A-A-- | --- | -G |
| GB549    | 4g | AT----- | -C--- | C--- | C--C- | TA-A- | --- | -T |
| GB438    | 4h | TG----- | -C--- | C--- | C---- | A-G-- | --- | -- |
| CAR4/1205 | 4i | -A--G-- | -C--- | C--- | ---- | A-A-- | --- | -C |
| CAR4/901  | 4? | T------ | -C--- | A--- | A---- | A-A-- | --- | -T |
| BE95  | 5a | GT----- | -G-T- | -C--- | C---- | -G--- | --- | -G |
| BE100 | 5a | GT----CG | -C--- | C---- | C---- | -T-AG | --- | -- |
| SA4   | 5a | GT----- | ---- | -C--- | C---- | -G--- | --- | -- |

Figure 5

| | SEQ ID | MSTNPKPQKKNKRNTNRRPQDVKFPGGGQIVGGVYLLPRRGPRLGVRATR |
|---|---|---|
| HCV1 1a | 1 | ------------------------------------------------- |
| HCVJ 1b | | -----R-T----------------------------------------- |
| HCJ6 2a | | -----R-T----------------------------------------- |
| HCJ8 2b | | -----R-T----------------------------------------- |
| NE92 2d | 144 | -----R-T----------------------------------------- |
| EB1 3a | | --R-T----I--------------V------------------C----- |
| NZL1 3a | | ---L-R-T----I--------------V--------------------- |
| HCV-TR 3b | | ---L---RQT----L----N--------V--------------V----- |
| BE98 3c | 148 | ---L---R-T----X---------------V---Q--------V----- |
| GB358 4c | 192 | -----R-T-----M----------------------------------- |
| GB809 4e | 164 | ---L-R-T-----M----------------------------------- |
| CAM600 4e | 166 | -----R-T-----M----------------------------------- |
| GB724 4? | 194 | -----R-T-----M----------------------------------- |
| EG-29 4? | | -----R-------M----------------------------------- |
| BE95 5a | 152 | -----R-T---------------------------M------------- |

|  |  |  |  | V-core |  |  |
|---|---|---|---|---|---|---|
|  |  | KTSERSQPRGRRQPIPKAR | RPEGRTWAQ | PGYPWPLYGNEGCGWAGWLLSP |
| HCV1 | 1a | ------------------- | --------- | ---------------------- |
| HCVJ | 1b | ------------------- | --------- | ------M--------------- |
| HCJ6 | 2a | ---------------D--- | -ST-KS-GK | ---------L------------ |
| HCJ8 | 2b | ---------------D--- | -ST-KS-GK | ---------------------- |
| NE92 | 2d | ---------------D--- | --T-KS-GK | ---------L------------ |
| EB1 | 3a | ------------------- | -S---S--- | ---------------------- |
| NZL1 | 3a | ------------------- | -S---S--- | ---------------------- |
| HCV-TR | 3b | ------KQ-HL-------- | SR----S-- | -------------K----L--- |
| BE98 | 3c | -------S-------R--- | -T---S--- | ---------------------- |
| GB358 | 4c | ------------------- | -S---S--- | ---------------------- |
| GB809 | 4e | ------------------- | -S---S--- | ---------------------- |
| CAM600 | 4e | ------------------- | -T---S--- | ---------------------- |
| GB724 | 4? | ------------------- | -S---S--- | A--------------------- |
| EG-29 | 4? | ------------------- | -S---S--- | ---------------------- |
| BE95 | 5a | ------------------- | Q-T--S-G- | ---------A---L-------- |

Figure 5 - Continued 2

```
                 101                        126
        RGSRPSWGPTDPRRRSRNLGKVIDTL
HCV1 1a -------------------------
HCVJ 1b -------------------------
HCJ6 2a ------------N----H----V---
HCJ8 2b ---------T--H----H-----R--
NE92 2d ------------H----H-------I

NZL1   3a ------------N------------
HCV-TR 3b ------------N------F------
BE98   3c ------------N-------------

GB809  4e ------------N-------------
CAM600 4e -X--X-------N---X---------
GB724  4? ------------N-------------

```
          127                                                              176
          TCGFADLMGYIPLVGAPLGGAARALAHGVRVLEDGVNYATGNLPGCSFSI
HCV-1     1a  --------------------------------------------------
HCVEC1    1a  --------------------------------------------------
HCVHCT18  1a  --------------------------------------------------
HCVHCT23  1a  -------------------R------------------------------
HCVHCT27  1a  --------------------------------------------------
HCVTH     1a  --------------------------------------------------
HCV-J     1b  ------------------------------------------------L-

HC-J6     2a  ----V------------V--------------F-----------------
HC-J8     2b  ----V-----------V-V-------------I-----------------
NE92      2d  ----V-----------V-V-------------I-----------------

HD10      3a  ----V-----------V-V-----A---I-F-------------------
BR33      3a  ----V-----------V-V-----A---I-F-------------------
BR36      3a  ----V-----------V-V-----A---I-F-------------------
NZL1      3a  ----V-----------V-V-----A---I-F-------------------
HCV-TR    3b  ----V-----------V-V-----A-G-----------------------
```

Figure 5 - Continued 4

| | | 127 | 176 |
|---|---|---|---|
| GB809_4 | 4a | ---------------------------- | ----------------------------- |
| GB116 | 4c | -------------------V--V----- | ----------------AV---] ------- |
| GB215 | 4c | -------------------V--V----- | ------------E---AV---] ------- |
| GB358 | 4c | -------------------V--V----- | ------------E---AV---] ------- |
| GB809_2 | 4e | -------------------V--V----- | ----------------AV---] ------- |
| CAM600 | 4e | -------------------V--V----- | ----------------AV---] ------- |
| CAMG22 | 4f | -------------------t--V----- | ----------------AV---] ------- |
| CAMG27 | 4f | ------S------------V--V----- | ----------------AV---] ------- |
| GB549 | 4g | -------------------V--V----- | ----------------AV---] ------- |
| GB438 | 4h | -------------------V--V----- | ----------------AV---] ------- |
| CAR4/1205 | 4i | -------------------V--V----- | ----------------A----] ------- |
| CAR4/901 | 4? | A------------------V--V----- | ----------------AV---] ------- |
| BE95 | 5a | -------------------G-V--V--- | ----------------------P------- |
| BE100 | 5a | ---V---------------G-V--V--- | ------------------------------ |

Figure 5 - Continued 5

```
                         177                                                              226
                          |                                                                |
                          E1                   V1                                  V2
                          ↓   ┌─────────────────────────────────┐       ┌──────────────────────┐
            FLLAALLSCLTVPASA  YQVRNSTGLYHV       TNDCPNSSI      VYEAADAILHT  PGC
HCV-1    1a ----------------  ------------       ---------      -----------  ---
HCVEC1   1a ----------------  -----S------       ---------      -----------  ---
HCVHCT18 1a -------T--------  --H---------       ---------      ---------A-  ---
HCVHCT23 1a ----------------  ------------       ---------      ----T--T--S  ---
HCVHCT27 1a ----------------  ----S-I-----       ---------      -----------  ---
HCVTH    1a ----------------  ------------       ---------      ---------A-  ---
HCV-J    1b -------I--------  -E---VS-I---       ----S----      ------M-M--  ---

HC-J6    2a -----I-T-V-----   AE-K-ISTG-M-       --T-D----      TWQLQA-V--V  ---
HC-J8    2b -------V----V--   VE---ISSS-YA       --S-N----      TWQLT-V--L   ---
S83      2c -----I---------   VE-KDTGDS-MP       ----S----      -WQLEG-V--L  ---
NE92     2d -----I---V-G---   L--K-TSSS-M-       ----Q----      -WQLR-V--V   ---

HD10     3a ---F---IH--AS--   LEW--TS---VL       ----S----      ----D-V----  ---
BR33     3a ---F---IH--AG--   LEW--TS---VL       ----S----      ----D-V---A  ---
BR36     3a ---F---IH--AS--   LEW--TS---VL       ----S----      ----D-V----  ---
NZL1     3a ---F---IH--AS--   LEW--TS---VL       ----S----      ----D-V----  ---
HCV-TR   3b ---F----C----G-   LEYT-TS---VL       ----S-G--      ----E-V---L  ---
```

Figure 5 - Continued 6

| | | 177 | | V1 | | V2 | 226 |
|---|---|---|---|---|---|---|---|
| GB809_4 | 4a | ------- | - | EHY---AS-I--I | ---V | ---TDHH----L | --- |
| Z4 | 4a | ------- | - | EHY---AS-I--I | ---- | ---DHH-----L | --- |
| Z1 | 4b | ------- | - | VHY---AS-V--- | ---- | ---TENH-M-L | --- |
| GB116 | 4c | S------ | - | VNY---AS-V--I | ---T | ---DYH----L | --- |
| GB215 | 4c | Y------ | - | IHY---AS-V--I | ---- | ---DHH----L | --- |
| GB358 | 4c | ------T | - | VNY---AS-V--I | ---- | ---TEHH----L | --- |
| Z6 | 4c | ------- | - | VNY---AS-V--- | ---- | ---EHQ----L | --- |
| Z7 | 4c | ------- | - | VNYH--AS-V--I | ---- | M---EHH----L | --- |
| DK13 | 4d | ------- | - | -NY----S-V--- | ---- | ---TDYH----L | --- |
| GB809_2 | 4e | ------G | - | VNY---AS-V--I | ---A | ---TDNH----L | --- |
| CAM600 | 4e | ------T | - | VNY---AS-I--I | ---A | ---TENH----L | --- |
| CAMG22 | 4f | ------- | - | VHYH--TS-I--L | ---- | ---F--VHH----L | --- |
| CAMG27 | 4f | ------- | - | VHYH--TS-I--I | ---- | ---F--EHH----L | --- |
| GB549 | 4g | ------- | - | QHY---IS-I--- | ---- | ---DHH-M-L | --- |
| GB438 | 4h | ---V---R | - | QHY---AS-I--- | ---- | ---DHH-M-L | --- |
| CAR4/1205 | 4i | S---E--- | - | IHY---ASDG--YI | ---- | ---ENH----L | --- |
| CAR4/901 | 4? | X------ | - | QHY---VS-I--- | ---- | ---DHH-M-L | --- |
| BE95 | 5a | -I----- | - | VPY---AS-I--- | ---- | ---DNL----A | --- |
| BE100 | 5a | -I----- | - | VPY---AS-I--- | ---- | ---D-L----A | --- |
| SA4 | 5a | ------- | - | VPY---AS-V--- | ---- | ---DNL----A | --- |
| HK2 | 6a | ------- | - | LTYG--S-----L | ---- | -L--DAM----L | --- |

Figure 5 - Continued 7

|  |  | 227 | V3 |  | V4 |  | 276 PUTATIVE |
|---|---|---|---|---|---|---|---|
|  |  | VPC | VREGNASRCVVAM | TPTVA | TRDGKLPATQ | LRRHID | LLVGSATLCSALY |
| HCV-1 | 1a | --- | ------------- | ----- | ---------- | ------ | ------------- |
| HCVEC1 | 1a | --- | --H----V----- | ----- | ---------- | ------ | ------------- |
| HCVHCT18 | 1a | --- | --H----V----- | ----- | ------T--- | ------ | ------------- |
| HCVHCT23 | 1a | --- | ---D-V------- | ----- | ------T--- | ------ | ------------- |
| HCVHCT27 | 1a | --- | ------K---PV | A---- | --K----N--- | ------ | ------------- |
| HCVTH | 1a | --- | ------------- | ----- | ---R---T--- | ------ | ------------- |
| HCV-J | 1b | --- | ---S-F------- | ---L- | A-NSSI-T-T | I---V- | ----A--A---M- |
| HC-J6 | 2a | --- | EKV--T----IPV | S-N-- | VQQPGALTQG | --T--- | MV-M--------- |
| HC-J8 | 2b | --- | ENDNGTLH--IQV | --N-- | VKHRGALTRS | --T-V- | MI-MA--A----- |
| S83 | 2c | --- | E-TA-V-----PV | A-NL- | ISQPGALTKG | --A--- | II-M---V----- |
| NE92 | 2d | --- | EEK--I-----IPV | S-NI- | VSQPGALTKG | --T--- | TIIA----F---- |
| HD10 | 3a | --- | -QD--T-A--TPV | ----- | V-YVGATTAS | I---V- | M----A---M--- |
| BR33 | 3a | --- | -QD--T-T--TPV | ----- | V-YVGATTAS | I-S-V- | -----A---M--- |
| BR36 | 3a | I-- | -QD--T-T--TPV | ----- | VKYVGATTAS | I-S-V- | -----A---M--- |
| NZL1 | 3a | --- | -QD--T-T--TPV | ----- | V-YVGATTAS | I-S-V- | -----A---M--- |
| HCV-TR | 3b | --- | -TT--Q-S--TTV | ST--- | V-TLGVTTAS | I-T-V- | M----ARQ----- |

Figure 5 - Continued 8

| | | 227 V3 | | V4 | | 276 PUTATIVE |
|---|---|---|---|---|---|---|
| GB809_4 | 4a | ---A--V----TPV | --- | AVSMDA-LES | F----V | -M--A---V-- |
| Z4 | 4a | -MT--T----TPV | --- | VAHPGA-LES | F----V | -M--A------ |
| Z1 | 4b | ---TE-T-----PL | --- | APYPNA-LES | M----V | -M--A--M--- |
| GB116 | 4c | ---V--Q-----L | --- | APYVGA-LES | ---S-V | -M--A--V--F |
| GB215 | 4c | ---V--Q-----L | S--- | APYIGA-VES | F----V | -M--A--V--- |
| GB358 | 4c | ---V--Q-----L | --- | APYIGA-LES | ---S-V | MM--A--V--- |
| Z6 | 4c | ---V--Q-----L | --- | VSYIGA-LDS | -----V | -M--A--A--- |
| Z7 | 4c | ---V--Q-----L | --- | APYIGA-LES | I----V | -M--A--V--- |
| DK13 | 4d | ----K-T----SL | --- | AQHLNA-LES | -----V | -M--G------ |
| GB809_2 | 4e | ---KT-Q-----L | --- | SPYVGA-LEP | -----V | -M--A--V--- |
| CAM600 | 4e | ----T--Q-----L | --- | SPYAGA-LEP | -----V | -M--A--M--- |
| CAMG22 | 4f | ----T--Q-----L | -L- | APYLGA-LES | M----V | -M--A--T--- |
| CAMG27 | 4f | ----T-----I-L | -L- | APHIGA-LES | M----V | -M--T------ |
| GB549 | 4g | ----T--T----PL | --- | APYVGA-LES | -----V | -M--A--V--- |
| GB438 | 4h | ----T--V----IPL | --- | VPYLGA-L-S | V-Q-V | -M--A------ |
| CAR4/1205 | 4i | ----KT-Q-----L | -L- | APHLRA-LSS | ---A-V | -M--A--A--- |
| CAR4/901 | 4? | I---T--V-----SL | --- | APYLGA-L-S | -----V | -M--A--A--F |
| BE95 | 5a | ---MT--V-----QI | ---LS | APSLGAVTAP | ---AV | Y-A-G-A---- |
| BE100 | 5a | ---KD-V-----QI | ---LS | APSFGAVTAP | ---AV | Y---G-A---- |
| SA4 | 5a | ---QD-V-K---QI | ---LS | APNLGAVTAP | ---AV | Y-A-G-A---- |
| HK2 | 6a | L----VDDR-T---H-V | ----L- | IPNAST----G | F----V | --A-A-VV--S-- |

Figure 5 - Continued 9

```
        277                                        319
        TRANSMEMBRANE              V5
         DOMAIN
         VGDLCGSVFLVGQLFTF SPRRHWTTQG CNCSIYPGHITGHRMA
HCV-1      1a  ---------------- ---------- ----------------
HCVEC1     1a  ---------------- ---------- ----------------
HCVHCT18   1a  -----I---------- ---------- ----------------
HCVHCT23   1a  ---------------- -------D-- ----------------
HCVHCT27   1a  -----I---------- -------D-- ----------------
HCVTH      1a  ---------------- ---------- ----------------
HCV-J      1b  ----------S----- ---YE-V-D- -------VS-------
HC-J6      2a  ---G-M-AA-M-IV-- -QH--FV-D- -------T--------
HC-J8      2b  -V-A-MILS-A-MV-- -Q--NF--E- -------Q--------
S83        2c  -V-ALM-AA-VVVV-- -QII-TFV-E -------R--------
NE92       2d  I-A-M-AS-V-II--- -QII-KFV-D ----------------
HD10       3a  ---M--A---------A R----Q-V-T ---L----LS------
BR33       3a  ---M--A---------A R----Q-V-T ---L----LS------
BR36       3a  ---M--A---------A R----Q-V-T ---L----LS------
NZL1       3a  ---M--A---------A R----Q-V-T ---L----LS------
HCV-TR     3b  ---AF-A---------A R----T-V-T -------VS-------
```

Figure 5 - Continued 10

|  |  | 277 TRANSMEMBRANE DOMAIN |  | V5 |  | 319 |
|---|---|---|---|---|---|---|
| GB809_4 | 4a | -----GA-----M- | --- | Q------D | ----- | --T------- |
| Z4 | 4a | -----GA--M--MI | --- | R------E | ----- | --T------- |
| Z1 | 4b | I----G------- | D-- | R------D | ----- | --VS------ |
| GB116 | 4c | I----G------- | S-- | Q------D | ----- | --A--V---- |
| GB215 | 4c | I----G-----M- | S-- | R------D | ----- | ---A----G- |
| GB358 | 4c | I----G-----M- | S-- | Q------D | ----- | --A--V---- |
| Z6 | 4c | I----GA----M- | S-- | Q------D | ----- | --A--V---- |
| Z7 | 4c | I----G-----M- | --- | Q------D | ----- | --A--V---- |
| DK13 | 4d | I--V-G------- | --- | Q------D | ----- | --A------- |
| GB809_2 | 4e | I----GL----M- | --- | Q------D | ----- | --T------- |
| CAM600 | 4e | I----GL----M- | --- | R----L-E | ----- | ---T------ |
| CAMG22 | 4f | I----GI--A-M- | --- | R----L-E | ----- | ---------- |
| CAMG27 | 4f | I----GI----M- | N-- | R------D | ----- | ---D------ |
| GB549 | 4g | I----G-----M- | --- | Q------D | ----- | ---V------ |
| GB438 | 4h | I--I-G--A--MV | S-- | Q------D | ----- | ---S------ |
| CAR4/1205 | 4i | I----G---A--- | --I | R--I-E--D | ----- | ---V------ |
| CAR4/901 | 4? | I----G------- | --- | Q------D | ----- | ---V------ |
| BE95 | 5a | ---A--AL----M- | -Y- | R-Q-A-V-N | ----- | ---S--V--- |
| BE100 | 5a | ---A--AL----M- | -Y- | R-Q-A-V-D | ----- | ---S--V--Q |
| SA4 | 5a | ---A--A-----M- | -Y- | R-Q-T-V-D | ----- | ---S------ |
| HK2 | 6a | I------L--A---- | --- | Q------V-D | ----- | ----T--V--- |

Figure 6

```
           4648                                                    4698
       GTGTGCCAGGACCATCTTGAATTTTGGGAGGGCGTCTTTACAGGCCTCACT
HCV-1  --C-------------C--A--G--C-----A-----C-------------C
HCV-J  ---------A------------G--------CA--T--C--C------A
HC-J6  --A--T--A-----C--G--G--C-----A-CG--------T--------A
HC-J8  ------------------------------------------------
HCC153 -----------------A--C----------A-------C--T--A--A---
EB1
EB2
EB6
EB7
                                      ↑
                                    4664

4699                                                    4750
       CATATAGATGCCCACTTTCTATCCCAGACAAAGCAGAGTGGGGAGAACCTT
HCV-1  ---C-------------CT-G-------C--A-----GCA--A--C-----C
HCV-J  ---C----------------------C--T--A-------ATCG----A--TT-C
HC-J6  ---C--T--C-------C----C-------G--------AG-A--A--T--
HC-J8  ---C-------------------------G--A--T-------CAG--ACTC---T-C
HCC153 ---C---------------------------------------CAG--ACTC---T-C
EB1                                              ----CAG--ACTC---T-C
EB2                                              A---CAG--ACTC---T-C
EB6                                              A----CAG--ACTC---T-C
EB7                                                     ↑
                                                      4731
```

Figure 6 - continued 1

```
              4751                                              4800
HCV-1   CCTTACCTGGTAGCGGTACCAAGCCACCCGTGTGCGCTAGGGCTCAAGCCCC
HCV-J   --C-------------A-------C-----A---------G--T-------
HC-J6   G-A---T-AAC---C-----G-T-A---------CA----------------
HC-J8   G-G--T--AACG--C-----G---A--A---C---AA-G-------------
HCC153  T-G-T----ACT--C-----------T-----------C-C-G-G--T---
EB1     T-G------AACT--C-----------T------CC-C-G--G--T-T
EB2     T-G------AACT--C-----------T------CC-C-G--G--T--
EB6     T-G------AACT--C-----------T------CC-C-G--G--T--
EB7     T-G------AACT--C-----------T------CC-C-G--G--T--

4801                                             4849
HCV-1   TCCCCCATCGTGGGACCAGATGTGGAAGTGTTTGATTCGCCTCAAGCCCA
HCV-J   A--T----------------A-------------C-C-A--G--A----
HC-J6   C----G--C-----GTC-------------------C--A---------
HC-J8   ---T-T------GT------------------C-A-C-A-G----A--T-
HCC153  -----AGT-----G-----C------A-----C-CG-A--G--T----A-
EB1     -----AGT-----G-----C------A-----C-CG-G--G--T----A-
EB2     -----AGT-----G-----C------A-----C-CG-G--A-------A-
EB6     -----AGT-----G------------A-----C-CG-G--G-------A-
EB7     -----AGT-----G------------A-----C-CG-G--G-------A-
```

Figure 6 - continued 2

```
                            4850                                                  4900
          SEQ ID NO         CCCTCCATGGGCCAACACCCCTGCTATACAGACTGGGGCGCTGTTCAGAAT
HCV-1                       -A--G-------G-------G-----G--A--A--C-----A---
HCV-J                       -A---GTG--C--C-----T--C--G--C--CT-----T----ACC---C
HC-J6                       -A--GAC---T--C-----C--C--G---CT-----T--C--GACC---
HC-J8                       -A--A----A--T--G---T--T---TC-GT----GC---C--A---
HCCl53        29                                      ↑
                                                      4863
HD10-1-25     31                                                      -C--A---
HD10-1-3      33                                                      -C--A---
BR36-20-164   35                                                      -C--A---
BR36-20-166   37                                                      -C--A---
BR36-20-165   39                                                      -C--A---
                                                                      ↑
                                                                      4892

```
             4901                                                    4949
HCV-1        GAAATCACCCTGACGCCACCCAGTCACCAAATACATCATGACATGCATGTC
HCV-J        --GG----T--C--A-----CA-A-----------G--------------
HC-J6        --GG--------C----T--T--G-G-------GCC--C-----CA
HC-J8        --GG--------T-------C--G-G-------GCC--G-----CA
HCC153       -------TG-T-----A---CA----A--------G---------------
HD10-1-25    -------TG-T-----A---C-----------T--G---------------
HD10-1-3     -------TG-T-----A---C-----------T--G---------------
BR36-20-164  -------TG-T-----A---CA----A--------G---------------
BR36-20-166  -------TG-T-----A---CA----A--------G---------------
BR36-20-165  -------TG-T-----A---CA----A--------G---------------

4950                                              4990
HCV-1        GGCCGACCTGGAGGTCGTCACGAGCACCTGGGTGTCTCGTTG
HCV-J        --T------------------T---------A--A-
HC-J6        A-------T-----A-G--C-----G----CT-A-C--
HC-J8        A--T----C---A--A-G--A---T-A-----C--G-CG-
HCC153       A
HD10-1-25    A--T---A--T-----A--AAC---C----------T-GC---
HD10-1-3     A--T---A--T-----A--AAC---C----------T-GC---
BR36-20-164  A--T---A--T-----A--AAC---C----------TT-GC---
BR36-20-166  A--T---A--T-----A--AAC---C----------TT-GC---
BR36-20-165  A--T---A--T-----A--AAC---C----------TT-GC---
```

Figure 6 - continued 4

```
              4991                                          5040
HCV-1         GCGGCGTCCTGGCTGCTTTGGCCGGCGTATTGCCTGTCAACAGGCTGCGTG
HCV-J         ----A----T--G---C--------C-----A-G-----A---------
HC-J6         -G--G----T----G--CG-C--------C-----G-G--C--G--T--T
HC-J8         -G--G--G--A--C--CG----A--T--C-----G-G--T-----A-T
HD10-1-25     -A--G-------C--G--CC-A--G--C--T-----GTC---------T
HD10-1-3      -A--G-------C--G--CC-A--G--C--T-----GTC---------T
BR36-20-164   -A--G-------C--G--CC-A--G--C--T-----GTC--T--T--T
BR36-20-166   -A--G-------C--G--CC-A--G--C--T-----GTC--T--T--T
BR36-20-165   -A--G-------C--G--CC-A--G--C--T-----GTC--T--T--T 5041                                          5090
HCV-1         GTCATAGTGGGCAGGGTCGTCTTGTCCGGGAAGCCGGCAATCATACCTGA
HCV-J         ---T-------A--A--------G---A--TG-T--T--C--
HC-J6         TG---CA-C----C-CT-GCA-G-TAA-CA-CGAG-C-TCG-TGC---G--
HC-J8         TC---CA-T----C-CC-ACA-C--AAT-ATCG-GT--TTG-GGCC--C--
HD10-1-25     --A--C-----TCATA---AGC---GGG--C-----C--G-T--A--
HD10-1-3      --A--C-----TCATA---AGC---GGG--C-----C--G-T--A--
BR36-20-164   --G--T-----TCATA---AGC---GGG--C--------G-T--A--
BR36-20-166   --G--T-----TCATA---AGC---GGG--C--------G-T--A--
BR36-20-165   --G--T-----TCATA---AGC---GGG--C--------G-T--A--
```

Figure 6 - continued 5

```
            5091                                              5140
HCV-1       CAGGGAAGTCCTCTACCGAGAGTTCGATGAGATGGAAGAGTGCTCTCAGC
HCV-J       -------------------AG-------------------TG--TCA-
HC-J6       --A---G-----TGAG-CT--T-------G--A--TG-CTCTA
HC-J8       --A---A--T-A--TGAG-CC--T-------A---G-CTCCA
HD10-1-25   --A---G--GT-G--T-A-C---A-------G-------G--AG
HD10-1-3    --A---G--GT-G--T-A-C---A---------G-----G--AG
BR36-20-164 --AA--G--GT-G--T-A-C-A-A------------A--AG
BR36-20-166 --AA--G--GT-G--T-A-C-A-A------------A--AG
BR36-20-165 --AA--G--GT-G--T-A-C-A-A------------A--AG 5141                                              5190
HCV-1       ACTTACCGTACATCGAGCAAGGGATGATGCTCGCCGAGCAGTTCAAGCAG
HCV-J       --C-C--T----------A---CA-----A-----A---
HC-J6       GAGCGG-TCT---T--AG-G---CA-CG-A-A-----AT-C-G---TCC
HC-J8       -AGCCG-CCT---T--G------CA-CG-A-G--G---AT-C----ATCT
HD10-1-25   C-GCC--A------A----CTCA-G-AA-A---C-C------G--
HD10-1-3    C-GCC--A------A----CTCA-G-AA-A---C-C------G--
BR36-20-164 CTGCC--A--T---A----CTCA-G-AA-A--TC-C-----GGA
BR36-20-166 CTGCC--A--T---A----CTCA-G-AA-A--TC-C------G-A
BR36-20-165 CTGCC--A--T---A----CTCA-G-AA-A--TC-C------G-A
```

Figure 6 - Continued 6

```
              5191                                                    5240
HCV-1         AAGGCCCTCGGCCTCCTGCAGACCGGCGTCCCGTCAGGCAGAGGTTATCGC
HCV-J         ----G-----AT-G-----A---A--CA---AAG--A---G-----C-GCT--
HC-J6         ---AT--AA---T-AT-----CAA--T-----AAA--A--TC-A-AC--ACA
HC-J8         ---ATA-AA---------A--ACAG--CA-AA--G--A--TC-A-AC--ACA
HD10-1-25     --AAT---T--A--G-------CGA---CA----AA--ACA--CT--C--T-A
HD10-1-3      --AAT---T--A--G-------CGA---CA----AA--ACA--CT--C--T-A
BR36-20-164   --A-T---T--AT-G-------CGA---CA----AA--ACA--CT--C--T-A
BR36-20-166   --A-T---T--AT-G-------CGA---CA----AA--ACA--CT--C--T-A
BR36-20-165   --A-T---T--AT-G-------CGA---CA----AA--ACA--CT--C--T-A 5241                                                   5290
HCV-1         CCCTGCTGTCCAGACCAACTGGCAAAAACTCGAGACCTTTCTGGGCGAAGC
HCV-J         T--C-TG--GG--T---G----G-GCC--T---GT--------A-
HC-J6         A--C-----G---G-TTCT----CC--GG-A---CAA--------C-A---
HC-J8         G--A---A--A---T-ATCA----CC--G--T--ACAA--T----C-A---
HD10-1-25     G---C-TAA-AGCTT------------G--T--A--------CAC------
HD10-1-3      G---C-TAA-AGCTT------------G--T--A--------CAC------
BR36-20-164   G---CATA--AACT-------------G--T---G----T---CAC------
BR36-20-166   G---CATA--AACT-------------G--T---G----T---CAC------
BR36-20-165   G---CATA--AACT-------------G--T---G----T---CAC------
```

Figure 6 - continued 7

| | 5292 |
|---|---|
| HCV-1 | AT |
| HCV-J | -C |
| HC-J6 | -C |
| HC-J8 | -C |
| HD10-1-25 | -- |
| HD10-1-3 | -- |
| BR36-20-164 | -- |
| BR36-20-166 | -- |
| BR36-20-165 | -- |

Figure 7

| | SEQ ID NO | 1290 | 1300 | 1310 | 1320 | 1330 |
|---|---|---|---|---|---|---|
| HCV-1 | | ITTGSPITYSTYGKFLADGGCSGGAYDIIICDECHSTDATSILGIG | | | | |
| HCV-J | | ----G-------------C--------------------------- | | | | |
| HC-J6 | | V---A---------------------A-----------S-T----- | | | | |
| HC-J8 | | V---DS--------------I-----AA-------V---T----- | | | | |
| BE95 | 270 | ----AS-------------------------V-------Q---T----- | | | | |

| | 1340 | 1350 | 1360 | 1370 | 1380 |
|---|---|---|---|---|---|
| HCV-1 | TVLDQAETAGARLVVLATATPPGSVTVPHPNIEEVALSTTGEIPFYGKAI | | | | |
| HCV-J | ---------------------------------I------------N------------ | | | | |
| HC-J6 | -------V---T---------------------T----------------GQE------R-- | | | | |
| HC-J8 | -------V---------------------T--T--S---------GHE------------ | | | | |
| BE95 | -------------------------------------T----------------PQE--V----R-- | | | | |

Figure 7 - Continued 1

```
                1390       1400       1410       1420      1430
HCV-1    PLEVIKGGRHLIFCHSKKKCDELAAKLVALGINAVAYYRGLDVSVIPTSG
HCV-J    -I-A--------------------------TG--L---------------
HC-J6    --SY---------------------A-RGM-L-------------Q----
HC-J8    --AF---------------------A-RGM-V-------------Q----
BE95     --AF------------------KQ-TS--V---------A-----A----

1440       1450       1460       1470      1480
HCV-1    DVVVVATDALMTGYTGDFDSVIDCNTCVTQTVDFSLDPTFTIETITLPQD
HCV-J    ------------F-------------------------------T-----
HC-J6    ------------F-----------VA---V----------T-Q-V----
HC-J8    ------------------------VA-S-I----------T-Q-V----
BE95     ---CS-------F---------SA----------------T-V------
```

Figure 7 - Continued 2

```
                 1490      1500      1510      1520      1530
HCV-1   AVSRTQRRGRTGRGKPGIYRFVAPGERPSGMFDSSVLCECYDAGCAWYEL
HCV-J   ----A---------------RS-----T--------------------
HC-J6   ----S---------------RL---Y-ST---A-----V-----A---
HC-J8   ----S---------------RL-V-Y-SS--------V-----A---
BE95    ----S---------------RH---Y-SA--------V-----D---

1540      1550      1560      1570      1580
HCV-1   TPAETTVRLRAYMNTPGLPVCQDHLEFWEGVFTGLTHIDAHFLSQTKQSG
HCV-J   ----S---------L-------------------S-------------A-
HC-J6   --------------F-------------A-----S-----------G-
HC-J8   --------------F-------------A-----------N---M-G-
BE95    --------------I-------------------------------Q-
BR36                          D---S-

SEQ ID NO
HCV-1
HCV-J
HC-J6
HC-J8
BE95
BR36     223
```

Figure 7 - Continued 3

|      | 1590       1600       1610       1620       1630 |
|------|---|
| HCV-1 | ENLPYLVAYQATVCARAQAPPPSWDQMWKCLIRLKPTLHGPTPLLYRLGA |
| HCV-J | D------------------------------------------------ |
| HC-J6 | --FA--T----------K-------T-------V-------------S |
| HC-J8 | --FA--T----------K-------T-------T-------------- |
| BE95  | --F---------------V-K----T-------ML------T-----P |
| BR36  | L-FST-T-------------------------E--V------T-----P |

|      | 1640       1650       1660       1670       1680 |
|------|---|
| HCV-1 | VQNEITLTHPVTKYIMTCMSADLEVVTSTWVLVGGVLAALAAYCLSTGCV |
| HCV-J | ----V-----A------------------------------T--S--- |
| HC-J6 | -T--V-----A---Q---M----A-------V------A-----T--- |
| HC-J8 | -T--V-----A---Q---IM--S---A----V------A-----A--I |
| BE95  | ------------------------I--------V-------TV-S--- |
| BR36  | ------C----I-----A-----T--------L--------V------ |

Figure 7 - Continued 4

|        | 1690       | 1700         | 1710        | 1720         | 1730    |
|--------|------------|--------------|-------------|--------------|---------|
|        |            | NS4-1        |             | NS4-5        |         |
| HCV-1  | VIVGRVV    | LSGKPAIIPDREVLYREFDE MEEC | SQHLPYIEQGMM | LAEQFKQ |
| HCV-J  | ----II     | ---R--V------Q----  ---- | AS---------Q | ------- |
| HC-J6  | C-I--LH    | VNQRAVVA--K----EA-- ---- | ASRAAL--E-QR | I--ML-S |
| HC-J8  | S-I--LH    | -NDRVVVA--K-I--EA-- ---- | ASKAAL--E-QR | M--ML-S |
| BR36   | ---HIE     | -G-----V--K----QQY- ---- | --AA----AQV  | I-H---E |
| BE95   | A----II    | -----------A--QQ--- ---- | --AS---MDETRA| I-G---E |

|        | 1740         | 1750        | 1760        |
|--------|--------------|-------------|-------------|
|        | NS4-7        |             |             |
| HCV-1  | K|ALGLLQTASRQA EVIAPAVQTNWQKLETFWAKH|--- |
| HCV-J  | -  ----TK--   -AA--V-ESK-RA--V----   --- |
| HC-J6  | -  IQ----Q--K QD-Q----AS-P-V-Q-----  --- |
| HC-J8  | -  IQ----Q--T QD-Q--I-SS-P----Q-----  --- |
| BR36   | -  V----R-TQ-Q A--E-I-T-----A---N--   --- |
| BE95   | -  V--FIS-TGQK- -TLK--ATSV-N-A--Q--XIY   |

Figure 9

|  | SEQ ID NO | 1                                                  50 |
|---|---|---|
| PC-3-4 | 49 | ATGAGCACGAATCCTAAACCTCAAAGAAAAACCAAAAGAAACACCAACCG |
| PC-3-8 | 51 | -------------------------------------------------- |
| PC-2-1 | 41 | -------------------------------------------------- |
| PC-2-6 | 43 | -------------------------------------------------- |
| PC C/E1 | 53 | -------------------------------------------------- |

|  | 51                                                 100 |
|---|---|
| PC-3-4 | TCGCCCACAGGACGTCAAGTTCCCGGGGGTGGTCAGATCGTTGGGCGGAG |
| PC-3-8 | -------------------------------------------------- |
| PC-2-1 | -------------------------------------------------- |
| PC-2-6 | -------------------------------------------------- |
| PC C/E1 | -------------------------------------------------- |

Figure 9 - Continued 1

```
        101                                           150
PC-3-4  TTTACTTGTTGCCGCGGCAGGGGCCCTAGGATGGGTGTGCCGGCGACTCGG
PC-3-8  --------------------------------------------------
PC-2-1  --------------------------------------------------
PC-2-6  --------------------------------------------------
PC C/E1 --------------------------------------------------

151                                           200
PC-3-4  AAGACTTCGGAACGGTCGCAACCCCGTGGACGGCGTCAGCCTATTCCCAA
PC-3-8  --------------------------------------------------
PC-2-1  --------------------------------------------------
PC-2-6  --------------------------------------------------
PC C/E1 --------------------------------------------------
```

Figure 9 - Continued 2

```
       201                                                 250
PC-3-4 GGCGCGGCCAGCCCACGGGGCCGGTCCTGGGGTCAACCCGGGTACCCCTTGGC
PC-3-8 ----------------------------------------------------
PC-2-1 ----------------------------------------------------
PC-2-6 ----------------------------------------------------
PC C/E1 ----------------------------------------------------

251                                                 300
PC-3-4 CCCTTTACGCCAATGAGGGCCTCGGGTGGGCAGGGTGGCTGCTCTCCCCT
PC-3-8 -------------------------------------------------
PC-2-1 -------------------------------------------------
PC-2-6 -------------------------------------------------
PC C/E1 -------------------------------------------------
```

Figure 9 - Continued 3

```
       301                                               350
PC-3-4 CGAGGCTCTCGGCCTAATTGGGGCCCCAATGACCCCCGGGCGAAAATCGCG
PC-3-8 -------------------------------------------------
PC-2-1 -------------------------------------------------
PC-2-6 -------------------------------------------------
PC C/E1 -------------------------------------------------

351                                               400
PC-3-4 TAATTTGGGTAAGGTCATCGATACCCTAACGTGCGGATTCGCCGATCTCA
PC-3-8 -------------------------------------------------
PC-2-1 -------------------------------------------------
PC-2-6 -------------------------------------------------
PC C/E1 -------------------------------------------------
```

Figure 9 - Continued 4

```
          401                                              450
          TGGGGTATATCCCGCTCGTAGGCGGCCCCATTGGGGCGTCGCAAGGGCT
PC-3-4    -------C----------------------------------------
PC-3-8    ------------------------------------------------
PC-2-1    ------------------------------------------------
PC-2-6    ------------------------------------------------
PC-4-1    ----------------------------G-------------------
PC-4-6    ------------------------------------------------
PC C/E1   --------Y-------------------R-------------------

SEQ ID NO   451                                              500
                      CTCGCACACGGTGTGAGGGTCCTTGAGGACGGGGTAAACTATGCAACAGG
PC-3-4                --------------------------------------------------
PC-3-8                --------------------------------------------------
PC-2-1                --------------------------------------------------
PC-2-6                --------------------------------------------------
PC-4-1    45          -----------------------------C--------------------
PC-4-6    46          --------------------------------------------------
PC C/E1               -------------------------------------S------------
```

Figure 9 - Continued 5

```
          501                                              550
PC-3-4    GAATTTACCCGGTTGCTCTTTCTCTATCTTTATTCTTGCTCTTCTCGT
PC-3-8    ------------------------------------------------
PC-2-1    ------------------------------------------------
PC-2-6    ------------------------------------------------
PC-4-1    ------------------------------------------------
PC-4-6    ------------------------------------------------
PC C/E1   ------------------------------------------------

551                                              600
PC-3-4    GTCTGACCGTTCCGGCCTCTGCAGTTCCCCTACCGAAATGCCTCTGGGATT
PC-3-8    --------------------------------------------------
PC-4-1    --------------------------------------------------
PC-4-6    --------------------------------------------------
PC C/E1   --------------------------------------------------
```

Figure 9 - Continued 6

```
       601                                            650
PC-3-4  TATCATGTTACCAATGATTGCCCAAACTCTTCCATAGTCTATGAGGCAGA
PC-3-8  --------------------------------------------------
PC-4-1  --------------------------------------------------
PC-4-6  --------------------------------------------------
PC C/E1 --------------------------------------------------

651                                            700
PC-3-4  TAACCTGATCCTACACGGCACCTGGTTGCCTGCCTTGTGTCATGACAGGTA
PC-3-8  --------------------------------------------------
PC-4-1  --------------------------------------------------
PC-4-6  --------------------------------------------------
PC C/E1 --------------------------------------------------
```

Figure 9 - Continued 7

```
          701                                            750
PC-3-4    ATGTGAGTAGATGCTGGGTCCAAATTACCCCTACACTGTCAGCCCCGAGC
PC-3-8    --------------------------------------------------
PC-4-1    --------------------------------------------------
PC-4-6    --------------------------------------------------
PC C/E1   --------------------------------------------------

751                                            800
PC-3-4    CTCGGGAGCAGTCACGGGCTCCTCTTCGGAGAGCCGTTGACTACCTAGCGGGG
PC-3-8    --------------------------------------------------
PC-4-1    --------------------------------------------------
PC-4-6    --------------------------------------------------
PC C/E1   --------------------------------------------------
```

Figure 9 - Continued 8

```
                                                   850
    801 AGGGGCTGCCCTCTGCTCCGGGTTATACGTAGGAGACGGCGTGTGGGGCA
PC-3-4  --------------------------------------------------
PC-3-8  --------------------------------------------------
PC-4-1  --------------------------------------------------
PC-4-6  --------------------------------------------------
PC C/E1 --------------------------------------------------

900
    851 CTATTCTTGGGTAGGCCAAATGTTCACCTATAGGCCTCGCCAGCACGCTACG
PC-3-4  --------------------------------------------------
PC-3-8  --------------------------------------------------
PC-4-1  --------------------------------------------------
PC-4-6  --------------------------------------------------
PC C/E1 --------------------------------------------------
```

Figure 9 - Continued 9

```
        901                                                950
PC-3-4  GTGCAGAACTGCAACTGTTCCATTTACAGTGGCCATGTTACCGGCCACCG
PC-3-8  --------------------------------------------------
PC-4-1  --------------------------------------------------
PC-4-6  --------------------------------------------------
PC C/E1 --------------------------------------------------

951
PC-3-4  GATGGCA
PC-3-8  -------
PC-4-1  -------
PC-4-6  -------
PC C/E1 -------
```

Figure 10

```
         SEQ ID NO                                                            3890
HCV-1               ACCACTGGCAGCCCCATCACGTACTCCACCTACGG                  1a
HCV-J               ----G---G-------------------------- TT--             1b
HC-J6               --G--C--GGCG----------------A--T---                  2a
HC-J8               --G--C--GGCG----------T-----------TT-T--             2b
PC1_37    197       ----C--GGA-T-T----T---------------T----              5a
C1_48     199       ----C--AGCTT-T------A-------T------                  5a
BR36      222       ----C--AGCTT-T------A-------T------                  3a 3891                                                      3940
HCV-1               CAAGTTCCTTGCCGACGGCGGGTGCTCGGGGGCGCTTATGACATAATAA    1a
HCV-J               -------------------T-A------C-----------C------      1b
HC-J6               ---A----------C-----T-G-C---G-A--C-----C---C--C     2a
HC-J8               ------TA-C--A-T-A--C--TG-A-CC--T--C-----C---C--C     2b
PC1_37              ---------T--T-T-A----T--A----C----GC----G-G--C-      5a
C1_48               ---------T--T-T-A----T--A----C----------G-G--C-      5a
BR36                ---------T--T-T-A----T--A----C----G-----G-G--C-      3a 3941                                                      3990
HCV-1               TTTGTGACGAGTGCCACTCCACGGATGCCACATCCATCTTGGGCATCGGC   1a
HCV-J               -A----T--A-------A--T--CT-G--TA--------------        1b
HC-J6               -A--C--T--A----TG--GT---CT-T--CA----TC-C------A      2a
HC-J8               -A--C----A----T--AGT--C--T--TA----C-T----T--A        2b
PC1_37              -A--C--------T----CA--C-----CA----TC-T--G--A---      5a
C1_48               -A--C--------T----CA--C-----CA----TC-T--G--A---      5a
BR36                -A--C--------T----CA--C-----CA----TC-T--G--A---      3a
```

Figure 10 - Continued 1

```
         3991                                              4040
HCV-1    ACTGTCCTTGACCAAGCAGAGACTGCGGGGGCGAGACTGGTTGTGCTCGC
HCV-J    --A-----G--T--G-----T--G-----C--G--C--C--------
HC-J6    --A-----C--T--------A--C-----TC--G--AAC--A--G----
HC-J8    --A---------------------T----C--A--C-TC--G--A--G--TT--G--
PC1_37   ----------------------G--------G--T--A--T--G--C--C--C--G--
PC1_48   ------------------------G-----G--T--A--T--G--C--C--CT--G--
BR36     ------------------------G-----G--T--A--T--G--C--C--CT--G--

4041                                              4090
HCV-1    CACCGGCCACCCCTCCGGGCTCCGTCACTGTGCCCCATCCCAACATCGAGG
HCV-J    ----------G--------A--GA-----C-----A--C-----------
HC-J6    T--G--T--G--C--C--G--A--G--AACC-----C--------A-----
HC-J8    ---A----G-----C--TA-G--G--AACT------CAGT------A-----
PC1_37   ----G----------------C----AGT--G--AAC-----C---------
PC1_48   ----G----------------C----AGT--G--AAC-----C---------
BR36     ----G----------------C-----AGT--G--AAC-----C---------

4091                                              4140
HCV-1    AGGTTGCTCTCTGTCCACCACCGGAGAGATCCCTTTTTACGGCAAGGCTATC
HCV-J    -A--G--C-----------A--T-----T--C--C--T-----A--C---
HC-J6    ----G--C--CGGGCAGGAG--T--------C--C--T--G--G--G--T
HC-J8    ----G--C--TGGTCA-GAG--C--------T-----A-----T
PC1_37   -A--G--C--C-TCAGGAG--G--C--T--C--------GA--C--T
PC1_48   -A--G--C--C-TCAGGAG--G--C--T--C--------GA--C--T
BR36     -A--G--C--C-TCAGGAG--G--C--T--C--------GA--C--T
```

Figure 10 - Continued 2

```
              4141                                              4190
HCV-1    CCCCTCGAAGTAATCAAGGGGGGAGACATCTCATCTTCTGTCATTCAAA
HCV-J    ---A-T--G-CC--------------A--G--------C-----C----
HC-J6    ----GTC-TAC---------A--A----CT-G------C-----C----
HC-J8    ----A-CTT-C---------C-------CT-G------C-----C----
PC1_37   ----T-CTT-T--A------C-------T--G------C-----C----
PC1_48   ----T-CTT-T--A------T-------T--G------C-----C----
BR36     ----T-CTT-T--A------T-------T--G------C-----C----

4191                                              4240
HCV-1    GAAGAAGTGCGACGAACTCGCCCGCAAAGCTGGTCGCGCATTGGGCATCAATG
HCV-J    -----------T--------G-----------ACA-GCC-C--AC--------
HC-J6    -----------T--------G-----------G--GGCC---TCGG-GTA----T-G--C---
HC-J8    -----------T--------G-----------A--GGCC---CCGG-GCA----TG-------
PC1_37   ---A--A--T--T-------------------AAGC-A----AC-AGCC-----G-G--C---
PC1_48   ---A--A--T--T-------------------AAGC-A----AC-AGCC-----G-G--C---
BR36     ---A--A--T--T-------------------AAGC-A----AC-AGCC-----G-G--C---

4241                                              4290
HCV-1    CCGTGGCCCTACTACCGCGGTCTTGACGTGTCCGTCATCCCGACCAGCGGC
HCV-J    -T--A--G--T-----G---C--T--------A----T-----A
HC-J6    -A-----------A--A--G--G-----C-------A--A---TCAG--A
HC-J8    ----T--A----TA-G------C-----C-------T--A---TCAA--A
PC1_37   ----A--T--TA-A------A------CG-------A--C--A-CA--A
PC1_48   ----A--T--TA-A------A------CG-------A--C--A-CA--A
BR36     ----A--T--TA-A------A-------CG------C--AGCA--A
```

Figure 10 - Continued 3

```
                4291                                                      4340
HCV-1   GATGTTGTCGTCGTGGCAACCGATGCCCTCATGACCGGCTATACCGGCGA
HCV-J   ---C--C--T-------A--C--T--A-------G--T--------
HC-J6   --C--A--G-----C--C--C-------G--G--T--T--A---
HC-J8   --C--G--G--T--C--C--T-----A-----T--G--C-----
PC1_37  --C--G-----GTGCAGC-----C--G-------G--A--TC-----
PC1_48  --C--G-----GTGCAGC-----C--G-------G--A--TC-----
BR36    ----G-----------------------------------------

4341                                                      4390
HCV-1   CTTCGACTCGGGTGATAGACTGCAATACGTGTGTCACCCAGACAGTCGATT
HCV-J   ---T------A---C-----C--A------------------
HC-J6   ---T------C---C-----CGTAGCG----T--AGTT--A--C-
HC-J8   ---T--C--C--C-----T---GTTGCA---T--T--TT--T--C-
PC1_37  ---T--T--T--C--------CT-CGCC----T------G--G--C-
PC1_48  ---T--T--T--C--------CT-CGCC----T------G--G--C-
BR36    ---T--T--T--C--------CT-CGCC----T------G--G--C-

4391                                                      4440
HCV-1   TCAGCCCTTGACCCTACCTTCACCATTGAGACAATCACGCTCCCCAGGAT
HCV-J   ---T-G--T--C---G--CA----G----A--C
HC-J6   ---T-G-----C--A-----AACC--CAG--TG---T--A--C
HC-J8   ---A-----A---------CACC--TCAA--CG---T-----C
PC1_37  ---T-G--T--C--T--T----T-C--AG-G--------C
PC1_48  ---T-G--T--C--T--T----T-C--AG-G--------C
BR36    ---T-G--T--C--T--T----T-C--AG-G--------C
```

Figure 10 – Continued 4

```
         4441                                                      4490
HCV-1    GCTGTCTCCCGCACTCAACGTCGGGCAGGACTGGCAGGGGGAAGCCAGG
HCV-J    --G--G---TG-G--G--G--A--T-------------C-G-AGT---
HC-J6    ------A--T-GC--G---C-------C--G-------A-GA-TG---
HC-J8    -------------T-G-----A-A--G--A------G------CGATTG--
PC1_37   --A--G---A-A-GC---G---T-------C-C--G--A--T-G--AC--
PC1_48   --A--G---A-A-GC---G---A-------C-C--G--A--T-G--AC--
BR36     ---------------------------------------------------

4491                                                      4550
HCV-1    CATCTACAGATTTGTGGCACCGGGGGAGCGCCCCTCCGGCATGTTCGACT
HCV-J    ------G-----A-T--A--A--A---G----A------------
HC-J6    T--T--T-G-A----TT-CA-T--T----AG----A--A----T---A
HC-J8    -G-T----G-A----TT-GT-A---C---A-G--G--T--G------
PC1_37   ----A----C-G-A---CT-GG-T--A---A-A--G--T--------
PC1_48   ----A----C-G-A---CT-GG-T--A---A-A--N--T-A------A
BR36     ---------------------------------------------

4551                                                      4590
HCV-1    CGTCCGTCCTCTGTGAGTGCTATGACGCAGGCTGTGCTTGGTATGAGCTC
HCV-J    -C--G---G-------------------C---------------
HC-J6    GTGTA--G-----C------C--T----GGCC--A--------
HC-J8    GCGTA--G-----C------T--C--GGCA--C-----C----T
PC1_37   -CGTG--G------------C--T--C--A----A----C--T--G
PC1_48   -CGTG--G------------C--T--C--A----A----C--T--G
BR36     ---------------------------------------------
```

Figure 10 - Continued 5

```
                4591                                                      4640
HCV-1    ACGCCCGCCGAGACTACAGTTAGGCTACGAGCGTACATGAACACCCCGGG
HCV-J    ------T-------CT-G-------T-G--G--T---C-A--T--A--A---
HC-J6    ---A--A--G------C---C---CA----A--TT-C----A--T---
HC-J8    ---A--T--T------G--G--A--C--G--T--TT-C---TT-C----G--C---
PC1_37   ----T--T-----------T--T--T-----C--G------T-G--C-------C---
PC1_48   ----T--T-----------C--G------T-G---C-----T--N-A----------C---
BR36     -------------------C--G---T-G---C----T------A---------C---

4641                                                      4690
HCV-1    GCTTCCCGTGTGCCAGGACCATCTTGAATTTTGGGAGGGCGTCTTTACAG
HCV-J    -T-G---C---------C--A--G--C-----A-----C---
HC-J6    TT-G---T-------A-------G-----CA--T--C---C
HC-J8    TT-G---A-T--A------C--G--G--C-----A-CG---
PC1_37   ----C--T--C------T---------T-G-------C----G--G--C--G---
PC1_48   ----C--T--C------T---------T-G-------C----G--G--C--G---
BR36     -----------------------A--C------------G--G--G--T---

4691                                                      4740
HCV-1    GCCTCACTCATATAGATGCCCACTTTCTATCCCAGACAAAGCAGAGTGGG
HCV-J    -----C--C---------CT-G-----C--A----GCA--A
HC-J6    -----A--C------C--T--A---------ATCG---
HC-J8    --T--A--C--T-C------C--C-----G--------AG-A--A
PC1_37   -G-----A-C--C--C--T---A-G--G---A--C--A---G---
PC1_48   -G-----A-C--C--T--------A-G--G---A--C--A---G---
BR36     -A--A----C----------------------G--A---T----CAG--A
```

Figure 10 - Continued 6

```
                    4741                                              4790
        HCV-1   GAGAACCTTCCTTACCTGGTAGCGTACCAAGCCACCGTGTGCGCTAGGGC
        HCV-J   ---C-----C--C-------------A-------------C---------
        HC-J6   --A--TT-CG-A---T-AAC---C------G--T--A-------------
        HC-J8   --A--T--G-G--T--AACG---C------G-----A-------C-----
        PC1_37  -----TT-C--A-------T-----------A--A---C--T-T-C--C-
        PC1_48  -----TT-N--A----T----------------A--A---C--T-C-C--
        BR36    CTC----T-CT-G-T----ACT---C-----T------------C-C---

4791                                              4840
        HCV-1   TCAAGCCCCCTCCCCCATCGTGGGACCAGATGTGGAAGTGTTTGATTCGCC
        HCV-J   ---G--T--A--T---------------A----------C--C--A--G-
        HC-J6   CA-----C-----G--C-------GTC--------------C---A----
        HC-J8   AA-G-------T--T------GT------------------C-A-C-A-G-
        PC1_37  GA---G--C----CAGC------------A---CA---C-C--T------
        PC1_48  GA---G--C----CAGC------------A---CA---C-C--T------
        BR36    G---G--T-----AGT------G------------C--CG-A--G-----

4841                                              4890
        HCV-1   TCAAGCCCCACCCCTCCATGGGCCAACACCCCTGCTATACAGACTGGGGCT
        HCV-J   -A-------A--G----C--------G-----G----G-A--A--C----
        HC-J6   -----A--GTG----T--C--C----T--C--G---C-CT---T------
        HC-J8   ----A--GAC----T--C--C----T--C--G---C-CT---T--C----
        PC1_37  ----A--G--NT-AAC---C--T--T----CT-G----G----GC-C---
        PC1_48  ----A--G--TT-AAC---C--T--T----CT-G----G----GC-C---
        BR36    -T----A--A---A----A--T--G--T--T---TC-GT----GC-----
```

Figure 10 - Continued 7

```
              4891                                              4940
HCV-1   GTTCAGAATGAAATCACCCTGACGCACCCAGTCACCAAATACATCATGAC
HCV-J   ----------A------GG----T--C--A----CA-A-------G----
HC-J6   ---ACC---C---GG-------C-----T--T--G--G-----GCC----
HC-J8   --GACC---C---GG-------T-------C--G--G-----GCC----
PC1_37  --C----------G----------A-------CA-------T---G----
PC1_48  --C----N-----G----------A-------CA-------T---G----
BR36    --C---A---------TG-T--A------CA----A-------G----

4941                                              4990
HCV-1   ATGCATGTCGGCCGACCTGGAGGTCGTCACGAGCACCTGGGTGCTCGTTG
HCV-J   ---------T--------T------T-------A--A----
HC-J6   C-----CAA-------T-----A--G-C--G---CT-A-C-
HC-J8   G-----CAA-------T-----A--A-G--A--T-A---C--G-CG--
PC1_37  T------T--G-----T-----A-T--C--T---T--G--G-
PC1_48  T------T--G-----T-----A-T--C--N--T---T--G--G-
BR36    ---A--T--T-------A--AAC---C-------TT-GC---

4991                                              5040
HCV-1   GCGGGCGTCCTGGCTGCTGCTTGGCCGTATTGCCTGTCAACAGGCTGCGTG
HCV-J   ---A----T--G--C--------A-G----A--
HC-J6   -G--G----T---CG-C---------G--G--C--G--T--T
HC-J8   -G--G--A--C--CG-----A--T--C-----G--G--T----A-T
PC1_37  -G----TG-----CC-----G--CC--C--T--A-GGTG--T-CG--A
PC1_48  -G----TG-----CC-----G--CC--C--T--A-GGTG--T-CG--A
BR36    -A--G-----C--G-----CC-A--G--C--C---T-----GTC--T--T--T
```

Figure 10 - Continued 8

```
         5041                                              5090
HCV-1    GTCATAGTGGGCAGGGTCGTCTTGTCCCGGAAGCCGGCAATCATACCTGA
HCV-J    ----T-------A--A------------G---A--TG-T--T--C----
HC-J6    TG-----CA-C---C--CT-GCA-G-TAA-CA-CGAG-C-TCG-TGC--
HC-J8    TC-----CA-T---C--CC-ACA-C--AAT-ATCG-GT--TTG-GGCC-C---
PC1_37   ---C-------C---T--A---C-C--T----A--T--C----T--C--
PC1_48   ---C-------C---T--A---A-C-C-T-----A--T--C----T--C--
BR36     ---G---T-----TCATA---AGC--GGG--C---------G-T--A--

5091                                              5140
HCV-1    CAGGGAAGTCCCTCTACCGAGAGTTCGATGAGATGGAAGAGTGCTCTCAGC
HCV-J    ---------------------AG-----------------TG--TCA--
HC-J6    --A----G--------TGAG-CT---T-------G---A--TG-CTCTA
HC-J8    --A----A--T-A---TGAG-CC---T-----------A--G-CTCCA
PC1_37   T----G--AT-A---AGC-A--T-------G--------------GGCCT
PC1_48   T----G-CAT-A---AGC-A--T-------G--------------GGCCT
BR36     --AA---G--GT-G--T-A-C-A--------------------A---AG 5141                                              5190
HCV-1    ACTTACCGTACATCGAGCAAGGGGATGATGCTCGCCGAGCAGTTCAAGCAG
HCV-J    --C-C--G--T---------------A---CA------A---A-----
HC-J6    GAGCGG-TCT---T---AG-G---CA-CG-A-A-----AT-C-G---TCC
HC-J8    -AGCCG-CCT---T---G-----CA-CG-A-G--G---AT-C----ATCT
PC1_37   CG--G---C---T---G---CG--ACACGTGCCA---T----GA--A----AG--
PC1_48   CG--G---C---T---G---CG--GACACGTGCCA--T----GA--A----AG--
BR36     CTGCC---A-----T-----A----CTCA-G-AA-A--TC-C-------G-A
```

|        |
|--------|
| HCV-1  |
| HCV-J  |
| HC-J6  |
| HC-J8  |
| PC1_37 |
| PC1_48 |
| BR36   |

Figure 10 – Continued 9

```
             5191                                                  5240
HCV-1    AAGGCCCTCGGCCTCCTGCAGACCGCGTCCCGTCAGGCAGAGGTTATCGC
HCV-J    -----G---AT-G----A--CA--AAG--A--G----C-GCT--
HC-J6    ---AT--AA--T-AT-----CAA--T---AAA--A--TC-A-AC--ACA
HC-J8    ---ATA-AA----------A--ACAG--CA-AA-G--A--TC-A-AC--ACA
PC1_37   ---A-TG------T--A-CAGC--GA-CGG--AGA----T---AAC-C-GAA
PC1_48   ---A-TG------T--A-CAGC--GA-CGG--AGA----T---AAC-C-GAA
BR36     ---A-T----T--AT-G------CGA--CA----AA--ACA--CT--C--T-A 5241                                                  5290
HCV-1    CCCTGCTGTCCAGACCAACTGGCAAAAACTGAGACCTTCTGGGCGAAGC
HCV-J    T--C-TG--GG--T---G----G-GCC--T---GT-----A-
HC-J6    A--C----G----G-TTCT----CC--GG-A---CAA-----C--A-
HC-J8    G--A---A--T-ATCA----CC--G--T--ACAA---T-----C--A-
PC1_37   G--G--A-C-AC-T-TGTG---A-C--GGCT---CAG------N-C-CAT
PC1_48   G--G--A-C-AC-T-TGTG---A-C--GGCT---CAG------C-CAT
BR36     G--CATA--AACT------------G--T----G----T---CAC---

5291
HCV-1    AT
HCV-J    -C
HC-J6    -C
HC-J8    -C
PC1_37   -C
PC1_48   -C
BR36     --
```

Figure 11

```
        1286                                              SEQ ID NO
HCV-1   TTGSPITYSTYGKFLADGGCSGGAYDIIICDECHSTDATSILGIGTVLDQAETAGARLVV
HCV-J   ---G--------C-----------------------------S-T--------------
HC-J6   ---A-------------------A--------------AV-S-T--------V--T---
HC-J8   ---DS-----------I------AA-----------------V-T--------V-----
PC-1-48 ---AS----------------------------V----------T--------------
PC-1-37 ---AS----------------------H-V------------Q-T--------------

56
                                                              58

1346
HCV-1   LATATPPGSVTVPHPNIEEVALSTTGEIPFYGKAIPLEVIKGGRHLIFCHSKKKCDELAA
HCV-J   -------------I-----------------N------------------I-A------
HC-J6   -------------------T---------GQE--------R----SY------------
HC-J8   ----------T--T--S--------------GHE-----------AF------------
PC-1-48 -X-X---------T--------------PQE--V----XR----AF------------
PC-1-37 ---X---------T--------------PQE--V----R-----AF----N--------
```

Figure 11 - Continued 1

```
        1406
HCV-1   KLVALGINAVAYYRGLDVSVIPTSGDVVVVATDALMTGYTGDFDSVIDCNTCVTQTVDFS
HCV-J   ----TG--L---------------------------F-----------------------
HC-J6   A-RGM-L---------------Q-------------F--------------VA----V--
HC-J8   A-RGM-V---------------Q----------------------------VA-S-I--

1466
HCV-1   LDPTFTIETITLPQDAVSRTQRRGRTGRGKPGIYRFVAPGERPSGMFDSSVLCECYDAGC
HCV-J   ------------------T-----A--------------RS----T--------------
HC-J6   -----T-Q-V--------S--------------RL---Y-ST---A-------V-----A
HC-J8   -----T-Q-V--------S--------------RL-V-Y-SS-----------V-----A

1526
HCV-1   AWYELTPAETTVRLRAYMNTPGLPVCQDHLEFWEGVFTGLTHIDAHFLSQTKQSGENLPY
HCV-J   --------------S------L----------------S---------------------
HC-J6   ---------------------F------------------A----------A-D---FA-
HC-J8   ---------------------F------------------A----------G----FA-
```

Figure 11 - Continued 2

```
        1586
HCV-1   LVAYQATVCARAQAPPPSWDQMWKCLIRLKPTLHGPTPLLYRLGAVQNEITLTHPVTKYI
HCV-J   ------------------------------------------------------V----I--
HC-J6   --T---------K------V---T-----V-----------------S-T--V------
HC-J8   --T---------K------V---T-----V-----------------T--V--------

1646
HCV-1   MTCMSADLEVVTSTWVLVGGVLAALAAYCLSTGCVVIVGRVVLSGKPAIIPDREVLYREF
HCV-J   -A--------------------------------T-S-----II--R--V------Q---
HC-J6   A---Q-----M------A-----V-----A----C-I---LHVNQRAVVA--K----EA-
HC-J8   A---Q-----IM--S--A-----V-----A---IS-I---LH-NDRVVVA--K-I---EA-
PC-1-48 -A--------I--X-------V-X-------TV-S-A----II---------A--XQ-
PC-1-37 -AF-------I--X---P---I-X---V-T-XX---TV-S-A----II-------X-----QQ- 1706                                                    1764
HCV-1   DEMEECSQHLPYIEQGMMLAEQFKQKALGLLQTASRQAEVIAPAVQTNWQKLETFWAKH
HCV-J   -----------------Q---------------------TK---AA--V-ESK-RA--V----
HC-J6   -----ASRAAL--E-QRI--ML-S-IQ----Q--K--QD-Q---AS-P-V-Q------
HC-J8   -----ASKAAL--E-QRM--ML-S-IQ----Q-T---QD-Q--I-SS-P---Q------
PC-1-48 -----AS---MDETRAI-G---E-V--FIS-TGQK--TLK--ATSV-N-AXQ---TY
PC-1-37 -----AS---MDETRXI-G---E-V--FIS-TGQK--TLK--ATSV-N-ADQ--XTY
```

Figure 12

```
                330        340        350        360        370
                |          |          |          |          |
HCV1   PTTALVMAQLLRIPQAILDMIAGAHWGVLAGIAYFSMVGNWAKVLVVLLL
HCVJ   ----VS-------VV------L--Y--------I-M--
HCJ6   --ATMIL-YAM-V-EV-I-I-G-----MF-L----Q-A---V-I---
HCJ8   --LTMIL-YAA-V-ELV-EI-F-G-----VF-L----Q-A---IAI---
NZL1   -AVGM-V-HV--L--TLF-IM-----I---L--Y--Q----AIIMVM
HCVTR  --IG--ISH-M-L--TLF-LVS-T----M-L---Q-----VI--IM
BE95   ----LV------VVI--I---S-----FAA--YAS--A--T--VL--F--

380        390        400        410   420
                |          |          |          |     |   *
                                                         *
       FAGVDA|ETHVTGGSAGHTVSGFVSLLAPGAKQNVQLINTNGSWHLNSTAL
HCV1         E2
HCVJ   ----G|H------RVASSTQSL--W-SQ-PS-KI--V------I-R---
HCJ6   A----|Q--TV---TA-NARTLTGMFSL--R-KI--------I-R---
HCJ8   V----|-------R--A--AG-FTT----LY--------I-R---
NZL1   -S---|H-YT---T-SRHTQA-AG-FDI-PQ-KL---V------I----
HCVTR  -S---|N-YT-A--MAQSIYRLTDIFST-PS-KL--V-S----------
BE95   -----|T-QIS---SAQ-TY-IA-FITR--Q-KL--------I-R---
```

Figure 12 - Continued 1

```
             430       440       450       460       470
              *         *         *  -       -         *
HCV1    NCNDSLNTGWLAGLFYHHKFNSSGCPERLASCRPLTDFDQGWGPISY AN
HCVJ    -----Q---FI-A---A-R--A-----M-----IDE-A-----TH DM
HCJ6    -----H--F--S----T-S--------MSA--SIEA-RV----ALQ-ED-
HCJ8    -----Q--F--S----T----------S---G-D--RI----TLE-ET-
NZL1    ---E-I----FI-----Y-----T---Q--S--K-I-F-R-----LTD --
HCVTR
BE95    -----Q---FI-----Y--------D-M----A-AT-----T--- --

480       490       500       510       520
HCV1    GSGP/DQRPYCWHYPPKPCGIVPAKSVCGPVYCFTPSPVVVGTTDRSGAP
HCVJ    PESS/------A-R----SQ--------------------------F---
HCJ6    VTN-E-M-----RQ--V-S-S-------------------------L---
HCJ8    VTNDG-M------R-----RT-----------------------KQ-V--
NZL1    IT--S-D-----A-R--D----S--
HCVTR
BE95    I----S-DK------R---V---QE-------------------SK-H-
```

Figure 12 - Continued 2

```
                        530           540
                        |              *
HCV1    1a      TYSWGENDTDVFVLNNTRPPL
HCVJ    1b      -----E----LL--TRP-QG
HCJ6    2a      --T--E----L---S----Q
HCJ8    2b      --T--E----L---S----R
NZL1    3a      --T--E----L---S----R
HCVTR   3b      ---N-S-V--F--LM-----I
BE95    5a      ---N-S-V--F--LM-----I
```

Figure 13

```
                SEQ ID        980
                         CCCCTACGACGGGCGTTGGTAATGGCTCAGCTGCTCCGGATCCCACAAGCC
HCV-1     1a
HCH-H     1a             -----------G-A-------GG-A-----------A--------------
HC-J1     1a             -----------G---------G-----------------------------
HCV-J     1b             -A---------A----CC-A--GG-AT-G-----A----------------
HCV-BK    1b             -G--C---A--A----CC-A--GG---T-G----T-A-------------T
HC-J4.83  1b             -A------A--A----CC-A--GG---T-G----T---------------T
HC-J4.91  1b             -A------A--A----CC-A--GG---T-G----T----------------
HCV-JTA   1b             -G------A--A----CC-A--GG---T-G----T-A--------------
HCV-JTB   1b             -G------A--A----CC-A--GG---T-G----T-A-------------T
HCV-CHINA 1b             -G------A--A----CC-A--GG---T-G----T-A--------------
HCV-T     1b             -G------A--A----TC-A--GG---T-G----T------T---------
HCV-JK1   1b             -G---------A----C-----GG---T-G----T-A-----T--------
HCUNK     1b             -A------A--A----CC-A--GG-AT-G-----A----------------
HCV-N     1b             -A------A--A----CC-C--G----T-G----T-A-------------T
HC-J6     2a             -G---C----G-TA-CA--A-CC---GT-CGC-A-G--CG----CG-G-T-
HC-J8     2b             -T---A--TCTTA-CA--A-CC-C--CT-CGCCGCT-TG-T--CG--CTG
HC-J5     2a             -A---C----G-CA-CA--A-CC---GT-CGC-A-G--CG----CG-G-TT
HC-J7     2b             -A---A--TCTTA-CA--A-CC-C--CT-TGCCGCT-TG-T--TG-GCTA
NZL1      3a             ----CG-TGT--GTA----GG----TG-C--G--TT-A--C---GA----
HEM26     3a             ----CG-TGT--GTA----GG----CG-C--G--TT-G--C---GA----
TH85      3a             ----CG-CGT--GTA----GG-A--TG-C--G--TT-G--C---GA----
US114     3a             ----CG-CGT--GTA----GG----CG-T--G--CG-G--TC-G--GA----
BE95      5a        157  -A---------A--TC--C-GG----C----T-A--G----T--C----TG
```

Figure 13 - Continued 1

```
                 1030
                 ATCTTGGACATGATCGCTGGTGCTCACTGGGGAGTCCTGGCGGGCATAGC
HCV-1     1a     ---A---------------------C--C--------------------AA
HCH-H     1a     ---A---------------------------------------------
HC-J1     1a     ---------T---------------------------------C-T---
HCV-J     1b     G--G-----------G--G--G---C-----------T------A----
HCV-BK    1b     G--G-----------G--G--G---C-----------------------C-T---
HC-J4.83  1b     G--G-----------G--G--G---C-----------------------C-T---
HC-J4.91  1b     G--G-----------G--G--G---C-----------------------C-T---
HCV-JTA   1b     G--G-----T-----G--G--G---C-----------------A-----C-T---
HCV-JTB   1b     G--G-----T-----G--G--G---C-----------------A-----C-T---
HCV-CHINA 1b     G--A-----------G--G-TG---C-----------------------C-T---
HCV-T     1b     G--G-----T-----G--G-GG---C-----------------------C-T---
HCV-JK1   1b     G--G-----------G--G-TG---C-----------------------C-T---
HCUNK     1b     G--G-----------G-GA-A---GT-C-----------A---------C-T---
HCV-N     1b     G--A-C---------G--G--G---C-----------------------C-T---
HC-J6     2a     ---A-A---C---T-GC---G-----T-----C---A---TTC---T---
HC-J8     2b     G--C-C---A---T--TTTC--C-GC--T-----T--GG--TTT--T-G---
HC-J5     2a     ---A-A---C---TAGC---G-----------C---A---TTC---C---
HC-J7     2b     G--C-T--GG-TG--TTC--C-GC--T-----T--GG--TTT--T-G---
NZL1      3a     T-G--C---A--G--C---G--C---T-----CA--T-----C-G---
HEM26     3a     T-G--C---A--A--C---G--C---T-----CA--T-----C-----
TH85      3a     T-G--C---A--A--C---G--C---T-----CA--T-----C-----
US114     3a     T-G--C-T-AG-A--C---G--C---T-----CA--T-----C-----
BE95      5a     G--A-T---C-----A--GAGC-----------G---T--TTT-C-GCC--
```

Figure 13 - Continued 2

```
                        1080
          GTATTTCTCCATGGTGGGGAACTGGGGCCGAAGGTCCTGGTAGTGCTGCTGC
HCV-1    1a  --------------------------------------------------
HCH-H    1a  --------------------------------------------T-----
HC-J1    1a  --------------------------------------------------A-
HCV-J    1b  C---C-AT------------------T----T---A-T---A--------A-
HCV-BK   1b  C---C-AT-----C------------T----T---A-T---A--------A-
HC-J4.83 1b  C---C-AT------A-----------T----T---A-T---GC-------A-
HC-J4.91 1b  C---C-AT------A-----------T----T---A-T---GC-------A-
HCV-JTA  1b  C---C-AT------------------T----T---A-T---A--------A-
HCV-JTB  1b  C---C-AT------------------T----T---A-T---A--T-----A-
HCV-CHINA 1b C---C-ATG-----------T-----T----T---A-T---A--T-----A-
HCV-T    1b  C---C-AT------------------T----T---TT--A-T---A----A-
HCV-JK1  1b  C---C-AT------------------T----T---T--AA-T---A----A-
HCUNK    1b  C---C-AT------------------T----T---T---A-T---A----A-
HCV-N    1b  C---C-AT------------------T----T---T--AA-T-C-A----A-
HC-J6    2a  C---C-----T---CA---AGCG---T----A--A---G-T--CA-T--TT-
HC-J8    2b  C---C--------CAA---AGCG---T----C--A--C-CCA-C--C---T-
HC-J5    2a  C---C-----T---CA---AGCG------------G-T--CA-C---T----
HC-J7    2b  C---C---------CA---AGCG---T----C--A--A-T-CCA-C--C---C-
NZL1     3a  C----A--------CA---C------T----C------A-T-CCA-C--C---C-
HEM26    3a  C----A--------CA---C--T---T----C-----------------C-
TH85     3a  C----A--------CAA--C------T----C---GCAA-CA--CA--G-TA
US114    3a  C----A--------CA---C------T----C---GCTA-CA--CG--G-TA
BE95     5a  A---C-ATG-ATC----CT-------T----A--C---G---CT--T-T-
```

Figure 13 - Continued 3

```
              1130
HCV-1     1a  TATTTGCCGGCGTCGACGCGGAAACCCACGTCACCGGGGAAGTGCCGGC
HCH-H     1a  ------------------------------------------A-----
HC-J1     1a  -G----------------------------AT-----T-----CAA--C--
HCV-J     1b  -C----------T-------T---G-C-C-----G--A-------G-TA-C-
HCV-BK    1b  -T----T-----T-------T---G-----T--G--A-----GGGCGCAA-C-
HC-J4.83  1b  -C---C------T-------C-------G-----G--T--ACGT-G---GGCG--A--
HC-J4.91  1b  -C----------T-------T-------G-----T--ACGT-G----GGTG----
HCV-JTA   1b  -C----------T-------T-------G--TC-TT--ACG--A---GTCGCAA-CT
HCV-JTB   1b  -C----------T-------T-------G--TC-TT--ACG--A---GTCGCAA-CT
HCV-CHINA 1b  -C----------T-------T-------G--TC--T---ACG--A---GGCGCAG--
HCV-T     1b  -C---C------T-------T-------T-G---T----CGT-T-----G-CA-TG-C-
HCV-JK1   1b  -T----------T-------T-------G-AGT----AT---GT-A---A--G-CA-TG-C-
HCUNK     1b  -C----------T-------T-------G-ACT----T----GT-A-T--GCA--AA--
HCV-N     1b  -C----------T-------T-------GAACC--------G--A-----GGCGCAA--T
HC-J6     2a  -T----------T-------T---G-C-C-----C------T-ACA--G----GCAC--T-C-
HC-J8     2b  -GGCC-------G---G---G---C---------TAC-GTT-----TTC-A---CG
HC-J5     2a  -TG---G--A--G---G---T--AACC---T-TTC--G---CCAGGAA--G--T
HC-J7     2b  -GGCC-T--A--G---G---T---A-C--G-AC-GTT-C---TTC---T-CG
NZL1      3a  -TG-C-A--A--G---G---T--AGC----------A---T--C---CAA--G-C-
HEM26     3a  -G--CT-A--G-----G---T--CC-C----AT-TAC------T--C-C----ATCT
TH85      3a  -G---T-A--G-----G---T--C-------AT-TAC------T--C----TG-CT
US114     3a  -G---T-A--G-----G---T--C--G--A-G-A-----------T--C-C---A-CT
BE95      5a  -G----A--G-----T---T--CAGC--A--TA--------T--CTC-ATG-CT
              -G-----A--G--T--T--TACT----GA-TT-G--C---CTCCAG--C-
```

Figure 13 – Continued 4

| | | 1180 | | | | |
|---|---|---|---|---|---|---|
| HCV-1 | 1a | CACACTGTGTCTGGATTTGTTAGCCTCCTCGCACCAGGCCCAAGCAGAA |
| HCH-H | 1a | -G----CAC-G----GC-----G-T-----TA--------------- |
| HC-J1 | 1a | -G-G-CA-------C------T--T--A-------T----------- |
| HCV-J | 1b | TC--GCACCCAGA-CC-C--GTC-TGG---T----A----C-ATCT-- |
| HCV-BK | 1b | A-A--CACCAACA-GC-C--GTC-A-GT----AGT--GC-GTCT---- |
| HC-J4.83 | 1b | -----CACC--CACGC-C-CGTC------T---T---G--GTCT---- |
| HC-J4.91 | 1b | -----CACC--C--G--CACGTC------T---T---G--GTCT---- |
| HCV-JTA | 1b | -G--CACACCCAGA-CG--CACGTC-T--T---A-C-A--GC-GGCC--G |
| HCV-JTB | 1b | -G-CACACCCAG--GG-C-CGTC-T--T---A-C----GC-GGCC--G |
| HCV-CHINA | 1b | -G-T-CACCCTC--G--CACGTC------T--TA---T--G--TCT-- |
| HCV-T | 1b | -G-----CACCCACA-TC-C-CGTCT---T-TA---A---G--GTCC-- |
| HCV-JK1 | 1b | -G----CACCCGGC-CG---CGTC-T---T---AGT--T---T-GGCT-- |
| HCUNK | 1b | -GGG-C-CTAGCTCGC-AACGTC-----T--TAGC--T--GC-GGTT---C |
| HCV-N | 1b | ---CTCACCAGC--G---C-CGG------T--TA----T--GC-GTCT---G |
| HC-J6 | 2a | --T-AC-CCAGGACCC-CACCG--A-GT--T-C-TT---T--G---- |
| HC-J8 | 2b | -GT--C--CG-G--G---C-C-G----T-TA-TA-T-------- |
| HC-J5 | 2a | GCA--CACCAGG--C--CACC---A-GT--T-CT-T---T-G----- |
| HC-J7 | 2b | --T--C--TAGA---G-C-CC---A--T--AGC--T---T--CG---G |
| NZL1 | 3a | -GTCA-ACCCAA-CG----C-G-T--TT-T-ACAT----C--C-A-- |
| HEM26 | 3a | --TG--ACCAGA--GA-A-C----T--TT-TA-TGTG--------- |
| TH85 | 3a | --TGA----C-ACA--G----C----T--TT--AAT-GG----CGC-- |
| US114 | 3a | -GTGA----C-ACA--G--CAC-G--T-TT----C-GG----C--CGA--A- |
| BE95 | 5a | --A--GAC---A---CA-C-CCTCAT-TA--A-C-GC----GC----- |

Figure 13 - Continued 5

```
                    1230
          CGTCCAGCTGATCAACACCAACGGGCAGTTGGCACCTCAATAGCACGGCCC
HCV-1  1a  -A-----A---------------------------A---------------
HCH-H  1a  -A-------------------------------------------------T
HC-J1  1a  -A-------------------------------------A-----------T
HCV-J  1b  AA----A--CG-G---------------C--------A--------C--G--T
HCV-BK 1b  AA----T--A-----T--G----------A------A--------C--G--T
HC-J4.83 1b AA---TG-G--T-----------------C--------A--------C--G--T
HC-J4.91 1b AA---TG-G--T-----------------C--------A--------C--G--T
HCV-JTA 1b AA----C--A----T--------------C--------A--------C--G--T
HCV-JTB 1b AA----C--A----T--------------C--------A--------C--G--T
HCV-CHINA 1b GA----T--A--T----T-T--C--------------TA-------C--G--T
HCV-T  1b  AA----T--A--------------------C-------A--------C--G--T
HCV-JK1 1b AA--A--TG-T----T--------------C-------A--------C--G--T
HCUNK  1b  -C-------------C---------------------TA-------C--G--C
HCV-N  1b  AA----T--A----T-------------C--------A--------C--G--T
HC-J6  2a  AA-------C-------------------------A-A--------CC-G--C
HC-J8  2b  -C-T-TT-A----------T---------------A--A--------CC-G--T
HC-J5  2a  -C-T----C--T------T--------T---------A--------CC-G--C
HC-J7  2b  -C-T----C------T------------C--------A-A--------CC-G--C
NZL1   3a  TA--AGT--A------------------------T---A--------CC-G--C
HEM26  3a  AC-G----G--------------T---T--TCG------A--------C--T--T
TH85   3a  AC-G----G--------------T---T--TCG------A--------C--T--T
US114  3a  -C-G---T-G-------------T---T--TCG------A-------A--C-----T
BE95   3a  -C-G----G--------------T---T--TCG-----TA--------CC-----T
       5a  AC-G----C--A--T--------A---------A--C--A--------C--G--C
```

Figure 13 - Continued 6

```
           1280
HCV-1      TGAACTGCAATGATAGCCTCAACACCGGCTGGTTGGCAGGGCTTTCTAT
HCH-H      ------------A-------------------A---------------
HC-J1      ------------A-------T-----------A---------------
HCV-J      ---T---CTC--C-A---G-TCA-T--T-C----G--------C----
HCV-BK     -------CTCT-C-G---G-TTC-T--C-C----G-------------
HC-J4.83   -------CTC--C-----G-TCC-T--C-C----G-------------
HC-J4.91   -A-----CTC--C-----G-TCC-T--C-C----G-------------
HCV-JTA    -A-T---ATC--------G-TC--T--C-CA---G-------------
HCV-JTB    -------ATC--------G-TC--T--C-CA---G-------------
HCV-CHINA  -------CTC-----T--G-TTC-T--C-CTC--G-------------
HCV-T      -A---C-CTC--C-G---G-TC--T--C-C----G-------------
HCV-JK1    ---T-C-GTC--A-----G-TC--T--C-C----G-------------
HCUNK      ---G---CTC--------G-TTG-T--C-C----G-------------
HCV-N      -------CTC--C-G---G-TCC-T--C-CC---G--C----------
HC-J6      -------CTCTT-GC-------TCC-C--GTCA--G-------------
HC-J8      -C-T---C--T-AC-G--G--T-TCC-C--TTCCT-G--T--------
HC-J5      ---T---CTC--T-G------G--TCC-C---GTCC--G---------
HC-J7      -C-T-----T-GC-A--A--T-TC--C--T-CC--G--T---------
NZL1       -A--T--GTC-A-A------G-TTA-A--T-----T-G--T-------
HEM26      ---------GTC-A-A----G-TCA-A--T-----T-A--T-------
TH85       --------TC-A-A------G-TCA-A--TA----T-G--T-------
US114      --------GTC-A-A-----G-TCA-A--T-----T-GC-T-------
BE95       -T-T----C------C-G--G-TCA-A--C-----C--C---------
```

HCV-1      1a
HCH-H      1a
HC-J1      1a
HCV-J      1b
HCV-BK     1b
HC-J4.83   1b
HC-J4.91   1b
HCV-JTA    1b
HCV-JTB    1b
HCV-CHINA  1b
HCV-T      1b
HCV-JK1    1b
HCUNK      1b
HCV-N      1b
HC-J6      2a
HC-J8      2b
HC-J5      2a
HC-J7      2b
NZL1       3a
HEM26      3a
TH85       3a
US114      3a
BE95       5a

Figure 13 - Continued 7

| | | 1330 | | | | | | |
|---|---|---|---|---|---|---|---|---|
| HCV-1 | 1a | CACCACAAGTTCAACTCTTCAGGCTGTCCTGAGAGGCTAGCCAGCTGCCG |
| HCH-H | 1a | --G----A----------------------------------T-G---- |
| HC-J1 | 1a | --A----A----------------------------------T-G---- |
| HCV-J | 1b | GCA----G---------G--G---C--G--C--A---C-CA-G--T--- |
| HCV-BK | 1b | ACA--T-GT-------------G--C--G--C--A---C-CA-G--CAG- |
| HC-J4.83 | 1b | ACA----G---------------G--C--G--C--A---C-CA-G---- |
| HC-J4.91 | 1b | ACA--------------------G--C--G--C--G---C-CA-G---- |
| HCV-JTA | 1b | ACA--------------------G--C--A--C--A---C-CA-G---A |
| HCV-JTB | 1b | GCA--------------------G--C--A--C--A---C-CA-G---A |
| HCV-CHINA | 1b | ACA----G---------G--G--C--C--A--CG-A---C-CA-G---- |
| HCV-T | 1b | GCG----G---------G--G--C--C--G--C--A---C-CA-G---- |
| HCV-JK1 | 1b | GTAA-G-----------------G--T--A--CT-A---C-CA-G--T- |
| HCUNK | 1b | A-AT---G---------G--G--C--C--G--C--CT-G---CG----- |
| HCV-N | 1b | ACAT---G---------G--G--C--C--A--G-C-CA-G-------- |
| HC-J6 | 2a | AC-----GC--------G-----C--A-----C--AC-CA-GT--GC-- |
| HC-J8 | 2b | AC----------AGC--T-----C--C-----C--C--CT-GT-TTC-- |
| HC-J5 | 2a | GT-A--CGC----T--G-----A----CC-TC-C--CT-GT----T--- |
| HC-J7 | 2b | GT-AGACGT---AGC--T-----A----C--C--CT-GT-TTC----- |
| NZL1 | 3a | T----T----------------A-T--A----C-A----CAG----AA |
| HEM26 | 3a | T-T--T----------------A-T--A----C-C----CAG---TAA |
| TH85 | 3a | T----T----------------A-T--A----C-A----CAG----AA |
| US114 | 3a | T-TA-T----------------A-T--A----C-A----CAG--T--AA |
| BE95 | 5a | T----T--------------T----A--C--G--TC--A-G--T--TA- |

Figure 13 - Continued 8

|  |  | 1380 |  |  |  |
|---|---|---|---|---|---|
| HCV-1 | 1a | ACCCCTTACCGATTTTGACCAGGGCTGGGGCCCTATCAGTTAT | | | GCCA |
| HCH-H | 1a | --G--------------------C------------------ | | | ---- |
| HC-J1 | 1a | --G---------------------------------C----- | | | ---- |
| HCV-J | 1b | C---A--CGAT--G--C-CT------G-------T---C-C- | | | -AT- |
| HCV-BK | 1b | CA--A--GA-A-G--C---------A-------T-C--T-C- | | | --TG |
| HC-J4.83 | 1b | C---A--GA-TGG--C-C-------A-------T---C-CC- | | | A-TG |
| HC-J4.91 | 1b | C---A--GA--GG--C-C-------A-------T---C-CC- | | | A-TG |
| HCV-JTA | 1b | CT--A--CGA-A-G--C-CT-----A-----------C-CC- | | | A--G |
| HCV-JTB | 1b | CT--A--GA-A-G--C-CT------A-------T---C-CC- | | | A--G |
| HCV-CHINA | 1b | C---A--GATACA--C--T--------------T---C-CC- | | | A-TG |
| HCV-T | 1b | TT--A--GA-A-G--C---T-----A-------T---C-CC- | | | A-TG |
| HCV-JK1 | 1b | T---A--GA-AGG--C-CT---A--G-------T---CCC- | | | --TG |
| HCUNK | 1b | C---A--GATACA--C-CG------G-----------C--C- | | | A-TG |
| HCV-N | 1b | CT--A--GA-A-G--C--------A-------T---C-C- | | | --TG |
| HC-J6 | 2a | CAGTA-CGAG-CC---CGGGT----A-----G-CT-ACAA---GAG-A- | | | ---- |
| HC-J8 | 2b | CGGG--GGA-------CG-ATC---------AA-CT-GGAA--CGAAA- | | | ---- |
| HC-J5 | 2a | CAG-A-CGAG-C---CCGGATA--G------A-CT-GCAA--CGAG-AT | | | ---- |
| HC-J7 | 2b | TAAG--GGAT-----CG-ATC---G------AA-CT-GGAA--GAGA-- | | | ---- |
| NZL1 | 3a | G---A-C--TTTC--CAGG-----A-------CT-A-CAG- | | | --T- |
| HEM26 | 3a | G---A-C--TTCC--CAGG-----G----T-CT-G-CAG- | | | --T- |
| TH85 | 3a | G---A-C---TCC--CA-T-----G-------CT-G-CAG- | | | --AA |
| US114 | 3a | G---A-C--TTCC--CAGG-----G----T-CT-G-CAG- | | | --T- |
| BE95 | 5a | GG-----G---AC-----------------AA--------C- | | | ---- |

Figure 13 - Continued 9

| | | 1430 | | |
|---|---|---|---|---|
| HCV-1 | 1a | ACGGAAGCGGCCCC | | GACCAGCGCCCCTACTGCTGGCACTACCCCCA |
| HCH-H | 1a | ------T- | | ---G-A--------------------T----- |
| HC-J1 | 1a | -------- | | ---A----------T--T-------------- |
| HCV-J | 1b | TGCCTGAGA--T-G | | -----A-G--A---T----------G-G---T |
| HCV-BK | 1b | -GTCT---A-AT-A | | -----A--A---------------A--T |
| HC-J4.83 | 1b | -GCCTGA-A----G | | --T--A-G--T---T----------G-G---T |
| HC-J4.91 | 1b | -GCCT-A-A----G | | --T--A-G--T---T----------G-G---T |
| HCV-JTA | 1b | -GCCT---G-A--TG | | --T--A-G--T---T----------G-A---T |
| HCV-JTB | 1b | -GCCTG-G-A--TTG | | -----A-G--T---T----------G-G---T |
| HCV-CHINA | 1b | -GCCTGATA--T-G | | -----A-G--T---T----------G-A---T |
| HCV-T | 1b | -G-CTGA-AT--AG | | -----A--G-T---T----------G-A---C |
| HCV-JK1 | 1b | -GTCTC--A--T-G | | ----AA-G------T----------G-A---T |
| HCUNK | 1b | -GCCTCAT-ATTTG | | --T--A-G--T---T----------G-G---T |
| HCV-N | 1b | -TCCT-AA-A---G | | -----A-G------T-------T--G-A---G |
| HC-J6 | 2a | -T-TC-C-AAT--AGAG | | -TAT-A-A--A----------A------A--- |
| HC-J8 | 2b | --TC-C-AA-GATGGG | | -AT-A-G--G-----------A- |
| HC-J5 | 2a | -T-TC-C-AAT--AGAA | | -TAT-A-A--A---------A------A--- |
| HC-J7 | 2b | -T-TT-C-AA-GAGGAG | | -AT-A-A--G-----------G---T--G |
| NZL1 | 3a | --ATC-C---T--TTCT | | -TG-CA-A--A----------A---G-A---T |
| HEM26 | 3a | --ATCTC---TT-GTCC | | -AG-CAAA--G----------G---G-A---T |
| TH85 | 3a | ---ATC-C---T---TCT | | -TG-CAAA--A---------------G-A---T |
| US114 | 3a | --ATC-C--ATT-TTCT | | -TG-CAAA--G---------------G-A---T |
| BE95 | 5a | --AT-TCG--T---AGT | | -TG-CAAA--A---T----------T------- |

Figure 13 - Continued 10

```
                      1480
HCV-1       1a   AAACCTTGCGGGTATTGTGCCCGCGAAGAGTGTG
HCH-H       1a   -G-----T--C-------------A----C----
HC-J1       1a   -------------------C----A----C---A
HCV-J       1b   CG-----G---C-----G-C----T---TC-CAG
HCV-BK      1b   CC--AA--TACC---C--A--T---TC-GAG---
HC-J4.83    1b   CG-----G--T------C--A----TC-CAG---
HC-J4.91    1b   CG-----G--T------C--A----TC-CAG---
HCV-JTA     1b   CGG-AG--T--------C--A--T-TC-CAG---
HCV-JTB     1b   CGG-AG--T--------C--A----TC-CAG---
HCV-CHINA   1b   CG-AAG--T--------C--A----TC-CAG---
HCV-T       1b   CGG----G--T------C--A----TC-CAG---
HCV-JK1     1b   C------G--T------C-------TT-CAG---
HCUNK       1b   C------G--T----------A---TT-CAG---
HCV-N       1b   C---AG--T-------CA-A---CG-TCCGAG-C
HC-J6       2a   -G--AG--T---G-A--CT------GCTC-----
HC-J8       2b   --GG-------------C--C--G--T-G--CG--T
HC-J5       2a   ----G---T---C--A--C------G-TC-----
HC-J7       2b   -G------------C--CT-G--T----CG----C
NZL1        3a   -G-----T-AC------C--G--ATCA-------C
HEM26       3a   -G-----TACCG-----C--A--ATCA-------C
TH85        3a   -G-----TAAA-G----C--A--ATCA-------C
US114       3a   -G-T---T-A--CC---C--G--ATCA-------C
BE95        5a   CGG----G----AG-G------A--CC-AGAG--C
```

SEQUENCES OF HEPATITIS C VIRUS GENOTYPES AND THEIR USE AS THERAPEUTIC AND DIAGNOSTIC AGENTS

This application is a continuation of application Ser. No. 08/362,455, filed Jan. 11, 1995, which is a 371 U.S. national phase of PCT/EP94/01323, filed Apr. 27, 1994, which designated the U.S., the entire content of which is hereby incorporated by reference in this application.

The present invention relates to new nucleotide and amino acid sequences corresponding to the coding region of a new type 2 subtype 2d, type-specific sequences corresponding to HCV type 3a, to new sequences corresponding to the coding region of a new subtype 3c, and to new sequences corresponding to the coding region of HCV type 4 and type 5 subtype 5a; a process for preparing them, and their use for diagnosis, prophylaxis and therapy.

The technical problem underlying the present invention is to provide new type-specific sequences of the Core, the E1, the F2, the NS3, the NS4 and the NS5 regions of HCV type 4 and type 5, as well as of new variants of HCV type 2 and 3. These new HCV sequences are useful to diagnose the presence of type 2 and/or type 3 and/or type 4 and/or type 5 HCV genotypes in a biological sample. Moreover, the availability of these new type-specific sequences can increase the overall sensitivity of HCV detection and should also prove to be useful for therapeutic purposes.

Hepatitis C viruses (HCV) have been found to be the major cause of non-A, non-B hepatitis. The sequences of cDNA clones covering the complete genome of several prototype isolates have been determined (Kato et al., 1990; Choo et al., 1991; Okamoto et al., 1991; Okamoto et al., 1992). Comparison of these isolates shows that the variability in nucleotide sequences can be used to distinguish at least 2 different genotypes, type 1 (HCV-J and HCV-1) and type 2 (HC-J6 and HC-J8), with an average homology of about 68%. Within each type, at least two subtypes exist (e.g. represented by HCV-1 and HCV-J), having an average homology of about 79%. HCV genomes belonging to the same subtype show average homologies of more than 90% (Okamoto et al., 1992). However, the partial nucleotide sequence of the NS5 region of the HCV-T isolates showed at most 67% homology with the previously published sequences, indicating the existence of a yet another HCV type (Mori et al., 1992). Pans of the 5' untranslated region (UR), core, NS3, and NS5 regions of this type 3 have been published, further establishing the similar evolutionary distances between the 3 major genotypes and their subtypes (Chan et al., 1992).

The identification of type 3 genotypes in clinical samples can be achieved by means of PCR with type-specific primers for the NS5 region. However, the degree to which this will be successful is largely dependent on sequence variability and on the virus titer present in the serum. Therefore, routine PCR in the open reading frame, especially for type 3 and the new type 4 and S described in the present invention and/or group V (Cha et al., 1992) gels can be predicted to be unsuccessful. A new typing system (LiPA), based on v on in the highly conserved 5' UR, proved to be more usefull because the 5 major HCV genotypes and their subtypes can be determined (Stuyver et al., 1993). The selection of high-titer isolates enables to obtain PCR fragments for cloning with only 2 primers, while nested PCR requires that 4 primers match the unknown sequences of the new type 3, 4 and 5 genotypes.

New sequences of the 5' untranslated region (5'UR) have been listed by Bukh et al. (1992). For some of these, the E1 region has recently been described (Bukh et al., 1993). Isolates with similar sequences in the 5'UR to a group of isolates including DK12 and HK10 described by Bukh et al. (1992) and E-b1 to E-b8 described and classified as type 3 by Chan et al. (1991), have been reported and described in the 5'UR, the carboxyterminal part of E1, and in the NS5 region as group IV by Cha et al. (1992; WO 92/19743), and have also been described in the 5'UR for isolate BR56 and classified as type 3 by the inventors of tis application (Stuyver et al., 1993).

The aim of the present invention is to provide new HCV nucleotide and amino acid sequences enabling the detection of HCV infection.

Another aim of the present infection is to provide new nucleotide and amino acid HCV sequences enabling the classification of infected biological fluids into different serological groups unambiguously linked to types and subtypes at the genome level.

Another aim of the present invention is to provide new nucleotide and amino acid HCV sequences ameliorating the overall HCV detection rate.

Another aim of the present invention is to provide new HCV sequences, useful for the design of HCV vaccine compositions.

Another aim of the present invention is to provide a pharmaceutical composition consisting of antibodies raised against the polypeptides encoded by these new HCV sequences, for therapy or diagnosis.

The present invention relates more particularly to a composition comprising or consisting of at least one polynucleic acid containing at least 5, and preferably 8 or more contiguous nucleotides selected from at least one of the following HCV sequences:

an HCV type 3 genomic sequence, more particularly in any of the following regions:
  the region spanning positions 417 to 957 of the Core/E1 region of HCV subtype 3a,
  the region spanning positions 4664 to 4730 of the NS3 region of HCV type 3,
  the region spading positions 4892 to 5292 of the NS3/4 region of HCV type 3,
  the region spanning positions 8023 to 8235 of the NS5 region of the BR36 subgroup of HCV subtype 3a,
an HCV subtype 3c genomic sequence,
more particularly the coding regions of the above-specified regions;
an HCV subtype 2d genomic sequence, more particularly the coding region of HCV subtype 2d;
an HCV type 4 genomic sequence, more particularly the coding region, more particularly the coding region of subtypes 4a, 4e, 4f, 4g, 4h, 4i, and 4j,
an HCV hype 5 genomic sequence, more particularly the coding region of HCV type 5, more particularly the regions encoding Core, E1, E2, NS3, and NS4
  with said nucleotide numbering being with respect to the numbering of HCV nucleic acids as shown in Table 1, and with said polynucleic acids containing at least one nucleotide difference with known HCV (type 1, type 2, and type 3) polynucleic acid sequences in the above-indicated regions, or the complement thereof.

It is to be noted that the nucleotide difference in the polynucleic acids of the invention may involve or not an amino acid difference in the corresponding amino acid sequences coded by said polynucleic acids.

According to a preferred embodiment, the present invention relates to a composition comprising or containing at least one polynucleic acid encoding an HCV polyprotein, with said polynucleic acid containing at least 5, preferably at least 8 nucleotides corresponding to at least part of an HCV nucleotide sequence encoding an HCV polyprotein, and with said HCV polyprotein containing in its sequence at least one of the following amino acid residues L7, Q43, M44, S60, R67, Q70, T71, A79, A87, N106, K115, A127, A190, V134, G142, I144, E152, A157, V158, P165, S177 or Y177, 1178, V180 or E180 or F182, R184, I186, H187, T189, A190, S191 or G191, Q192 or L192 or 1192 or V192 or E192, N193 or H193 or P193, W194 or Y194, H195, A197 or I197 or V197 or T197, V202, L103 or L203, Q208, A210, V212, F214, T216, R217 or D217 or E217 or V217, H218 or N218, H219 or V219 or L219, L227 or I227, M231 or E231 or Q231, T232 or D232 or A232 or K232, Q235 or I235, A237 or T237, I242, I246, S247, S248, V249, S250 or Y250, I251 or V251 or M251 or F251, D252, T254 or V254, L255 or V255, E256 or A256, M258 or F258 or V258, A260 or Q260 or S260, A261, T264 or Y264, M265, I266 or A266, A267, G268 or T268, F271 or M271 or V271, I277, M280 or H280, 1284 or A284 or L84, V274, V291, N292 or S292, R293 or I293 or Y293, Q294 or R294, L297 or 1297 or Q297, A299 or Q299, N303 or T303, M308 or L308, T310 or F310 or A310 or D310 or V310, L313, G317 or Q317, L333, S351, A358, A359, A363, S364, A366, T369, L373, F376, I387, S392, I399, F402, I1403, R40S, D454, A461, A463, T464, K484, Q500, E501, S521, K522, H524, N528, S531, S532, V534, F536, F537, M539, I546, C1282, A1283, H1310, V1312, Q1321, P1368, V1372, V1373, K1405, Q1406, S1409, A1424, A1429, C1435, S1436, S1456, H1496, A1504, D1510, D1529, I1543, N1567, D1556, N1567, M1572, Q1579, L1581, S1583, F1585, V1595, E1606 or T1606, M1611, V1612 or L1612, P1630, C1636, P1651, T1656 or I1656, L1663, V1667, V1677, A1681, H1685, E1687, G1689, V1695, A1700, Q1704, Y1705, A1713, A1714 or S1714, M1718, D1719, A1721 or T1721, R1722, A1723 or V1723, H1726 or G1726, E1730, V1732, F1735, I1736, S1737, R1738, T1739, G1740, Q1741, K1742, Q1743, A1744, T1745, L1746, E1747 or K1747, I1749, A1750, T1751 or A1751, V1753, N1755, K1756, A1757, P1758, A1759, H1762, T1763, Y1764, P2645, A2647, K2650, K2653 or L2653, S2664, N2673, F2680, K2681, L 2686, H2692, Q2695 or L2695 or 12695, V2712, F2715, V2719 or Q2719, T2722, T2724, S2725, R2726, G2729, Y2735, H2739, I2748, G2746 or I2746, I2748, P2752 or K2752, P1754 or T2754, T2757 or P2157, with said notation being composed of a letter representing the amino acid residue by its one-letter code, and a number representing the amino acid numbering according to Kato et al., 1990.

Each of the above-mentioned residues can be found in any of FIGS. 2, 5, 7, 11 or 12 showing the new amino acid sequences of the present invention aligned with known sequences of other types or subtypes of HCV for the Core, E1, E2, NS3, NS4, and NS5 regions.

More particularly, a polynucleic acid contained in the composition according to the present invention contains at least 5, preferably 8, or more contiguous nucleotides corresponding to a sequence of contiguous nucleotides selected from at least one of HCV sequences encoding the following new HCV amino acid sequences:

- new sequences spanning amino acid positions 1 to 319 of the Core/E1 region of HCV subtype 2d, type 3 (more particularly new sequences for subtypes 3a and 3c), new type 4 subtypes (more particularly new sequences for subtypes 4a, 4e, 4f, 4g, 4h, 4i and 4j) and type 5a, as shown in FIG. 5;
- new sequences spanning amino acid positions 328 to 546 of the E1/E2 region of HCV subtype 5a as shown in FIG. 12;
- new sequences spanning amino acid positions 1556 to 1764 of the NS3/NS4 region of HCV type 3 (more particularly for new subtypes 3a sequences), and subtype 5a, as show in FIGS. 7 or 11;
- new sequences spanning amino acid positions 2645 to 2757 of the NS5B region of HCV subtype 2d, type 3 (more particularly for new subtypes 3a and 3c), new type 4 subtypes (more particularly subtypes 4a, 4e, 4f, 4g, 4h, 4i and 4j) and subtype 5a, as shown in FIG. 2.

Using the LiPA system mentioned above, Brazilian blood donors with high titer type 3 hepatitis C virus, Gabonese patients with high-titer type 4 hepatitis C virus, and a Belgian patient with high-titer HCV type 5 infection were selected. Nucleotide sequences in the core, E1, NS5 and NS4 regions which have not yet been reported before, were analyzed in the frame of the invention. Coding sequences (with the exception of the core region) of any type 4 isolate are reported for the fist time in the present invention. The NS5b region was also analyzed for die new type 3 isolates. After having determined the NS5b sequences, comparison with the Ta and Tb subtypes described by Mori et al. (1992) was possible, and the type 3 sequences could be identified as type 3a genotypes. The new type 4 isolates segregated into 10 subtypes, based on homologies obtained in the NS5 and E1 regions. New type 2 and 3 sequences could also be distinguished from previously described type 2 or 3 subtypes from sera collected in Belgium and the Netherlands.

The term "polynucleic acid" refers to a single stranded or double stranded nucleic acid sequence which may contain at least 5 contiguous nucleotides to the complete nucleotide sequence (f.i. at least 6, 7, 8, 9, 10, 11, 12, 13, 14, 15 or more contiguous nucleotides). A polynucleic acid which is up till about 100 nucleotides in length is often also referred to as an oligonucleotide. A polynucleic acid may consist of deoxyribonucleotides or ribonucleotides, nucleotide analogues or modified nucleotides, or may have been adapted for therapeutic purposes. A polynucleic acid may also comprise a double stranded cDNA clone which can be used for cloning purposes, or for in vivo therapy, or prophylaxis.

The term "polynucleic acid composition" refers to any kind of composition comprising essentially said polynucleic acids. Said composition may be of a diagnostic or a therapeutic nature.

The expression "nucleotides corresponding to" refers to nucleotides which are homologous or complementary to an indicated nucleotide sequence or region within a specific HCV sequence.

The term "coding region" corresponds to the region of the HCV genome that encodes the HCV polyprotein. In fact, it comprises the complete genome with the exception of the 5' untranslated region and 3' untranslated region.

The term "HCV polyprotein" refers to the HCV polyprotein of the HCV-J isolate (Kato et al., 1990). The adenine residue at position 330 (Kato et al., 1990) is the first residue of the ATG codon that initiate the long HCV polyprotein of 3010 amino acids in HCV-J and other type 1b isolates, and of 3011 amino acids in HCV-1 and other type 1a isolates, and of 3033 amino acids in type 2 isolates HC-J6 and HC-J8 (Okamoto et al., 1992).

This adenine is designated as position 1 at the nucleic acid level, and this methionine is designated as position 1 at the amino acid level, in the present invention. As type 1a isolates contain 1 extra amino acid in the NS5a region, coding sequences of type 1a and 1b have identical numbering in the Core, E1, NS3, and NS4 region, but will differ in the NS5b region as indicated in Table 1. Type 2 isolates have 4 extra amino acids in the E2 region, and 17 or 18 extra amino acids in the NS5 region compared to type 1 isolates, and will differ in numbering from type 1 isolates in the NS3/4 region and NS5b regions as ted in Table 1.

TABLE 1

|  | Region | Positions described in the present invention* | Positions described for HCV-J (Kato et al., 1990) | Positions described for HCV-1 (Choo et al., 1991) | Positions described for HC-J6, HC-J8 (Okamoto et al., 1992) |
| --- | --- | --- | --- | --- | --- |
| Nucleotides | NS5b | 8023/8235 | 8352/8564 | 8026/8238 | 8433/8645 |
|  |  | 7932/8271 | 8261/8600 | 7935/8274 | 8342/8681 |
|  | NS3/4 | 4664/5292 | 4993/5621 | 4664/5292 | 5017/5645 |
|  |  | 4664/4730 | 4993/5059 | 4664/4730 | 5017/5083 |
|  |  | 4892/5292 | 5221/5621 | 4892/5292 | 5245/5645 |
|  |  | 3856/4209 | 4185/4528 | 3856/4209 | 4209/4762 |
|  |  | 4936/5292 | 5265/5621 | 4936/5292 | 5289/5645 |
|  |  | coding region of present invention | 330/9359 | 1/9033 | 342/9439 |
| Amino Acids | NS5b | 2675/2745 | 2675/2745 | 2676/2746 | 2698/2768 |
|  |  | 2645/2757 | 2645/2757 | 2646/2758 | 2668/2780 |
|  | NS3/4 | 1556/1764 | 1556/1764 | 1556/1764 | 1560/1768 |
|  |  | 1286/1403 | 1286/1403 | 1286/1403 | 1290/1407 |
|  |  | 1646/1764 | 1646/1764 | 1646/1764 | 1650/1768 |

Table 1: Comparison of the HCV nucleotide and amino acid numbering system used in the present invention (*) with the numbering used for other prototype isolates. For example, 8352/8564 indicates the region designated by the numbering from nucleotide 8352 to nucleotide 8564 as described by Kato et al. (1990). Since the numbering system of the present invention starts at the polyprotein initiation site, the 329 nucleotides of the 5' untranslated region described by Kato et al. (1990) have to be substracted, and the corresponding region is numbered from nucleotide 8023 ("8352–329") to 8235 ("8564–329").

The term "HCV type" corresponds to a group of HCV isolates of which the complete genome shows more than 74% homology at the nucleic acid levels or of which the NS5 region between nucleotide positions 7932 and 8271 shows more than 74% homology at the nucleic acid level, or of which the complete HCV polyprotein shows more than 78% homology at the amino acid level, or of which the NS5 region between amino acids at positions 2645 and 2757 shows more than 80% homology at the amino acid level, to polyproteins of the other isolates of the group, with said numbering beginning at the first ATG codon or first methionine of the long HCV polyprotein of the HCV-J isolate (Kato et al., 1990). Isolates belonging to different type of HCV exhibit homologies, over the complete genome, of less than 74% at the nucleic acid level and less than 78% at the amino acid level. Isolates belonging to the same type usually show homologies of about 92 to 95% at the nucleic acid level and 95 to 96% at the amino acid level when belonging to the same subtype, and those belonging to the same type but different subtypes preferably show homologies of about 79% at the nucleic acid level and 85–86% at the amino acid level.

More preferably the definition of HCV types is concluded from the classification of HCV isolates according to their nucleotide distances calculated as detailed below:

(1) based on phylogenetic analysis of nucleic acid sequences in the NS5b region between nucleotides 7935 and 8274 (Choo et al., 1991) or 8261 and 8600 (Kato et al., 1990) or 8342 and 8681 (Okamoto et al., 1991), isolates belonging to the same HCV type show nucleotide distances of less than 0.34, usually less than 0.33, and more usually of less than 0.32, and isolates belonging to the same subtype show nucleotide distances of less than 0.135, usually of less than 0.13, and more usually of less than 0.125, and consequently isolates belonging to the same type but different subtypes show nucleotide distances ranging from 0.135 to 0.34, usually ranging from 0.1384 to 0.2477, and more usually ranging from 0.15 to 0.32, and isolates belonging to different HCV types show nucleotide distances greater than 0.34, usually greater that 0.35, and more usually of greater than 0.358, more usually ranging from 0.1384 to 0.2977.

(2) based on phylogenetic analysis of nucleic acid sequences in the core/E1 region between nucleotides 378 and 957, isolates belonging to the same HCV type show nucleotide distances of less than 0.38, usually of less than 0.37, and more usually of less than 0.364, and isolates belonging to the same subtype show nucleotide distances of less than 0.17, usually of less than 0.16, and more usually of less than 0.15, more usually less than 0.135, more usually less than 0.134, and consequently isolates belonging to the same type but different subtypes show nucleotide distances ranging from 0.15 to 0.38, usually ranging from 0.16 to 0.37, and more usually ranging from 0.17 to 0.36, more usually ranging from 0.133 to 0.379, and isolate belonging to different HCV types show nucleotide distances greater than 0.34, 0.35, 0.36, usually more than 0.365, and more usually of greater than 0.37.

(3) based on phylogeneic analysis of nucleic acid sequences in the NS3/NS4 region between nucleotides 4664 and 5292 (Choo et al., 1991) or bet nucleotides 4993 and 5621 (Kato et al., 1990) or between nucleotides 5017 and 5645 (Okamoto et al., 1991), isolates belonging to the same HCV type show nucleotide distances of less than 0.35, usually of less than 0.34, and more usually of less than 0.33, and isolates belonging to the same subtype show nucleotide distances of less than 0.19, usually of less than 0.18, and more usually of less than 0.17, and consequently isolates belonging to the same type but different subtypes show nucleotide distances ranging from 0.17 to 0.35, usually ranging from 0.18 to 0.34, and more usually ranging from 0.19 to 0.33, and isolates belonging to different HCV types show nucleotide distances greater than 0.33, usually greater than 0.34, and more usually of greater than 0.35.

TABLE 2

Molecular evolutionary distances

| Region | Core/E1<br>579 bp | E1<br>384 bp | NS5B<br>340 bp | NS5B<br>222 bp |
|---|---|---|---|---|
| Isolates* | 0.0017–0.1347 | 0.0026–0.2031 | 0.0003–0.1151 | 0.000–0.1323 |
|  | (0.0750 ± 0.0245) | (0.0969 ± 0.0289) | (0.0637 ± 0.0229) | (0.0607 ± 0.0205) |
| Subtypes* | 0.1330–0.3794 | 0.1645–0.4869 | 0.1384–0.2977 | 0.117–0.3538 |
|  | (0.2786 ± 0.0363) | (0.3761 ± 0.0433) | (0.2219 ± 0.0341) | (0.2391 ± 0.0399) |
| Types* | 0.3479–0.6306 | 0.4309–0.9561 | 0.3581–0.6670 | 0.3457–0.7471 |
|  | (0.4703 ± 0.0525) | (0.6308 ± 0.0928) | (0.4994 ± 0.0495) | (0.5295 ± 0.0627) |

*Figures created by the PHYLIP program DNADIST are expressed as minimum to maximum (average ± standard deviation). Phylogenic distances for isolates belonging to the same subtype ('isolates'), to different subtypes of the same type ('subtypes'), and to different types ('types') are given.

In a comparative phylogenetic analysis of available sequences, ranges of molecular evolutionary distances for different regions of the genome were calculated, based on 19,781 pairwise comparisons by means of the DNA DIST program of the phylogeny inference package PHYLIP version 3.5C (Felsenstein, 1993). The results are shown in Table 2 and indicate that although the majority of distances obtained in each region fit with classification of a certain isolate, only the ranges obtained in the 340 bp NS5B-region are non-overlapping and therefore conclusive. However, as was performed in the present invention, it is preferable to obtain sequence information from at least 2 regions before final classification of a given isolate.

Designation of a number to the different types of HCV and HCV types nomenclature is based on chronological discovery of the different types. The numbering system used in the present invention might still fluctuate according to international conventions or guidelines. For example, "type 4" might be changed into "type 5" or "type 6".

The term "subtype" corresponds to a group of HCV isolates of which the complete polyprotein shows a homology of more than 90% both at the nucleic acid and amino acid levels, or of which the NS5 region between nucleotide positions 7932 and 8271 shows a homology of more than 90% at the nucleic acid level to the corresponding parts of the genomes of the other isolates of the same group, with said numbering beginning with the adenine residue of the initiation codon of the HCV polyprotein. Isolates belonging to the same type but different subtypes of HCV show homologies of more than 74% at the nucleic acid level and of more than 78% at the amino acid level.

The term "BR36 subgroup" refers to a group of type 3a HCV isolates (BR36, BR33, BR34) that are 95%, preferably 95.5%, most preferably 96% homologous to the sequences as represented in SEQ ID NO 1, 3, 5, 7, 9, 11 in the NS5b region from position 8023 to 8235.

It is to be understood that extremely variable regions like the E1, E2 and NS4 regions will exhibit lower homologies than the average homology of the complete genome of the polyprotein Using these criteria, HCV isolates can be classified into at least 6 types. Several subtypes can clearly be distinguished in types 1, 2, 3 and 4: 1a, 1b, 2a, 2b, 2c, 2d, 3a, 3b, 4a, 4 b, 4c, 4d, 4e, 4f, 4g, 4h, 4i and 4j based on homologies of the 5' UR and coding regions including the part of NS5 between positions 7932 and 8271. An overview of most of the reported isolates and their proposed classification according to the typing system of the present invention as well as other proposed classifications is presented in Table 3.

TABLE 3

HCV CLASSIFICATION

|  | OKA-MOTO | MORI | NAKAO | CHA | PROTOTYPE |
|---|---|---|---|---|---|
| 1a | I | I | Pt | GI | HCV-1, HCV-H, HC-J1 |
| 1b | II | II | KI | GII | HCV-J, HCV-BK, HCV-T, HC-JK1, HC-J4, HCV-CHINA |
| 1c |  |  |  |  | HC-G9 |
| 2a | III | III | K2a | GIII | HC-J6 |
| 2b | IV | IV | K2b | GIII | HC-J8 |
| 2c |  |  |  |  | S83, ARG6, ARG8, I10, T983 |
| 2d |  |  |  |  | NE92 |
| 3a | V | V | K3 | GIV | E-b1, Ta, BR36, BR33, HD10, NZL1 |
| 3b |  | VI | K3 | GIV | HCV-TR, Tb |
| 3c |  |  |  |  | BE98 |
| 4a |  |  |  |  | Z4, GB809-4 |
| 4b |  |  |  |  | Z1 |
| 4c |  |  |  |  | GB116, GB358, GB215, Z6, Z7 |
| 4d |  |  |  |  | DK13 |
| 4e |  |  |  |  | GB809-2, CAM600, CAM736 |
| 4f |  |  |  |  | CAM622, CAM627 |
| 4g |  |  |  |  | GB549 |
| 4h |  |  |  |  | GB438 |

TABLE 3-continued

HCV CLASSIFICATION

| OKAMOTO | MORI | NAKAO | CHA | PROTOTYPE |
|---|---|---|---|---|
| 4i | | | | CAR4/1205 |
| 4j | | | | CAR1/501 |
| 4k | | | | EG29 |
| 5a | | | GV | SA3, SA4, SA1, SA7, SA11, BE95 |
| 6a | | | | HK1, HK2, HK3, HK4 |

The term "complement" refers to a nucleotide sequence which is complementary to an indicated sequence and which is able to hybridize to the indicated sequences.

The composition of the invention can comprise many combinations. By way of example, die composition of the invention can comprise:

two (or more) nucleic acids from the same region or, two nucleic acids (or more), respectively from different regions, for the same isolate or for different isolates, or nucleic acids from the same regions and from at least two different regions (for the same isolate or for different isolate).

The present invention related more particularly to a polynucleic acid composition as defined above, wherein said polynucleic acid corresponds to a nucleotide sequence selected from any of the following HCV type 3 genomic sequences:

an HCV genomic sequence having a homology of at least 67%, preferably more than 69%, more preferably 71%, even more preferably more than 73%, or most preferably more than 76% to any of the sequences as represented in SEQ ID NO 13, 15, 17, 19, 21, 23, 25 or 27 (HD10, BR36 or BR33 sequences) in the region spanning positions 417 to 957 of the Core/E1 region as shown in FIG. 4;

an HCV genomic sequence having a homology of at least 65%, preferably more than 67%, preferably more than 69%, even preferably more than 70%, most preferably more than 74% to any of the sequences as represented in SEQ ID NO 13, 15, 17, 19, 21, 23, 25 or 27 (HD10, BR36 or BR33 sequences) in the region spacing positions 574 to 957 of the E1 region as shown in FIG. 4;

an HCV genomic sequence as having a homology of at least 79%, more preferably at least 81%, most preferably more than 83% or more to any of the sequences as represented in SEQ ID NO 147 (representing positions 1 to 346 of the Core region of HCV type 3c, sequence BE98) in the region spanning positions 1 to 378 of the Core region as shown in FIG. 3;

an HCV genomic sequence of HVC type 3a having a homology of at least 74%, more preferably at least 76, 7, most preferably more than 78% or more to any of the sequences as represented in SEQ ID NO 13, 15, 17, 19, 21, 23, 25 or 27 (HD10, BR36 or BR33 sequences) in the region spanning positions 417 to 957 in the Core/E1 region as shown in FIG. 4;

an HCV genomic sequence of HCV type 3a as having a homology of at least 74%, preferably more than 76%, most preferably 78% or more to any of the sequences as represented in SEQ ID NO 13, 15, 17, 19, 21, 23, 25 or 27 (HD10, BR36 or BR33 sequences) in the region spanning positions 574 to 957 in the E1 region as shown in FIG. 4;

an HCV genomic sequence as having a homology of more than 73.5%, preferably more than 74%, most preferably 75% homology to the sequence as represented in SEQ ID NO 29 (HCC153 sequence) in the region spanning positions 4664 to 4730 of the NS3 region as shown in FIG. 6;

an HCV genomic sequence having a homology of more than 70%, preferably more than 72%, most preferably more than 74% homology to any of the sequences as represented in SEQ ID NO 29, 31, 33, 35, 37 or 39 (HCC153, HD10, BR36 sequences) in the region spanning positions 4892 to 5292 in the NS3/NS4 region as shown in FIG. 6 or 10;

an HCV genomic sequence of the BR36 subgroup of HCV type 3a as having a homology of more than 95%, preferably 95, 5%, most preferably 96% homology to any of the sequences as represented in SEQ ID NO 5, 7, 1, 3, 9 or 11(BR34, BR33, BR36 sequences) in the region spanning positions 8023 to 8235 of the NS5 region as shown in FIG. 1;

an HCV genomic sequence of the BR36 subgroup of HCV type 3a as having a homology of more than 96%, preferably 96.5%, most preferably 97% homology to any of the sequences as represented in SEQ ID NO 5, 7, 1, 3, 9 or 11 (BR34, BR33, BR36 sequences) in the region spanning positions 8023 to 8192 of the NS5B region as shown in FIG. 1;

an HCV genomic sequence of HCV type 3c being characterized as having a homology of more than 79%, more preferably more than 81%, and most preferably more than 83% to the sequence as represented in SEQ ID NO 149 (BE98 sequence) in the region spanning positions 7932 to 8271 in the NS5B region as shown in FIG. 1.

Preferentially the above-mentioned genomic HCV sequences depict sequences from the coding regions of all the above-mentioned sequences.

According to the nucleotide distance classification system (with said nucleotide distances being calculated as explained above), said sequences of said composition are selected from:

an HCV genomic sequence being characterized as having a nucleotide distance of less than 0.44, preferably of less than 0.40, most preferably of less than 0.36 to any of the sequences as represented in SEQ ID NO 13, 15, 17, 19, 21, 23, 25 or 27 in the region spanning positions 417 to 957 of the Core/E1 region as shown in FIG. 4;

an HCV genomic sequence being characterized having a nucleotide distance of less than 0.53, preferably less than 0.49, most preferably of less than 0.45 to any of the sequence as represented in SEQ ID NO 19, 21, 23, 25 or 27 in the region spanning positions 574 to 957 of the E1 region as shown in FIG. 4;

an HCV genomic sequent charaterized having a nucleotide distance of less than 0.15, preferably less than 0.13, and most preferably less than 0.11 to any of the sequences as represented in SEQ ID NO 147 in the region spanning positions 1 to 378 of the Core region as shown in FIG. 3;

an HCV genomic sequence of HVC type 3a being characterized as having a nucleotide distance of less than 0.3, preferably less than 0.26, most preferably of less than 0.22 to any of the sequences as represented in SEQ ID NO 13, 15, 17, 19, 21, 23, 25 or 27 in the region spanning positions 417 to 957 in the Core/E1 region as shown in FIG. 4;

an HCV genomic sequence of HCV type 3a being characterized as having a nucleotide distance of less than 0.35, preferably less than 0.31, most preferably of less than 0.27 to any of the sequences as represented in SEQ ID NO 13, 15, 17, 19, 21, 23, 25 or 27 in the region spanning positions 574 to 957 in the E1 region as shown in FIG. 4;

an HCV genomic sequence of the BR36 subgroup of HCV type 3a being characterized as having a nucleotide sequence of less than 0.0423, preferably less than 0.042, preferably less than 0.0362 to any of the sequences as represented in SEQ ID NO 5, 7, 1, 3, 9 or 11 in the region spanning positions 8023 to 8235 of the NS5 region as shown in FIG. 1;

an HCV genomic sequence of HCV Ape 3c being characterized as having a nucleotide distance of less than 0.255, preferably of less than 0.25, more preferably of less than 0.21, most preferably of less than 0.17 to the sequence as represented in SEQ ID NO 149 in the region spanning positions 7932 to 8271 in the NS5B region as shown in FIG. 1.

In the present application, the E1 sequences encoding the antigenic ectodomain of the E1 protein, which does not overlap the carboxyterminal signal-anchor sequences of E1 disclosed by Cha et al. (1992; WO 92/19743), in addition to the NS4 epitope region, and a part of the NS5 region are disclosed for 4 different isolates: BR33, BR34, BR36, HCC153 and HD10, all belonging to type 3a (SEQ ID NO 1, 3, 5, 7, 9, 11, 13, 15, 17, 19, 21, 23, 25, 27, 29, 31, 35, 37 or 39).

Also within the present invention are new subtype 3c sequences (SEQ ID NO 147, 149 of the isolate BE98 in the Core and NS5 regions (see FIGS. 3 and 1).

Finally the present invention also relates to a new subtype 3a sequence as represented in SEQ ID NO 217 (see FIG. 1)

Also included within the present invention are sequence variants of the polynucleic acids as selected from any of the nucleotide sequences as given in any of the above mentioned SEQ ID numbers, with said sequence variants containing either deletions and/or insertions of one or more nucleotides, mainly at the extremities of oligonucleotide (either 3' or 5'), or substitutions of some non-essential nucleotides by others (including modified nucleotides an/or inosine), for example, a type 1 or 2 sequence might be modified into a type 3 sequence by replacing some nucleotides of the type 1 or 2 sequence with type-specific nucleotides of type 3 as shown in FIG. 1 (NS5 region), FIG. 3 (Core region), FIG. 4 (Core/E1 region), FIGS. 6 and 10 (NS31/NS4 region).

According to another embodiment, the present invention relates to a polynucleic acid composition as defined above, wherein said polynucleic acids correspond to a nucleotide sequence selected from any of the following HCV type 5 genomic sequences:

an HCV genomic sequence as having a homology of more than 85%, preferably more than 86%, most preferably more than 87% homology to any of the sequences as represented in SEQ ID NO 41, 43, 45, 47, 49, 51, 53 (PC sequences) or 151 (BE95 sequence) in the region spanning positions 1 to 573 of the Core region as shown in FIGS. 9 and 3;

an HCV genomic sequence as having a homology of more than 61%, preferably more than 63%, more preferably more than 65% homology, even more preferably more than 66% homology and most preferably more than 67% homology (f.i. 69 and 71%) to any of the sequences as represented in SEQ ID NO 41, 43, 45, 47, 49, 51, 53 (PC sequences), 153 or 155 (BE95, BE100 sequences) in the region spanning positions 574 to 957 of the E1 region as shown in FIG. 4;

an HCV genomic sequence having a homology of more than 76.5%, preferably of more than 77%, most preferably of more than 78% homology with any of the sequences as represented in SEQ ID NO 55, 57, 197 or 199 (PC sequences) in the region spanning positions 3856 to 4209 of the NS3 region as shown in FIG. 6 or 10;

an HCV genomic sequence having a homology of more than 68%, preferably of more the 70%, most preferably of more than 72% homology with the sequence as represented in SEQ ID NO 157 (BFE95 sequence) in the region spanning positions 980 to 1179 of the E1/E2 region as shown in FIG. 13;

an HCV genomic sequence having a homology of more than 57%, preferably more than 59%, most preferably more than 61% homology to any of the sequences as represented in SEQ ID NO 59 or 61 (PC sequences) in the region s g positions 4936 to 5296 of the NS4 region as shown in FIGS. 6 or 10;

an HCV genomic sequence as having a homology of more than 93%, preferably more than 93.5%, most preferably more than 947% homology to any of the sequences as represented in SEQ ID NO 159 or 161 (BE95 or BE96 sequences) in the region spanning positions 7932 to 8271 of the NS5B region as shown in FIG. 1.

Preferentially the above-mentioned genomic HCV sequences depict sequences from die coding regions of all the above-mentioned sequences.

According to the nucleotide distance classification system (with said nucleotide distances being calculated as explained above), said sequence of said composition are selected from:

a nucleotide distance of less than 0.53, preferably less than 0.51, more preferably Less than 0.49 for the E1 region to the type 5 sequences depicted above;

a nucleotide distance of less than 0.3, preferably less than 0.28, more preferably of less tan 0.26 for the Core region to the type 5 sequences depicted above;

a nucleotide distance of less than 0.072, preferably less than 0.071, more preferably less than 0.070 for the NS5B region to the type 5 sequences as depicted above.

Isolates with similar sequences in the 5'UR to a group of isolates including SA1, SA3, and SA7 described in the 5'UR by Bukh et al. (1992), have been reported and described in the 5'UR and NS5 region as group V by Cha et al. (1992; WO 92/19743). This group of isolates belongs to type 5a as described in the present invention (SEQ ID NO 41, 43, 45, 47, 49, 51, 53, 55, 57, 59, 61, 151, 153, 155, 157, 159, 161, 197 and 199).

Also included within the present invention are sequence variants of the polynucleic acids as selected from any of the nucleotide sequences as given in any of the above given SEQ ID numbers with said sequence variants containing either deletion and/or insertions of one or more nucleotides, mainly at the extremities of oligonucleotide (either 3' or 5'), or substitutions of some non-essential nucleotides (i.e. nucleotides not essential to discriminate between different genotypes of HCV) by others (including modified nucleotides an/or inosine), for example, a type 1 or 2 sequence might be modified into a type 5 sequence by replacing some nucleotides of the type 1 or 2 sequence with type-specific nucleotides of type 5 as shown in FIG. 3 (Core region), FIG. 4 (Core/E1 region). FIG. 10 (NS3/NS4 region), FIG. 14 (E1/E2 region).

Another group of isolates including BU74 and BU79 having similar sequences in the 5'UR to isolates including Z6 and Z7 as described in the 5'UR by Bukh et al. (1992), have been described in the 5'UR and classified as a new type 4 by the inventors of this application (Stuyver et al., 1993). Coding sequences, including core, E1 and N55 sequences of several new Gabonese isolates belonging to this group, are disclosed in the present invention (SEQ ID NO 106, 108, 110, 112, 114, 116, 118, 120 and 122).

According to yet another embodiment, the present invention Tess to a composition as defined above, wherein said polynucleic acids correspond to a nucleotide sequence selected from any of the following HCV type 4 genomic sequences:

an HCV genomic sequence having a homology of more than 66%, preferably more than 68%, most preferably more than 70% homology in the E1 region spanning positions 574 to 957 to any of the sequences as represented in SEQ ID) NO 118, 120 or 122 (GB358, GB549, GB809 sequences) as shown in FIG. 4:

- an HCV genomic sequence having a homology of more than 71%, preferably more than 72%, most preferably more than 74% homology to any of the sequences as represented in SEQ ID NO 118, 120 or 122 (GB358, GB549, GB809 sequences) in the region spanning positions 379 to 957 of the E1 region as shown in FIG. 4;
- an HCV genomic sequence having a homology of more than 92%, preferably more than 93%, most preferably more than 94% homology to any of the sequences as represented in SEQ ID NO 163 or 165 (GB809, CAM600 sequences) in the region spanning positions to 378 of the Core/E1 region as shown in FIG. 4;
- an HCV genomic sequence (subtype 4c) having a homology of more than 85%, preferably more than 86%, more preferably more than 86.5% homology, most preferably more than 87, more the 88 or more than 89% homology to any of the sequences as represented in SEQ ID NO 183, 185 or 187 (GB116, GB215, GB809 sequences) in the region spanning positions 379 to 957 of the E1 region as shown in FIG. 4;
- an HCV genomic sequence (subtype 4a) having a homology of more than 81%, preferably more than 83%, most preferably more than 85% homology to the sequence as represented in SEQ ID NO 189 (GB908 sequence) in the region spanning positions 379 to 957 of the E1 region as shown in FIG. 4;
- an HCV genomic sequence (subtype 4e) having a homology of more than 85%, preferably more than 87%, most preferably more than 89% homology w any of the sequences as represented in SEQ ID NO 167 or 169 (CAM600, GB908 sequences) in the region spanning positions 379 to 957 of the E1 region as shown in FIG. 4;
- an HCV genomic sequence (subtype 4f) having a homology of more than 79%, preferably more than 81%, most preferably more than 83% homology lo any of the sequences as represented in SEQ ID NO 171 or 173 (CAMG22, CAMG27 sequences) in the region spanning positions 379 to 957 of the E1 region as shown in FIG. 4;
- an HCV genomic sequence (subtype 4g) having a homology of more than 84%, preferably more than 86%, most preferably more than 88% homology to the sequence as represented in SEQ ID NO 175 (GB549 sequence) in the region spanning positions 379 to 957 of the E1 region as shown in FIG. 4;
- an HCV genomic sequence (subtype 4h) having a homology of more than 83%, preferably more than 85%, most preferably more than 87% homology to the sequence as represented in SEQ ID NO 177 (GB438 sequence) in the region spanning positions 379 to 957 of the E1 region as shown in FIG. 4;
- an HCV genomic sequence (subtype 4i) as having a homology of more than 76%, preferably more than 78%, most preferably more than 80% homology to the sequence as represented in SEQ ID NO 179 (CAR4/1205 sequence) in the region spanning positions 379 to 957 of the E1 region as shown in FIG. 4;
- an HCV genomic sequence (subtype 4j?) having a homology of more than 84% preferably more than 86%, most preferably more than 88% homology to the sequence as represented in SEQ ID NO 181 (CAR4/901 sequence) in the region spanning positions 379 to 957 of the E1 region as shown in FIG. 4;
- an HCV genomic sequence as having a homology of more than 73%, preferably more than 75%, most preferably more than 77% homology to any of the sequences as represented in SEQ ID NO 106, 108, 110, 112, 114, or 116 (GB48, GB116, GB215, GB358, GB549, GB809 sequences) in the region spanning positions 7932 to 8271 of the NS5 region as shown in FIG. 1:
- an HCV genomic sequence (subtype 4c) having a homology of more than 88%, preferably more than 89%, most preferably more than 90% homology to any of the sequences as represented in SEQ ID NO 106, 108, 110, or 112 (GB48, GB116, GB215, GB358 sequences) in the region spanning positions 7932 to 8271 of the NS5 region as shown in FIG. 1;
- an HCV genomic sequence (subtype 4e) having a homology of more than 88%, preferably more than 89%, most preferably more than 90% homology to any of the sequences as represented in SEQ ID NO 116 or 201 (GB809 or CAM 600 sequences) in the region spanning positions 7932 to 8271 of the NS5 region as shown in FIG. 1:
- an HCV genomic sequence (subtype 4f) having a homology of more than 87%, preferably more than 89%, most preferably more than 90% homology to the sequence as represented in SEQ ID NO 203 (CAMG22 sequence) in the region Spanning positions 7932 to 8271 of the NS5 region as shown in FIG. 1;
- an HCV genomic sequence (subtype 4g) as having a homology of more than 85%, preferably more than 87%, most preferably more than 89% homology to the sequence as represented in SEQ ID NO 114 (GB549 sequence) in the region spanning positions 7932 to 8271 of the NS5 region as shown in FIG. 1;
- an HCV genomic sequence (subtype 4h) as having a homology of more than 86%, preferably more than 87%, more preferably more than 88% homology, more preferably more than 89% homology to the sequence as represented in SEQ ID NO 207 (GB437 sequence) in the region spanning positions 7932 to 8271 of the NS5 region as shown in FIG. 1:

an HCV genomic sequence (subtype 4i) having a homology of more than 84%, preferably more than 86%, most preferably more than 88% homology to the sequence as represented in SEQ ID NO 209 (CAR4/1205 sequence) in the region spanning positions 7932 to 8271 of the NS5 region as shown in FIG. 1;

an HCV genomic sequence (subtype 4j) having a homology of more than 81%, preferably more than 83%, most preferably more than 85% homology to the sequence as represented in SEQ ID NO 211 (CAR1/501 sequence) in the region spanning positions 7932 to 8271 of the NS5 region as shown in FIG. 1.

Preferentially the above-mentioned genomic HCV sequences depict sequences from the coding regions of all the above-mentioned sequences.

According to the nucleotide distance classification system (with said nucleotide distances being calculated as explained above), said sequences of said composition are selected from:

an HCV genomic sequence (type 4) being characterized as having a nucleotide distance of less than 0.52, 0.50, 0.4880, 0.46, 0.44, 0.43 or most preferably less than 0.42 in the region spanning positions 574 to 957 to any of the sequences as represented in SEQ ID NO 118, 120 or 122 in the region spanning positions 1 to 957 of the Core/E1 region as shown in FIG. 4;

an HCV genomic sequence (type 4) being characterized as having a nucleotide distance of less than 0.39, 0.36 0.34 0.32 or most preferably less than 0.31 to any of the sequences as represented in SEQ ID NO 118, 120 or 122 in the region spanning positions 379 to 957 of the E1 region as shown in FIG. 4;

an HCV genomic sequence (subtype 4c) being characterized as having a nucleotide distance of less than 0.27, 0.26, 0.24, 0.22, 0.20, 0.18, 0.17, 0.162, 0.16 or most preferably less than 0.15 to any of the sequences as represented in SEQ ID NO 183, 185 or 187 in the region spanning positions 379 to 957 of the E1 region as shown in FIG. 4;

an HCV genomic sequence (subtype 4a) being characterized as having a nucleotide distance of less than 0.30, 0.28, 0.26, 0.24, 0.22, 0.21 or most preferably of less than 0.205 to the sequence as represented in SEQ ID NO 189 in the region spanning positions 379 to 957 of the E1 region as shown in FIG. 4;

an HCV genomic sequence (subtype 4e) being characterized as having a nucleotide distance of less than 0.26, 0.25, 0.23, 0.21, 0.19, 0.17, 0.165, most preferably less than 0.16 to any of the sequences as represent in SEQ ID NO 167 or 169 in the region spanning positions 379 to 957 of the E1 region as shown in FIG. 4;

an HCV genomic sequence (sub type 4f) being characterized as having a nucleotide distance of less than 0.26, 0.24, 0.22, 0.20, 0.18, 0.16, 0.15 or most preferably less than 0.14 to any of the sequences as represented in SEQ ID NO 171 or 173 in the region spanning positions 379 to 957 of the E1 region as shown in FIG. 4;

an HCV genomic sequence (subtype 4g) being characterized as having a nucleotide distance of less than 0.20, 0.19, 0.18, 0.17 or most preferably of less than 0.16 to the sequence as represented in SEQ ID NO 175 in the region spanning positions 379 to 957 of the E1 region as shown in FIG. 4;

an HCV genomic sequence (subtype 4h) being characterized as having a nucleotide distance of less than 0.20, 0.19, 0.18, 0.17 and most preferably of less than 0.16 to the sequence as represented in SEQ ID NO 177 in the region spanning positions 379 to 957 of the E1 region as shown in FIG. 4;

an HCV genomic sequence (subtype 4i) being characterized as having a nucleotide distance of less than 0.27, 0.25, 0.23, 0.21 and preferably less than 0.16 to the sequence as represented in SEQ ID NO 179 in the region spanning positions 379 to 957 of the E1 region as shown in FIG. 4;

an HCV genomic sequence (subtype 4j?) being characterized as having a nucleotide distance of less than 0.19, 0.18, 0.17, 0.165 and most preferably of less than 0.6 to the sequence as represented in SEQ ID NO 181 in the region spanning positions 379 to 957 of the E1 region as shown in FIG. 4;

an HCV genomic sequence (type 4) being characterized as having a nucleotide distance of less tan 0.35, 0.34, 0.32 and most preferably of less than 0.30 to any of the sequences as represented in SEQ ID NO 106, 108, 110, 112, 114, or 116 in the region spanning positions 7932 to 8271 of the NS5 region as shown in FIG. 1;

an HCV genomic sequence (subtype 4c) being characterized as having a nucleotide distance of less than 0.18, 0.16, 0.14, 0.135, 0.13, 0.1275 or most preferably less than 0.125 to any of the sequences as represented in SEQ ID NO 106, 108, 110, or 112 in the region spanning positions 7932 to 8271 of the NS5 region as shown in FIG. 1;

an HCV genomic sequence (subtype 4e) being characterized as having a nucleotide distance of less than 0.15, 0.14, 0.135, 0.13 and most preferably of less than 0.125 to any of the sequences as represented in SEQ ID NO 116 or 201 in the region spuming positions 7932 to 8271 of the NS5 region as shown in FIG. 1;

an HCV genomic sequence (subtype 4f) being characterized as having a nucleotide distance of less than 0.15, 0.14, 0.135, 0.13 or most preferably less than 0.125 to the sequence as represented in SEQ ID NO 203 in the region spanning positions 7932 to 8271 of the NS5 region as shown in FIG. 1;

an HCV genomic sequence (subtype 4g) being characterized as having a nucleotide distance of less than 0.17, 0.16, 0.15, 0.14, 0.13 or most preferably less than 0.5 to the sequence as represented in SEQ ID NO 114 in the region spanking positions 7932 to 8271 of the NS5 region as shown in FIG. 1;

an HCV genomic sequence (subtype 4h) being characterized as having a nucleotide distance of less than 0.155, 0.15, 0.145, 0.14, 0.135, 0.13 or most preferably less than 0.125 to the sequence as represented in SEQ ID NO 207 in the region spanning positions 7932 to 8271 of the NS5 region as shown in FIG. 1;

an HCV genomic sequence (subtype 4i) being characterized as having a nucleotide distance of less than 0.17, 0.16, 0.15, 0.14, 0.13 or most preferably of less than 0.125 to the sequence as represented in SEQ ID NO 209 in the region spanning positions 7932 to 8271 of the NS5 region as shown in FIG. 1;

an HCV genomic sequence (subtype 4j) being characterized as having a nucleotide distance of less than 0.21, 0.20, 0.19, 0.18, 0.17, 0.16, 0.15, 0.14, 0.13 and most preferably of less than 0.125 to the sequence as represented in SEQ ID NO 211 in the region spanning positions 7932 to 8271 of the NS5 region as shown i FIG. 1.

Also included within the present invention are sequence variants of the polynucleic acids as selected from any of the nucleotide sequences as given in any of the above given SEQ ID numbers with said sequence variants containing either deletion and/or insertions of one or more nucleotides, mainly at the extremities of oligonucleotide (either 3' or 5'), or substitutions of some non essay nucleotides (i.e. nucleotides not essential to dilute between different genotypes of HCV) by others (including modified nucleotides an/or inosine), for example, a type 1 or 2 sequence might be modified into a type 4 sequence by replacing some nucleotides of the type 1 or 2 sequence with type-specific nucleotides of type 4 as shown in FIG. 3 (Core region), FIG. 4 (Core/E1 region), FIG. 10 (NS3/NS4 region), FIG. 14 (E1/E2 region).

The present invention also relates to a sequence as represented in SEQ ID NO 193 (GB724 sequence).

After aligning NS5 or E1 sequences of G348, GB, 116, GB215, GB358, GB549 and GB809, these isolates clearly segregated into 3 subtypes within type 4 : GB48, GB116, GB215 and GB358 belong to the subtype designated 4c, GB549 to subtype 4g and GB809 to subtype 4e. In NS5, GB809 (subtype 4e) showed a higher nucleic acids homology to subtype 4c isolates (85.6–86.8%) than to GB549 (subtype 4g, 79.7%), while GB549 showed similar homologies to both other subtypes (78.8 to 80% to subtype 4c and 79.7% to subtype 4e). In E1, subtype 4c showed equal nucleic acid homologies of 75.2% to subtypes 4g and 4e while 4g and 4e were 78.4% homologous. At the amino acid level however, subtype 4e showed a normal homology to subtype 4c (80.2%), while subtype 4g was more homologous to 4c (83.3%) and 4e (84.1%).

According to yet another embodiment, the present invention relates to a composition as defined above, wherein said polynucleic acids correspond to a nucleotide sequence selected from any of the following HCV type 2d genomic sequences:

an HCV genomic sequence as having a homology of more than 78%, preferably more than 80%, most preferably more than 82% homology to the sequence as represented in SEQ ID NO (NE92) 143 in the region spanning positions 379 to 957 of the Core/E1 region as shown in FIG. 4;

an HCV genomic sequence as having a homology of more than 74%, preferably more than 76%, most preferably more than 78% homology to the sequence as represented in SEQ ID NO 143 (NE92) in the region spanning positions 574 to 957 as shown in FIG. 4;

an HCV genomic sequence as having a homology of more than 87%, preferably more than 89%, most preferably more than 91% homology to the sequence as represented in SEQ ID NO 145 (NE92) in the region spanning positions 7932 to 8271 of the NS5B region as shown in FIG. 1.

Preferentially the above-mentioned genomic HCV sequences depict sequences from the coding regions of all the above-mentioned sequences.

According to the nucleotide distance classification system (with said nucleotide distances being calculated as explained above), said sequences of said composition are selected from:

a nucleotide distance of less than 0.32, preferably less than 0.31, more preferably less than 0.30 for the E1 region (574 to 957) to any of the above specified sequences;

a nucleotide distance of less than 0.08, preferably less than 0.07, more preferably less than 0.06 for the Core region (1 to 378) to any of the above given sequences a nucleotide distance of less than 0.15, preferentially less than 0.13, more preferentially less than 0.12 for the NS5B region to any of the above-specified sequences.

Polynucleic acid sequences according to the present invention which are homologous to the sequences as represented by a SEQ ID NO can be characterized and isolated according to any of the techniques known in the art, such as amplification by means of type or subtype specific primers, hybridization with type or subtype specific probes under more or less stringent conditions, serological screening methods (see examples 4 and 11) or via the LiPA typing system.

Polynucleic acid sequences of the genomes indicated above from regions not yet depicted in the present examples, figures and sequence listing can be obtained by any of the techniques known in the art, such as amplification techniques using suitable primers from the type or subtype specific sequences of the present invention.

The present invention relates also to a composition as defined above, wherein said polynucleic acid is liable to act as a primer for amplifying the nucleic acid of a certain isolate belonging to the genotype from which the primer is derived.

An example of a primer according to this embodiment of the invention is HCPr 152 as shown in table 7 (SEQ ID NO 79).

The term "primer" refers to a single stranded DNA oligonucleotide sequence capable of acting as a point of initiation for synthesis of a primer extension product which is complementary to the nucleic acid sand to be copied. The length and the sequence of the primer must be such that they allow to prime the synthesis of the extension products. Preferably the primer is about 5–50 nucleotides. Specific length and sequence will depend on the complexity of the required DNA or RNA targets, as well as on the conditions of or use such as temperature and ionic strength.

The fact than amplification primers do not have to match exactly with corresponding template sequence to warrant proper amplification is amply documented in the liters (Kwok et al., 1990).

The amplification method used can be either polymerase chain reaction (PCR, Saiki et al., 1988), ligase chain reaction (LCR; Lidgren et al., 1988; Wu & Wace, 1989; Barany, 1991), nucleic acid sequence-based amplification (NASBA; Guatelli et al., 1990; Compton, 1991), transcription-based amplification system CTAS; Kwoh et al. 1989), strand displacement amplification (SDA; Duck, 1990; Walker et al., 1992) or amplification by means of Qβ replicase (Lizardi et al., 1988; Lomeli et al., 1989) or any other suitable method to amplify nucleic acid molecules using primer extension. During amplification, the amplified products can be conveniently labelled either using labelled primers or by incorporating labelled nucleotides. Labels may be isotopic ($^{35}$P, $^{35}$S, etc.) or non-isotopic (biotin, digoxigenin etc.). The amplification reaction is repeated between 20 and 80 times, advantageously between 30 and 50 times.

The present invention also relates to a composition as defined above, wherein said polynucleic acid is able to act as a hybridization probe for specific detection and/or classification into types of a nucleic acid containing said nucleotide sequence, with said oligonucleotide being possibly labelled or attached to a solid substrate.

The term "probe" refers to single stranded sequence-specific oligonucleotide which have a sequence which is complementary to the target sequence of the HCV genotype (s) to be detected.

Preferably, these probes are about 5 to 50 nucleotides long, more preferably from about 10 to 25 nucleotides.

The term "solid support" can refer to any substrate to which an oligonucleotide probe can be coupled, provided that it retains its hybridization characteristics and provided that the background level of hybridization remains low. Usually the solid subtract will be a microtiter plate, a membrane (e.g. nylon or nitrocellulose) or a microsphere (bead). Prior to application to the membrane or fixation it may be convenient to modify the nucleic acid probe in order to facilitate fixation or improve the hybridization efficiency. Such modifications may encompass homopolymer tailing, coupling with different reactive groups such as aliphatic group, $NH_2$ groups, SH groups, carboxylic groups, or coupling with biotin or haptens.

The present invention also relates to the use of a composition as defined above for detecting the presence of one or more HCV genotypes, more particularly for detecting the presence of a nucleic acid of any of the HCV genotypes having a nucleotide sequence as defined above, present in a biologic sample liable to contain them, comprising at least the following steps:

(i) possibly extracting sample nucleic acid, (ii) possibly amplifying the nucleic acid with at least one of the primers as defined above or any other HCV subtype 2d, HCV type 3, HCV type 4, HCV type 5 or universal HCV primer, (iii) hybrizing the nucleic acids of the biological sample, possibly under denatured conditions, and with said nucleic acids being possibly labelled during or after amplification, at appropriate conditions with one or more probes as defined above, with said probes being preferably attached to a solid substrate, (iv) washing at appropriate conditions, (v) detecting the hybrids formed, (vi) inferring the presence of one or more HCV genotypes present from the observed hybridization pattern, Preferably, this technique could be performed in the Core or NS5B region. The term "nucleic acid" can also be referred to as analyze strand and corresponds to a single- or double-stranded nucleic acid molecule. This analyze strand is preferentially positive- or negative stranded RNA, cDNA or amplified cDNA.

The term "biological sample" refers to any biological sample (tissue or fluid) containing HCV nucleic acid sequences and refers more particularly to blood serum or plasma samples.

The term "HCV subtype 2d primer" refers to a primer which specifically amplifies HCV subtype 2d sequences present in a sample (see Examples section and figures).

The term "HCV type 3 primer" refers to a primer which specifically amplifies HCV type 3 sequences present in a sample (see Examples section and figures).

The term "HCV type 4 primer" refers to a primer which specifically amplifies HCV type 4 genomes present in a sample.

The term "universal HCV primer" refers to oligonucleotide sequences complementary to any of the conserved regions of the HCV genome.

The term "HCV type 5 primer" refers to a primer which specifically amplifies HCV type 5 genomes present in a sample. The term "universal HCV primer" refers to oligonucleotide sequence complementary to any of the conserved regions of the HCV genome.

The expression "appropriate" hybridization and washing condition s are to be as stringent and are generally known in the art (e.g. Maniatis et al., Molecular Cloning: A Laboratory Manual, New York, Cold Spring Harbor Laboratory, 1982).

However, according to the hybridization solution (SSC, SSPE, etc.), these probes should be hybridized at their appropriate temperature in order to an sufficient specificity.

The term "labelled" refers to the use of labelled nucleic acids. This may include the use of labelled nucleotides incorporated during the polymerase step of the amplification such as illustrate by Saiki et al. (1988) or Bej et al. (1990) or labelled primers, or by any other method known to the person skilled in the art.

The process of the invention comprises the steps of contacting any of the probes as defined above, with one of the following elements:

either a biological sample in which the nucleic acids are made available for hybridiztion, or the purified nucleic acids contained in the biological sample or a single copy derived from the purified nucleic acids, or an amplified copy derived from the purified nucleic acids, with said elements or with said probes being attached to a solid subsume.

The expression "inferring the presence of one or more HCV genotypes present from the observed hybridization pattern" refers to the identification of the presence of HCV genomes in the sample by analyzing the pattern of binding of a panel of oligonucleotide probes. Single probes may provide useful information concerning the presence or absence of HCV genomes in a sample. On the other hand, the variation of the HCV genomes is dispersed nature , so rarely is any one probe able to identify uniquely a specific HCV genome. Rather, the identity of an HCV genotype may be inferred from the pattern of binding of a panel of oligonucleotide probes, which are specific for (different) segments of the different HCV genomes. Depending on the choice of these oligonucleotide probes, each known HCV genotype will correspond to a specific hybridization pattern upon use of a specific combination of probes. Each HCV genotype will also be able to be discriminated from any other HCV genotype amplified with the same primers depending on the choice of the oligonucleotide probes. Comparison of the generated pattern of positively hybridizing probes for a sample containing one or more unkown HCV sequences to a scheme of expected hybridization patterns, allows one to clearly infer the HCV genotypes present in said sample.

The present invention thus relates to a method as defined above, wherein one or more hybridization probes are selected from any of SEQ ID NO 1, 3, 5, 7, 9, 11, 13, 15, 17, 19, 21, 23, 25, 27, 29, 31, 33, 35, 37, 39, 41, 43, 45, 47, 49, 51, 53, 55, 57, 59 or 61, 106, 108, 110, 112, 114, 116, 118, 120, 122, 143, 145, 147, 149, 151, 153, 155, 157, 159, 161, 163, 165, 167, 169, 171, 173, 175, 177, 179, 181, 183, 185, 187, 198, 191, 193, 195, 197, 199, 201, 203, 205, 207, 209, 211, 213, 215, 217, 222, 269 or sequence variants thereof, with said sequence variants containing deletions and/or insertions of one or more nucleotides, mainly at their extremities (either 3' or 5'), or substitutions of some non-essential nucleotides (i.e. nucleotides not essential to discriminate between genotypes) by others (including modified nucleotides or inosine), or with said variants consisting of the complement of any of the above-mentioned oligonucleotide probes, or with said variants consisting of ribonucleotides instead of deoxyribonucleotides, all provided that said variant probes can be caused to hybridize with the same specificity as the oligonucleotide probes from which they are derived.

In order to distinguish the amplified HCV genomes from each other, the target polynucleic acids are hybridized to a set of sequence-specific DNA probes targetting HCV genotypic regions located in the HCV polynucleic acids.

Most of these probes target the most type-specific regions of HCV genotypes, but some can be caused to hybridize to more than one HCV genotype.

According to the hybridization solution (SSC, SSPE, etc.), these probes should be stringently hybridized at their appropriate temperature in order to attain sufficient specificity. However, by slightly modifying the DNA probes, either by adding or deleting one or a few nucleotide at their extremities (either 3' or 5'), or substituting some non essential nucleotides (i.e. nucleotides not essential to discriminate between types) by others (including modified nucleotides or inosine) these probes or variants thereof can be caused to hybridize specifically at the same hybridization conditions (i.e. the same temperature and the same hybridization solution). Also changing the amount (concentration) of probe used may be beneficial to obtain more specific hybridization results. It should be noted in this context, that probes of the same length, regardless of their GC content, will hybridize specifically at approximately the same temperature in TMACl solutions (Jacobs et al., 1988).

Suitable assay methods for purposes of the present invention to detect hybrids formed between the oligonucleotide probes and the nucleic acid sequences in a sample may comprise any of the assay formats known in the art, such as the conventional dot-blot format, sandwich hybridizaton or reverse hybridization. For example, the detection can be accomplished using a dot blot format the unlabelled amplified sample being bound to a membrane, the membrane being incorporated with at least one labelled probe meter suitable hybridization and wash conditions, and the presence of bound probe being monitored.

An alternative and preferred method is a "reverse" dot-blot format, in which the amplified sequence contains a label. In this format, the unlabelled oligonucleotide probes are bound to a solid support and exposed to the labelled sample under appropriate stringent hybridization and subsequent washing conditions. It is to be understood that also any other assay method which relies on the formation of a hybrid between the nucleic acids of the sample and the oligonucleotide probes according to the present invention may be used.

According to an advantageous embodiment, the process of detecting one or more HCV genotypes contained in a biological sample comprises the steps of contacting amplified HCV nucleic acid copies derived from the biological sample, with oligonucleotide probes which have been immobilized as parallel lines on a solid support.

According to this advantageous method, the probes are immobilized in a Line Probe Assay (LiPA) format. This is a reverse hybridization format (Saiki et al., 1989) using membrane strips onto which several oligonucleotide probes (including negative or positive control oligonucleotide) can be conveniently applied as parallel lines.

The invention thus also relates to a solid support, preferably a membrane strip, carrying on its surface, one or more probes as defined above, coupled to the support in the form of parallel lines.

The LiPA is a very rapid and user-friendly hybridization test. Results can be read 4 h. after the start of the amplification. After amplification during which usually a non-isotopic label is incorporated in the amplified product, and alkaline denaturation, the amplified product is contacted with the probes on the membrane and the hybridization is carried out for about 1 to 1.5 h hybridized polynucleic acid is detected. From the hybridization pattern generated, the HCV type can be deduced either visually, but preferably using dedicated software. The LiPA format is completely compatible with commercially available scanning devices, thus rendering automatic interpretation of the results very reliable. All those advantages make the LiPA format liable for the use of HCV detection in a routine setting. The LiPA format should be particularly advantageous for detecting the presence of different HCV genotypes.

The present invention also relates to a method for detecting and identifying novel HCV genotypes, different from the known HCV genomes, comprising the step of:

determining to which HCV genotype the nucleotide present in a biological sample belong, according to the process as defied above, in the case of observing a sample which does not generate a hybridization pattern compatible with those defined in Table 3, sequencing the portion of the HCV genome sequence corresponding to the any hybridizing probe of the new HCV genotype to be determined, The present invention also relates to the use of a composition as defined above, for detecting one or more genotypes of HCV present in a biological sample liable to contain them, comprising the steps of:

(i) possibly extracting sample nucleic acid, (ii) amplifying the nucleic acid with at least one of the primers as defined above, (iii) sequencing the amplified products (iv) inferring the HCV genotypes present from the determine sequences by comparison to all known HCV sequences.

The present invention also relates to a composition consisting of or comprising at least one peptide or polypeptide comprising a contiguous sequence of at least 5 amino acids corresponding to a contiguous amino acid sequence encoded by at least one of the HCV genomic sequences as defined above, having at least one amino acid differing from the corresponding region of known HCV (type 1 and/or type 2 and/or type 3) polyprotein sequences as shown in Table 3, or muteins thereof.

It is to be noted that, at the level of the amino acid sequence, an amino acid difference (with respect to known HCV amino acid sequences) is necessary, which means that the polypeptides of the invention correspond to polynucleic acids having a nucleotide difference (with known HCV polynucleic acid sequences) involving an amino acid difference.

The new ammo acid sequences, as deduced from the disclosed nucleotide sequences (see SEQ ID NO 1 to 62 and 106 to 123 and 143 to 218, 223 and 270), show homologies of only 59.9 to 78% with prototype sequences of type 1 and 2 for the NS4 region, and of only 53.9 to 68.8% with prototype sequences of type 1 and 2 for the E1 region. As the NS4 region is known to contain several epitopes, for example characterized in patent application EP-A-0 489 968, and as the E1 protein is expected to be subject to immune attack as part of the viral envelope and expected to contain epitopes, the NS4 and E1 epitopes of the new type 3, 4 and 5 isolates will consistency differ from the epitopes present in type 1 and 2 isolates. This is exampified by the type-specificity of NS4 synthetic peptides as presented in example 4, and the type-specificity of recombinant E1 proteins in example 11.

After aligning the new subtype 2d type 3, 4 and 5 (see SEQ ID NO 1 to 62 and 106 to 123 and 143 to 218, 223 and 270) amino acid sequences with the prototype sequence of type 1a, 1b, 2a, and 2b, type- and subtype-specific variable regions can be delineated as presented in FIGS. 5 and 7.

As to the muteins derived from the polypeptides of the invention, Table 4 gives an overview of the amino acid substitutions which could be the basis of some of the muteins as defined above.

The peptides according to the present invention contain preferably at least 5 contiguous HCV amino acids, preferably however at least 8 contiguous amino acids, at least 10 or at least 15 (for instead at least 9, 11, 12, 13, 14, 20 or 25 amino acids) of the new HCV sequences of the invention.

TABLE 4

| Amino acids | Synonymous groups |
| --- | --- |
| Ser (S) | Ser, Thr, Gly, Asn |
| Arg (R) | Arg, His, Lys, Glu, Gln |
| Leu (L) | Leu; Ile, Met, Phe, Val, Tyr |
| Pro (P) | Pro, Ala, Thr, Gly |
| Thr (T) | Thr, Pro, Ser, Ala, Gly, His, Gln |
| Ala (A) | Ala, Pro, Gly, Thr |
| Val (V) | Val, Met, Ile, Tyr, Phe, Leu, Val |
| Gly (G) | Gly, Ala, Thr, Pro, Ser |
| Ile (I) | Ile, Met, Len, Phe, Val, Ile, Tyr |
| Phe (F) | Phe, Met, Tyr, Ile, Len, Trp, Val |
| Tyr (Y) | Tyr, Phe, Trp, Met, Ile, Val, Leu |
| Cys (C) | Cys, Ser, Thr, Met |
| His (H) | His, Gln, Arg, Lys, Gln, Thr |
| Gln (Q) | Gln, Glu, His, Lys, Asn, Thr, Arg |
| Asn (N) | Asn, Asp, Ser, Gln |
| Lys (K) | Lys, Arg, Glu, Gln, His |
| Asp (D) | Asp, Asn, Gln, Gln |
| Glu (E) | Glu, Gln, Asp, Lys, Asn, His, Arg |
| Met (M) | Met, Ile, Len, Phe, Val |

The polypeptides of the invention, and particularly the fragments, can be prepared by classical chemical synthesis.

The synthesis can be carried out in homogeneous solution or in solid phase.

For instance the synthesis technique in homogeneous solution which can be used is the one described by Houben-weyl in the book entitled "Methode der organischen chemie" (Method of organic chemistry) edited by E. Wunsh, vol. 15-I et II. THIEME, Stuttgart 1974.

The polypeptides of the invention can also be prepared in solid phase according to the methods described by Atherton and Shepard in their book entitled "Solid phase peptide synthesis" (IRL Press, Oxford, 1989).

The polypeptides according to this invention can be prepared by means of recombinant DNA techniques as described by Maniaitis et al., Molecular Cloning: A Library Manual, New York, Cold Spring Harbor Laboratory, 1982).

The present invention relates particularly to a polypeptide or peptide composition as defined above, wherein said contiguous sequence contains in its sequence at least one of the following amino acid residues: L7, Q43, M44, S60, R67, Q70, T71, A79, A87, N106, K115, A127, A199, S130, V134, G142, I144, E152, A157, V158, P165, S177 or Y177, I178, V180 or E180 or F182, R184, I186, H187, T189, A190, S191 or G191, Q192 or L192 or I192 or V192 or E192, N193 or H193 or P193, W194 or Y194, I1195, A197 or I197 or V197 or T197, V202, L203 or L203, Q208, A210, V212, F214, T216, R217 or D217 or E217 or V217, H218 or N218, H219 or V219 or L219, L227 or I227, M231 or E231 or Q231, T232 or D232 or A232 or K232, Q235 or I1235, A237 or T237, I242, I246, S247, S248, V249, S250 or Y250, I251 or V251 or M251 or F251, D252, I254 or V254, L255 or V255, E256 or A256, M258 or F258 or V258, A260 or Q260 or S260, A261, I264 or Y264, M265, I266 or A266, A267, G268 or T268, F271 or M271 or V271, I277, M280 or H280, C284 or A284 or L84, V274, V291, N292 or S292, R293 or I293 or Y293, Q294 or R294, L297 or I297 or Q297, A299 or K299 or Q299, N303 or T303, T308 or L308, T310 or F310 or A310 or D310 or V310, L313, G317 or Q317, L333, S351, A358, A359, A363, S364, A366, T369, L373, F376, Q386, I387, S392, 1399, F402, I403, R405, D454, A461, A463, T464, K484, Q500, E501, S521, K522, H524, N528, S531, S532, V534, F536, F537, M539, I546, C1282, A1283, H1310, V1312, Q1321, P1368, V1372, V1373, K1405, Q1406, S1409, A1424, A1429, C1435, S1436, S1456, H1496, A1504, D1510, D1529, I1543, N1567, D1556, N1567, M1572, Q1579, L1581, S1583, F1585, V1595, E1606 or T1606, M1611, V1612 or L1612, P1630, C1636, P1651, T1656 or I1656, L1663, V1667, V1677, A1681, H1685, E1687, G1689, V1695, A1700, Q1704, Y1705, A1713, A1714 or S1714, M1718, D1719, A1721 or T1721, R1722, A1723 or V1723, H1726 or G1726, E1730, V1732, F1735, I1736, S1737, R1738, T1739, G1740, Q1741, K1742, Q1743, A1744, T1745, L1746, E1747 or K1747, L1749, A1750, T1751 or A1751, V1753, N1755, K1756, A1757, P1758, A1759, H1762, T1763, Y1764, P2645, A2647, K2650, K2653 or L2653, S2664, N2673, F2680, K2681, L2686, H2692, Q2695 or L2695 or I2695, V2712, P2715, V2719 or Q2719, T2722, T2724, S2725, R2726, G2729, Y2735, H2739, I2748, G2746 or I2746, I2748, P2752 or K2752, P2754 or T2754, T2757 or P2757, with said notation being composed of a letter representing the amino acid residue by its one-letter code, and a number representing the amino acid numbering according to Kato et al., 1990 as shown in Table 1 (comparison with other isolates). See also the numbering in FIGS. 2, 5, 7, and 11 (alignment amino acid sequences).

Within the group of unique and new amino acid residues of the present invention, the following residues were found to be specific for the following types of HCV according to the HCV classification system used in the present invention:

Q208, R217, E231, I235, I246, T264, I266, A267, F271, K299, L2686, Q2719 which are specific for the HCV subtype 2d sequences of the present invention as shown in FIGS. 5 and 2:

Q43, S60, R67, F182, I186, H187, A190, S191, L192, W194, V202, L203, V219, Q231, D232, A237, T254, M280, Q299, T303, L308, and/or L313 which are specific for the Core/E1 region of HCV type 3 of the invention as shown in FIG. 5;

D1556, Q1579, L1581, S1584, F1585, E1606, V1612, P1630, C1636, T1656, L1663, H1685, E1687, G1689, V1695, Y1705, A1713, A1714, A1721, V1723, H1726, R1738, Q1743, A1744, E1747, I1749, A1751, A1759 and/or H1762 which are specific for the NS3/4 region of HCV type 3 sequences of the invention as shown in FIG. 7;

K2665, D2666, R2670 which are specific for the NS5B region of HCV type 3 of the invention as shown in FIG. 2;

L7, A79, A127, S130, E152, V158, I177 or Y177, V180 or E180, R184, T189, Q192 or E192 or 1192, N193 or H193, 1197 or V197, 1203, A210, V212, E217, H218, I4219, L227, A232, V249, I251 or M251, D252, L255 or V255, E256, M258 or V258 or F258, A260 or Q260, M265, T268, V271, V274, M280, I284, N292 or S292, Q294, L297 or I297, T308, A310 or D310 or V310 or T310, and G317 which are specific for the core/E1 region of HCV type 4 sequences of the present invention as shown in FIG. 5;

P2645, K2650, P2653, G2656, V2658, I2668, N2673 or N2673, K2681, H2686, D2691, L2692, Q2695 or L2695 or I2695, Y2704, V2712, P715, V2719, I2722, S2725, G2729, Y2735, G2746 or I2746, P2752 or K2752, Q2753, P2754 or T2754, T2757 or P2757 which are specific for the NS5B region of the HCV type 4 sequences of the present invention as shown in FIG. 2;

M44, Q70, A87, N106, K115, V137, G142, P165, I178, F251, A299, N303, Q317 which are specific for the Core/E1 region of the HCV type 5 sequence of the present invention as shown in FIG. 5;

L333, S351, A358, A359, A363, S364, A366, T369, L373, F376, Q386, I387, S392, I399, F102, I403, R405, D454, A461, A463, T464, K484, Q500, E501, S521, K522, H524, N528, S532, V534, F537, M539, I546 which are specific for the E1/E2 region of the HCV type 5 sequences of the present invention as shown in FIG. 12;

C1282, A1283, V1312, Q1321, P1368, V1372, K1405, Q1406, S1409, A1424, A1429, C1435, S1436, S1456, H1496, A1504, D1510, D1529, I1543, N1567, M1572, V1595, T1606, M1611, L1612, I1656, V1667, A1681, A1700, A1713, S1714, M1718, D1719, T1721, R1722, A1723, G1726, F1735, I1736, S1737, T1739, G1740, K1742, T1745, L1746, K1747, A1750, V1753, N1755, A1757, D1758, T1763, and Y1764 which are specific for the NS3/NS4 region of HCV type 5 sequences of the invention as shown in FIG. 7;

A2647, I2653, S2674, F2680, T2724, R2726, Y2730, H2739 which are specific for the NS5B region of the HCV type 5 sequences of the present invention as shown in FIG. 2;

A256, P1631, V1677, Q1704, E1730, V1732, Q1741 and T1751 which are specific for the HCV type 3 and 5 sequences of the present invention as shown in FIGS. 5 and 7;

T71, A157, I227, T237, T240, Y250, V251, S260, M271, I2673, T2722, I2748 which are specific for the HCV type 3 and 4 sequences of the present invention as shown in FIGS. 5 and 2, V192, Y194, A197, P249, S250, R294 which are specific for the HCV type 4 and 5 sequences of the present invention as shown in FIG. 5;

I293 which is specific for the HCV type 4 and subtype 2d sequence of the present invention as shown in FIG. 5;

D217 and R294 which are specific for the HCV type 3, 4 and 5 sequences of the present invention as shown in FIG. 5;

L192 which is specific for the HCV type 3 and subtype 2d sequences of the present invention as shown in FIG. 5;

G191 and T197 which are specific for the HCV type 3, 4 and subtype 2d sequences of the preset invention as shown in FIG. 5;

K232 which is specific for the HCV subtype 2d en type 5 sequences of the present invention as shown in FIG. 5.
and with said notation being composed of a letter, unambiguously representing the amino acid by its one-letter code, and a number representing the amino acid numbering according to Kato et al., 1990 (see also Table 1 for comparison with other isolates), as well as FIG. 2 (NS5 region), FIG. 5 (Core/E1 region), FIG. 7 (NS3/NS4 region), FIG. 12 (E1/E2 region). Some of the above-mentioned amino acids may be contained in type or subtype Specific epitopes.

For example M231 (detected in type 5) refers to a methionine at position 231. A glutamine (Q) is present at the same position 231 in type 3 isolates, whereas this position is occupied by an arginine in type 1 isolate and by a lysime (K) or asparagine (N) in type 2 isolates (see FIG. 5).

The peptide or polypeptide according to this embodiment of the invention may be possibly labelled, or attached to a solid substrate, or coupled to a carrier molecule such as biotin or mixed with a proper adjuvant.

The variable region in the core protein (V-CORE in FIG. 5) has been shown to be useful for serotyping (Machida et al., 1992). The sequence of the disclosed type 5 sequence in this region shows type-specific features. The peptide from amino acid 70 to 78 shows the following unique sequence for the sequences of the present invention (see FIG. 5):

QPRGRSWGQ (SEQ ID NO 93)
RSEGRTSWAQ (SEQ ID NO 220)
and RTEGRTSWAQ (SEQ ID NO 221)

Another preferred V-Core spanning region is the peptide spanning positions 60 to 78 of subtype 3c with sequence:

SRRQPIPRARRTEGRSWAQ (SEQ ID NO 268)

Five type-specific variable regions (V to V5) can be identified after aligning E1 amino acid sequences of the 4 genotypes, as shown in FIG. 5.

Region V1 encompasses amino acids 192 to 203, this is the amino-terminal 10 ammo acids of the E1 protein. The following unique sequences as shown in FIG. 5 can be deduced:

LEWRNTSGLYVL (SEQ ID NO 83)
VNYRNASGIYHI (SEQ ID NO 126)
QHYRNISGIYHV (SEQ ID NO 127)
EHYRNASGIYHI (SEQ ID NO 128)
IHYRNASGIYHI (SEQ ID NO 224)
VPYRNASGIYHV (SEQ ID NO 84)
VNYRNASGIYHI (SEQ ID NO 225)
VNYRNASGVYHI (SEQ ID NO 226)
VNYHNTSGIYHL (SEQ ID NO 227)
QHYRNASGIYHV (SEQ ID NO 228)
QHYRNVSGIYHV (SEQ ID NO 229)
IHYRNASDGYYI (SEQ ID NO 230)
LQVKNTSSSYMV (SEQ ID NO 231)

Region V2 encompasses amino acids 213 to 223. The following unique sequences can be found in the VZ region as shown in FIG. 5:

VYEADDVILHT (SEQ ID NO 85)
VYETEHHILHL (SEQ ID NO 129)
VYEADHHIMHL (SEQ ID NO 130)
VYETDHHILHL (SEQ ID NO 131)
VYEADNLILHA (SEQ ID NO 86)
VWQLRAIVLHV (SEQ ID NO 232)
VYEADYHILHL (SEQ ID NO 233)
VYETDNHILHL (SEQ ID NO 234)
VYETENHILHL (SEQ ID NO 235)
VFETVHHILHL (SEQ ID NO 236)
VFETEHHILHL (SEQ ID NO 237)
VFETDHHIMHL (SEQ ID NO 238)
VYETENHILHL (SEQ ID NO 239)
VYEADALILHA (SEQ ID NO 240)

Region V3 encompasses the amino acids 230 to 242. The following unique V3 region sequence can be deduced from FIG. 5:

VQDGNTSTCWTPV (SEQ ID NO 87)
VQDGNTSACWTPV (SEQ ID NO 241)

VRVGNQSRCWVAL (SEQ ID NO 132)
VRTGNTSRCWVPL (SEQ ID NO 133)
VRAGNVSRCWTPV (SEQ ID NO 134)
EEKGNISRCWIPV (SEQ ID NO 242)
VKTGNQSRCWVAL (SEQ ID NO 243)
VRTGNQSRCWVAL (SEQ ID NO 244)
VKTGNQSRCWIAL (SEQ ID NO 245)
VKTGNVSRCWIPL (SEQ ID NO 247)
VKTGNVSRCWISL (SEQ ID NO 248)
VRKDNVSRCWVQI (SEQ ID NO 249)

Region V4 encompasses the amino acids 248 to 257. The following V4 region sequences can be deduced from FIG. 5:

VRYVGATTAS (SEQ ID NO 89)
APYIGAPLES (SEQ ID NO 135)
APYVGAPLES (SEQ ID NO 136)
AVSMDAPLES (SEQ ID NO 137)
APSLGAVTAP (SEQ ID NO 90)
APSFGAVTAP (SEQ ID NO 250)
VSQPGALTKG (SEQ ID NO 251)
VKYVGATTAS (SEQ ID NO 252)
APYIGAPVES (SEQ ID NO 253)
AQHLNAPLES (SEQ ID NO 254)
SPYVGAPLEP (SEQ ID NO 255)
SPYAGAPLEP (SEQ ID NO 256)
APYLGAPLEP (SEQ ID NO 257)
APYLGAPLES (SEQ ID NO 258)
APYVGAPLES (SEQ ID NO 259)
VPYLGAPLTS (SEQ ID NO 260)
APHLRAPLSS (SEQ ID NO 261)
APYLGAPLTS (SEQ ID NO 262)

Region V5 encompasses the amino acids 294 to 303. The following unique V5 region peptides can be deduced from FIG. 5:

RPRRHQTVQT (SEQ ID NO 91)
QPRRHWTTQD (SEQ ID NO 138)
RPRRHWTTQD (SEQ ID NO 139)
RPRQHATVQN (SEQ ID NO 92)
RPRQHATVQD (SEQ ID NO 263)
SPQHHKFVQD (SEQ ID NO 264)
RPRRLWTTQE (SEQ ID NO 265)
PPRIHETTQD (SEQ ID NO 266)

The variable region in the E2 region (HVR-2) of type 5a as shown in FIG. 12 spanning amino acid positions 471 to 484 is also a preferred peptide according to the present invention with the following sequence:

TISYANGSGPSDDK (SEQ ID NO 267)

The above given list of peptides are particularly suitable for vaccine and diagnostic development.

Also comprised in the present invention is any synthetic peptide or polypeptide containing at least 5 contiguous amino acids derived from the above-defined peptides in their peptidic chain.

According to a specific embodiment, the present invention relates to a composition as defined above, wherein said contiguous sequence is selected from any of the following HCV amino acid type 3 sequences:

a sequence having a homology of more than 72%, preferably more than 74%, more preferably more than 77% and most preferably more than 80 or 84% homology to any of the amino acid sequences as represented in SEQ ID NO 14, 16, 18, 20, 22, 24, 26 or 28 (HD10, BR36, BR33 sequences) in the region spanning positions 140 to 319 in the Core/E1 region as shown in FIG. 5;

a sequence having a homology of more than 70%, preferably more than 72%, more preferably more than 75% homology, most preferably more than 81% homology to any of the amino acid sequences as represented in SEQ ID NO 14, 16, 18, 20, 22, 24, 26 or 28 (HD10, BR36, BR33 sequences) in the E1 region spanning positions 192 to 319 as shown in FIG. 5;

a sequence having a homology of more than 86%, preferably more thy 88%, and most preferably more than 90% homology to the amino acid sequences as representd in SEQ ID NO 148 (type 3c); BE98 in the region spanning positions 1 to 110 in the Core region as shown in FIG. 5;

a sequence having a homology of more than 76%, preferably more than 78%, most preferably more than 80% to any of the amino acid sequences as represented in SEQ ID NO 30, 32, 34, 36, 38 or 40 (HCC153, HD10, Br36 sequences) in the region spanning positions 1646 to 1764 in the NS3/NS4 region as shown in FIGS. 7 and 11;

a sequence having a homology of more than 81%, preferably more than 83%, and most preferably more than 86% homology to any of the amino acid sequences as represented in SEQ ID NO 14, 16, 18, 20, 22, 24, 26 or 28 (HD10, BR36, BR33 sequences) in the region spanning positions 140 to 319 in the Core/E1 region as shown in FIG. 5;

a sequence having a homology of more than 81.5%, preferably more than 83%, and most preferably more than 86% homology to any of the amino acid sequences as represented in SEQ ID NO 14, 16, 18, 20. 22, 24, 26 or 28 (HD10, BR36, BR33 sequences) in the E1 region spanning positions 192 to 319 as shown in FIG. 5;

a sequence having a homology of more than 86%, preferably more than 88%, and most preferably more than 90% to the amino acid sequence as represented in SEQ ID NO 150; (type 3c BE98) in the region spanning positions 2645 to 2757 in the NS5B region as shown in FIG. 2.

According to yet another embodiment, the present invention relates to a composition as defined above, wherein said contiguous sequence is selected from any of the following HCV amino acid type 4 sequences:

a sequence having a homology of more than 80%, preferably more than 82%, most preferably more than 84% homology to any of the amino acid sequences as represented in SEQ ID NO 119, 121, and 123 (GB358, GB549, GB809 sequences) in the region spanning positions 127 to 319 of the Core/E1 region as shown in FIG. 5;

a sequence having a homology of more than 80%, preferably more than 82%, most preferably more than 84% homology to any of the amino acid sequences as represented in SEQ ID NO 119, 121, and 123 (GB358, GB549, GB809 sequences) in the region spanning positions 127 to 319 of the Core/E1 region as shown in FIG. 5;

a sequence having a homology of more than 73%, preferably more than 75%, most preferably more than 78% homology in the E1 region spanning positions 192 to 319 to any of the amino acid sequences as represented in SEQ ID NO 119, 121, and 123 (GB358, GB549, GB809 sequences) in the region spanning positions 140 to 319 of the Core/E1 region as shown in FIG. 5;

a sequence having more than 85%, preferably more than 86%, most preferably more than 87% homology to any of the amino acid sequences as represented in SEQ ID NO 19, 121, or 123 (GB358, GB549, GB809 sequences) in the region spanning positions 192 to 319 of E1 as shown in FIG. 5;

a sequence showing more than 73%, preferably more than 74%, most preferably more than 75% homology to any of the amino acid sequences as represented in SEQ ID NO 107, 109, 111, 113, 115 or 117 (GB48, GB116, GB215, GB358, GB549, GB809 sequences) in the region spanning positions 2645 to 2757 of the NS5B region as shown in FIG. 2;

a sequence having any of the sequences as represented in SEQ ID NO 164 or 166 (GB809 and CAM600 sequences) in the Core region as shown in FIG. 5;

a sequence having any of the sequences as represented in SEQ ID NO 168, 170, 172, 174, 176, 178, 180, 182, 184, 186, 188 or 190 (CAM600, GB809, CAMG22, CAMG27, GB549, GB438, CAR4/1205, CAR4/901, GB116, GB215, GB958, GB809-4 sequences) in the Core/E1 region as shown in FIG. 5;

a sequence having any of the sequences as represented in SEQ ID NO 194, 196, 148, 200, 202, 204, 206, 208, 210, 212 (GB358, GB724, BE100, PC, CAM600, CAMG22, etc.) in the NS5B region or in SEQ ID NOs: 198, 200 in the NS3/4 region.

The above-mentioned type 4 peptides polypeptides comprise at least an amino acid sequence selected from any HCV type 4 polyprotein with the exception of core sequence as disclosed by Simmonds et al. (1993, EG-29, see FIG. 5).

According to yet another aspect, the present invention relates to a composition as defined above, wherein said contiguous sequence is selected from any of the following HCV amino acid type 5 sequences:

a sequence having more than 93%, preferably more than 94%, most preferably more than 95% homology in the region spanning Core positions 1 to 191to any of the amino acid sequences as represented in SEQ ID NO 42, 44, 46, 48, 50, 52 or 54 (PC sequences) and SEQ ID NO 152 (BE95) as shown in FIG. 5;

a sequence having more than 73%, preferably more than 74%, most preferably more than 76% homology in the region spanning E1 positions 192 to 319 to any of the amino acid sequences as represented in SEQ ID NO 42, 44, 46, 48, 50, 52 or 54 (PC sequences) as shown in FIG. 5;

a sequence having a more than 78%, preferably more than 80%, most preferably more than 83% homology to any of the amino acid sequences as represented in SEQ ID NO 42, 44, 46, 48, 50, 52, 54, 154, 156 (BE95, BE100) (PC sequences) in the region spanning positions 1 to 319 of the Core/E1 region as shown in FIG. 5;

a sequence having more than 90%, preferably more than 91%, most preferably more than 92% homology to any of the amino acid sequences represented in SEQ ID NO 56 or 58 (PC sequences) in the region spanning positions 1286 to 1403 of the NS3 region as shown in FIGS. 7 or 11;

a sequence having more than 66%, more particularly 68%, most particularly 70% or more homology to any of the amino acid sequences as represented in SEQ ID NO 60 or 62 (PC sequences) in the region spanning positions 1646 to 1764 of the NS3/4 region as shown in FIGS. 7 or 11.

According to yet another embodiment, the present invention relates to a composition as defined above, wherein said contiguous sequence is selected from any of the following HCV amino acid type 2d sequences:

a sequence having more than 83%, preferably more than 85%, most preferably more than 87% homology to the amino acid sequence as represented in SEQ ID NO 144 (NE92) in the region spanning positions 1 to 319 of the Cor/E1 region as shown in FIG. 5;

a sequence having more than 79%, preferably more than 81%, most preferably more than 84% homology in the region spanning E1 positions 192 to 319 to the amino acid sequence as represented in SEQ ID NO 144 (NE92) as shown in FIG. 12;

a sequence having more than 95%, more particularly 96%, most particularly 97% or more homology to the amino acid sequence as represented in SEQ ID NO 146 (NE92) in the region spanning positions 2645 to 2757 of the NS5B region as shown in FIG. 2.

The present invention also relates to a recombinant vector, particularly for cloning and/or expression, with said recombinant vector comprising a vector sequence, an appropriate prokaryotic, eukaryotic or viral promoter sequence followed by the nucleotide sequences as defined above, with said recombinant vector allowing the expression of any one of the HCV type 2 and/or HCV type 3 and/or type 4 and/Dr type 5 derived polypeptides as defied above in a prokaryotic, or eukaryotic host or in living mammals when injected as naked DNA, and more particularly a recombinant vector allowing the expression of any of the following HCV type 2d, type 3, type 4 or type 5 polypeptides spanning the following amino acid positions:

a polypeptide starting at position 1 and ending at any position in the region between positions 70 and 326, more particularly a polypeptide spanning positions 1 to 70, 1 to 85, positions 1 to 120, positions 1 to 150, positions 1 to 191, positions 1 to 200, for expression of the Core protein, and a polypeptide spanning positions 1 to 263, positions 1 to 326, for expression of the Core and E1 protein;

a polypeptide starting at any position in the region between positions 117 and 192, and ending at any position in the region between positions 263 and 326, for expression of E1, or forms that have the putative membrane anchor deleted (positions 264 to 293 plus or minus 8 amino acids);

a polypeptide starting at any position in the region between positions 1556 and 1688, and ending at any position in the region between positions 1739 and 1764, for expression of the NS4 regions, more particularly a polypeptide starting at position 1658 and ending at position 1711 for expression of the NS4a antigen, and more particularly, a polypeptide starting at position 1712 and ending between positions 1743 and 1972, for example 1712–1743, 1712–1764, 1712–1782, 1712–1972, 1712 to 1782 and 1902 to 1972 for expression of the NS4b protein or parts thereof.

The term “vectors” may comprise a plasmid, a cosmid, a phage, or a virus.

In order to carry out the expression of the polypeptide of the invention in bacteria such as *E. coli* or in eukaryotic cells such as in *S. cerevisiae*, or in cultured vertebrate or invertebrate hosts such as insect cells. We Hamster Ovary (CHO), COS, BHK, and MDCK cells, the following steps are carried out:

transformation of an appropriate cellular host with a recombinant vector, in which a nucleotide sequence coding for one of the polypeptides of the invention has been inserted under the control of the appropriated regulatory elements, particularly a promoter recognized by the polymerases of the cellular host and, in the case of a prokaryotic host, an appropriate ribosome binding site (RBS), enabling the expression in said cellular host of said nucleotide sequence. In the case of an eukaryotic host any artificial signal sequence or pre/pro sequence might be provided, or the natural HCV signal sequence might be employed, e.g. for expression of E1 the signal sequence starting between amino acid positions 117 and 170 and ending at amino acid position 191 can be used, for expression of NS4, the signal sequence starting between amino acid positions 1646 and 1659 can be used, culture of said transformed cellular host-under conditions enabling the expression of said insert.

The present invention also relates to a composition as defined above, wherein said polypeptide is a recombinant polypeptide expressed by means of an expression vector as defied above.

The present invention also relates to a composition as defined above, for use in a method for immunizing a mammal, preferably humans, against HCV comprising administering a sufficient amount of the composition possibly accompanied by pharmaceutically acceptable adjuvants, to produce an immune response, more particularly a vaccine composition including HCV type 3 polypeptides derived from the Core, E1 or the NS4 region and/or HCV type 4 and/or HCV type 5 polypeptides and/or HCV type 2d polypeptides.

The present invention also relates to an antibody raised upon immunization with a composition as defined above by means of a process as defined above, with said antibody being reactive with any of the polypeptides as defined above, and with said antibody being preferably a monoclonal antibody.

The monoclonal antibodies of the invention can be produced by any hybridoma liable to be formed according to classical methods from splenic cells of an animal, particularly from a mouse or rat, immunized against the HCV polypeptides according to the invention, or muteins thereof, or fragments thereof as defined above on the one hand, and of cells of a myeloma cell line on the other hand, and to be selected by the ability of the hybridoma to produce the monoclonal antibodies recognizing the polypeptides which has been initially used for the immunization of the animals.

The antibodies involved in the invention can be labelled by an appropriate label of the enzymatic, fluorescent, or radioactive type.

The monoclonal antibodies according to this preferred embodiment of the invention may be humanized versions of mouse monoclonal antibodies made by means of recombine DNA technology, departing from parts of mouse and/or human genomic DNA sequences coding for H and L chains or from cDNA clones coding for H and L chains.

Alternatively the monoclonal antibodies according to this preferred embodiment of the invention may be human monoclonal antibodies. These antibodies according to the present embodiment of the invention can also be derived from human peripheral blood lymphocytes of patients infected with type 3, type 4 or type 5 HCV, or vaccinated against HCV. Such human monoclonal antibodies are prepared, for instance, by means of human peripheral blood lymphocytes (PBL) repopulation of severe combined immune deficiency (SCID) mice (for recent review, see Duchosal et al. 1992).

The invention also relates to the use of the proteins of the invention, muteins thereof, or peptides derived therefrom for the selection of recombinant antibody by the process of repertoire cloning (Persson et al., 1991).

Antibodies directed to peptides derived from a certain genotype may be used either for the detection of such HCV genotypes, or as therapeutic agents.

The present invention also relates to the use of a composition as defined above for incorporation into an immunoassy for detecting HCV, present in biological sample liable to contain it, comprising at least the following steps:

(i) contacting the biological sample to be analyzed for the presence of HCV antibodies with any of the compositions as defined above preferably in an immobilized form under appropriate conditions which allow the formation of an immune complex, wherein said polypeptide can be a biotinyl polypeptide which is covalently bound to a solid substrate by means of streptavidin or avidin complexes, (ii) removing unbound components, (iii) incubating the immune complexes formed with heterologous antibodies, which specifically bind to the antibodies present in the sample to be analyzed, with said heterologous antibodies having conjugated to a detectable label under appropriate conditions, (iv) detecting the presence of said inmmunecomplexes visually or by means of densitometry and inferring the HCV serotype present from the observed hybridization pattern The present invention also relates to the use of a composition as defined above, for incorporation into a serotyping assay for detecting one or more serological types of HCV present in a biological sample liable to contain it, more particularly for detecting E1 and NS4 antigens or antibodies of the different types to be detected combined in one assay format, comprising at least the following steps:

(i) contacting the biological sample to be analyzed for the presence of HCV antibodies or antigens of one or more serological types, with at least one of the compositions as defined above, an immobilized form under appropriate conditions which allow the formation of an immunecomplex, (ii) removing unbound components, (iii) incubating the immunecomplexes formed with heterologous antibodies, which specifically bind to the antibodies present in the sample to be analyzed, with said heterologous antibodies having conjugated to a detectable label under appropriate conditions, (iv) detecting the presence of said immunecomplexes visually or by means of densitometry and interring the presence of one or more HCV serological types present from the observed binding pattern.

The present invention also relates to the use of a composition as defined above, for immobilization on a solid substrate and incorporation into a reversed phase hybridization assay, preferably for immobilization as parallel lines onto a solid support such as a membrane strip, for determining the presence or the genotype of HCV according to a method as defied above.

The present invention thus also relates to a kit for determining the presence of HCV genotypes as defined above present in a biological sample liable to contain them, comprising:

possibly at least one primer composition containing any primer selected from those defined above or any other HCV type 3 and/or HCV type 4, and/or HCV type 5, or universal HCV primers, at least one probe composition as defined above, with said probes being preferentially immobilize on a solid substrate, and more preferentially on one and the same membrane strip, a buffer or components necessary for producing the buffer enabling hybridiztion reaction between these probes and the possibly amplified products to be carried out, means for detecting the hybrids resulting from the preceding hybriziation, possibly also including an automated scanning and interpretation device for inferring the HCV genotypes present in the sample from the observed hybridization pattern.

The genotype may also be detected by means of a type-specific antibody as defined above, which is linked to any polynucleic sequence that can afterwards be amplified by PCR to detect the immune complex formed (Immuno-PCR, Sano et al., 1992);

The present invention also relates to a kit for determining the presence of HCV antibodies as defined above present in a biological sample liable to contain them, comprising:

at least one polypeptide composition as defined above, preferentially in combination with other polypeptides or peptides from HCV type 1, HCV type 2 or other types of HCV, with said polypeptides being preferentially immobilized on a solid substrate, and more preferentially on one and the same membrane strip, a buffer or components necessary for producing the buffer enabling binding reaction between these polypeptides and the antibodies against HCV present in the biological sample, means for detecting the immunecomplexes formed in the preceding binding reaction, possibly also including an automated scanning and interpretation device for inferring tie HCV genotypes present in the sample from the observed binding pattern.

BRIEF DESCRIPTION OF THE DRAWINGS

FIG. 1

Figure 8:
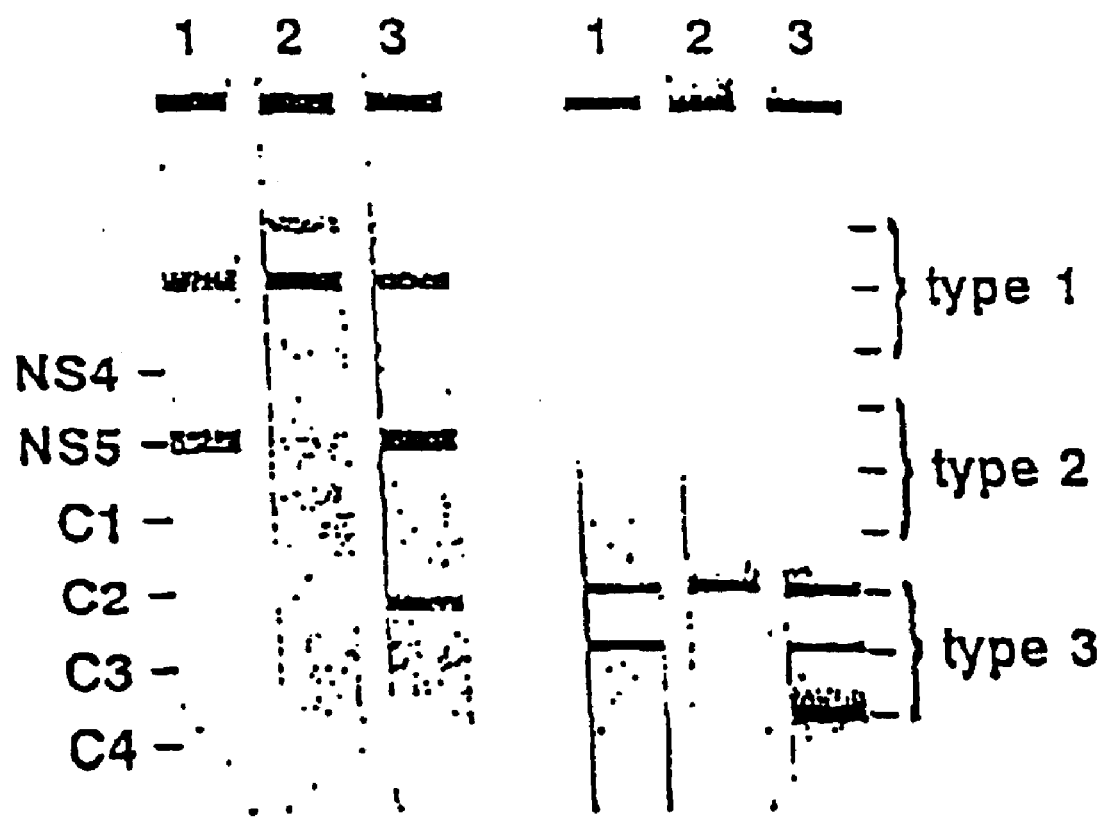

Alignment of consensus nucleotide sequences for each of the type 3a isolates BR34, BR36, and BR33, deduced from the clones with SEQ ID NO 1, 5, 9; type 4 isolates GB48, GBB 116, GB215, GB358, GB549, GB809, CAM600, CAMG22, G1438, CAR4/1205, CAR1/501 (SEQ ID NO. 106, 108, 110, 112, 114, 116, 201, 203, 205, 207, 209 and 211); type 5a isolates BE95 and BE96 (SEQ ID NO 159 and 161) and type 2d isolate NE92 (SEQ ID NO 145) from the region between nucleotides 7932 and 8271, with known sequences from the corresponding region of isolates HCV-1, HCV-J, HC-J6, HC-J8, T1 and T9, and others as shown in Table 3.

FIG. 2

Figure 1:
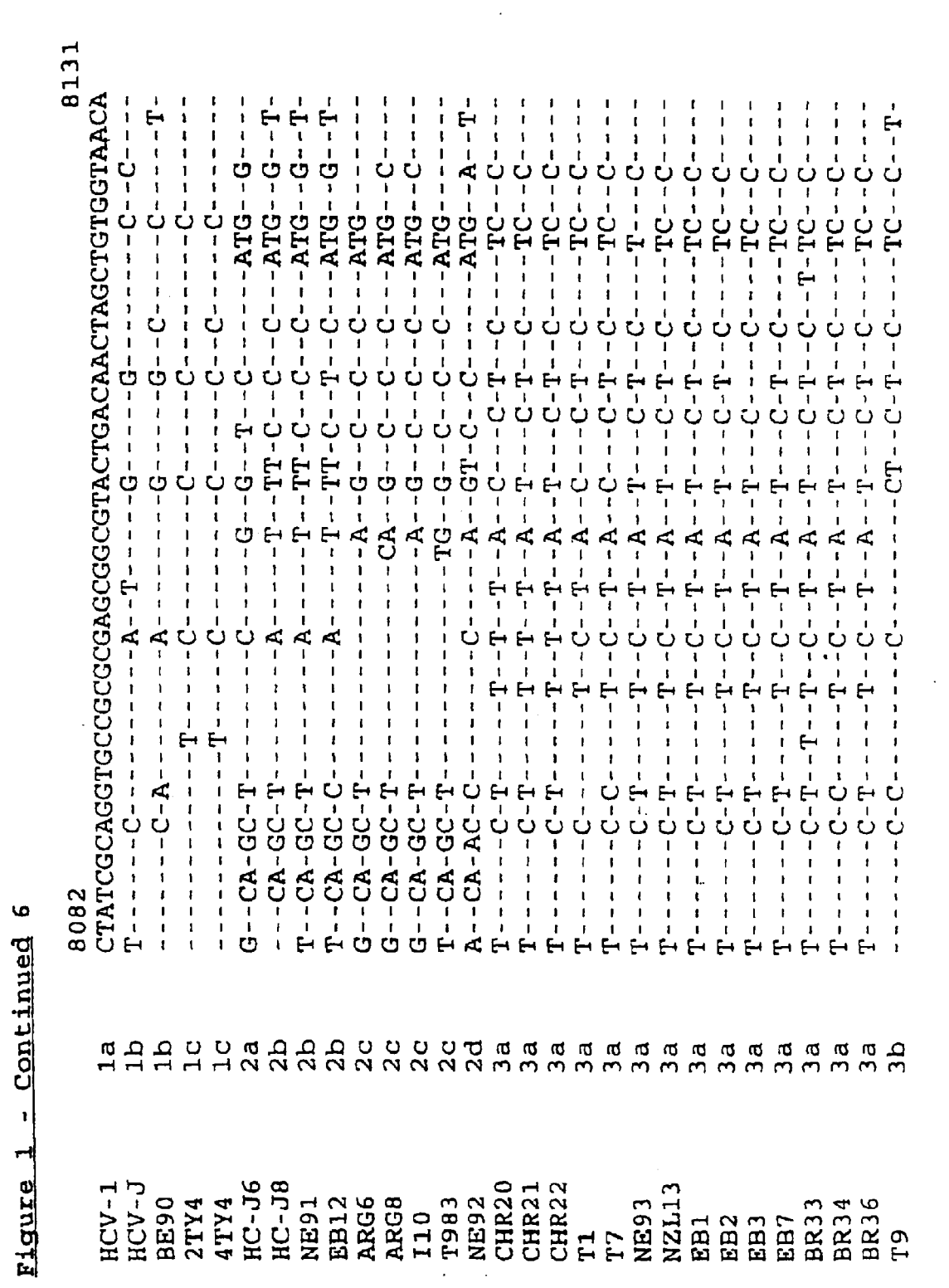

Alignment of amino acids sequences deduce from the nucleic acid sequences as represented in FIG. 1 from the subtype 3a clones BR34 (SEQ ID NO 2, 4), BR36 (SEQ ID NO 6, 8) and BR33 (SEQ ID NO 10, 12), the subtype 3c clone BE98 (SEQ ID NO 150), and the type 4 clones GB48 (SEQ ID NO 10f7), GB116 (SEQ ID NO 109), GB215 (SEQ ID NO 111), GB358 (SEQ ID NO 113), GB549 (SEQ ID NO 115) GB809 (SEQ ID NO 117); CAM600, CAMG22, GB438, CAR4/1205, CAR1/501 (SEQ ID NO 202, 204, 206, 208, 210, 212): the type 5a clones BE95 and BE96 (SEQ ID NO 160 and 162); as well as the subtype 2d isolate NE92 (SEQ ID NO 146) from the region between amino acids 2645 to 2757 with known sequences from die corresponding region of isolates HCV-1, HCV-J, HC-J6, and HC-J8, T1 and T9, and other sequences as shown in Table 3.

FIG. 3

Alignment of type 2d, 3c, 4 and 5a nucleotide sequences from isolates NE92, BE98, GB358, GB809, CAM600, GB3724, BE95 (SEQ ID NO 143, 147, 191, 163, 165, 193 and 151) in the Core region between nucleotide positions 1 and 500, with known sequences from the corresponding region of type 1, type 2, type 3 and type 4 sequences.

FIG. 4

Alignment of nucleotide sequences for the subtype 2d isolate NE92 (SEQ ID NO 143), the type 4 isolates GB358 (SEQ ID NO 118 and 187), GB549 (SEQ ID NO 120 and 175), and GB809-2 (SEQ ID NO 122 and 169), GB 809-4, BG116, GB215, CAM600, CAMG22, CAMG27, GB438, CAR4/1205, CAR4/901 (SEQ ID NO 189, 183, 185, 167, 171, 173, 177, 179, 181), sequences for each of de subtype 3a isolates HD10, 8R36, and BR33, (SEQ ID NO 13, 15, 17 (HD10), 19, 21 (BR36) and 23, 25 or 27 (BR23) and the subtype 5a isolates BE95 and BE100(SEQ ID NO 143 and 195) from the region between nucleotide 379 and 957, with known sequences from the corresponding region of type 1 and 2 and 3.

FIG. 5

Alignment of amino acid sequences from the new HCV nucleotide sequences of the Core/E1 region of isolates BR33, BR36, HD10, GB358, GB549, and GB809, PC or BE95, CAM600, and GB724 (SEQ ID NO. 14, 20, 24, 119 or 192, 121, 123 or 164, 54 or 152, 166 and 194) from the region between positions 1 and 319, with known sequences from type 1a (HCV-1), type 1b (HCV-J), type 2a (HC-JG), type 2b (RC-J8), NZL1, RCV-TR, positions 7–89 of type 3a (E-b1), and positions 8–88 of type 4a (EG-29). V-Core, variable region with type-specific features in the core protein, V1, variable region 1 of the E1 protein, V2, variable region 2 of the E1 protein, V3, variable region 3 of the E1 protein, V4, variable region 4 of the E1 protein, V5, variable region 5 of the E1 protein.

FIG. 6

Alignment of nucleotide sequences of isolates HCl53, HD10 and BR36, deduced from clones with SEQ ID NO 29, 31, 33, 35, 37 and 39, from die NS314 region between nucleotides 4664 to 5292, with known sequences from the corresponding region of isolates HCV-1, HCV-J, HC-J6, and HC-J8, EB1, EB2, EB6 and EB7.

FIG. 7

Alignment of amino acid sequences deduced from the new HCV nucleotide sequences of the NS3/NS4 region of isolate BR36 (SEQ ID NO 36, 38 and 40) and BE95 (SEQ ID NO 270). NS4-1, indicates the region that was synthesized as synthetic peptide 1 of the NS4 region, NS4-5, indicates the region that was synthesized as synthetic peptide 5 of the NS4 region; NS4-7, indicates the region that was synthesized as synthetic peptide 7 of the NS4 region.

FIG. 8

Reactivity of the LIPA-selected (Stuyver et al., 1993) type 3 sera on the Inno-LIA HCV Ab II assay (Imnogenetics) (left), and on the NS4LIA test For the NS4-LIA test, NSA-1, NS4-5, and NS4-7 peptides were synthesized based on the type 1 (HCV-1), type 2 (HC-J6) and type 3 (BR36) prototype isolate sequences as shown in Table 4, and applied as parallel lines onto a membrane strip as indicated, 1, serum BR33, 2, serum HD10, 3, serum DKH.

FIG. 9

Nucleotide sequences of Core/E1 clones obtained from the PCR fragment PC-2, PC-3, and PC-4, obtained from serum BE95 (PC-2-1 (SEQ ID NO 41), PC-2-6 (SEQ ID NO 43), PC-4 -1 (SEQ ID NO 45), PC-4-6 (SEQ ID NO 47), PC-3-4 (SEQ ID NO 49), and PC-3-8 (SEQ ID NO 51)) of subtype Sa isolate BE95.

A consensus sequence is shown for die Core and E1 region of isolate BE95, presented as PC C/E1 with SEQ ID NO 53, Y, C or T, R, A or G, S, C or G.

FIG. 10

Alignment of nucleotide sequences of clones with SEQ ID NO 197 and 199 (PC sequences, see also SEQ ID NO 55, 57, 59) and SEQ ID NO 35, 37 and 39 (BR36 sequences) from the NS3/4 region between nucleotides 3856 to 5292, with known sequences from the corresponding region of isolates HCV-1, HCV-1, HC-J6, and HC-J8.

FIG. 11

Alignment of amino acid sequences of subtype 5a BE95 isolate PC clones with SEQ ID NO 56 and 58, from the NS3/4 region between amino acids 1286 to 1764, with known sequences from the corresponding region of isolates HCV-1, HCV-J, HC-J6, and HC-J8.

FIG. 12

Alignment of amino acid sequences of subtype 5a isolate BE9S (SEQ ID NO 158) in the E1/E2 region spanning positions 328 to 546, with in sequences from the corresponding region of isolates HCV-1, HCV-J, HC-J6, HC-J8, NZL1 and HCV-TR (see Table 3).

FIG. 13

Alignment of the nucleotide sequences of subtype 5a isolate BE95 (SEQ ID NO 157) in the E1/E2 region with known HCV sequences as shown in Table 3.

EXAMPLE

Example 1

The NS5b Region of HCV Type 3

Type 3 sera, selected by means of the INNO-LiPA HCV research kit (Stuyver et al., 1993) from a number of Brazilian blood donors, were positive in the HCV antibody ELISA (Innotest HCV Ab II; Innogenetics) and/or in the INNO-LIA HCV Ab n confirmation test (Innogenetics). Only those sera that were positve after the first round of PCR reactions (Stuyver et al., 1993) were retained to further study.

Reverse transcription and nested PCR: RNA was extracted from 50 µl serum and subjected to cDNA synthesis as described (Stuyver et al., 1993). This cDNA was used as template for PCR, for which the total volume was increased to 50 µl containing 10 pmoles of each primer, 3 µl of 10× Pfu buffer 2 (Stratagene) and 2.5 U of Pfu DNA polymerase (Stratagene). The cDNA was amplified aver 45 cycles consisting of 1 mn 94° C., 1 min 50° C. and 2 min 72° C. The amplified products were separated by electrophoresis, isolated, cloned and sequenced as described (Stuyver et al., 1993).

Type 3a and 3b-specific primers in the NS5 region were selected from the published sequences (Mori et al., 1992) as follows:

for type 3a:
HCPr161(+):
5'-ACCGGAGGCCAGGAGAGTGATCTCCTCC-3' (SEQ ID NO 63) and
HCPr162(−):
5'-GGGCTGCTCTATCCTCATCGACGCCATC-3' (SEQ ID NO 64);

for type 3b:
HCPr163(+):
5'-GCCAGAGGCTCGGAAGGCGATCAGCGCT-3' (SEQ ID NO 65) and

HCPr164(−):
5'-GAGCTGCTCTGTCCTCCTCGACGCCGCA-3' (SEQ ID NO 66)

Using the Line Probe Assay (LiPA) (Stuyver et al., 1993), seven high-titer type 3 sera were selected and subsequently analyzed with the primer sets HCPr161/162 for type 3a, and HCPr163/164 for type 3b. None of these sera was positive with the type 3b primers. NS5 PCR fragments obtained using the type 3a primers from serum BR36 (BR36-23), serum BR33 (BR33-2) and serum BR34 (BR34-4) were selected for cloning. The following sequences were obtained from the PCR fragments:

From fragment BR34-4:
BR34-4-20 (SEQ ID NO 1), BR34-4-19 (SEQ ID NO 3)

From fragment BR36-23;
BR36-23-18 (SEQ ID NO 5), BR36-23-20 (SEQ ID NO 7)

From fragment BR33-2:
BR33-2-17 (SEQ ID NO 9), BR33-2-21 (SEQ ID NO 11)

An alignment of sequences with SEQ ID NO 1, 5 and 9 with known sequences is given in FIG. 1. An alignment of the deduced amino acid sequences is shown in FIG. 2. The 3 isolates are very closely related to each other (mutual homologies of about 95%) and to the published sequences of type 3a (Mori et al., 1992), but are only distantly related to type 1 and type 2 sequences (Table 5). Therefore, it is clearly demonstrated that NS5 sequences from LiPA-selected type 3 sera are indeed derived from a type 3 genome. Moreover, by analyzing the NS5 region of serum BR34, for which no 5'UR sequences were determined as described in Stuyver et al. (1993), the excellent correlation between typing by means of the LiPA and genotyping as deduced from nucleotide sequencing was further proven.

Example 2

The Core/E1 Region of HCV Type 3

After aligning the sequences of HCV-1 (Choo et al., 1991). HCV-J (Kato et al., 1990), HC-J6 (Okamoto et al., 1991), and HC-J8 (Okamoto et al., 1992), PCR primers were chosen in those regions of little sequence variation. Primers HCPr23(+): 5'-CTCATGGGGTACATTCCGCT-3' (SEQ ID NO 67) and HCP54(−): 5'-TATTACCAGTTCATCATCATATCCCA-3' (SEQ ID NO 68), were synthesized on a 392 DNA/RNA synthesizer (Applied Biosystems). This set of primers was selected to amplify the sequence from nucleotide 397 to 957 encoding amino acids 140 to 319 (Kato et al., 1990): 52 amino acids from the carboxyterminus of core and 128 amino acids of E1 (Kato et al., 1990). The amplification products BR36-9, BRR33-1, and HD10-2 were cloned as described (Stuyver et al., 1993). The following clones were obtained from the PCR fragments:

From fragment HD10-2:
HD10-2-5 (SEQ ID NO 13), HD10-2-14 (SEQ ID NO 15), HD10-2-21 (SEQ ID NO 17)

From fragment BR36-9:
BR36-9-13 (SEQ ID NO 19), BR36-9-20 (SEQ ID NO 21).

From fragment BR33-1:
BR33-1-10 (SEQ ID NO 23), BR33-1-19 (SEQ ID NO 25), BR33-1-20 (SEQ ID NO 27).

Figure 4:
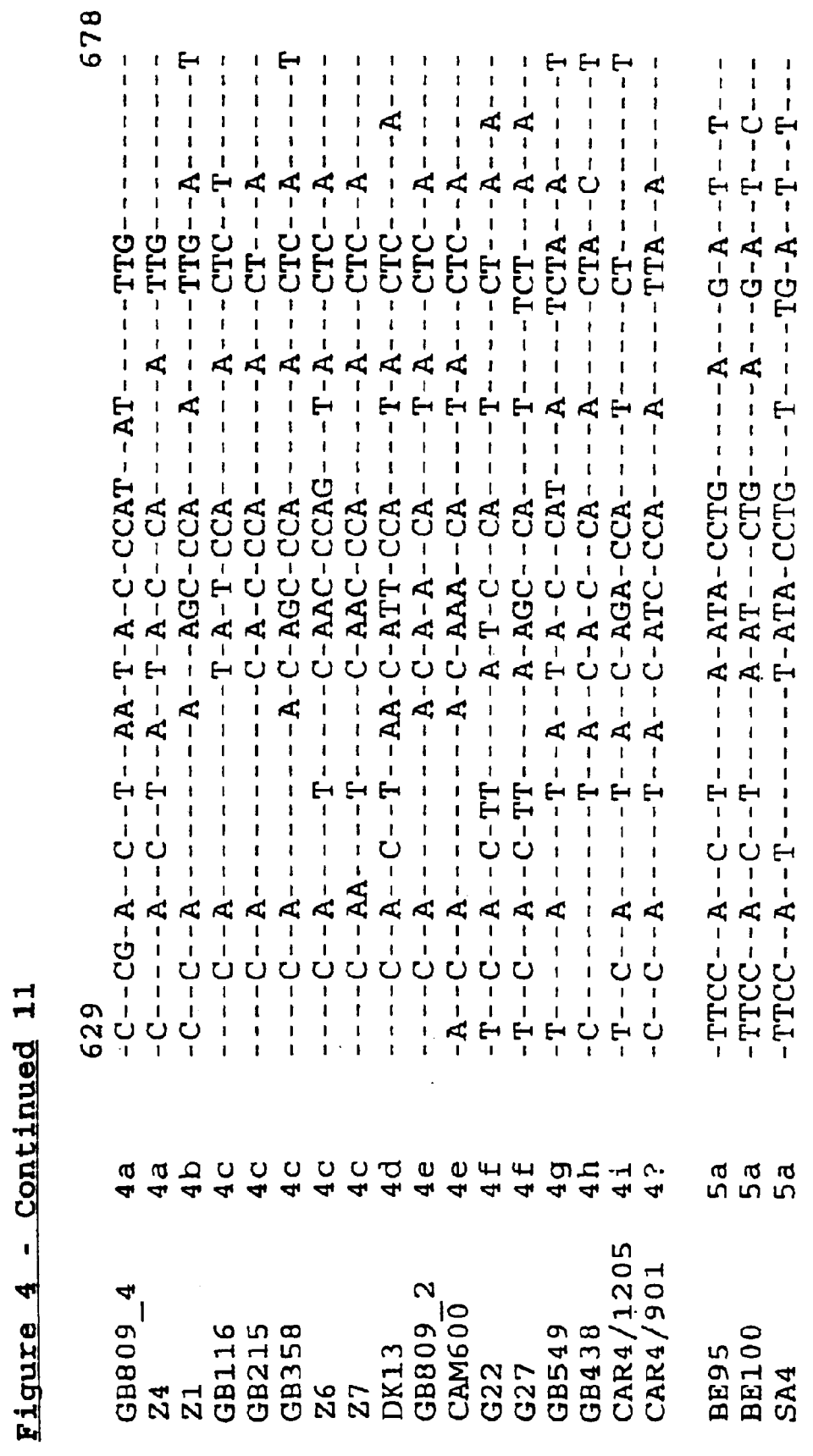

An alignment of the type 3 E1 nucleotide sequences (HD10, BR36, BR33) with SEQ ID NO 13, 19 and 23 with known E1 sequences is presented in FIG. 4. Four variations were detected in the E1 clones from serum HD10 and BR36, while only 2 were found in BR33. All are silent third letter variations, with the exception of mutations at position 40 (L to P) and 125 (M to I). The homologies of the type 3 E1 region (without core) with type 1 and 2 prototype sequences are depicted in Table 5.

In total, 8 clones covering the core/E1 region of 3 different isolates were sequenced and the E1 portion was compared with the known genotypes (Table 3) as shown in FIG. 5. After computer analysis of the deduced amino acid sequence, a signal-anchor sequence at the core carboxy terminus was detected which might, through analogy with type 1b (Hijikata et al., 1991), promote cleavage before the LEWRN sequence (position 192, FIG. 5; SEQ ID NO:271). The L-to-P mutation in one of the HD10-2 clones resides in this signal-anchor region and potentially impairs recognition by signal peptidase (computer prediction). Since no examples of such substitutions were found at this position in previously described sequences, this mutation might have resulted from reverse transcriptase or Pfu polymerase misincorporation. The 4 amino-terminal potential N-linked glycosylation sites, which are also present in HCV types 1a and 2, remain conserved in type 3. The N-glycosylation site in type 1b (aa 250, Kato et al., 1990) remains a unique feature of this subtype. All E1 cysteines, and the putative transmembrane region (aa 264 to 293, computer prediction) containing the aspartic acid at position 279, are conserved in all three HCV types. The following hypervariable regions can be delineated: V1 from aa 192 to 203 (numbering according to Kato et al., 1990), V2 (213–223), V3 (230–242), V4 (248–257and V5 (294–303). Such hydrophilic regions are thought to be exposed to the host defense mechanisms. This variability might therefore have been induced by the host's immune response. Additional putative N-linked glycosylation sites in the V4 region in all type 1b isolates known today and in the V5 region of HC-J8 (type 2b) possibly further contribute to modulation of the immune response. Therefore, analysis of this region, in the present invention, for type 3 and 4 sequences has been instrumental in the delineation of epitopes that reside in the V-regions of E1, which will be critical for future vaccine and diagnostics development.

Example 3

The NS3/NS4 Region of HCV Type 3

For the NS3/NS4 border region, the following sets of primers were selected in the regions of little sequence variability after aligning the sequences of HCV-1 (Choo et al., 1991), HCV-J (Kato et al.,1990), HC-J6 (Okamoto et al., 1991), and HC-J8 (Okamoto et al., 1992) (smaller case lettering is used for nucleotides added for cloning purposes):

set A:
HCPr116(+): 5'-ttttAAATACATCATGRCITGYATG-3' (SEQ ID NO 69)
HCPr66 (−): 5'-ctattaTTGTATCCCRCTGATGAART CCACAT-3' (SEQ ID NO 70)

set B:
HCPr116(+): 5'-ttttAAATACATCATGRC TTGYATG-3' (SEQ ID NO 69)
HCPr118(−): 5'-actagtcgactaYTGIATICCRCTIATRWAR TTCCACAT-3 ' (SEQ ID NO 71)

set C:
HCPr117(+): 5'-ttttAAATACATCGCIRCITGCAT GCA-3' (SEQ ID NO 72)

HCPr66 (−): 5'-ctattaTTGTATCCCRCTGATGAA RTCCACAT-3' (SEQ ID NO 70)

set D:
HCPr117(+): 5'-ttttATACATCGCIRCITGCATGCA-3' (SEQ ID NO 72)
HCPr118(−): 5'-actagtcgactaYTGIATICCRCTIATRWART TCCACAT-3' (SEQ ID NO 71)

set E:
HCPr116(+): 5'-tttAAATACATCATGRCITGYATG-3' (SEQ ID NO 69)
HCPr119(−): actagtcgactaRTTIGCGCIATIAGC-CGTRTT CCAYTG-3' (SEQ ID NO 73)

set F:
HCPr117(+): 5'-ttttATACATCGCIRCITGCATGCA-3' (SEQ ID NO 72)
HCPr119(−): actagtcgactaRTTIGCIATIAGCCGTRTT CATCCAYTG-3' (SEQ ID NO 73)

set G:
HCPr131 (+): 5'-ggaattctagaCCITCITGGGAYGA RAYITGGAARTG-3' (SEQ ID NO 74)
HCPr66 (−): 5'-cattaTTGTATCCCRCTGATGAA RTTCCACAT-3' (SEQ ID NO 70)

set H:
HCPr130(+): 5'-ggaattctagACIGCITAYCARGCIACIG TITGYGC-3' (SEQ ID NO 75)
HCPr66 (−): 5'-ctattaTTGTATCCCRCTGATGAA RTCCACAT-3' (SEQ ID NO 70)

set I:
HCPr134(+): 5'-CATATAGATGCCCACTTATC-3' (SEQ ID NO 76)
HCPr66 (−): 5'-ctattaTTGTATCCCRCTGATGAA RTTCCACAT-3' (SEQ ID NO 70)

set J:
HCPr131(+): 5'-ggaattctagaCCITCITGGGAYGARA YITGGAARTG-3' (SEQ ED NO 74)
HCPr118(−): 5'-actagtcgactaYTGIATICCRCTIATR WARTTCCACAT-3' (SEQ ID NO 71)

set K:
HCPr130(+): 5'-ggaattctagACIGCITAYCARGCIA CIGTITGYGC-3' (SEQ ID NO 75)
HCPr118(−): 5'-actagtcgactaYTGIATICCRCTIATR WARTTCCACAT-3' (SEQ ID NO 71)

set L:
HCPr134(+): 5'-CATATAGATGCCCACTTCCTATC-3' (SEQ ID NO 76)
HCPr118(−): 5'-actatcgactaYTGIATICCRCTIATRW ARTTCCACAT-3(SEQ ID NO71)

set M:
HCPr3(+): 5'-GTGTGCCAGGACCATC-3' (SEQ ID NO 77) and
HCPr4(−): 5'-GACATGCATGTCATGATGTA-3 (SEQ ID NO 78)

set N:
HCPr3(+): 5'-GTGCCAGGACCATC-3' (SEQ ID NO 77 and
HCPr118(−): 5'-actagtcgactaYTGIATICCRCTIATR WARTTCCACAT-3' (SEQ ID NO 71)

set O:
HCPr3(+): 5'-GTGTGCCAGGACCATC-3' (SEQ ID NO 77) and
HCPr66 (−): 5'-ctattaTTGTATCCCRCGATG AARTTCCACAT-3' (SEQ ID NO 70)

No PCR products could be obtained with the sets of primers A, B, C, D, E, F, G, H, I, J, K, L, M, and N, on random-primed cDNA obtained from type 3 sera With the primer set O, no fragment could be amplified from type 3 sera. However, a smear containing a few weakly stainable bands was obtained from serum BR36. After sequence analysis of several DNA fragments, purified and cloned from the area around 300 bp on the agarose gel, only one clone, HCC153 (SEQ ID NO 29), was shown to contain HCV information. This sequence was used to design primer HCPr152.

A new primer set P was subsequently tested on several sera.

set P:
HCPr152(+): 5'-TACGCCTCTTCATATCGGT GGGGCCTG-3' (SEQ ID NO 79) and
HCPr66(−): 5'-CTATTATGTATCCCRCTGATG AARTTCCACAT-3' (SEQ ID NO 70)

The 464-bp HCPr152/66 fragment was obtained from serum BR36 (BR3620) and serum HD10 (HD10-1). The following clones were obtained from these PCR products:

From fragment HD10-1:
HD10-1-25 (SEQ ID NO 31), HD10-1-3 (SEQ ID NO 33),
From fragment BLR36-20:
BR36-20-164 (SEQ ID NO 35), BR36-20-165 (SEQ ID NO 37), BR36-20-166 (SEQ ID NO 39).

The nucleotide sequences obtained from clones with SEQ ID NO 29, 31, 33, 35, 37 or 39 are shown aligned with the sequences of prototype isolates of other type of HCV in FIG. 6. In addition to one silent 3rd letter variation, one 2nd letter mutation resulted in an E to G substitution at position 175 of the deduced amino acid sequence of BR36 (FIG. 7). Serum HD10 clones were completely identical. The two type 3 isolates were nearly 94% homologous in this NS4 region. The homologies with other types are presented in Table 5.

Example 4

Analysis of the Anti-NS4 Response to Type-specific Peptides

As the NS4 sequence contains the information for an important epitope cluster, and since antibodies towards this region seem to exhibit little cross-reactivity (Chan et al., 1991), it was worthwhile to investigate the type-specific antibody response to this region. For each of the 3 genotypes, HCV-1 (Choo et al., 1991), HC-J6 (Okamoto et al., 1991) and BR36 (present invention), three 20-mer peptides were synthesized covering the epitope region between acids 1688 and 1743 (as depicted in table 6). The synthetic peptides were applied as parallel lines onto membrane strips. Detection of anti-NS4 antibodies and color development was performed according to the procedure described for the INNO-LIA HCV Ab II kit (Innogenetics, Antwerp). Peptide synthesis was carried out on a 9050 PepSynthesizer (Millipore). After incubation with 15 LiPA-selected type 3 sera, 9 samples showed reactivity towards NS4 peptides of at least 2 different types, but a clearly positive reaction was observed for 3 sera (serum BR33, RD30 and DKH) on the type 3 peptides, while negative (serum BR33 and HD30) or indeterminate (serum DKH) on the type 1 and type 2 NS4 peptides; 3 sera tested negative for anti-NS4 antibodies (FIG. 8). Using the same membrane strips coated with the 9 peptides as indicated above and as shown in FIG. 8, 38 type 1 sera (10 type 1a and 28 type 1b), 11 type 2 sera (10 type 2a and 1 type 2b), 12 type 3a 2 type 4 sera (as determined by the LiPA procedure) were also tested. As shown in Table 8, the sera reacted in a genotype-specific manner with the NS4 epitopes. These results demonstrate that type-specific anti-NS4 antibodies can be detected in the sera of some patients. Such genotype-specific synthetic peptides might be employed to develop serotyping assays, for example a mixture of the nine peptides as indicated above, or combined with the NS4 peptides from the HCV type 4 or 6 genotype or from new genotypes corresponding to the region between amino acids 1688 and 1743, or synthetic peptides of the NS4 region between amino acids 1688 and 1743 of at least one of the 6 genotypes, combined with the E1 protein or deletion mutants thereof, or synthetic E1 peptides of at least one of the genotypes. Such compositions could be further extended with type-specific peptides or proteins, including for example the region between amino acids 68 and 91 of the core protein, or more preferably the region between amino acids 68 and 78. Furthermore, such type-specific antigens may be advantageously used to improve current diagnostic screening and confirmation assays and/or HCV vaccines.

Example 5

The Core and E1 Regions of HCV Type 5

Sample BE95 was selected from a group of sera that reacted positive in a prototype Line Probe Assay as described earlier (Stuyver et al., 1993), because a high-titer of HCV RNA could be detected, enabling cloning of fragments by a single round of PCR. As no sequences from any coding region of type 5 has been disclosed yet, synthetic oligonucleotide for PCR amplification were chosen in the regions of little sequence variation after aligning the sequences of HCV-1 (Choo et al., 1991), HCV-J (Kato et al., 1990), HC-J6 (Okamoto et al., 1991), HC-J8 (Okamoto et al., 1992), and the new type 3 sequences of the present invention HD10, BR33, and BR36 (see FIG. 5, Example 2). The following sets of primers were synthesized on a 392 DNA/RNA synthesizer (Applied Biosystems):

Set 1:
HCPr52(+):
5'-atgTTGGGTAAGGTCATCGATACCCT-3' (SEQ ID NO 80) and
HCPr54(−):
5'-ctattaCCAGTTCATCATCATATCCCA-3' (SEQ ID NO 78)
Set 2:
HCPr41(+):
5'-CCCGGGAGGTCTCGTAGACCGTGCA-3' (SEQ ID NO 81) and
HCPr40(−):
5'-ctattaAAGATAGAGAAAGAGCAACCGGG-3' (SEQ ID NO 82)
Set 3:
HCPr41(+):
5'-CCCGGGAGGTCTCGTAGACCGTGCA-3' (SEQ ID NO 81) and
HCPr54(−):
5'-ccattaCCAGTTCATCATCATATCCCA-3' (SEQ ID NO 78)

The three sets of primers were employed to amplify the regions of the type 5 isolate PC as described (Stuyver et al., 1993). Set 1 was used to amplify the E1 region and yielded fragment PC-4, set 2 was designed to yield the Core region and yielded fragment PC-2. Set 3 was used to amplify the Core and E1 region and yielded fragment PC-3. These fragments were cloned as described (Stuyver et al., 1993). The following clones were obtained from the PCR fragments:

From fragment PC-2:
PC-2-1 (SEQ ID NO 41), PC-2-6 (SEQ ID NO 43),
From fragment PC-4:
PC4-1 (SEQ ID NO 45), PC-4-6 (SEQ ID NO 47),
From fragment PC-3:
PC-3-4 (SEQ ID NO 49), PC-3-8 (SEQ ID NO 51)

An alignment of sequences with SEQ ID NO 41, 43, 45, 47, 49 and 51, is given in FIG. 9. A consensus amino acid sequence (PC C/E1 ; SEQ ID NO 54) can be deduced from each of the 2 clones cloned from each of the three PCR fragments as depicted in FIG. 5, which overlaps the region between nucleotides 1 and 957 (Kato et al., 1990). The 6 clones are very closely related to each other (mutual homologies of about 99.7%).

An alignment of nucleotide sequence with SEQ ID NO 53 or 151 (PC C/E1 from isolate BE95) with known nucleotide sequences from the Core/E1 region is given in FIG. 3. The clone is only distantly related to type 1, type 2, type 3 and type 4 sequences (Table 5).

Example 6

NS3/NS4 Region of HCV Type 5

Attempts were undertaken to clone the NS3/NS4 region of the isolate BE95, described in example 5. The following sets of primers were selected in the regions of little sequence variability after aligning the sequences of HCV-1 (Choo et al., 1991), HCV-J (Kato et al., 1991), HC-J6 (Okamoto et al., 1991), and HC-J8 (Okamoto et al., 1992) and of the sequences obtained from type 3 sera of the present invention (SEQ ID NO 31, 33, 35, 37 and 39); smaller case lettering is used for nucleotides added for cloning purposes:

set A:
HCPr116(+): 5'-ttttAAATACATCATGRCITGYATG-3' (SEQ ID NO 66)
HCPr66 (–): 5'-ctattaTTGTATCCCRCTGATGAA RTTCCACAT-3' (SEQ ID NO 70)

set B;
HCPr116(+): 5'-ttttAAATACATCATGRCITGYATG-3' (SEQ ID NO 69)
HCPr118(–): 5'-actagtcgactaYTGIATICCRTIATR WARTTCCACAT-3' (SEQ ID NO71)

set C:
HCPr117(+): 5'-ttttAAATACATCGCIRCITGCATGCA-3' (SEQ ID NO 72)
HCPr66 (–): 5'-ctatta-TTGTATCCCRCTGATG AARTTCCACAT-3' (SEQ ID NO 70)

set D:
HCPr117(+): 5'-ttttAAATACATCGCIRCITGCATGCA-3' (SEQ ID NO 72)
HCPr118(–): 5'-actagtcgactaYTGIATICCRCTIATR WARTCCACAT-3' (SEQ ID NO 71)

set E:
HCPr116(+): 5'-ttttAAATACATCATGRCITGYATG-3' (SEQ ID NO 69)
HCPr119(–): actagtcgactaRTTCIATIAGCCG/ TRTTCATCCAYTG-3' (SEQ ID NO 73)

set F:
HCPr117(+): 5'-ttttAAATACATCGCIRCITGCATGCA-3' (SEQ ID NO 72)

HCPr119(–): actagtcgactaRTTIGCIATIAGCCG/ TRTTCATCCAYTG-3' (SEQ ID NO 73)

set G:
HCPr131(+): 5'-ggaattctagaCCITCITGGGAYGA RAYITGGAARTG-3' (SEQ ID NO 74)
HCPr66 (–): 5'-ctattaTTGTATCCCRCTGATGAA RTTCCACAT-3' (SEQ ID NO 70)

set H:
HCPr130(+): 5'-ggaattctagCIGCITAYCARGCIACIGTTGYGC-3' (SEQ ID NO 75)
HCPr66 (–): 5'-ctattaTTGTATCCCRCTGATGAA RTTCCACAT-3' (SEQ ID NO 70)

set I:
HCPr134(+): 5'-CATATAGATGCCCACTTCCTATC-3' (SEQ ID NO 76)
HCPr66 (–): 5'-ctattaTTGTATCCCRCTGATGAA RTTCCACAT-3' (SEQ ID NO 70)

set J:
HCPr131(+): 5'-ggaattctagaCCITCITGGGAYGARA YITGGAARTG-3' (SEQ ID NO 74)
HCPr118(–): 5'-actagtcgactaYTGIATICCRCTIATR WARTTCCACAT-3' (SEQ ID NO 71)

set K:
HCPr130(+): 5'-ggaarttctagACIGCITAYCARGCI ACIGTITGYGC-3' (SEQ ID NO 75)
HCPr118(–): 5'-actagtcgactaYTGIATICCRCTIATR WARTTCCACAT-3' (SEQ ID NO 71)

set L:
HCPr134(+): 5'-CATATAGATGCCCACTTCCTATC-3' (SEQ ID NO 76)
HCPr118(–): 5'-actgtcgactaYTGIATICCRCTIATR WARTTCCACAT-3' (SEQ ID NO 71)

set M:
HCPr3(+): 5'-GTTGCCAGGACCATC-3' (SEQ ID NO 77) and
HCPr4(–): 5'-GACATGCATGTCATGATGTA-3' (SEQ ID NO 78)

set N:
HCPr3(+): 5'-GTGTGCCAGGACCATC-3' (SEQ ID NO 77) and
HCPr 118(–): 5-acagtcgactaYTGIATICCRCTIATR WARTFCCACAT-3' (SEQ ID NO 71)

set O:
HCPr3(+): 5'-GTGTGCCAGGACCATC-3' (SEQ ID NO 77) and
HCPr66 (–): 5'-ctattaTTGTATCCCRCTGATG AARTTCCACAT-3' (SEQ ID NO 70)

No PCR products could be obtained with the sets of primers A, B, C, D, E, F, G, H, I, J, K, L, M, and N, on random-primed cDNA obtained from type 3 sera. However, set O yielded what appeared to be a PCR artifact fragment estimated about 1450 base pairs, instead of the expected 628 base pairs. Although it is not expected that PCR artifact fragments contain information of the gene or genome that was targetted in the experiment, efforts were put in cloning of this artifact fragment, which was designated fragment PC-1.

The following clones, were obtained from fragment PC-1: PC-1-37 (SEQ ID NO 59 and SEQ ID NO 55), PC-1-48 (SEQ ID NO 61 and SEQ ID NO 57)

The sequences obtained from the 5' and 3' ends of the clone are given in SEQ ID NOS 55, 57, 59, and 61, and the complete sequences with SEQ ID NO 197 and 199 are shown aligned with the sequences of prototype isolates of other types of HCV in FIG. 10 and the alignment of the deduced amino acid sequences is shown in FIG. 11 and 7. Surprisingly, the PCR artifact clone contained HCV information. The positions of the sequences within the HCV genome are compatible with a contiguous HCV sequence of 1437 nucleotides, which was the estimated size of the cloned PCR artifact fragment. Primer HCPr66 primed correctly at the expected position in the HCV genome. Therefore, primer HCPr3 must have incidentally misprimed at a position 809 nucleotides upstream of its legitimate position in the HCV genome. This could not be expected since no sequence information was available from a coding region of type 5.

Example 7

The E2 Region of HCV Type 5

Serum BE95 was chosen for experiments aimed at amplifying a part of the E2 region of HCV type 5.

After aligning the sequences of HCV-1 (2), HCV-J(1), HC-J6 (3), and HC-J8 (4), PCR primers were chosen in those regions of little sequence variation.

Primers HCPr109(+): 5'-TGGGATATGATGATGAACTGGTC-3' (SEQ ID NO 141) and HCPr14(-): 5'-CCAGGTACAACCGAACCAATTGCC-3' (SEQ ID NO 142) were combined to amplify the aminoterminal region of the E2/NS1 region, and were synthesized on a 392 DNA/RNA synthesizer (Applied Biosystems). With primers HCPr109 and HCPr14, a PCR fragment of 661 bp was generated, containing 169 nucleotides corresponding to the E1 carboxyterminus and 492 bases from the region encoding the E2 aminoterminus.

An alignment of the type 5 E1/E2 sequences with seq ID NO. 158 with known sequences is presented in FIG. 10. The deduced protein sequence was compared with the different genotypes (FIG. 12, amino acids 328–546). In the E1 region, there were no extra structural important motifs found. The aminoterminal of E2 was hypervariable when compared with the other genotypes. All 6 N-glycosylation sites and all 7 cysteine residue's were conserved in this E2 region. To preserve alignment, it was necessary to introduce a gap between aa 474 and 475 as for type 3a, but not between aa 480 and 481, as for type 2.

Example 8

The NS5b Region of HCV Type 4

Type 4 sera GB48, GB116, GB215, and GB358, selected by means of the line probe assay (LiPA, Stuyver et al., 1993), as well as sera GB549 and GB809 that could not be typed by means of this LiPA (only hybridization was observed with the universal probes), were selected from Gabonese patients. All these sera were positive after the first round of PCR reactions for the 5 untranslated region (Stuyver et al., 1993) and were retained for further study.

RNA was isolated from the sera and cDNA synthesized as described in example 1.

Universal primers in the NS5 region were selected a alignment of the published sequences as follows:
HCPr206(+):
5'-TGGGGATCCCCGTATGATACCCGCTGCITGA-3' (SEQ ID NO. 124) and
HCPr207(-):
5'-GGCGGAATCCTGTCATAGCCTCCGTGAA-3' (SEQ ID NO. 125);

and were synthesized on a 392 DNA/RNA synthesizer (Applied Biosystems). Using the Line Probe Assay (LiPA), four high-titer type 4 sera and 2 sera that could not be classified were selected and subsequently analysed with the primer set HCPr206/207. NS5 PCR fragments obtained using these primers from serum GB48 (GB48-3), serum GB 116 (GB 116-3), serum GB215 (GB215-3), serum GB358 (GB358-3), serum GB549 (GB549-3), and serum GB809 (GB809-3), were selected for cloning. The following sequences were obtained from the PCR fragments:

From fragment G48-3: GB48-3-10 (SEQ ID NO. 106)
From fragment GB116-3: GB116-3-5 (SEQ ID NO. 108)
From fragment GB215-3: GB215-3-8 (SEQ ID NO. 110)
From fragment GB358-3: GB358-3-3 (SEQ ID NO. 112)
From fragment GB549-3: GB549-3-6 (SEQ ID NO. 114)
From fragment GB809-3: GB809-3-1 (SEQ ID NO. 116)

An alignment of nucleotide sequences with SEQ ID NO. 106, 108, 110, 112, 114, and 116 with known sequences is given in FIG. 1. An alignment of deduced amino acid sequences with SEQ ID NO. 107, 109, 111, 113, 115, and 117with known sequences is given in FIG. 2. The 4 isolates that had been typed as type 4 by means of LiPA arm very closely related to each other (mutual homologies of about 95%), but are only distantly related to type 1, type 2, and type 3 sequences (e.g. GB358 shows homologies of 65.6 to 67.7% with other genotypes, Table 4). The sequence obtained from sera GB549 and GB809 also show similar homologies with genotypes 1, 2, and 3 (65.9 to 68.9% for GB549 and 65.0 to 68.5% for GB809, Table 4), but an intermediate homology of 79.7 to 86.8% (often observed between subtypes of the same type) exists between GB549 or GB509 with the group of isolates consisting of GB48, GB116, GB215, and GB358, or between GB549 and GB809. These data indicate the discovery of 3 new subtypes within the HCV genotype 4: in the present invention, these 3 subtypes are designated subtype 4c, represented by isolates GB48, GB 116, GB215, and GB358, subtype 4g, represented by isolate GB549, and subtype 4e, represented by isolate GB809. Although the homologies observed between subtypes in the NS5 region seem to indicate a closer relationship between subtypes 4c and 4e, the homologies observed in the E1 region indicate that subtypes 4g and 4e show the closest reason (see example 8).

Example 9

The Core/E1 Region of HCV Type 4

From each of the 3 new type 4 subtypes, one representative serum was selected for cloning experiments in the Core/E1 region. GB549 (subtype 4g) and GB809 (subtype 4e) were anayzed together with isolate GB358 that was chosen from the subtype 4c group. Synthetic oligonucleotide:

After aligning the sequences of HCV-1 (2), HCV-J(1), HC-J6 (3), and HC-J8 (4), PCR primers were chosen in those regions of little sequence variation.
Primers HCPr52(+): 5'-atgTTGGGTMGGTCATCGATACCCT-3' (SEQ ID NO:80), HCPr23(+): 5'-CTCATGGGGTACATTCCGCT-3' (SEQ ID NO:67), and HCPr54(-): 5'-CTATTACCAGTTCATCATCATATCCCA-3' (SEQ ID NO:68), were synthesized on a 392 DNA/RNA synthesizer (Applied Biosystems). The sets of primers HCPr23/54 and HCPr52/54 were used, but only with the primer set HCPr52/54, PCR fragments could be obtained. This set of primers amplified the sequence from nucleotide 379 to 957 encoding amino acids 127 to 319: 65 amino acids from the carboxyterminus of core and 128 amino acids of E1. The amplification products GB358-4, GB549-4, and GB804-4 were cloned as described in example 1. The following were obtained from PCR fragments:

From fragment GB358-4: GB358-4-1 (SEQ ED NO 118)
From fragment GB549-4: GB549-4-3 (SEQ ID NO 120)
From fragment GB809-4: GB809-4-3 (SEQ ID NO 122)

An alignment of the type 4 Core/E1 nucleotide sequences with seq ID NO. 118, 120, and 122 with Known sequences is presented in FIG. 4. The homologies of the type 4 E1 region (without core) with type 1, type 2, type 3, and type 5 prototype sequences are depicted in Table 4. Homologies of 53 to 66% are observed with representative isolates of non-type 4 genotypes. Observed homologies in the E1 region within type 4, between the different subtypes, ranges from 75.2 to 78.4%. The recently disclosed sequences of the care region of Egyptian type 4 isolates (for example EG-29 in FIG. 3) described by Simmonds et al. (1993) do not allow alignment with the Gabonese sequences (as described in the present invention) in the NSB region and may belong to different type 4 subtypes(s) as can be deduced from the core sequences. The deduced amino acid sequences with SEQ ID NO 119, 121, and 123 are aligned with other prototype sequences in FIG. 5. Again, type-specific variation mainly resides in the variable V regions, designated in the present invention, and therefore, type-4-specific amino acids or V regions will be instrumental in diagnosis and therapeutics for HCV type 4.

Example 10

The Core/E1 and NS5 b Regions of new HCV Type 2, 3 and 4 Subtype

Samples NE92(subtype 2d), BE98 (subtype 3c), CAM600 and GB809 (subtype 4e), CAMG22 and CAMG27 (subtype 4f), GB438 (subtype 4h), CAR4J1205 subtype (4i), CAR1/501 (subtype 4j), CAR1/901 (subtype 4?), and GB724 (subtype 4?) were selected from a group of sera that reacted positive but aberrantly in a prototype Line Probe Assay as described earlier (Stuyver et al., 1993). Another type 5a isolate BE100was also analyzed in the C/E1 region, and yet another type 5a isolate BE96 in the NS5b region. A high-titer of HCV RNA could be detected, enabling cloning of fragments by a single round of PCR. As no sequences from any coding region of these subtypes had been disclosed yet, synthetic oligonucleotide for PCR amplification were chosen in the regions of little sequence variation after aligning the sequences of HCV-1 (Choo et al., 1991), HCV-1 (Kato et al., 1990). HC-J6 (Okamoto et al., 1991). HC-J8 (Okamoto et al., 1992), and the other new sequences of the present invention.

The above mentioned sets 1, 2 and 3 (see example 5) of primers were used but only with set 1, PCR fragments could be obtained from all isolates (except for BE98. GB724, and CAR1/501). This set of primers amplified the sequence from nucleotide 379 to 957 encoding amino acids 127 to 319: 65 amino acids from the carboxyterminus of core and 128 amino acids of E1. With set 3, the core/E1 region from isolate NE92 and BE98 could be amplified, and with set 2, the core region of GB358, GB724, GB809, and CAM600 could be amplified. The amplification products were cloned as described in example 1. The following clones were obtained from the PCR fragments:

From isolate GB724, the clone with SEQ ID NO 193 from the core region.

From isolate NE92, the clone with SEQ ID NO 143
From isolate BE98, the clone from the core/E1 region of which part of the sequence has been analyzed and is given in SEQ ID NO 147,
From isolate CAM600, the clone with SEQ ID NO 167 from the E1 region, or SEQ ID NO 165 from the Core/E1 region as shown in FIG. 3,
From isolate CAMG22, the clone with SEQ ID NO 171 from the E1 region as shown in FIG. 4,
from isolate GB358, the clone with SEQ ID NO 191 in the core region,
from isolate CAMG27, the clone with SEQ ID NO 173 from the core/E1 region,
from isolate GB438, the clone with SEQ ID NO 177 from the core/ E1 region,
from isolate CRA4/1205, the clone with SEQ ID NO 179 from the core/E1 region,
from isolate CAR1/901, the clone with SEQ ID NO 181 from the core/E1 region,
from isolate GB809, the clone GB809-4 with SEQ ID NO 189 from the core/E1 region,
clone GB809-2 with SEQ ID NO 169 from the core/E1 region and the clone with SEQ ID NO 163 from the core region, and from isolate BE100, the clone with SEQ ID NO 155 from the Core/E1 region as shown in FIG. 4.

An alignment of these Core/E1 sequences with known Core/E1 sequences is presented in FIG. 4. The deduced amino acid sequences with SEQ ID NO 144, 148, 164, 168, 170, 172, 174, 178, 180, 182, 190, 192, 194, 156, 166 are aligned with other prototype sequences in FIG. 5. Again, type-specific variation mainly resides in the variable V regions, designated in the present invention, and therefore, type 2d, 3c and type 4-specific amino acids or V regions will be instrumental in diagnosis and therapeutics for HCV type (subtype) 2d, 3c or the different type 4 subtypes.

The NS5 b region of isolates NE92, BE98, CAM600, CAMG22, GB438, CAR4/1205, CAR1/501, and BE96 was amplified with primers HCPr206 and HCPr207 (Table 7). The corresponding clones were cloned and sequenced as in example 1 and the corresponding sequences (of which BE98 was partly sequenced) received the following identification numbers.

NE92: SEQ ID NO 145
BE98: SEQ ID NO 149
CAM600: SEQ ID NO 201
CAMG22: SEQ ID NO 203
GB438: SEQ ID NO 207
CAR4/1205: SEQ ID NO 209
CAR1/501: SEQ ID NO 211
BE95: SEQ ID NO 159
BE96: SEQ ID NO 161

An alignment of these NS5b sequences with know NS5b sequences is presented in FIG. 1. The deduced amino acid sequences with SEQ ID NO 146, 150, 202, 204, 206, 208, 210, 212, 160, 162 are alignment with other prototype sequences in FIG. 2. Again, subtype-specific variations can be observed, and therefore, type 2d, 3c and type 4-specific amino acids or V regions will be instrumental in diagnosis and therapeutics for HCV type (subtype) 2d, 3c or the different type 4 subtypes.

Example 11

Genotype-specific Reactivity of Anti-E1 Antibodies (Serotyping)

E1 proteins were expressed from vanccinia virus constructs containing a core/E1 region extending from nucleotide positions 355 to 978 (Core/E1 clones described in previous examples including the primers HCPr52 and HCPr54), and expressed proteins from L119 (after the initiator methionine) to W326 of the HCV polyprotein. The expressed protein was modified upon expression in the appropriate host cells (e.g. HeLa, RK13, HuTK-, HepG2) by cleavage between amino acids 191 and 192 of the HCV polyprotein and by the addition of high-mannose type carbohydrate motifs. Therefore, a 30 to 32 kDa glycoprotein could be observed on western blot by means of detection with serum from patients with hepatitis C.

As a reference, a genotype 1b clone obtained form the isolate HCV-B was also expressed in an identical way as described above, and was expressed from recombinant vaccinia virus vvHCV-11A.

A panel of 104 genotyped sera was first tested for reactivity with a cell lysate containing type 1b protein expressed from the recombinant vaccinia virus vvHCV-11A, and compared with cell lysate of RK13 cells infected with a wild type vaccinia virus ('E1/WT'). The lysates were coated as a 1/20 dilution on a normal ELISA microtiter plate (Nunc maxisorb) and left to react with a 1120 diluation of the respective sera. The panel consisted of 14 type 1a, 38 type 1b, 21 type 2, 21 type 3a, and 9 type 4 sera. Human antibodies ware subsequently detected by a goat anti-human IgG conjugated with peroxidase and the enzyme activity was detected. The optical density values of the E1 and wild type lysates were divided and a factor 2 was taken as the cut-off. The results are giving in the table A. Eleven out of 14 type 1a sera (79%), 25 out of 38 type 1b sera (66%), 6 out of 21 (29%), 5 out of 21 (24%), and none of the 9 type 4 or the type 5 serum reacted (0%). These experiments clearly show the high prevalence of anti-E1 antibodies reactive with the type 1 E1 protein in patients infected with type 1(36/52 (69%)) (either type 1a or type 1b), but the low prevalence or absence in non-type 1sera (11/52 (21%)).

TABLE A

| serum | E1/WT |
|---|---|
| type 1a | |
| 3748 | 3.15 |
| 3807 | 3.51 |
| 5282 | 1.99 |
| 9321 | 3.12 |
| 9324 | 2.76 |
| 9325 | 6.12 |
| 9326 | 10.56 |
| 9356 | 1.79 |
| 9388 | 3.5 |
| 8366 | 10.72 |
| 8380 | 2.27 |
| 10925 | 4.02 |
| 10936 | 5.04 |
| 10938 | 1.36 |
| type 1b | |
| 5205 | 2.25 |
| 5222 | 1.33 |
| 5246 | 1.24 |
| 5250 | 13.58 |
| 5493 | 0.87 |
| 5573 | 1.75 |
| 8243 | 1.77 |
| 8244 | 2.05 |
| 8316 | 1.21 |
| 8358 | 5.04 |
| 9337 | 14.47 |
| 9410 | 5 |
| 9413 | 5.51 |

TABLE A-continued

| serum | E1/WT |
|---|---|
| 10905 | 1.26 |
| 10919 | 5.00 |
| 10928 | 8.72 |
| 10929 | 8.26 |
| 10931 | 2.3 |
| 10932 | 4.41 |
| 44 | 2.37 |
| 45 | 3.14 |
| 46 | 4.37 |
| 47 | 5.68 |
| 48 | 2.97 |
| 49 | 1.18 |
| 50 | 9.85 |
| 51 | 4.51 |
| 52 | 1.11 |
| 53 | 5.20 |
| 54 | 0.98 |
| 55 | 1.48 |
| 56 | 1.06 |
| 57 | 3.85 |
| 58 | 7.6 |
| 59 | 3.28 |
| 60 | 3.23 |
| 61 | 7.82 |
| 62 | 1.92 |
| type 2 | |
| 23 | 0.91 |
| 24 | 1.16 |
| 25 | 2.51 |
| 26 | 0.96 |
| 27 | 1.20 |
| 28 | 0.96 |
| 29 | 2.58 |
| 30 | 8.05 |
| 31 | 0.92 |
| 32 | 0.82 |
| 33 | 5.75 |
| 34 | 0.79 |
| 35 | 0.86 |
| 36 | 0.85 |
| 37 | 0.76 |
| 38 | 0.92 |
| 39 | 1.08 |
| 40 | 2.33 |
| 41 | 2.83 |
| 42 | 1.21 |
| 43 | 0.91 |
| type 3 | |
| 1 | 6.88 |
| 2 | 1.47 |
| 3 | 3.06 |
| 4 | 6.52 |
| 5 | 10.24 |
| 6 | 2.72 |
| 7 | 1.11 |
| 8 | 1.54 |
| 9 | 1.60 |
| 10 | 1.21 |
| 11 | 1.07 |
| 12 | 1.00 |
| 13 | 0.85 |
| 14 | 0.96 |
| 15 | 0.51 |
| 16 | 1.00 |
| 17 | 1.09 |
| 18 | 0.99 |
| 19 | 1.04 |
| 20 | 1.04 |
| 21 | 0.96 |
| type 4 | |
| 22 | 0.87 |
| GB48 | 0.49 |
| GB113 | 0.68 |
| GB116 | 0.73 |

TABLE A-continued

| serum | E1/WT |
|---|---|
| GB215 | 0.52 |
| GB358 | 0.56 |
| GB359 | 0.71 |
| GB438 | 1.08 |
| GB516 | 1.04 |
| type 5 | |
| BE95 | 0.86 |

Core/E1 clones of isolates BR36 (type 3a) and BE95 (type 5a) were subsequently recombined into the viruses vvHCV-62 and vvHCV-63, respectively. A genotyped panel of sera was subsequently tested onto cell lysates obtained from RK13 cells infected with the recombinant viruses vvHCV-62 and vvHCV-63. Tests were carried out as described above and the results are given in the table given below (TABLE B). From these rests, it can clearly be seen that, although some cross-reactivity occurs (especially between type 1 and 3), the obtained values of a given serum are usually higher on its homologous E1 protein than on an E1 protein of another genotype. For type 5 sera, none of the 5 sera were reactive on type 1 or 3 E1 proteins, while 3 out of 5 were shown to contain anti-E1 antibodies when tested on their homologous type 5 protein. Therefore, in this simple test system, a considerable number of sera can already be serotyped. Combined with the reactivity to type-specific NS4 epitopes or epitopes derived from other type-specific parts of the HCV polyprotein, a serotyping assay may be developed for discriminating the major types of HCV. To overcome the problem of cross-reactivity, the position of cross-reactive epitopes may be determined by someone skilled in the art (e.g. by means of competition of the reactivity with synthetic peptides), and the epitopes evoking cross-reactivity may be left out of the composition to be included in the serotyping assay or may be included in sample diluent to outcompete cross-reactive antibodies.

TABLE B

| serum | $E1^{1b}$/WT | $E1^{3a}$/WT | $E1^{5a}$/WT |
|---|---|---|---|
| type 1b | | | |
| 8316 | 0.89 | 0.59 | 0.80 |

TABLE B-continued

| serum | $E1^{1b}$/WT | $E1^{3a}$/WT | $E1^{5a}$/WT |
|---|---|---|---|
| 8358 | 2.22 | 2.65 | 1.96 |
| 9337 | 1.59 | 0.96 | 0.93 |
| 9410 | 16.32 | 9.60 | 3.62 |
| 9413 | 9.89 | 2.91 | 2.85 |
| 10905 | 1.04 | 0.96 | 1.05 |
| 10919 | 3.17 | 2.56 | 2.96 |
| 10928 | 4.39 | 2.28 | 2.07 |
| 10929 | 2.95 | 2.07 | 2.08 |
| 10931 | 3.11 | 1.49 | 2.11 |
| 5 | 0.86 | 0.86 | 0.96 |
| 6 | 3.48 | 1.32 | 1.32 |
| 7 | 6.76 | 4.00 | 3.77 |
| 8 | 10.88 | 3.44 | 4.04 |
| 9 | 1.76 | 1.88 | 1.58 |
| 10 | 9.88 | 7.48 | 7.20 |
| 11 | 8.48 | 8.99 | 8.45 |
| 12 | 0.76 | 0.72 | 0.76 |
| 13 | 5.04 | 5.67 | 5.37 |
| 14 | 10.48 | 10.54 | 11.22 |
| 15 | 5.18 | 1.62 | 1.65 |
| type 3 | | | |
| 8332 | 3.39 | 4.22 | 0.66 |
| 10907 | 3.24 | 4.39 | 0.96 |
| 10908 | 0.99 | 0.94 | 0.98 |
| 10934 | 0.86 | 0.90 | 0.90 |
| 10927 | 2.58 | 2.71 | 2.44 |
| 8210 | 0.82 | 0.80 | 0.86 |
| 8344 | 1.09 | 6.66 | 1.17 |
| 8351 | 1.21 | 1.29 | 1.22 |
| 30 | 0.85 | 4.11 | 0.98 |
| 32 | 0.85 | 2.16 | 1.04 |
| type 5 | | | |
| | 0.78 | 0.95 | 1.54 |
| BE110 | 0.79 | 1.01 | 4.95 |
| BE95 | 0.47 | 0.52 | 0.65 |
| BE111 | 0.71 | 0.75 | 8.33 |
| BE112 | 1.01 | 1.27 | 2.37 |
| BE113 | 1.11 | 1.35 | 1.60 |

TABLE 5

Homologies of new HCV sequences with other known HCV types

| Region | Isolate | 1a | 1b | 2a | 2b | 3a | | 3b | |
|---|---|---|---|---|---|---|---|---|---|
| (nucleotides) | (type) | HCV-1 | HCV-J | HC-J6 | HC-J8 | T1 | T7 | T9 | T10 |
| Core (1–573) | PC (5) | 83.8 (91.6) | 84.8 (92.1) | 82.6 (90.1) | 82.4 (89.0) | | | | |
| E1 (574–957) | HD10 (3) | 61.5 (68.0) | 64.6 (68.8) | 57.8 (55.5) | 56.3 (59.4) | | | | |
| | BR36 (3) | 62.0 (66.4) | 62.5 (67.2) | 56.5 (53.9) | 55.2 (58.6) | | | | |
| | BR33 (3) | 60.7 (67.2) | 63.3 (68.0) | 56.5 (54.7) | 56.0 (58.6) | | | | |
| | PC (5) | 61.4 (64.0) | 62.4 (64.8) | 54.1 (49.6) | 53.3 (47.2) | | | | |
| | GB358 (4a) | 62.5 (69.1) | 62.8 (65.9) | 59.4 (54.0) | 54.4 (54.0) | | | | |
| | GB549 (4b) | 66.0 (72.2) | 62.8 (69.8) | 59.1 (56.4) | 56.5 (54.0) | | | | |
| | GB809 (4c) | 63.3 (69.1) | 60.7 (64.3) | 56.7 (53.2) | 53.0 (51.6) | | | | |
| NS3 (3856–4209) | PC (5) | 74.7 (89) | 76.1 (86.4) | 76.1 (89.8) | 78.0 (89.0) | | | | |
| NS4 (4892–5292) | BR36 (3) | 67.8 (78.5) | 69.8 (75.1) | 62.0 (67.5) | 61.7 (66.0) | | | | |
| | HD10 (3) | 69.8 (74.6) | 66.6 (69.7) | 57.8 (59.9) | 59.1 (59.9) | | | | |

TABLE 5-continued

Homologies of new HCV sequences with other known HCV types

| Region | Isolate | 1a | 1b | 2a | 2b | 3a | | 3b | |
|---|---|---|---|---|---|---|---|---|---|
| (nucleotides) | (type) | HCV-1 | HCV-J | HC-J6 | HC-J8 | T1 | T7 | T9 | T10 |
| NS4 (4936–5292) | PC (5) | 61.3 (62.2) | 63.0 (65.5) | 52.9 (46.2) | 54.3 (43.7) | | | | |
| NS5b (8023–8235) | BR34 (3) | 65.7 | 66.7 | 63.9 | 64.3 | 94.8 | 93.9 | 75.6 | 77.0 |
| | BR36 (3) | 64.3 | 67.6 | 64.8 | 66.7 | 94.8 | 93.4 | 75.1 | 76.5 |
| | BR33 (3) | 65.7 | 67.1 | 64.3 | 64.8 | 94.8 | 93.9 | 76.0 | 77.5 |
| | GB358 (4a) | 67.7 (76.1) | 65.6 (77.0) | 66.5 (70.8) | 65.6 (71.7) | | | | |
| | GB549 (4b) | 68.8 (76.1) | 67.1 (77.0) | 65.9 (71.7) | 65.9 (74.4) | | | | |
| | GB809 (4c) | 68.5 (73.5) | 65.0 (73.5) | 67.7 (69.9) | 67.7 (73.5) | | | | |

Shown are the nucleotide homologies (the amino-acid homology is given between brackets) for the region indicated in the left column.

TABLE 6

NS4 sequences of the different genotypes

| prototype position-> | TYPE | SYNTHETIC PEPTIDE NS4-1 (NS4a) 1690    1700 | SYNTHETIC PEPTIDE NS4-5 (NS4b) 1720    1730 | SYNTHETIC PEPTIDE NS4-7 (NS4b) 1730    1740 |
|---|---|---|---|---|
| | | ** * ** ** | * * * | * * * * |
| HCV-I | 1a | LSG KPAIIPDREV LY<u>R</u>EFDE (SEQ ID NO:272) | SQ<u>H</u>LPYIEQ G<u>MML</u>AEQFKQ K (SEQ ID NO:273) | <u>L</u>AEQFKQ K<u>A</u>LGLLQTAS RQA (SEQ ID NO:274) |
| HCV-J | 1b | LSG RPAVIPDREV LYQEFDE (SEQ ID NO:275) | AS<u>H</u>LPYIEQ GM<u>Q</u>LAEQFKQ K (SEQ ID NO:276) | <u>L</u>AEQFKQ K<u>A</u>LGLLQTAT KQA (SEQ ID NO:277) |
| HC-J6 | 2a | <u>VNQ</u> RA<u>VV</u>APDKEV LY<u>E</u>AFDE (SEQ ID NO:278) | AS<u>RAAL</u>IEE G<u>QRI</u>AE<u>MLKS</u> K (SEQ ID NO:279) | IAE<u>MLKS</u> K<u>IQ</u>GLL<u>QQ</u>AS KQA (SEQ ID NO:280) |
| HC-J8 | 2b | L<u>ND</u> RVVVAPDKE<u>I</u> LY<u>E</u>AFDE (SEQ ID NO:281) | AS<u>KAAL</u>IEE G<u>QRM</u>AE<u>MLKS</u> K (SEQ ID NO:282) | <u>MAEMLKS</u> K<u>IQ</u>GLL<u>QQ</u>AT RQA (SEQ ID NO:283) |
| BR36 | 3a | L<u>GG</u> KPAI<u>V</u>PDKEV LYQQ*YDE* (SEQ ID NO:97) | SQ<u>AA</u>PYIEQ A<u>QVIAHQFKE</u> K (SEQ ID NO:99) | IA<u>HQFKE</u> K*V*LGLL<u>Q</u>RAT QQQ (SEQ ID NO:100) |
| PC | 5 | LSG KPAIIPDRE<u>A</u> LYQQFDE V (SEQ ID NO:102 and SEQ ID NO:103, respectively) | AASLPY<u>MDE</u> TRA*IA*G<u>Q</u>FK*E* K (SEQ ID NO:284) | IA<u>GQ</u>F*KE* K*V*LG*FISTTG Q*K*A* (SEQ ID NO:105) |

*, residues conserved in every genotype. Double underlined amino acids are type-specific, amino acids in italics are unique to type 3 and 5 sequences.

TABLE 7

| SEQ ID NO | Primer NO (polarity) | Sequence from 5' to 3' |
|---|---|---|
| 63 | HCPr161(+) | 5'-ACCGGAGGCCAGGAGAGTGATCTCCTCC-3' |
| 64 | HCPr162(-) | 5'-GGGCTGCTCTATCCTCATCGACGCCATC-3' |
| 65 | HCPr163(+) | 5'-GCCAGAGGCTCGGAAGGCGATCAGCGCT-3' |
| 66 | HCPr164(-) | 5'-GAGCTGCTCTGTCCTCCTCGACGCCGCA-3' |
| 67 | HCPr23(+) | 5'-CTCATGGGGTACATTCCGCT-3' |
| 68 | HCPr54(-) | 5'-CTATTACCAGTTCATCATCATATCCCA-3' |
| 69 | HCPr116(+) | 5'-ttttAAATACATCATGRCITGYATG-3' |
| 70 | HCPr66(-) | 5'-ctattaTTGTATCCCRCTGATGAARTTCCACAT-3' |
| 71 | HCPr118(-) | 5'actagtcgactaYTGIATICCRCTIATRWARTTCCACAT-3' |
| 72 | HCPr117(+) | 5'-ttttAAATACATCGCIRCITGCATGCA-3' |

TABLE 7-continued

| SEQ ID NO | Primer NO (polarity) | Sequence from 5' to 3' |
|---|---|---|
| 73 | HcPr119(-) | 5'-actagtcgactaRTTIGCIATIAGCCKRTTCATCCAYTG-3' |
| 74 | HCPr131(+) | 5'-ggaattctagaCCITCITGGGAYGARAYITGGAARTG-3' |
| 75 | HCPr130(+) | 5'-ggaattctagACIGCITAYCARGCIACIGTITGYGC-3' |
| 76 | HCPr134(+) | 5'-CATATAGATGCCCACTTCCTATC-3' |
| 77 | HCPr3(+) | 5'-GTGTGCCAGGACCATC-3' |
| 78 | HCPr4(-) | 5'-GACATGCATGTCATGATGTA-3' |
| 79 | HCPr152(+) | 5'-TACGCCTCTTCTATATCGGTTGGGGCCTG-3' |
| 80 | HCPr52(+) | 5'-atgTTGGGTAAGGTCATCGATACCCT-3' |
| 81 | HCPr41(+) | 5'-CCCGGGAGGTCTCGTAGACCGTGCA-3' |
| 82 | HCPr40(-) | 5'-ctattaAAGATAGAGAAAGAGCAACCGGG-3' |
| 124 | HCPR206 | 5'-tggggatcccgtatgatacccgctgctttga-3' |
| 125 | HCPR207 | 5'-ggcggaattcctggtcatagcctccgtgaa-3' |
| 141 | HCPR109 | 5'-tgggatatgatgatgaactggtc-3' |
| 142 | HCPR14 | 5'-ccaggtacaaccgaaccaattgcc-3' |

TABLE 8

NS4 SEROTYPING

| serum | Type 1 NS4 | | | Type 2 NS4 | | | Type 3 NS4 | | |
|---|---|---|---|---|---|---|---|---|---|
|  | 1 | 5 | 7 | 1 | 5 | 7 | 1 | 5 | 7 |
| type 1a | | | | | | | | | |
| 101 | 3 | 3 | 3 | – | 1 | 3 | +/– | +/– | 3 |
| 102 | 1 | +/– | 2 | – | – | 2 | – | – | 1 |
| 103 | 1 | 3 | 3 | – | +/– | 3 | – | +/– | 3 |
| 104 | 3 | 3 | 3 | 2 | 2 | 3 | 3 | +/– | 2 |
| 105 | 3 | 3 | 3 | – | 2 | 2 | +/– | +/– | 2 |
| 106 | 3 | 1 | 1 | – | 1 | 2 | +/– | +/– | +/– |
| 107 | 3 | 3 | 3 | – | 2 | 2 | 2 | – | 1 |
| 108 | 3 | 3 | 3 | – | +/– | 2 | +/– | 1 | 2 |
| 109 | 3 | 3 | 3 | +/– | 2 | 3 | 1 | – | 3 |
| 110 | 3 | 3 | 3 | – | +/– | 1 | – | – | 3 |
| type 1b | | | | | | | | | |
| 111 | +/– | +/– | – | – | – | – | – | – | – |
| 112 | – | 2 | 3 | – | – | 2 | – | – | 3 |
| 113 | 2 | 3 | 3 | – | – | 1 | – | – | 3 |
| 114 | 2 | 3 | 3 | 1 | + | 2 | + | 1 | 3 |
| 115 | 3 | 3 | 3 | – | + | 3 | – | – | 3 |
| 116 | 3 | 3 | 3 | – | +/– | 1 | – | – | 1 |
| 117 | 3 | – | – | 3 | +/– | +/– | +/– | – | – |
| 118 | 1 | 2 | 3 | – | +/– | 2 | – | +/– | 3 |
| 119 | +/– | 2 | 2 | +/– | +/– | 2 | + | 1 | 2 |
| 120 | – | 3 | 3 | – | 3 | +/– | +/– | – | – |
| 121 | 3 | 3 | 3 | +/– | 2 | 2 | 2 | 2 | 3 |
| 122 | 3 | 3 | 1 | – | 1 | 2 | 2 | 1 | 1 |
| 123 | 3 | 3 | 2 | – | 1 | 2 | – | 1 | 1 |
| 124 | 3 | 3 | 3 | – | +/– | 2 | – | – | 2 |
| 125 | 3 | 3 | 3 | 1 | 1 | 3 | 2 | 1 | 3 |
| 126 | 1 | 2 | 2 | 1 | 1 | 1 | 1 | 1 | 1 |
| 127 | 3 | 2 | +/– | – | +/– | 1 | +/– | +/– | +/– |
| 128 | 3 | 3 | 3 | – | +/– | 1 | 2 | +/– | +/– |
| 129 | 2 | 3 | 3 | – | – | 3 | – | – | 3 |
| 130 | – | 2 | 1 | +/– | – | – | – | – | – |
| 131 | – | 1 | 1 | – | – | – | – | +/– | – |
| 132 | – | – | – | +/– | – | +/– | – | – | – |
| 133 | 3 | 3 | 3 | – | 1 | 3 | – | 1 | 3 |
| 134 | – | 2 | 2 | – | – | – | – | – | – |
| 135 | 3 | 3 | 3 | 1 | + | 2 | 2 | 1 | 3 |
| 136 | – | 3 | 3 | +/– | +/– | +/– | +/– | – | 3 |
| 137 | +/– | +/– | +/– | +/– | +/– | +/– | +/– | – | – |
| 138 | 3 | 3 | 3 | +/– | 2 | 2 | 1 | + | 3 |
| type 2a | | | | | | | | | |
| 139 | 3 | – | – | 3 | 3 | +/– | 1 | – | – |
| 140 | +/– | – | – | 3 | 3 | 3 | 3 | – | – |
| 141 | 2 | – | – | 2 | 1 | +/– | 2 | – | – |
| 142 | – | – | – | – | +/– | – | – | – | – |
| 143 | – | +/– | +/– | 1 | 2 | 1 | 1 | +/– | +/– |
| 144 | 1 | 1 | + | 1 | 3 | 2 | 1 | 1 | 2 |
| 145 | – | +/– | +/– | 3 | 1 | 2 | 2 | +/– | – |
| 146 | – | – | – | +/– | +/– | – | – | – | – |
| 147 | – | +/– | – | 3 | 1 | 3 | – | – | – |
| 148 | – | – | – | +/– | – | – | +/– | – | – |
| type 2b | | | | | | | | | |
| 149 | – | +/– | +/– | 3 | 3 | 1 | 2 | +/– | +/– |
| type 3 | | | | | | | | | |
| 150 | +/– | +/– | +/– | +/– | +/– | +/– | 1 | 3 | 3 |
| 151 | – | – | – | – | – | – | 2 | – | 2 |
| 152 | +/– | – | – | – | – | – | 3 | – | – |
| 153 | – | – | – | – | – | – | – | 1 | – |
| 154 | +/– | 1 | 3 | – | +/– | 2 | 2 | 1 | 3 |
| 155 | – | 2 | 3 | – | 2 | 2 | 1 | 1 | 3 |
| 156 | – | – | – | – | – | – | – | – | – |
| 157 | – | – | – | +/– | +/– | – | +/– | 2 | 2 |
| 158 | 2 | – | – | – | 1 | 2 | 3 | 2 | 2 |
| 159 | – | – | – | – | +/– | +/– | – | 3 | 3 |
| 160 | – | – | – | – | +/– | – | – | 2 | 3 |
| 161 | – | – | – | – | 1 | 1 | +/– | 3 | 2 |

TABLE 8-continued

NS4 SEROTYPING

| | Type 1 NS4 | | | Type 2 NS4 | | | Type 3 NS4 | | |
|---|---|---|---|---|---|---|---|---|---|
| serum | 1 | 5 | 7 | 1 | 5 | 7 | 1 | 5 | 7 |
| type 4 | | | | | | | | | |
| 162 | 1 | – | – | – | – | – | – | – | – |
| 163 | 2 | – | – | – | +/– | +/– | +/– | – | – |

REFERENCES

Barany F (1991). Genetic disease detection and DNA amplification using cloned thermostable ligase. Proc Natl Acad Sci USA 88: 139–193.

Bej A, Mahbubani M, Miller R, Di Cesare J, Haff L, Atlas R (1990) Mutiplex PCR amplification and immobilized capture probes for detection of bacterial pathogens and indicators in water. Mol Cell Probes 4:353–365.

Bukh J, Purcell R, Miller R (1992). Sequence analysis of the 5' noncoding region of hepatitis C virus. Proc Natl Acad Sci USA 89:4942–4946.

Bukh J, Purcell R, Miller R (1993). At least 12 genotypes... PNAS 90,8234–8238.

Cha T, Beal E, Irvine B, Kolberg J, Chien D, Kuo G, Urdea M (1992) At least five related, but distinct, hepatitis C viral genotypes exist Proc Natl Acad Sci USA 89:7144–7148.

Cham S-W, Simmonds P. McOmish F, Yap P, Mitchell R, Dow B, Follet E (1991) Serological responses to infection with three different types of hepatitis C virus. Lancet 338:1991.

Chan S-W, McOmish F, Holmes E, Dow B, Peutherer J, Follett E, Yap P, Simmonds P (1992) Analysis of a new hepatitis C virus type and its phylogenetic relationship to existing variants. J Gen Virol 73:1131–1141.

Chomczynski P, Sacchi N (1987) Single step method of RNA isolation by acid guanidinium thiocyanate-phenol-chloroform extraction. Anal Biochem 162:156–159.

Choo Q, Richlman K, Han J, Berger K, Lee C, Dong C, Gallegos C, Coit D, Medina-Selby A, Barr P, Weiner A, Bradley D, Kuo G, Houghton M (1991) Genetic organization and diversity of the hepatitis C virus. Proc Natl Acad Sci USA 88:2451–2455.

Compton J (1991). Nucleic acid sequence-based amplification Nature, 350: 91–92.

Duclosal A, Eming S, Fisher P (1992) Immunization of hu-PBL-SCID mice and the resue of human monoclonal Fab fragments through combinatorial libraries. Nature 355:258–262.

Duck P (1990). Probe amplifier system based on chimeric cycling oligonucleotide. Biotechniques 9, 142–147.

Guatelli J, Whitfield K, Kwoh D, Barringer K, Richman D, Gengeras T (1990) Isothermal, in vitro amplification of nucleic acids by a multienzyme reaction modeled after retroviral replication. Proc Natl Acad Sci USA 87: 1874–1878.

Hijikata M, Kato N, Ootsuyama Y, Nakagawa M, Shimotohmo K (1991) Gene mapping of the putative structural region of the hepatitis C virus genome by in vitro processing analysis. Proc Natl Acad Sci USA 88, 5547–5551.

Jacobs K, Rudersdorf R, Neill S, Dougherty J. Brown E, Fritsch E (1988) The thermal stability of oligonucleotide duplexes is sequence independent in tetraalkylammonium salt solutions: application to identifying recombinant DNA clones. Nucl Acids Res 16:4637–4650.

Kato N, Hijikata M, Ootsuyama Y, Nakagawa M, Ohkoshi S, Sugimura T, Shimotohno K (1990) Molecular cloning of the human hepamtitis C virus genome from Japanese patients with non-A, non-B hepatitis. Proc Natl Acad Sci USA 87:9524–9528.

Kwoh D, Davis G, whitfield K, Chappelle H, Dimichele L, Gingeras T (1989). Transcription-based amplification system and detection of amplified than immunodeficiency virus type 1 with a bead-based sandwich hybridization format Proc Natl Acad Sci USA, 86: 1173–1177.

Kwok S, Kellogg D, Mckinney N, Spasic D, Goda L, Levenson C, Sinisky J, (1990). Effects of primer-template mismatches on the polymerase chain reaction: Human immunodeficiency views type 1 model studies. Nucl. Acids Res., 18: 999.

Landgren U, Kaiser R, Sanders J, Hood L (1 988). A ligase-mediated gene detection technique. Science 241:1077–1080.

Lizardi P, Guerra C, Lomeli H, Tussie-Luna I, Kramer F (1988) Exponential amplification of recombinant RNA hybrization probes. Bio/Technology 6:1197–1202.

Lomeli H Tyagi S, Printchard C, Lisardi P, Kramer F (1989) Quanitative assays based on the use of replicatable hybridization probes. Clin Chem 35: 1826–1831.

Machida A, Ohnuma H, Tsuda F, Mumelata E, Tanaka T, Akahane Y, Ocamoto H. Mishiro S (1992) Hepatology 16, 886–891.

Maniatis T, Fritsch E, Sambrook J (1982) Molecular cloning: a laboratory manual. Cold Spring Harbor Laboratory Press, Cold Spring Harbor, N.Y.

Mori S, Kato N, Yagyu A, Tanaka T, Ikeda Y, Petchclai B, Chiewsilp P, Kurimura T, Shimotohno K (1992) A new type of hepatitis C virus in patient in Thailand. Biochem Biophys Res Comm 183:334–342.

Okamoto H, Okada S, Sugiyama Y, Kurai K, Lizuka H, Machida A, Miyakawa Y, Mayumi M (1991) Nucleotide sequence of the genomic RNA of hepatitis C virus isolated from a human carrier: comparison with reported isolates for conserved and divergent regions. J Gen Virol 72:2697–2704.

Okamoto H, Kurai K, Okada S, Yamamoto , Lizuka H, Tanaka T, Fukuda S, Tsuda F, Mishiro S (1992) Full-length sequences of a hepatitis C virus genome having poor homology to reported isolates: comparative study of four distinct genotype. Virology 188:331–341.

Persson M, Caothien R, Burton D (1991). Generation of diverse high-affinity human monoclonal antibodies by repertoire cloning. Proc Natl Acad Sci USA 89:2432–2436. Saiki R, Gelfand D, Stoffel S, Scharf S, Higuchi R, Horn G, Mullis K, Erlich H (1988). Primer-directed enzymatic amplification of DNA with a thermo-stable DNA polymerase Science 239:487–491.

Saiki R, Walsh P. Levenson C, Erlich H (1989) Genetic analysis of amplified DNA with immobilized sequence-specific oligonucleotide probes (1989) Proc Natl Acad Sci USA 86:6230–6234.

Sano T, Smith C, Cantor C (1992) Immumno-PCR: very sensitive antigen detection by means of specific antibody-DNA conjugates. Science 258:120–122.

Simmonds P, McOmsh F, Yap P, Chan S, Lin C, Dusheiko G, Saeed A, Holmes E (1993), Sequence variability in the 5' noncoding region of hepatitis C virus: identification of a new virus type and restrictions on sequence diversity. J Gen Virology, 74:661–668.

Stuyver L, Rossau R, Wyseur A, Duhamel M, Vanderborght B, Van Heuverswyn H, Maertens G (1993) Typing of hepatitis C virus (HCV) isolates and characterization of a new (sub)types using a Line Probe Assay. J Gen Virology, 74: 1093–1102.

Waller G, Little M, Nadeau J, Shank D (1992). Isothermal in vitro amplification of DNA by a restriction enzyme/ DNA polymerase system. Proc Natl Acad Sci USA 89:392–396.

Wu D, Wallace B (1989). The ligation amplification reaction (LAR)—amplification of specific DNA sequences using sequential rounds of template-dependent ligation Genomics 4:560–569.

What is claimed is:

1. An isolated polynucleic acid sequence consisting of 8 or more contiguous nucleotides selected from:

an HCV type 3a genomic sequence selected from the region spanning positions 417 to 957 of the Core/E1 region of HCV subtype 3a, wherein said polynucleic acid sequence is capable of hybridizing to HCV subtype 3a, but not another subtype of HCV;

the complement of said polynucleic acid, wherein said polynucleic acid contains at least one genotype 3a-specific nucleotide.

2. A recombinant vector comprising a vector sequence; and a prokaryotic, eukaryotic or viral promoter sequence operably linked to a polynucleic acid sequence of claim 1.

3. A kit for determining the presence of HCV genotypes comprising a polynucleic acid sequence of claim 1.

4. A method of detecting or screening for one or more HCV genotypes present in a biological sample, comprising the following steps:

(i) providing a sample nucleic acid, (ii) determining the presence of a polynucleic acid sequence according to claim 1, by means of a sequencing reaction, and, (iii) inferring from the presence of one or more of these HCV polynucleic acid sequences of step (ii) the genotype(s) present in said sample.

5. A method of detecting or screening for one or more HCV genotypes present in a biological sample, comprising the following steps:

(i) providing a sample nucleic acid, (ii) specifically amplifying a polynucleic acid sequence according to claim 1, and, (iii) inferring from the presence of one or more amplified HCV polynucleic acid sequences of step (ii) the genotype(s) present in said sample.

6. An isolated HCV polynucleic acid according to claim 1, wherein said polynucleic acid is capable of acting as a primer for HCV type- or subtype-specific amplification.

7. An isolated HCV polynucleic acid according to claim 1, wherein said polynucleic acid is capable of acting as a probe for HCV type- or subtype-specific hybridisation hybridization.

8. A method for detecting HCV nucleic acids present in a biological sample comprising the following steps:

(i) providing a sample nucleic acid, (ii) determining the sequence of one or more HCV polynucleic acids according to claim 1, present in said sample.

* * * * *

```
                              SEQUENCE LISTING

<160> NUMBER OF SEQ ID NOS: 284

<210> SEQ ID NO 1
<211> LENGTH: 213
<212> TYPE: DNA
<213> ORGANISM: hepatitis C virus

<400> SEQUENCE: 1
ctcacggaac ggctttactg cgggggccct atgttcaaca gcaagggggc ccagtgtggt      60
tatcgccgct gccgtgccag tggagttctg cctaccagct tcggcaacac aatcacttgc    120
tacatcaagg ccacagcggc tgcaagggcc gcaggcctcc ggaacccgga ctttcttgtc    180
tgcggagatg atctggtcgt ggtggctgag agt                                 213

<210> SEQ ID NO 2
<211> LENGTH: 71
<212> TYPE: PRT
<213> ORGANISM: hepatitis C virus

<400> SEQUENCE: 2

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Arg Ala Ala Gly Leu Arg Asn Pro Asp Phe Leu Val Cys Gly Asp Asp
    50                  55                  60

Leu Val Val Val Ala Glu Ser
65                  70

<210> SEQ ID NO 3
<211> LENGTH: 213
<212> TYPE: DNA
<213> ORGANISM: hepatitis C virus

<400> SEQUENCE: 3
ctcacggaac ggctttactg cgggggccct atgttcaaca gcaagggggc ccagtgtggt      60
tatcgccgct gccgtgccag tggagttctg cctaccagct tcggcaacac aatcacttgc    120
tacatcaagg ccacagcggc tgcaagggcc gcaggcctcc ggaacccgga ctttcttgtc    180
tgcggagatg atctggtcgt ggtggctgag agt                                 213

<210> SEQ ID NO 4
<211> LENGTH: 71
<212> TYPE: PRT
<213> ORGANISM: hepatitis C virus

<400> SEQUENCE: 4

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30
```

```
Ser Phe Gly Asn Thr Ile Thr Cys Tyr Ile Lys Ala Thr Ala Ala Ala
        35                  40                  45

Lys Ala Ala Gly Leu Arg Asn Pro Asp Phe Leu Val Cys Gly Asp Asp
    50                  55                  60

Leu Val Val Val Ala Glu Ser
65                  70

<210> SEQ ID NO 5
<211> LENGTH: 213
<212> TYPE: DNA
<213> ORGANISM: hepatitis C virus

<400> SEQUENCE: 5
ctcacggagc ggctttactg cgggggccct atgtttaaca gcaaggggc ccagtgtggt      60 tatcgccgtt gccgtgccag tggagttctg cctaccagct tcggcaacac aatcacttgt    120
tacatcaaag ccacagcggc cgcaaaagcc gcaggcctcc ggagcccgga ctttcttgtc    180
tgcggagatg atctggtcgt ggtggctgag agt                                  213

<210> SEQ ID NO 6
<211> LENGTH: 71
<212> TYPE: PRT
<213> ORGANISM: hepatitis C virus

<400> SEQUENCE: 6

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
        35                  40                  45

Lys Ala Ala Gly Leu Arg Ser Pro Asp Phe Leu Val Cys Gly Asp Asp
    50                  55                  60

Leu Val Val Val Ala Glu Ser
65                  70

<210> SEQ ID NO 7
<211> LENGTH: 213
<212> TYPE: DNA
<213> ORGANISM: hepatitis C virus

<400> SEQUENCE: 7
ctcacggagc ggctttactg cgggggccct atgtttaaca gcaaaggggc ccagtgtggt     60
tatcgccgtt gccgtgccag tggagttctg cctaccagct tcggcaacac aatcacttgt   120
tacatcaaag ccacagcggc cgcaaaagcc gcaggcctcc ggagcccgga ctttcttgtc   180
tgcggagatg atctggtcgt ggtggctgag agt                                 213

<210> SEQ ID NO 8
<211> LENGTH: 71
<212> TYPE: PRT
<213> ORGANISM: hepatitis C virus

<400> SEQUENCE: 8

Leu Thr Glu Arg Leu Tyr Cys Gly Gly Pro Met Phe Asn Ser Lys Gly
1               5                   10                  15

Ala Gln Cys Gly Tyr Arg Arg Cys Arg Ala Ser Gly Val Leu Pro Thr
            20                  25                  30

Ser Phe Gly Asn Thr Ile Thr Cys Tyr Ile Lys Ala Thr Ala Ala Ala
```

```
                35                  40                  45
Lys Ala Gly Leu Arg Ser Pro Asp Phe Leu Val Cys Gly Asp Asp
         50                  55                  60

Leu Val Val Val Ala Glu Ser
 65                  70

<210> SEQ ID NO 9
<211> LENGTH: 213
<212> TYPE: DNA
<213> ORGANISM: hepatitis C virus

<400> SEQUENCE: 9
ctcacggagc ggctttactg cgggggccct atgttcaaca gcaagggggc ccagtgtggt      60
tatcgccgtt gtcgtgccag tggagttctg cctaccagtt tcggcaacac aatcacttgt    120
tacatcaagg ccacagcggc tgcaaaagcc gcaggcctcc ggaacccgga ctttcttgtt    180
tgcggagatg atttggtcgt ggtggctgag agt                                 213

<210> SEQ ID NO 10
<211> LENGTH: 71
<212> TYPE: PRT
<213> ORGANISM: hepatitis C virus

<400> SEQUENCE: 10

Leu Thr Glu Arg Leu Tyr Cys Gly Gly Pro Met Phe Asn Ser Lys Gly
 1               5                  10                  15

Ala Gln Cys Gly Tyr Arg Arg Cys Arg Ala Ser Gly Val Leu Pro Thr
             20                  25                  30

Ser Phe Gly Asn Thr Ile Thr Cys Tyr Ile Lys Ala Thr Ala Ala Ala
         35                  40                  45

Lys Ala Gly Leu Arg Asn Pro Asp Phe Leu Val Cys Gly Asp Asp
         50                  55                  60

Leu Val Val Val Ala Glu Ser
 65                  70

<210> SEQ ID NO 11
<211> LENGTH: 213
<212> TYPE: DNA
<213> ORGANISM: hepatitis C virus

<400> SEQUENCE: 11
ctcacggagc ggctttactg cgggggccct atgttcaaca gcaagggggc ccagtgtggt      60
tatcgccgtt gtcgtgccag tggagttctg cctaccagtt tcggcaacac aatcacttgt    120
tacatcaagg ccacagcggc tgcaaaagcc gcaggcctcc ggaacccgga ctttcttgtt    180
tgcggagatg atttggtcgt ggtggctgag agt                                 213

<210> SEQ ID NO 12
<211> LENGTH: 71
<212> TYPE: PRT
<213> ORGANISM: hepatitis C virus

<400> SEQUENCE: 12

Leu Thr Glu Arg Leu Tyr Cys Gly Gly Pro Met Phe Asn Ser Lys Gly
 1               5                  10                  15

Ala Gln Cys Gly Tyr Arg Arg Cys Arg Ala Ser Gly Val Leu Pro Thr
             20                  25                  30

Ser Phe Gly Asn Thr Ile Thr Cys Tyr Ile Lys Ala Thr Ala Ala Ala
         35                  40                  45
```

```
Lys Ala Ala Gly Leu Arg Asn Pro Asp Phe Leu Val Cys Gly Asp Asp
 50                  55                  60

Leu Val Val Ala Glu Ser
 65              70
```

<210> SEQ ID NO 13
<211> LENGTH: 541
<212> TYPE: DNA
<213> ORGANISM: hepatitis C virus

<400> SEQUENCE: 13

```
cgtcggcgct cctgtaggag gcgtcgcaag agcccttgcg catggcgtga gggcccttga    60
agacgggata aatttcgcaa cagggaattt gcccggttgc tccttttcta tcttccttct   120
tgctctgttc tcttgcttaa tccatccagc agctagtcta gagtggcgga acacgtctgg   180
cctctatgtc cttaccaacg actgttccaa tagcagtatt gtgtatgagg ccgatgacgt   240
tattctgcac acacccggct gtgtaccttg tgttcaggac ggtaatacat ctgcgtgctg   300
gaccccagtg acacctacag tggcagtcag gtacgtcgga gcaaccaccg cttcgatacg   360
caggcatgta gacatgttgg tgggcgcggc cacgatgtgc tctgctctct acgtgggtga   420
tatgtgtggg gccgtcttcc tcgtgggaca agccttcacg ttcagacctc gtcgccatca   480
aacggtccag acctgtaact gctcactgta cccaggccat ctttcaggac accgaatggc   540
t                                                                   541
```

<210> SEQ ID NO 14
<211> LENGTH: 180
<212> TYPE: PRT
<213> ORGANISM: hepatitis C virus

<400> SEQUENCE: 14

```
Val Gly Ala Pro Val Gly Gly Val Ala Arg Ala Leu Ala His Gly Val
 1               5                  10                  15

Arg Ala Leu Glu Asp Gly Ile Asn Phe Ala Thr Gly Asn Leu Pro Gly
             20                  25                  30

Cys Ser Phe Ser Ile Phe Leu Leu Ala Leu Phe Ser Cys Leu Ile His
         35                  40                  45

Pro Ala Ala Ser Leu Glu Trp Arg Asn Thr Ser Gly Leu Tyr Val Leu
     50                  55                  60

Thr Asn Asp Cys Ser Asn Ser Ser Ile Val Tyr Glu Ala Asp Asp Val
 65                  70                  75                  80

Ile Leu His Thr Pro Gly Cys Val Pro Cys Val Gln Asp Gly Asn Thr
                 85                  90                  95

Ser Ala Cys Trp Thr Pro Val Thr Pro Thr Val Ala Val Arg Tyr Val
            100                 105                 110

Gly Ala Thr Thr Ala Ser Ile Arg Arg His Val Asp Met Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180
```

<210> SEQ ID NO 15
<211> LENGTH: 541
<212> TYPE: DNA
<213> ORGANISM: hepatitis C virus

<400> SEQUENCE: 15

```
cgtcggcgct cctgtaggag gcgtcgcaag agcccttgcg catggcgtga gggcccttga      60
agacgggata aatttcgcaa caggaatttt gcccggttgc tccttttcta tcttccttcc     120
tgctctgttc tcttgcttaa tccatccagc agctagtcta gagtggcgga acacgtctgg     180
cctctatgtc cttaccaacg actgttccaa tagcagtatt tgtatgagg ccgatgacgt      240
tattctgcac acaccggct gtgtaccttg tgttcaggac ggtaatacat ctgcgtgctg      300
gaccccagtg acacctacag tggcagtcag gtacgtcgga gcaaccaccg cttcgatacg     360
caggcatgta gacatattgg tgggcgcggc cacaatgtgc tctgctctct acgtgggtga     420
tatgtgtggg gccgtcttcc tcgtgggaca agccttcacg ttcagacctc gtcgccatca     480
aacggtccag acctgtaact gctcactgta cccaggccat ctttcaggac accgaatggc     540
t                                                                     541
```

<210> SEQ ID NO 16
<211> LENGTH: 180
<212> TYPE: PRT
<213> ORGANISM: hepatitis C virus

<400> SEQUENCE: 16

```
Val Gly Ala Pro Val Gly Gly Val Ala Arg Ala Leu Ala His Gly Val
 1               5                  10                  15

Arg Ala Leu Glu Asp Gly Ile Asn Phe Ala Thr Gly Asn Leu Pro Gly
            20                  25                  30

Cys Ser Phe Ser Ile Phe Leu Pro Ala Leu Phe Ser Cys Leu Ile His
        35                  40                  45

Pro Ala Ala Ser Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Thr Pro Gly Cys Val Pro Cys Val Gln Asp Gly Asn Thr
                85                  90                  95

Ser Ala Cys Trp Thr Pro Val Thr Pro Thr Val Ala Val Arg Tyr Val
            100                 105                 110

Gly Ala Thr Thr Ala Ser Ile Arg Arg His Val Asp Ile Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg His Gln
145                 150                 155                 160

Thr Val Gln Thr Cys Asn Cys Ser Leu Tyr Pro Gly His Leu Ser Gly
                165                 170                 175

His Arg Met Ala
            180
```

<210> SEQ ID NO 17
<211> LENGTH: 541
<212> TYPE: DNA
<213> ORGANISM: hepatitis C virus

<400> SEQUENCE: 17

-continued

```
cgtcggcgct cctgtaggag gcgtcgcaag agcccttgcg catggcgtga gggcccttga      60
agacgggata aatttcgcaa cagggaattt gcccggttgc tccttttcta tcttccttct     120
tgctctgttc tcttgcttaa tccatccagc agctagtcta gagtggcgga acacgtctgg     180
cctctacgtc cttaccaacg actgttccaa tagcagtatt gtgtatgagg ccgatgacgt     240
tattctgcac acacccggct gtgtaccttg tgttcaggac ggtaatacat ctgcgtgctg     300
gaccccagtg acacctacag tggcagtcag gtacgtcgga gcaaccaccg cttcgatacg     360
caggcatgta gacatattgg tgggcgcggc cacgatgtgc tctgctctct acgtgggtga     420
tatgtgtggg gccgtcttcc tcgtgggaca agccttcacg ttcagacctc gtcgccatca     480
aacggtccag acctgtaact gctcactgta cccaggccat ctttcaggac accgaatggc     540
t                                                                     541
```

<210> SEQ ID NO 18
<211> LENGTH: 180
<212> TYPE: PRT
<213> ORGANISM: hepatitis C virus

<400> SEQUENCE: 18

```
Val Gly Ala Pro Val Gly Gly Val Ala Arg Ala Leu Ala His Gly Val
1               5                   10                  15

Arg Ala Leu Glu Asp Gly Ile Asn Phe Ala Thr Gly Asn Leu Pro Gly
            20                  25                  30

Cys Ser Phe Ser Ile Phe Leu Leu Ala Leu Phe Ser Cys Leu Ile His
        35                  40                  45

Pro Ala Ala Ser Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Thr Pro Gly Cys Val Pro Cys Val Gln Asp Gly Asn Thr
                85                  90                  95

Ser Ala Cys Trp Thr Pro Val Thr Pro Thr Val Ala Val Arg Tyr Val
            100                 105                 110

Gly Ala Thr Thr Ala Ser Ile Arg Arg His Val Asp Ile Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180
```

<210> SEQ ID NO 19
<211> LENGTH: 541
<212> TYPE: DNA
<213> ORGANISM: hepatitis C virus

<400> SEQUENCE: 19

```
cgtcggcgct cccgtaggag gcgtcgcaag agcccttgcg catggcgtga gggcccttga      60
agacgggata aatttcgcaa cagggaattt gcccggttgc tccttttcta ttttccttct     120
tgctctgttc tcttgcttaa ttcatccagc agctagtcta gagtggcgga atacgtctgg     180
```

-continued

```
cctctatgtc cttaccaacg actgttccaa tagcagtatt gtgtacgagg ccgatgacgt      240
tattctgcac acacccggct gcataccttg tgtccaggac ggcaatacat ccacgtgctg      300 gacccccagtg acacctacag tggcagtcaa gtacgtcgga gcaaccaccg cttcgatacg     360
cagtcatgtg gacctattag tgggcgcggc cacgatgtgc tcagcgctct acgtgggtga     420
tatgtgtggg gccgtcttcc ttgtgggaca agccttcacg ttcagacctc gtcgccatca     480
aacggtccag acctgtaact gctcgctgta cccaggccat ctttcaggac atcgaatggc     540
t                                                                     541
```

<210> SEQ ID NO 20
<211> LENGTH: 180
<212> TYPE: PRT
<213> ORGANISM: hepatitis C virus

<400> SEQUENCE: 20

```
Val Gly Ala Pro Val Gly Gly Val Ala Arg Ala Leu Ala His Gly Val
1               5                  10                   15

Arg Ala Leu Glu Asp Gly Ile Asn Phe Ala Thr Gly Asn Leu Pro Gly
            20                  25                   30

Cys Ser Phe Ser Ile Phe Leu Leu Ala Leu Phe Ser Cys Leu Ile His
        35                  40                  45

Pro Ala Ala Ser Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Thr Pro Gly Cys Ile Pro Cys Val Gln Asp Gly Asn Thr
                85                  90                  95

Ser Thr Cys Trp Thr Pro Val Thr Pro Thr Val Ala Val Lys Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180
```

<210> SEQ ID NO 21
<211> LENGTH: 541
<212> TYPE: DNA
<213> ORGANISM: hepatitis C virus

<400> SEQUENCE: 21

```
cgtcggcgct cccgtaggag gcgtcgcaag agcccttgcg catggcgtga gggcccttga      60
agacgggata aatttcgcaa cagggaattt gcccggttgc tccttttcta ttttccttct     120
tgctctgttc tcttgcttaa ttcatccagc agctagtcta gagtggcgga atacgtctgg    180
cctctatgtc cttaccaacg actgttccaa tagcagtatt gtgtacgagg ccgatgacgt     240
tattctgcac acacccggct gcataccttg tgtccaggac ggcaatacat ccacgtgctg     300 gacccccagtg acacctacag tggcagtcaa gtacgtcgga gcaaccaccg cttcgatacg    360
cagtcatgtg gacctattag tgggcgcggc cacgatgtgc tctgcgctct acgtgggtga    420
```

```
catgtgtggg gctgtcttcc tcgtgggaca agccttcacg ttcagacctc gtcgccatca      480
aacggtccag acctgtaact gctcgctgta cccaggccat ctttcaggac atcgaatggc      540
t                                                                       541
```

<210> SEQ ID NO 22
<211> LENGTH: 180
<212> TYPE: PRT
<213> ORGANISM: hepatitis C virus

<400> SEQUENCE: 22

```
Val Gly Ala Pro Val Gly Val Ala Arg Ala Leu Ala His Gly Val
1               5                   10                  15

Arg Ala Leu Glu Asp Gly Ile Asn Phe Ala Thr Gly Asn Leu Pro Gly
                20                  25                  30

Cys Ser Phe Ser Ile Phe Leu Leu Ala Leu Phe Ser Cys Leu Ile His
                35                  40                  45

Pro Ala Ala Ser Leu Glu Trp Arg Asn Thr Ser Gly Leu Tyr Val Leu
        50                  55                  60

Thr Asn Asp Cys Ser Asn Ser Ser Ile Val Tyr Glu Ala Asp Asp Val
65                  70                  75                  80

Ile Leu His Thr Pro Gly Cys Ile Pro Cys Val Gln Asp Gly Asn Thr
                85                  90                  95

Ser Thr Cys Trp Thr Pro Val Thr Pro Thr Val Ala Val Lys Tyr Val
                100                 105                 110

Gly Ala Thr Thr Ala Ser Ile Arg Ser His Val Asp Leu Leu Val Gly
            115                 120                 125

Ala Ala Thr Met Cys Ser Ala Leu Tyr Val Gly Asp Met Cys Gly Ala
        130                 135                 140

Val Phe Leu Val Gly Gln Ala Phe Thr Phe Arg Pro Arg His Gln
145                 150                 155                 160

Thr Val Gln Thr Cys Asn Cys Ser Leu Tyr Pro Gly His Leu Ser Gly
                165                 170                 175

His Arg Met Ala
            180
```

<210> SEQ ID NO 23
<211> LENGTH: 541
<212> TYPE: DNA
<213> ORGANISM: hepatitis C virus

<400> SEQUENCE: 23

```
cgtcggcgct cccgtaggag gcgtcgcaag agcccttgcg catggcgtga gggcccttga      60
ggacgggata aacttcgcaa cagggaattt gcccggttgc tccttttcta tcttccttct     120
tgctctgttc tcttgcttaa tccatccagc agctggtcta gagtggcgga atacgtctgg     180
cctctatgtc cttaccaacg actgttccaa tagtagtatt gtgtatgagg ccgatgacgt     240
tattctgcac gcgcccggct gtgtaccttg tgtccaggac ggcaatacgt ctacatgctg     300
gaccccagta acacctacag tggcagtcag gtacgtcggg gcaaccaccg cttcgatacg     360
cagtcatgtg gacctgttag taggcgcggc cacgatgtgc tctgcgcttt acgtgggtga     420
tatgtgtggg gccgtcttcc tcgtgggaca agccttcacg ttcagacccc gccgccatca     480
aacggtccag acctgtaact gctcgctgta cccaggccat ctttcaggac atcgcatggc     540
t                                                                       541
```

```
<210> SEQ ID NO 24
<211> LENGTH: 180
<212> TYPE: PRT
<213> ORGANISM: hepatitis C virus

<400> SEQUENCE: 24

Val Gly Ala Pro Val Gly Val Ala Arg Ala Leu Ala His Gly Val
1               5                   10                  15

Arg Ala Leu Glu Asp Gly Ile Asn Phe Ala Thr Gly Asn Leu Pro Gly
                20                  25                  30

Cys Ser Phe Ser Ile Phe Leu Leu Ala Leu Phe Ser Cys Leu Ile His
            35                  40                  45

Pro Ala Ala Gly Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Ala Pro Gly Cys Val Pro Cys Val Gln Asp Gly Asn Thr
                85                  90                  95

Ser Thr Cys Trp Thr Pro Val Thr Pro Thr Val Ala Val Arg Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
    130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180

<210> SEQ ID NO 25
<211> LENGTH: 541
<212> TYPE: DNA
<213> ORGANISM: hepatitis C virus

<400> SEQUENCE: 25
cgtcggcgct cccgtaggag gcgtcgcaag agcccttgcg catggcgtga gggcccttga      60
ggacgggata aacttcgcaa cagggaattt gcccggttgc tcttttttcta tcttccttct    120 tgctctgttc tcttgcttaa tccatccagc agctggtcta gagtggcgga atacgtctgg    180
cctctatgtc cttaccaacg actgttccaa tagtagtatt gtgtatgagg ccgatgacgt    240
tattctgcac gcgcccggct gtgtaccttg tgtccaggac ggcaatacgt ctacatgctg    300
gaccccagta acacctacag tggcagtcag gtacgtcggg gcaaccaccg cttcgatacg    360
cagtcatgtg gacctgttag taggcgcggc cacgatgtgc tctgcgcttt acgtgggtga    420
tatgtgtggg gccgtcttcc tcgtgggaca agccttcacg ttcagacccc gccgccatca    480
aacggtccag acctgtaact gctcgctgta cccaggccat ctttcaggac atcgaatggc    540
t                                                                    541

<210> SEQ ID NO 26
<211> LENGTH: 180
<212> TYPE: PRT
<213> ORGANISM: hepatitis C virus

<400> SEQUENCE: 26
```

```
Val Gly Ala Pro Val Gly Gly Val Ala Arg Ala Leu Ala His Gly Val
1               5                   10                  15

Arg Ala Leu Glu Asp Gly Ile Asn Phe Ala Thr Gly Asn Leu Pro Gly
            20                  25                  30

Cys Ser Phe Ser Ile Phe Leu Leu Ala Leu Phe Ser Cys Leu Ile His
        35                  40                  45

Pro Ala Ala Gly Leu Glu Trp Arg Asn Thr Ser Gly Leu Tyr Val Leu
    50                  55                  60

Thr Asn Asp Cys Ser Asn Ser Ser Ile Val Tyr Glu Ala Asp Asp Val
65                  70                  75                  80

Ile Leu His Ala Pro Gly Cys Val Pro Cys Val Gln Asp Gly Asn Thr
                85                  90                  95

Ser Thr Cys Trp Thr Pro Val Thr Pro Thr Val Ala Val Arg Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
            180

<210> SEQ ID NO 27
<211> LENGTH: 541
<212> TYPE: DNA
<213> ORGANISM: hepatitis C virus

<400> SEQUENCE: 27
cgtcggcgct cccgtaggag gcgtcgcaag agcccttgcg catggcgtga gggcccttga      60
ggacgggata aacttcgcaa cagggaattt gcccggttgc tcttttttcta tcttccttct    120
tgctctgttc tcttgcttaa tccatccagc agctggtcta gagtggcgga atacgtctgg    180
cctctatgtc cttaccaacg actgttccaa tagtagtatt gtgtatgagg ccgatgacgt    240
tattctgcac gcgcccggct gtgtaccttg tgtccaggac ggcaatacgt ctacatgctg    300
gaccccagta acacctacag tggcagtcag gtacgtcggg gcaaccaccg cttcgatacg    360
cagtcatgtg gacctgttag taggcgcggc cacgatgtgc tctgcgcttt acgtgggtga    420
tatgtgtggg gccgtcttcc tcgtgggaca agccttcacg ttcagacccc gccgccatca    480
aacggtccag acctgtaact gctcgctgta cccaggccat ctttcaggac atcgaatggc    540
t                                                                   541

<210> SEQ ID NO 28
<211> LENGTH: 180
<212> TYPE: PRT
<213> ORGANISM: hepatitis C virus

<400> SEQUENCE: 28

Val Gly Ala Pro Val Gly Gly Val Ala Arg Ala Leu Ala His Gly Val
1               5                   10                  15

Arg Ala Leu Glu Asp Gly Ile Asn Phe Ala Thr Gly Asn Leu Pro Gly
            20                  25                  30
```

-continued

```
Cys Ser Phe Ser Ile Phe Leu Leu Ala Leu Phe Ser Cys Leu Ile His
         35                  40                  45

Pro Ala Ala Gly Leu Glu Trp Arg Asn Thr Ser Gly Leu Tyr Val Leu
     50                  55                  60

Thr Asn Asp Cys Ser Asn Ser Ser Ile Val Tyr Glu Ala Asp Asp Val
 65                  70                  75                  80

Ile Leu His Ala Pro Gly Cys Val Pro Cys Val Gln Asp Gly Asn Thr
                 85                  90                  95

Ser Thr Cys Trp Thr Pro Val Thr Pro Thr Val Ala Val Arg Tyr Val
            100                 105                 110

Gly Ala Thr Thr Ala Ser Ile Arg Ser His Val Asp Leu Leu Val Gly
        115                 120                 125

Ala Ala Thr Met Cys Ser Ala Leu Tyr Val Gly Asp Met Cys Gly Ala
130                 135                 140

Val Phe Leu Val Gly Gln Ala Phe Thr Phe Arg Pro Arg Arg His Gln
145                 150                 155                 160

Thr Val Gln Thr Cys Asn Cys Ser Leu Tyr Pro Gly His Leu Ser Gly
                165                 170                 175

His Arg Met Ala
        180
```

<210> SEQ ID NO 29
<211> LENGTH: 287
<212> TYPE: DNA
<213> ORGANISM: hepatitis C virus

<400> SEQUENCE: 29

```
tagactttttg ggagagcgtc ttcactggac taactcacat agatgcccac tttctgtcac      60
agactaagca gcagggactc aacttctcgt tcctgactgc ctaccaagcc actgtgtgcg     120
ctcgcgcgca ggctcctccc ccaagttggg acgagatgtg gaagtgtctc gtacggctta     180
agccaacact acatggacct acgcctcttc tatatcggtt ggggcctgtc caaaatgaaa     240
tctgcttgac acccccatc acaaaataca tcatggcatg catgtca                    287
```

<210> SEQ ID NO 30
<211> LENGTH: 95
<212> TYPE: PRT
<213> ORGANISM: hepatitis C virus

<400> SEQUENCE: 30

```
Asp Phe Trp Glu Ser Val Phe Thr Gly Leu Thr His Ile Asp Ala His
 1               5                  10                  15

Phe Leu Ser Gln Thr Lys Gln Gln Gly Leu Asn Phe Ser Phe Leu Thr
             20                  25                  30

Ala Tyr Gln Ala Thr Val Cys Ala Arg Ala Gln Ala Pro Pro Pro Ser
         35                  40                  45

Trp Asp Glu Met Trp Lys Cys Leu Val Arg Leu Lys Pro Thr Leu His
     50                  55                  60

Gly Pro Thr Pro Leu Leu Tyr Arg Leu Gly Pro Val Gln Asn Glu Ile
 65                  70                  75                  80

Cys Leu Thr His Pro Ile Thr Lys Tyr Ile Met Ala Cys Met Ser
                 85                  90                  95
```

<210> SEQ ID NO 31
<211> LENGTH: 401
<212> TYPE: DNA
<213> ORGANISM: hepatitis C virus -continued

<400> SEQUENCE: 31

```
tccaaaatga aatctgcttg acacacccccg tcacaaaata cattatggca tgcatgtcag      60
ctgatctgga agtaaccacc agcacctggg tgttgcttgg aggggtcctc gcggccctag     120
cggcctactg cttgtcagtc ggctgcgttg taatcgtggg tcatatcgag ctggggggca     180
agccggcact cgttccagac aaggaggtgt tgtatcaaca gtacgatgag atggaggagt     240
gctcgcaagc cgccccatac atcgaacaag ctcaggtaat agcccaccag ttcaaggaga     300
aaatccttgg actgctgcag cgagccaccc aacaacaagc tgtcattgag cccgtaatag     360
cttccaactg gcaaaagctt gaaaccttct ggcacaagca t                         401
```

<210> SEQ ID NO 32
<211> LENGTH: 133
<212> TYPE: PRT
<213> ORGANISM: hepatitis C virus

<400> SEQUENCE: 32

```
Gln Asn Glu Ile Cys Leu Thr His Pro Val Thr Lys Tyr Ile Met Ala
1               5                   10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Leu Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Ile Leu Gly Leu Leu Gln Arg Ala Thr Gln Gln Gln
            100                 105                 110

Ala Val Ile Glu Pro Val Ile Ala Ser Asn Trp Gln Lys Leu Glu Thr
        115                 120                 125

Phe Trp His Lys His
        130
```

<210> SEQ ID NO 33
<211> LENGTH: 401
<212> TYPE: DNA
<213> ORGANISM: hepatitis C virus

<400> SEQUENCE: 33

```
tccaaaatga aatctgcttg acacacccccg tcacaaaata cattatggca tgcatgtcag      60
ctgatctgga agtaaccacc agcacctggg tgttgcttgg aggggtcctc gcggccctag     120
cggcctactg cttgtcagtc ggctgcgttg taatcgtggg tcatatcgag ctggggggca     180
agccggcact cgttccagac aaggaggtgt tgtatcaaca gtacgatgag atggaggagt     240
gctcgcaagc cgccccatac atcgaacaag ctcaggtaat agcccaccag ttcaaggaga     300
aaatccttgg actgctgcag cgagccaccc aacaacaagc tgtcattgag cccgtaatag     360
cttccaactg gcaaaagctt gaaaccttct ggcacaagca t                         401
```

<210> SEQ ID NO 34
<211> LENGTH: 133
<212> TYPE: PRT
<213> ORGANISM: hepatitis C virus -continued

```
<400> SEQUENCE: 34

Gln Asn Glu Ile Cys Leu Thr His Pro Val Thr Lys Tyr Ile Met Ala
1               5                   10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Leu Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Ile Leu Gly Leu Leu Gln Arg Ala Thr Gln Gln Gln
            100                 105                 110

Ala Val Ile Glu Pro Val Ile Ala Ser Asn Trp Gln Lys Leu Glu Thr
        115                 120                 125

Phe Trp His Lys His
    130

<210> SEQ ID NO 35
<211> LENGTH: 401
<212> TYPE: DNA
<213> ORGANISM: hepatitis C virus

<400> SEQUENCE: 35
tccaaaatga atctgcttg acacacccca tcacaaaata catcatggca tgcatgtcag    60
ctgatctgga agtaaccacc agcacctggg ttttgcttgg aggggtcctc gcggccctag   120
cggcctactg cttgtcagtc ggttgtgttg tgattgtggg tcatatcgag ctggggggca   180
agccggcaat cgttccagac aaagaggtgt tgtatcaaca atacgatgag atggaagagt   240
gctcacaagc tgccccatat atcgaacaag ctcaggtaat agctcaccag ttcaagggaa   300
aagtccttgg attgctgcag cgagccaccc aacaacaagc tgtcattgag cccatagtaa   360
ctaccaactg caaaagcctt gaggcctttt ggcacaagca t                       401

<210> SEQ ID NO 36
<211> LENGTH: 133
<212> TYPE: PRT
<213> ORGANISM: hepatitis C virus

<400> SEQUENCE: 36

Gln Asn Glu Ile Cys Leu Thr His Pro Ile Thr Lys Tyr Ile Met Ala
1               5                   10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Ile Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Gly Lys Val Leu Gly Leu Leu Gln Arg Ala Thr Gln Gln Gln
```

```
                    100                 105                 110
Ala Val Ile Glu Pro Ile Val Thr Thr Asn Trp Gln Lys Leu Glu Ala
        115                 120                 125

Phe Trp His Lys His
    130

<210> SEQ ID NO 37
<211> LENGTH: 401
<212> TYPE: DNA
<213> ORGANISM: hepatitis C virus

<400> SEQUENCE: 37
tccaaaatga aatctgcttg acacacccca tcacaaaata catcatggca tgcatgtcag        60
ctgatctgga agtaaccacc agcacctggg ttttgcttgg aggggtcctc gcggccctag       120
cggcctactg cttgtcagtc ggttgtgttg tgattgtggg tcatatcgag ctggggggca       180
agccggcaat cgttccagac aaagaggtgt tgtatcaaca atacgatgag atggaagagt       240
gctcacaagc tgccccatat atcgaacaag ctcaggtgat agctcaccag ttcaaggaaa       300
aagtccttgg attgctgcag cgagccaccc aacaacaagc tgtcattgag cccatagtaa       360
ctaccaactg gcaaaagctt gaggcctttt ggcacaagca t                           401

<210> SEQ ID NO 38
<211> LENGTH: 133
<212> TYPE: PRT
<213> ORGANISM: hepatitis C virus

<400> SEQUENCE: 38

Gln Asn Glu Ile Cys Leu Thr His Pro Ile Thr Lys Tyr Ile Met Ala
1               5                   10                  15

Cys Met Ser Ala Asp Leu Glu Val Thr Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Ile Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Val Leu Gly Leu Leu Gln Arg Ala Thr Gln Gln Gln
            100                 105                 110

Ala Val Ile Glu Pro Ile Val Thr Thr Asn Trp Gln Lys Leu Glu Ala
        115                 120                 125

Phe Trp His Lys His
    130

<210> SEQ ID NO 39
<211> LENGTH: 401
<212> TYPE: DNA
<213> ORGANISM: hepatitis C virus

<400> SEQUENCE: 39
tccaaaatga aatctgcttg acacacccca tcacaaaata catcatggca tgcatgtcag        60
ctgatctgga agtaaccacc agcacctggg ttttgcttgg aggggtcctc gcggccctag       120
cggcctactg cttgtcagtc ggttgtgttg tgattgtggg tcatatcgag ctggggggca       180
```

| agccggcaat cgttccagac aaagaggtgt tgtatcaaca atacgatgag atggaagagt | 240 |
| gctcacaagc tgccccatat atcgaacaag ctcaggtaat agctcaccag ttcaaggaaa | 300 |
| aagtccttgg attgctgcag cgagccaccc aacaacaagc tgtcattgag cccatagtaa | 360 |
| ctaccaactg gcaaaagctt gaggcctttt ggcacaagca t | 401 |

```
<210> SEQ ID NO 40
<211> LENGTH: 133
<212> TYPE: PRT
<213> ORGANISM: hepatitis C virus

<400> SEQUENCE: 40
```

Gln Asn Glu Ile Cys Leu Thr His Pro Ile Thr Lys Tyr Ile Met Ala
1               5                   10                  15

Cys Met Ser Ala Asp Leu Glu Val Thr Ser Thr Trp Val Leu Leu
            20                  25                  30

Gly Gly Val Leu Ala Ala Leu Ala Ala Tyr Cys Leu Ser Val Gly Cys
        35                  40                  45

Val Val Ile Val Gly His Ile Glu Leu Gly Gly Lys Pro Ala Ile Val
    50                  55                  60

Pro Asp Lys Glu Val Leu Tyr Gln Gln Tyr Asp Glu Met Glu Glu Cys
65                  70                  75                  80

Ser Gln Ala Ala Pro Tyr Ile Glu Gln Ala Gln Val Ile Ala His Gln
                85                  90                  95

Phe Lys Glu Lys Val Leu Gly Leu Leu Gln Arg Ala Thr Gln Gln Gln
            100                 105                 110

Ala Val Ile Glu Pro Ile Val Thr Thr Asn Trp Gln Lys Leu Glu Ala
        115                 120                 125

Phe Trp His Lys His
    130

```
<210> SEQ ID NO 41
<211> LENGTH: 509
<212> TYPE: DNA
<213> ORGANISM: hepatitis C virus

<400> SEQUENCE: 41
```

| ccatgagcac gaatcctaaa cctcaaagaa aaaccaaaag aaacaccaac cgtcgcccac | 60 |
| aggacgtcaa gttcccgggc ggtggtcaga tcgttggcgg agtttacttg ttgccgcgca | 120 |
| ggggccctag gatgggtgtg cgcgcgactc ggaagacttc ggaacggtcg caaccccgtg | 180 |
| gacggcgtca gcctattccc aaggcgcgcc agcccacggg ccggtcctgg ggtcaacccg | 240 |
| ggtacccttg gccccttttac gccaatgagg gcctcgggtg ggcagggtgg ctgctctccc | 300 |
| ctcgaggctc tcggcctaat tggggcccca atgaccccg gcgaaaatcg cgtaatttgg | 360 |
| gtaaggtcat cgataccota acgtgcggat tcgccgatct catggggtat atccogctcg | 420 |
| taggcggccc cattgggggc gtcgcaaggg ctctcgcaca cggtgtgagg gtccttgagg | 480 |
| acggggtaaa ctatgcaaca gggaattta | 509 |

```
<210> SEQ ID NO 42
<211> LENGTH: 169
<212> TYPE: PRT
<213> ORGANISM: hepatitis C virus

<400> SEQUENCE: 42
```

Met Ser Thr Asn Pro Lys Pro Gln Arg Lys Thr Lys Arg Asn Thr Asn
1               5                   10                  15

```
Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
            115                 120                 125

Gly Phe Ala Asp Leu Met Gly Tyr Ile Pro Leu Val Gly Gly Pro Ile
        130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu
                165
```

<210> SEQ ID NO 43
<211> LENGTH: 509
<212> TYPE: DNA
<213> ORGANISM: hepatitis C virus

<400> SEQUENCE: 43

```
ccatgagcac gaatcctaaa cctcaaagaa aaccaaaag aaacaccaac cgtcgcccac      60
aggacgtcaa gttcccgggc ggtggtcaga tcgttggcgg agtttacttg ttgccgcgca    120
ggggccctag gatgggtgtg cgcgcgactc ggaagacttc ggaacggtcg caaccccgtg    180
gacggcgtca gcctattccc aaggcgcgcc agcccacggg ccggtcctgg ggtcaacccg    240
ggtacccttg ccccttttac gccaatgagg gcctcgggtg ggcagggtgg ctgctctccc    300
ctcgaggctc tcggcctaat tggggcccca atgaccccg gcgaaaatcg cgtaatttgg     360
gtaaggtcat cgatacccta acgtgcggat tcgccgatct catggggtat atcccgctcg    420
taggcggccc cattgggggc gtcgcaaggg ctctcgcaca cggtgtgagg gtccttgagg    480
acggggtaaa ctatgcaaca gggaattta                                      509
```

<210> SEQ ID NO 44
<211> LENGTH: 169
<212> TYPE: PRT
<213> ORGANISM: hepatitis C virus

<400> SEQUENCE: 44

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80
```

```
Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Pro Ile
    130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu
                165
```

<210> SEQ ID NO 45
<211> LENGTH: 580
<212> TYPE: DNA
<213> ORGANISM: hepatitis C virus

<400> SEQUENCE: 45

```
aacgtgcgga ttcgccgatc tcatggggta tatcccgctc gtaggcggcc ccattggggg    60
cgtcgcaagg gctctcgcac acggtgtgag ggtccttgag gacggggtaa actatgcaac   120
agggaattta cccggttgct ctttctctat ctttattctt gctcttctct cgtgtctgac   180
cgttccggcc tctgcagttc cctaccgaaa tgcctctggg atttatcatg ttaccaatga   240
ttgcccaaac tcttccatag tctatgaggc agataacctg atcctacacg cacctggttg   300
cgtgccttgt gtcatgacag gtaatgtgag tagatgctgg gtccaaatta cccctacact   360
gtcagccccg agcctcggag cagtcacggc tcctcttcgg agagccgttg actacctagc   420
gggagggct gccctctgct ccgcgttata cgtaggagac gcgtgtgggg cactattctt   480
ggtaggccaa atgttcacct ataggcctcg ccagcacgct acggtgcaga actgcaactg   540
ttccatttac agtggccatg ttaccggcca ccggatggca                        580
```

<210> SEQ ID NO 46
<211> LENGTH: 193
<212> TYPE: PRT
<213> ORGANISM: hepatitis C virus

<400> SEQUENCE: 46

```
Thr Cys Gly Phe Ala Asp Leu Met Gly Tyr Ile Pro Leu Val Gly Gly
1               5                   10                  15

Pro Ile Gly Gly Val Ala Arg Ala Leu Ala His Gly Val Arg Val Leu
            20                  25                  30

Glu Asp Gly Val Asn Tyr Ala Thr Gly Asn Leu Pro Gly Cys Ser Phe
        35                  40                  45

Ser Ile Phe Ile Leu Ala Leu Leu Ser Cys Leu Thr Val Pro Ala Ser
    50                  55                  60

Ala Val Pro Tyr Arg Asn Ala Ser Gly Ile Tyr His Val Thr Asn Asp
65                  70                  75                  80

Cys Pro Asn Ser Ser Ile Val Tyr Glu Ala Asp Asn Leu Ile Leu His
                85                  90                  95

Ala Pro Gly Cys Val Pro Cys Val Met Thr Gly Asn Val Ser Arg Cys
            100                 105                 110

Trp Val Gln Ile Thr Pro Thr Leu Ser Ala Pro Ser Leu Gly Ala Val
        115                 120                 125
```

```
Thr Ala Pro Leu Arg Arg Ala Val Asp Tyr Leu Ala Gly Gly Ala Ala
    130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asn Cys Asn Cys Ser Ile Tyr Ser Gly His Val Thr Gly His Arg Met
            180                 185                 190

Ala
```

<210> SEQ ID NO 47
<211> LENGTH: 580
<212> TYPE: DNA
<213> ORGANISM: hepatitis C virus

<400> SEQUENCE: 47

```
aacgtgcgga ttcgccgatc tcatggggta tatcccgctc gtaggcggcc ccattggggg     60
cgtcgcaagg gctctcgcac acggtgtgag ggtccttgag gacgggtaa actatgcaac    120
agggaattta cccggttgct ctttctctat ctttattctt gctcttctct cgtgtctgac    180
cgttccggcc tctgcagttc cctaccgaaa tgcctctggg atttatcatg ttaccaatga    240
ttgcccaaac tcttccatag tctatgaggc agataacctg atcctacacg cacctggttg    300
cgtgccttgt gtcatgacag gtaatgtgag tagatgctgg gtccaaatta cccctacact    360
gtcagccccg agcctcggag cagtcacggc tcctcttcgg agagccgttg actacctagc    420
gggagggct gccctctgct ccgcgttata cgtaggagac gcgtgtgggg cactattctt    480
ggtaggccaa atgttcacct ataggcctcg ccagcacgct acggtgcaga actgcaactg    540
ttccatttac agtggccatg ttaccggcca ccggatggca                        580
```

<210> SEQ ID NO 48
<211> LENGTH: 193
<212> TYPE: PRT
<213> ORGANISM: hepatitis C virus

<400> SEQUENCE: 48

```
Thr Cys Gly Phe Ala Asp Leu Met Gly Tyr Ile Pro Leu Val Gly Gly
1               5                   10                  15

Pro Ile Gly Gly Val Ala Arg Ala Leu Ala His Gly Val Arg Val Leu
                20                  25                  30

Glu Asp Gly Val Asn Tyr Ala Thr Gly Asn Leu Pro Gly Cys Ser Phe
            35                  40                  45

Ser Ile Phe Ile Leu Ala Leu Leu Ser Cys Leu Thr Val Pro Ala Ser
    50                  55                  60

Ala Val Pro Tyr Arg Asn Ala Ser Gly Ile Tyr His Val Thr Asn Asp
65                  70                  75                  80

Cys Pro Asn Ser Ser Ile Val Tyr Glu Ala Asp Asn Leu Ile Leu His
                85                  90                  95

Ala Pro Gly Cys Val Pro Cys Val Met Thr Gly Asn Val Ser Arg Cys
            100                 105                 110

Trp Val Gln Ile Thr Pro Thr Leu Ser Ala Pro Ser Leu Gly Ala Val
        115                 120                 125

Thr Ala Pro Leu Arg Arg Ala Val Asp Tyr Leu Ala Gly Gly Ala Ala
    130                 135                 140

Leu Cys Ser Ala Leu Tyr Val Gly Asp Ala Cys Gly Ala Leu Phe Leu
145                 150                 155                 160
```

Val Gly Gln Met Phe Thr Tyr Arg Pro Arg Gln His Ala Thr Val Gln
            165                 170                 175

Asn Cys Asn Cys Ser Ile Tyr Ser Gly His Val Thr Gly His Arg Met
            180                 185                 190

Ala

<210> SEQ ID NO 49
<211> LENGTH: 959
<212> TYPE: DNA
<213> ORGANISM: hepatitis C virus

<400> SEQUENCE: 49
ccatgagcac gaatcctaaa cctcaaagaa aaaccaaaag aaacaccaac cgtcgcccac      60
aggacgtcaa gttcccgggc ggtggtcaga tcgttggcgg agtttacttg ttgccgcgca    120
ggggccctag gatgggtgtg cgcgcgactc ggaagacttc ggaacggtcg caacccgtg    180
gacggcgtca gcctattccc aaggcgcgcc agcccacggg ccggtcctgg ggtcaacccg    240
ggtaccttg gccccttac gccaatgagg gcctcgggtg ggcagggtgg ctgctctccc      300
ctcgaggctc tcggcctaat tggggcccca atgaccccg gcgaaaatcg cgtaatttgg     360
gtaaggtcat cgatacccta acgtgcggat tcgccgatct catggggtat atcccgctcg    420
taggcggccc cattgggggc gtcgcaaggg ctctcgcaca cggtgtgagg gtccttgagg    480
acggggtaaa ctatgcaaca gggaatttac ccggttgctc tttctctatc tttattcttg    540
ctcttctctc gtgtctgacc gttccggcct ctgcagttcc ctaccgaaat gcctctggga    600
tttatcatgt taccaatgat tgcccaaact cttccatagt ctatgaggca gataacctga    660
tcctacacgc acctggttgc gtgccttgtg tcatgacagg taatgtgagt agatgctggg    720
tccaaattac ccctacactg tcagccccga gcctcggagc agtcacggct cctcttcgga    780
gagccgttga ctacctagcg ggaggggctg ccctctgctc cgcgttatac gtaggagacg    840
cgtgtgggc actattcttg gtaggccaaa tgttcaccta taggcctcgc cagcacgcta    900
cggtgcagaa ctgcaactgt tccatttaca gtggccatgt taccggccac cggatggca    959

<210> SEQ ID NO 50
<211> LENGTH: 319
<212> TYPE: PRT
<213> ORGANISM: hepatitis C virus

<400> SEQUENCE: 50

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys

```
                115                 120                     125
Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Pro Thr Gly Asn Leu Pro Gly Cys Ser Phe Ser Ile
                165                 170                 175

Phe Ile Leu Ala Leu Leu Ser Cys Leu Thr Val Pro Ala Ser Ala Val
            180                 185                 190

Pro Tyr Arg Asn Ala Ser Gly Ile Tyr His Val Thr Asn Asp Cys Pro
        195                 200                 205

Asn Ser Ser Ile Val Tyr Glu Ala Asp Asn Leu Ile Leu His Ala Pro
210                 215                 220

Gly Cys Val Pro Cys Val Met Thr Gly Asn Val Ser Arg Cys Trp Val
225                 230                 235                 240

Gln Ile Thr Pro Thr Leu Ser Ala Pro Ser Leu Gly Ala Val Thr Ala
                245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Leu Phe Leu Val Gly
        275                 280                 285

Gln Met Phe Thr Tyr Arg Pro Arg Gln His Ala Thr Val Gln Asn Cys
    290                 295                 300

Asn Cys Ser Ile Tyr Ser Gly His Val Thr Gly His Arg Met Ala
305                 310                 315

<210> SEQ ID NO 51
<211> LENGTH: 959
<212> TYPE: DNA
<213> ORGANISM: hepatitis C virus

<400> SEQUENCE: 51
ccatgagcac gaatcctaaa cctcaaagaa aaaccaaaag aaacaccaac cgtcgcccac      60
aggacgtcaa gttcccgggc ggtggtcaga tcgttggcgg agtttacttg ttgccgcgca    120
ggggccctag gatgggtgtg cgcgcgactc ggaagacttc ggaacggtcg caaccccgtg    180
gacggcgtca gcctattccc aaggcgcgcc agcccacggg ccggtcctgg ggtcaacccg    240
ggtacccttg gcccctttac gccaatgagg gcctcgggtg ggcagggtgg ctgctctccc    300
ctcgaggctc tcggcctaat tggggcccca atgacccccg gcgaaaatcg cgtaatttgg    360
gtaaggtcat cgataccctα acgtgcggat tcgccgatct catgggtac atcccgctcg    420 taggcggccc cgttggggc gtcgcaaggg ctctcgcaca cggtgtgagg gtccttgagg    480
acggggtaaa ctatccaaca gggaatttac ccggttgctc tttctctatc tttattcttg    540
ctcttctctc gtgtctgacc gttccggcct ctgcagttcc ctaccgaaat gcctctggga    600
tttatcatgt taccaatgat tgcccaaact cttccatagt ctatgaggca gataacctga    660
tcctacacgc acctggttgc gtgccttgtg tcatgacagg taatgtgagt agatgctggg    720
tccaaattac ccctacactg tcagccccga gcctcggagc agtcacggct cctcttcgga    780
gagccgttga ctacctagcg ggaggggctg ccctctgctc cgcgttatac gtaggagacg    840
cgtgtggggc actattcttg gtaggccaaa tgttcaccta taggcctcgc cagcacgcta    900
cggtgcagaa ctgcaactgt tccatttaca gtggccatgt taccggccac cggatggca    959
```

-continued

<210> SEQ ID NO 52
<211> LENGTH: 319
<212> TYPE: PRT
<213> ORGANISM: hepatitis C virus

<400> SEQUENCE: 52

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
130                 135                 140

Gly Gly Val Ala Arg Ala Leu Ala His Gly Val Arg Val Leu Glu Asp
145                 150                 155                 160

Gly Val Asn Tyr Pro Thr Gly Asn Leu Pro Gly Cys Ser Phe Ser Ile
                165                 170                 175

Phe Ile Leu Ala Leu Leu Ser Cys Leu Thr Val Pro Ala Ser Ala Val
            180                 185                 190

Pro Tyr Arg Asn Ala Ser Gly Ile Tyr His Val Thr Asn Asp Cys Pro
        195                 200                 205

Asn Ser Ser Ile Val Tyr Glu Ala Asp Asn Leu Ile Leu His Ala Pro
210                 215                 220

Gly Cys Val Pro Cys Val Met Thr Gly Asn Val Ser Arg Cys Trp Val
225                 230                 235                 240

Gln Ile Thr Pro Thr Leu Ser Ala Pro Ser Leu Gly Ala Val Thr Ala
                245                 250                 255

Pro Leu Arg Arg Ala Val Asp Tyr Leu Ala Gly Gly Ala Ala Leu Cys
            260                 265                 270

Ser Ala Leu Tyr Val Gly Asp Ala Cys Gly Ala Leu Phe Leu Val Gly
        275                 280                 285

Gln Met Phe Thr Tyr Arg Pro Arg Gln His Ala Thr Val Gln Asn Cys
290                 295                 300

Asn Cys Ser Ile Tyr Ser Gly His Val Thr Gly His Arg Met Ala
305                 310                 315

<210> SEQ ID NO 53
<211> LENGTH: 959
<212> TYPE: DNA
<213> ORGANISM: hepatitis C virus

<400> SEQUENCE: 53
ccatgagcac gaatcctaaa cctcaaagaa aaccaaaag aaacaccaac cgtcgcccac     60
aggacgtcaa gttcccgggc ggtggtcaga tcgttggcgg agtttacttg ttgccgcgca   120

-continued

```
ggggccctag gatgggtgtg cgcgcgactc ggaagacttc ggaacggtcg caaccccgtg    180
gacggcgtca gcctattccc aaggcgcgcc agcccacggg ccggtcctgg ggtcaacccg    240 ggtaccttg gcccctttac gccaatgagg gcctcgggtg ggcagggtgg ctgctctccc     300
ctcgaggctc tcggcctaat tggggcccca atgaccccg gcgaaaatcg cgtaatttgg     360
gtaaggtcat cgatacccta acgtgcggat tcgccgatct catgggtay atcccgctcg     420 taggcggccc crttgggggc gtcgcaaggg ctctcgcaca cggtgtgagg gtccttgagg    480
acggggtaaa ctatscaaca gggaatttac ccggttgctc tttctctatc tttattcttg    540
ctcttctctc gtgtctgacc gttccggcct ctgcagttcc ctaccgaaat gcctctggga    600
tttatcatgt taccaatgat tgcccaaact cttccatagt ctatgaggca gataacctga    660
tcctacacgc acctggttgc gtgccttgtg tcatgacagg taatgtgagt agatgctggg    720
tccaaattac ccctacactg tcagccccga gcctcggagc agtcacggct cctcttcgga    780
gagccgttga ctacctagcg ggaggggctg ccctctgctc cgcgttatac gtaggagacg    840
cgtgtggggc actattcttg gtaggccaaa tgttcaccta taggcctcgc cagcacgcta    900
cggtgcagaa ctgcaactgt tccatttaca gtggccatgt taccggccac cggatggca     959
```

<210> SEQ ID NO 54
<211> LENGTH: 319
<212> TYPE: PRT
<213> ORGANISM: hepatitis C virus

<400> SEQUENCE: 54

```
Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Met Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Gln Pro Thr Gly Arg Ser Trp Gly Gln Pro Gly
65                  70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
            100                 105                 110

Arg Arg Lys Ser Arg Asn Leu Gly Lys Val Ile Asp Thr Leu Thr Cys
        115                 120                 125

Gly Phe Ala Asp Leu Met Gly Tyr Ile Pro Leu Val Gly Gly Pro Val
    130                 135                 140

Gly Gly Val Ala Arg Ala Leu Ala His Gly Val Arg Val Leu Glu Asp
145                 150                 155                 160

Gly Val Asn Tyr Pro Thr Gly Asn Leu Pro Gly Cys Ser Phe Ser Ile
                165                 170                 175

Phe Ile Leu Ala Leu Leu Ser Cys Leu Thr Val Pro Ala Ser Ala Val
            180                 185                 190

Pro Tyr Arg Asn Ala Ser Gly Ile Tyr His Val Thr Asn Asp Cys Pro
        195                 200                 205

Asn Ser Ser Ile Val Tyr Glu Ala Asp Asn Leu Ile Leu His Ala Pro
    210                 215                 220

Gly Cys Val Pro Cys Val Met Thr Gly Asn Val Ser Arg Cys Trp Val
```

```
                225                 230                 235                 240
Gln Ile Thr Pro Thr Leu Ser Ala Pro Ser Leu Gly Ala Val Thr Ala
                245                 250                 255

Pro Leu Arg Arg Ala Val Asp Tyr Leu Ala Gly Ala Ala Leu Cys
            260                 265                 270

Ser Ala Leu Tyr Val Gly Asp Ala Cys Gly Ala Leu Phe Leu Val Gly
            275                 280                 285

Gln Met Phe Thr Tyr Arg Pro Arg Gln His Ala Thr Val Gln Asn Cys
    290                 295                 300

Asn Cys Ser Ile Tyr Ser Gly His Val Thr Gly His Arg Met Ala
305                 310                 315

<210> SEQ ID NO 55
<211> LENGTH: 354
<212> TYPE: DNA
<213> ORGANISM: hepatitis C virus
<220> FEATURE:
<221> NAME/KEY: misc_feature
<222> LOCATION: (191)..(191)
<223> OTHER INFORMATION: "n" is any nucleotide

<400> SEQUENCE: 55
accaccggag cttctatcac atactccact tacggcaagt tccttgctga tggagggtgt      60
tcaggcggcg cgcatgacgt gatcatatgc gacgagtgcc attcccagga cgccaccacc    120
attcttggga taggcactgt ccttgaccag gcagagacgg ctggagctag gctcgtcgtc    180
ttggccacgg ncacccctcc cggcagtgtg acaacgcccc accccaacat cgaggaagtg    240
gccctgcctc aggaggggga ggttcccttc tacggcagag ccattcccct tgcttttata    300
aagggtggta ggcatctcat cttctgccat tccaagaaaa attgtgatga actc           354

<210> SEQ ID NO 56
<211> LENGTH: 118
<212> TYPE: PRT
<213> ORGANISM: hepatitis C virus
<220> FEATURE:
<221> NAME/KEY: MISC_FEATURE
<222> LOCATION: (64)..(64)
<223> OTHER INFORMATION: "Xaa" is any amino acid

<400> SEQUENCE: 56

Thr Thr Gly Ala Ser Ile Thr Tyr Ser Thr Tyr Gly Lys Phe Leu Ala
1               5                   10                  15

Asp Gly Gly Cys Ser Gly Gly Ala His Asp Val Ile Ile Cys Asp Glu
            20                  25                  30

Cys His Ser Gln Asp Ala Thr Thr Ile Leu Gly Ile Gly Thr Val Leu
        35                  40                  45

Asp Gln Ala Glu Thr Ala Gly Ala Arg Leu Val Val Leu Ala Thr Xaa
    50                  55                  60

Thr Pro Pro Gly Ser Val Thr Thr Pro His Pro Asn Ile Glu Glu Val
65                  70                  75                  80

Ala Leu Pro Gln Glu Gly Glu Val Pro Phe Tyr Gly Arg Ala Ile Pro
                85                  90                  95

Leu Ala Phe Ile Lys Gly Gly Arg His Leu Ile Phe Cys His Ser Lys
            100                 105                 110

Lys Asn Cys Asp Glu Leu
        115

<210> SEQ ID NO 57
```

```
<211> LENGTH: 354
<212> TYPE: DNA
<213> ORGANISM: hepatitis C virus
<220> FEATURE:
<221> NAME/KEY: misc_feature
<222> LOCATION: (185)..(185)
<223> OTHER INFORMATION: "n" is any nucleotide
<220> FEATURE:
<221> NAME/KEY: misc_feature
<222> LOCATION: (191)..(191)
<223> OTHER INFORMATION: "n" is any nucleotide
<220> FEATURE:
<221> NAME/KEY: misc_feature
<222> LOCATION: (276)..(276)
<223> OTHER INFORMATION: "n" is any nucleotide

<400> SEQUENCE: 57
accaccggag cttctatcac atactccact tacggcaagt tccttgctga tggagggtgt      60
tcaggcggcg cgtatgacgt gatcatatgc gacgagtgcc attcccagga cgccaccacc    120
attcttggga taggcactgt ccttgaccag gcagagacgg ctggagctag gctcgtcgtc    180
ttggncacgg ncacccctcc cggcagtgtg acaacgcccc accccaacat cgaggaagtg    240
gccctgcctc aggaggggga ggttcccttc tacggnagag ccattcccct tgcttttata    300
aagggtggta ggcatctcat cttctgccat tccaagaaaa aatgtgatga actt          354

<210> SEQ ID NO 58
<211> LENGTH: 133
<212> TYPE: PRT
<213> ORGANISM: hepatitis C virus
<220> FEATURE:
<221> NAME/KEY: MISC_FEATURE
<222> LOCATION: (62)..(62)
<223> OTHER INFORMATION: "Xaa" is any amino acid
<220> FEATURE:
<221> NAME/KEY: MISC_FEATURE
<222> LOCATION: (64)..(64)
<223> OTHER INFORMATION: "Xaa" is any amino acid
<220> FEATURE:
<221> NAME/KEY: MISC_FEATURE
<222> LOCATION: (92)..(92)
<223> OTHER INFORMATION: "Xaa" is any amino acid

<400> SEQUENCE: 58

Thr Thr Gly Ala Ser Ile Thr Tyr Ser Thr Tyr Gly Lys Phe Leu Ala
1               5                   10                  15

Asp Gly Gly Cys Ser Gly Gly Ala Tyr Asp Val Ile Ile Cys Asp Glu
            20                  25                  30

Cys His Ser Gln Asp Ala Thr Thr Ile Leu Gly Ile Gly Thr Val Leu
        35                  40                  45

Asp Gln Ala Glu Thr Ala Gly Ala Arg Leu Val Val Leu Xaa Thr Xaa
    50                  55                  60

Thr Pro Pro Gly Ser Val Thr Thr Pro His Pro Asn Ile Glu Glu Val
65                  70                  75                  80

Ala Leu Pro Gln Glu Gly Glu Val Pro Phe Tyr Xaa Arg Ala Ile Pro
                85                  90                  95

Leu Ala Phe Ile Lys Gly Gly Arg His Leu Ile Phe Cys His Ser Lys
            100                 105                 110

Lys Lys Cys Asp Glu Leu Arg Gln Ala Thr Asp Gln Pro Gly Arg Glu
        115                 120                 125

Arg Pro Trp Glu Tyr
    130

<210> SEQ ID NO 59
```

```
<211> LENGTH: 357
<212> TYPE: DNA
<213> ORGANISM: hepatitis C virus
<220> FEATURE:
<221> NAME/KEY: misc_feature
<222> LOCATION: (38)..(38)
<223> OTHER INFORMATION: "n" is any nucleotide
<220> FEATURE:
<221> NAME/KEY: misc_feature
<222> LOCATION: (76)..(76)
<223> OTHER INFORMATION: "n" is any nucleotide
<220> FEATURE:
<221> NAME/KEY: misc_feature
<222> LOCATION: (79)..(79)
<223> OTHER INFORMATION: "n" is any nucleotide
<220> FEATURE:
<221> NAME/KEY: misc_feature
<222> LOCATION: (151)..(151)
<223> OTHER INFORMATION: "n" is any nucleotide
<220> FEATURE:
<221> NAME/KEY: misc_feature
<222> LOCATION: (232)..(232)
<223> OTHER INFORMATION: "n" is any nucleotide
<220> FEATURE:
<221> NAME/KEY: misc_feature
<222> LOCATION: (349)..(349)
<223> OTHER INFORMATION: "n" is any nucleotide

<400> SEQUENCE: 59
atggctttca tgtctccgga cttggaggtc attaccanca cttgggttct ggtgggggc      60 gttgtggcga ccctgncgnc ctactgcttg acggtgggtt cggtagccat agtcggtagg    120
atcatcctct ctgggaaacc tgccatcatt nccgataggg aggtattata ccagcaattt    180
gatgagatgg aggagtgctc ggcctcgttg ccctatatgg acgaaacacg tnccattgcc    240
ggacaattca agagaaagt gctcggcttc atcagcacga ccggccagaa ggctgaaact     300
ctgaagccgg cagccacgtc tgtgtggaac aaggctgatc agttctggnc cacatac       357

<210> SEQ ID NO 60
<211> LENGTH: 128
<212> TYPE: PRT
<213> ORGANISM: hepatitis C virus
<220> FEATURE:
<221> NAME/KEY: MISC_FEATURE
<222> LOCATION: (13)..(13)
<223> OTHER INFORMATION: "Xaa" is any amino acid
<220> FEATURE:
<221> NAME/KEY: MISC_FEATURE
<222> LOCATION: (26)..(27)
<223> OTHER INFORMATION: "Xaa" is any amino acid
<220> FEATURE:
<221> NAME/KEY: MISC_FEATURE
<222> LOCATION: (51)..(51)
<223> OTHER INFORMATION: "Xaa" is any amino acid
<220> FEATURE:
<221> NAME/KEY: MISC_FEATURE
<222> LOCATION: (78)..(78)
<223> OTHER INFORMATION: "Xaa" is any amino acid
<220> FEATURE:
<221> NAME/KEY: MISC_FEATURE
<222> LOCATION: (117)..(117)
<223> OTHER INFORMATION: "Xaa" is any amino acid

<400> SEQUENCE: 60

Met Ala Phe Met Ser Pro Asp Leu Glu Val Ile Thr Xaa Thr Trp Val
1               5                   10                  15

Leu Val Gly Gly Val Val Ala Thr Leu Xaa Xaa Tyr Cys Leu Thr Val
            20                  25                  30

Gly Ser Val Ala Ile Val Gly Arg Ile Ile Leu Ser Gly Lys Pro Ala
        35                  40                  45
```

```
Ile Ile Xaa Asp Arg Glu Val Leu Tyr Gln Gln Phe Asp Glu Met Glu
 50                  55                  60

Glu Cys Ser Ala Ser Leu Pro Tyr Met Asp Glu Thr Arg Xaa Ile Ala
 65                  70                  75                  80

Gly Gln Phe Lys Glu Lys Val Leu Gly Phe Ile Ser Thr Thr Gly Gln
                 85                  90                  95

Lys Ala Glu Thr Leu Lys Pro Ala Ala Thr Ser Val Trp Asn Lys Ala
                100                 105                 110

Asp Gln Phe Trp Xaa Thr Tyr Met Trp Asn Phe Ile Ser Gly Ile Gln
                115                 120                 125
```

<210> SEQ ID NO 61
<211> LENGTH: 357
<212> TYPE: DNA
<213> ORGANISM: hepatitis C virus
<220> FEATURE:
<221> NAME/KEY: misc_feature
<222> LOCATION: (38)..(38)
<223> OTHER INFORMATION: "n" is any nucleotide
<220> FEATURE:
<221> NAME/KEY: misc_feature
<222> LOCATION: (70)..(70)
<223> OTHER INFORMATION: "n" is any nucleotide
<220> FEATURE:
<221> NAME/KEY: misc_feature
<222> LOCATION: (174)..(174)
<223> OTHER INFORMATION: "n" is any nucleotide
<220> FEATURE:
<221> NAME/KEY: misc_feature
<222> LOCATION: (339)..(339)
<223> OTHER INFORMATION: "n" is any nucleotide

<400> SEQUENCE: 61

```
atggcttgca tgtctgcgga cctggaggtc attaccanca cttgggttct ggtgggggc    60 gttgtggcgn ccctggcggc ctactgcttg acggtgggtt cggtagccat agtcggtagg   120
atcatcctct ctgggaaacc tgccatcatt cccgataggg aggcattata ccancaattt   180
gatgagatgg aggagtgctc ggcctcgttg ccctatatgg acgagacacg tgccattgcc   240
ggacaattca agagaaagt gctcggcttc atcagcacga ccggccagaa ggctgaaact    300
ctgaagccgg cagccacgtc tgtgtggaac aaggctganc agttctgggc cacatac     357
```

<210> SEQ ID NO 62
<211> LENGTH: 128
<212> TYPE: PRT
<213> ORGANISM: hepatitis C virus
<220> FEATURE:
<221> NAME/KEY: MISC_FEATURE
<222> LOCATION: (13)..(13)
<223> OTHER INFORMATION: "Xaa" is any amino acid
<220> FEATURE:
<221> NAME/KEY: MISC_FEATURE
<222> LOCATION: (24)..(24)
<223> OTHER INFORMATION: "Xaa" is any amino acid
<220> FEATURE:
<221> NAME/KEY: MISC_FEATURE
<222> LOCATION: (58)..(58)
<223> OTHER INFORMATION: "Xaa" is any amino acid
<220> FEATURE:
<221> NAME/KEY: MISC_FEATURE
<222> LOCATION: (113)..(113)
<223> OTHER INFORMATION: "Xaa" is any amino acid

<400> SEQUENCE: 62

```
Met Ala Cys Met Ser Ala Asp Leu Glu Val Ile Thr Xaa Thr Trp Val
 1               5                  10                  15

Leu Val Gly Gly Val Val Ala Xaa Leu Ala Ala Tyr Cys Leu Thr Val
```

```
                    20                  25                  30
Gly Ser Val Ala Ile Val Gly Arg Ile Ile Leu Ser Gly Lys Pro Ala
            35                  40                  45

Ile Ile Pro Asp Arg Glu Ala Leu Tyr Xaa Gln Phe Asp Glu Met Glu
 50                  55                  60

Glu Cys Ser Ala Ser Leu Pro Tyr Met Asp Glu Thr Arg Ala Ile Ala
 65                  70                  75                  80

Gly Gln Phe Lys Glu Lys Val Leu Gly Phe Ile Ser Thr Thr Gly Gln
                85                  90                  95

Lys Ala Glu Thr Leu Lys Pro Ala Ala Thr Ser Val Trp Asn Lys Ala
            100                 105                 110

Xaa Gln Phe Trp Ala Thr Tyr Met Trp Asn Phe Ile Ser Gly Ile Gln
        115                 120                 125

<210> SEQ ID NO 63
<211> LENGTH: 28
<212> TYPE: DNA
<213> ORGANISM: artificial
<220> FEATURE:
<221> NAME/KEY: misc_feature
<223> OTHER INFORMATION: HCPr161

<400> SEQUENCE: 63
accggaggcc aggagagtga tctcctcc                                    28

<210> SEQ ID NO 64
<211> LENGTH: 28
<212> TYPE: DNA
<213> ORGANISM: artificial
<220> FEATURE:
<221> NAME/KEY: misc_feature
<223> OTHER INFORMATION: HCPr162

<400> SEQUENCE: 64
gggctgctct atcctcatcg acgccatc                                    28

<210> SEQ ID NO 65
<211> LENGTH: 28
<212> TYPE: DNA
<213> ORGANISM: artificial
<220> FEATURE:
<221> NAME/KEY: misc_feature
<223> OTHER INFORMATION: HCPr163

<400> SEQUENCE: 65
gccagaggct cggaaggcga tcagcgct                                    28

<210> SEQ ID NO 66
<211> LENGTH: 28
<212> TYPE: DNA
<213> ORGANISM: artificial
<220> FEATURE:
<221> NAME/KEY: misc_feature
<223> OTHER INFORMATION: HCPr164

<400> SEQUENCE: 66
gagctgctct gtcctcctcg acgccgca                                    28

<210> SEQ ID NO 67
<211> LENGTH: 20
<212> TYPE: DNA
<213> ORGANISM: artificial
<220> FEATURE:
<221> NAME/KEY: misc_feature
```

<223> OTHER INFORMATION: HCPr23

<400> SEQUENCE: 67
ctcatggggt acattccgct        20

<210> SEQ ID NO 68
<211> LENGTH: 27
<212> TYPE: DNA
<213> ORGANISM: artificial
<220> FEATURE:
<221> NAME/KEY: misc_feature
<223> OTHER INFORMATION: HCPr54

<400> SEQUENCE: 68
ctattaccag ttcatcatca tatccca        27

<210> SEQ ID NO 69
<211> LENGTH: 24
<212> TYPE: DNA
<213> ORGANISM: artificial
<220> FEATURE:
<221> NAME/KEY: misc_feature
<223> OTHER INFORMATION: HCPr116

<400> SEQUENCE: 69
ttttaaatac atcatgrctg yatg        24

<210> SEQ ID NO 70
<211> LENGTH: 33
<212> TYPE: DNA
<213> ORGANISM: artificial
<220> FEATURE:
<221> NAME/KEY: misc_feature
<223> OTHER INFORMATION: HCPr66

<400> SEQUENCE: 70
ctattattgt atcccrctga tgaarttcca cat        33

<210> SEQ ID NO 71
<211> LENGTH: 36
<212> TYPE: DNA
<213> ORGANISM: artificial
<220> FEATURE:
<221> NAME/KEY: misc_feature
<223> OTHER INFORMATION: HCPr118

<400> SEQUENCE: 71
actagtcgac taytgatccr ctatrwartt ccacat        36

<210> SEQ ID NO 72
<211> LENGTH: 25
<212> TYPE: DNA
<213> ORGANISM: artificial
<220> FEATURE:
<221> NAME/KEY: misc_feature
<223> OTHER INFORMATION: HCPr117

<400> SEQUENCE: 72
ttttaaatac atcgcrctgc atgca        25

<210> SEQ ID NO 73
<211> LENGTH: 36
<212> TYPE: DNA
<213> ORGANISM: artificial
<220> FEATURE:
<221> NAME/KEY: misc_feature
<223> OTHER INFORMATION: HCPr119

```
<400> SEQUENCE: 73
actagtcgac tarttgcata gcckrttcat ccaytg                              36

<210> SEQ ID NO 74
<211> LENGTH: 34
<212> TYPE: DNA
<213> ORGANISM: artificial
<220> FEATURE:
<221> NAME/KEY: misc_feature
<223> OTHER INFORMATION: HCPr131

<400> SEQUENCE: 74
ggaattctag acctctggga ygaraytgga artg                                34

<210> SEQ ID NO 75
<211> LENGTH: 31
<212> TYPE: DNA
<213> ORGANISM: artificial
<220> FEATURE:
<221> NAME/KEY: misc_feature
<223> OTHER INFORMATION: HCPr130

<400> SEQUENCE: 75
ggaattctag acgctaycar gcacgttgyg c                                   31

<210> SEQ ID NO 76
<211> LENGTH: 23
<212> TYPE: DNA
<213> ORGANISM: artificial
<220> FEATURE:
<221> NAME/KEY: misc_feature
<223> OTHER INFORMATION: HCPr134

<400> SEQUENCE: 76
catatagatg cccacttcct atc                                            23

<210> SEQ ID NO 77
<211> LENGTH: 16
<212> TYPE: DNA
<213> ORGANISM: artificial
<220> FEATURE:
<221> NAME/KEY: misc_feature
<223> OTHER INFORMATION: HCPr3

<400> SEQUENCE: 77
gtgtgccagg accatc                                                    16

<210> SEQ ID NO 78
<211> LENGTH: 20
<212> TYPE: DNA
<213> ORGANISM: artificial
<220> FEATURE:
<221> NAME/KEY: misc_feature
<223> OTHER INFORMATION: HCPr4

<400> SEQUENCE: 78
gacatgcatg tcatgatgta                                                20

<210> SEQ ID NO 79
<211> LENGTH: 29
<212> TYPE: DNA
<213> ORGANISM: artificial
<220> FEATURE:
<221> NAME/KEY: misc_feature
<223> OTHER INFORMATION: HCPr152
```

```
<400> SEQUENCE: 79
tacgcctctt ctatatcggt tggggcctg                                    29

<210> SEQ ID NO 80
<211> LENGTH: 26
<212> TYPE: DNA
<213> ORGANISM: artificial
<220> FEATURE:
<221> NAME/KEY: misc_feature
<223> OTHER INFORMATION: HCPr52

<400> SEQUENCE: 80
atgttgggta aggtcatcga taccct                                       26

<210> SEQ ID NO 81
<211> LENGTH: 25
<212> TYPE: DNA
<213> ORGANISM: artificial
<220> FEATURE:
<221> NAME/KEY: misc_feature
<223> OTHER INFORMATION: HCPr41

<400> SEQUENCE: 81
cccgggaggt ctcgtagacc gtgca                                        25

<210> SEQ ID NO 82
<211> LENGTH: 29
<212> TYPE: DNA
<213> ORGANISM: artificial
<220> FEATURE:
<221> NAME/KEY: misc_feature
<223> OTHER INFORMATION: HCPr40

<400> SEQUENCE: 82
ctattaaaga tagagaaaga gcaaccggg                                    29

<210> SEQ ID NO 83
<211> LENGTH: 12
<212> TYPE: PRT
<213> ORGANISM: hepatitis C virus

<400> SEQUENCE: 83

Leu Glu Trp Arg Asn Thr Ser Gly Leu Tyr Val Leu
 1               5                  10

<210> SEQ ID NO 84
<211> LENGTH: 12
<212> TYPE: PRT
<213> ORGANISM: hepatitis C virus

<400> SEQUENCE: 84

Val Pro Tyr Arg Asn Ala Ser Gly Ile Tyr His Val
 1               5                  10

<210> SEQ ID NO 85
<211> LENGTH: 11
<212> TYPE: PRT
<213> ORGANISM: hepatitis C virus

<400> SEQUENCE: 85

Val Tyr Glu Ala Asp Asp Val Ile Leu His Thr
 1               5                  10

<210> SEQ ID NO 86
<211> LENGTH: 11
```

```
<212> TYPE: PRT
<213> ORGANISM: hepatitis C virus

<400> SEQUENCE: 86

Val Tyr Glu Ala Asp Asn Leu Ile Leu His Ala
1               5                   10

<210> SEQ ID NO 87
<211> LENGTH: 13
<212> TYPE: PRT
<213> ORGANISM: hepatitis C virus

<400> SEQUENCE: 87

Val Gln Asp Gly Asn Thr Ser Thr Cys Trp Thr Pro Val
1               5                   10

<210> SEQ ID NO 88
<211> LENGTH: 13
<212> TYPE: PRT
<213> ORGANISM: hepatitis C virus

<400> SEQUENCE: 88

Val Met Thr Gly Asn Val Ser Arg Cys Trp Val Gln Ile
1               5                   10

<210> SEQ ID NO 89
<211> LENGTH: 10
<212> TYPE: PRT
<213> ORGANISM: hepatitis C virus

<400> SEQUENCE: 89

Val Arg Tyr Val Gly Ala Thr Thr Ala Ser
1               5                   10

<210> SEQ ID NO 90
<211> LENGTH: 10
<212> TYPE: PRT
<213> ORGANISM: hepatitis C virus

<400> SEQUENCE: 90

Ala Pro Ser Leu Gly Ala Val Thr Ala Pro
1               5                   10

<210> SEQ ID NO 91
<211> LENGTH: 10
<212> TYPE: PRT
<213> ORGANISM: hepatitis C virus

<400> SEQUENCE: 91

Arg Pro Arg Arg His Gln Thr Val Gln Thr
1               5                   10

<210> SEQ ID NO 92
<211> LENGTH: 10
<212> TYPE: PRT
<213> ORGANISM: hepatitis C virus

<400> SEQUENCE: 92

Arg Pro Arg Gln His Ala Thr Val Gln Asn
1               5                   10

<210> SEQ ID NO 93
<211> LENGTH: 9
<212> TYPE: PRT
<213> ORGANISM: hepatitis C virus
```

```
<400> SEQUENCE: 93

Gln Pro Thr Gly Arg Ser Trp Gly Gln
1               5

<210> SEQ ID NO 94
<211> LENGTH: 8
<212> TYPE: PRT
<213> ORGANISM: hepatitis C virus

<400> SEQUENCE: 94

Val Gln Asp Gly Asn Thr Ser Thr
1               5

<210> SEQ ID NO 95
<211> LENGTH: 8
<212> TYPE: PRT
<213> ORGANISM: hepatitis C virus

<400> SEQUENCE: 95

Val Gln Asp Gly Asn Thr Ser Ala
1               5

<210> SEQ ID NO 96
<211> LENGTH: 10
<212> TYPE: PRT
<213> ORGANISM: hepatitis C virus

<400> SEQUENCE: 96

Val Lys Tyr Val Gly Ala Thr Thr Ala Ser
1               5                   10

<210> SEQ ID NO 97
<211> LENGTH: 20
<212> TYPE: PRT
<213> ORGANISM: hepatitis C virus

<400> SEQUENCE: 97

Leu Gly Gly Lys Pro Ala Ile Val Pro Asp Lys Glu Val Leu Tyr Gln
1               5                   10                  15

Gln Tyr Asp Glu
            20

<210> SEQ ID NO 98
<211> LENGTH: 20
<212> TYPE: PRT
<213> ORGANISM: hepatitis C virus

<400> SEQUENCE: 98

Leu Gly Gly Lys Pro Ala Leu Val Pro Asp Lys Glu Val Leu Tyr Gln
1               5                   10                  15

Gln Tyr Asp Glu
            20

<210> SEQ ID NO 99
<211> LENGTH: 20
<212> TYPE: PRT
<213> ORGANISM: hepatitis C virus

<400> SEQUENCE: 99

Ser Gln Ala Ala Pro Tyr Ile Glu Gln Ala Gln Val Ile Ala His Gln
1               5                   10                  15

Phe Lys Glu Lys
```

-continued

```
                20

<210> SEQ ID NO 100
<211> LENGTH: 20
<212> TYPE: PRT
<213> ORGANISM: hepatitis C virus

<400> SEQUENCE: 100

Ile Ala His Gln Phe Lys Glu Lys Val Leu Gly Leu Leu Gln Arg Ala
1               5                   10                  15

Thr Gln Gln Gln
            20

<210> SEQ ID NO 101
<211> LENGTH: 20
<212> TYPE: PRT
<213> ORGANISM: hepatitis C virus

<400> SEQUENCE: 101

Ile Ala His Gln Phe Lys Glu Lys Ile Leu Gly Leu Leu Gln Arg Ala
1               5                   10                  15

Thr Gln Gln Gln
            20

<210> SEQ ID NO 102
<211> LENGTH: 20
<212> TYPE: PRT
<213> ORGANISM: hepatitis C virus

<400> SEQUENCE: 102

Leu Ser Gly Lys Pro Ala Ile Ile Pro Asp Arg Glu Ala Leu Tyr Gln
1               5                   10                  15

Gln Phe Asp Glu
            20

<210> SEQ ID NO 103
<211> LENGTH: 20
<212> TYPE: PRT
<213> ORGANISM: hepatitis C virus

<400> SEQUENCE: 103

Leu Ser Gly Lys Pro Ala Ile Ile Pro Asp Arg Glu Val Leu Tyr Gln
1               5                   10                  15

Gln Phe Asp Glu
            20

<210> SEQ ID NO 104
<211> LENGTH: 20
<212> TYPE: PRT
<213> ORGANISM: hepatitis C virus

<400> SEQUENCE: 104

Ser Ala Ser Leu Pro Tyr Met Asp Glu Thr Arg Ala Ile Ala Gly Gln
1               5                   10                  15

Phe Lys Glu Lys
            20

<210> SEQ ID NO 105
<211> LENGTH: 20
<212> TYPE: PRT
<213> ORGANISM: hepatitis C virus

<400> SEQUENCE: 105
```

```
Ile Ala Gly Gln Phe Lys Glu Lys Val Leu Gly Phe Ile Ser Thr Thr
1               5                   10                  15

Gly Gln Lys Ala
            20
```

<210> SEQ ID NO 106
<211> LENGTH: 340
<212> TYPE: DNA
<213> ORGANISM: hepatitis C virus

<400> SEQUENCE: 106

```
ctccactgta accgaaaagg acatcagggt cgaggaggag gtctatcagt gttgtgacct      60
ggagcccgaa gcccgcaagg caattaccgc cctaacagag agactctacg tgggcggtcc     120
catgcataac agcaagggag acctgtgcgg gtatcgcaga tgtcgcgcaa gcggcgtcta     180
caccaccagc ttcgggaaca cactgacgtg ctacctcaaa gcctcagccg ctatcaaagc     240
ggcgggctg agagactgca ccatgttggt ctgtggtgat gacctggttg tcatcgctga      300
gagcgatggc gtagaggagg acaaacgacc cctcggagcc                           340
```

<210> SEQ ID NO 107
<211> LENGTH: 113
<212> TYPE: PRT
<213> ORGANISM: hepatitis C virus

<400> SEQUENCE: 107

```
Ser Thr Val Thr Glu Lys Asp Ile Arg Val Glu Glu Val Tyr Gln
1               5                   10                  15

Cys Cys Asp Leu Glu Pro Glu Ala Arg Lys Ala Ile Thr Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe
    50                  55                  60

Gly Asn Thr Leu Thr Cys Tyr Leu Lys Ala Ser Ala Ala Ile Lys Ala
65                  70                  75                  80

Ala Gly Leu Arg Asp Cys Thr Met Leu Val Cys Gly Asp Asp Leu Val
                85                  90                  95

Val Ile Ala Glu Ser Asp Gly Val Glu Glu Asp Lys Arg Pro Leu Gly
                100                 105                 110

Ala
```

<210> SEQ ID NO 108
<211> LENGTH: 340
<212> TYPE: DNA
<213> ORGANISM: hepatitis C virus

<400> SEQUENCE: 108

```
ctccactgta accgaaaagg acatcagggt cgaggaggag gtatatcagt gttgtgacct      60
ggagcccgag gcccgcagag caattaccgc cctaacagag agactctacg tgggcggtcc     120
catgcataac agcagggag acctgtgcgg gtatcgcaga tgccgtgcga gcggcgtcta      180
caccaccagc ttcgggaaca cactgacgtg ctatctcaaa gcctcagccg ctatcagagc     240
ggcgggctg agagactgca ccatgttggt ctgtggtgat gacctggtcg tcattgctga      300
aagcgatggc gtagaggagg acaaacgagc cctcggagcc                           340
```

<210> SEQ ID NO 109
<211> LENGTH: 113
<212> TYPE: PRT
<213> ORGANISM: hepatitis C virus

<400> SEQUENCE: 109

```
Ser Thr Val Thr Glu Lys Asp Ile Arg Val Glu Glu Glu Val Tyr Gln
1               5                   10                  15
Cys Cys Asp Leu Glu Pro Glu Ala Arg Ala Ile Thr Ala Leu Thr
                20                  25                  30
Glu Arg Leu Tyr Val Gly Gly Pro Met His Asn Ser Arg Gly Asp Leu
            35                  40                  45
Cys Gly Tyr Arg Arg Cys Arg Ala Ser Gly Val Tyr Thr Thr Ser Phe
        50                  55                  60
Gly Asn Thr Leu Thr Cys Tyr Leu Lys Ala Ser Ala Ala Ile Arg Ala
65                  70                  75                  80
Ala Gly Leu Arg Asp Cys Thr Met Leu Val Cys Gly Asp Asp Leu Val
                85                  90                  95
Val Ile Ala Glu Ser Asp Gly Val Glu Glu Asp Lys Arg Ala Leu Gly
            100                 105                 110
Ala
```

<210> SEQ ID NO 110
<211> LENGTH: 340
<212> TYPE: DNA
<213> ORGANISM: hepatitis C virus

<400> SEQUENCE: 110

```
ctccactgta accgaaaaag acatcagggt cgaggaggag gtatatcagt gttgtgacct      60
ggagcccgaa gcccgcaagg taattaccgc cctaacagag agactctatg tgggcggtcc     120
catgcataat agcaaaggag acctgtgcgg gtatcgcaga tgccgcgcaa gcggcgtcta     180
caccaccagc ttcgggaaca cactgacgtg ctatctcaaa gcctcagccg ccatcagggc     240
gtcaggctg agagactgca ctatgctggt ctatggtgac gacctggtcg tcattgccga      300
gagcgatggc gtagaggagg acaaacgagc cctcggagtc                            340
```

<210> SEQ ID NO 111
<211> LENGTH: 113
<212> TYPE: PRT
<213> ORGANISM: hepatitis C virus

<400> SEQUENCE: 111

```
Ser Thr Val Thr Glu Lys Asp Ile Arg Val Glu Glu Glu Val Tyr Gln
1               5                   10                  15
Cys Cys Asp Leu Glu Pro Glu Ala Arg Lys Val Ile Thr Ala Leu Thr
                20                  25                  30
Glu Arg Leu Tyr Val Gly Gly Pro Met His Asn Ser Lys Gly Asp Leu
            35                  40                  45
Cys Gly Tyr Arg Arg Cys Arg Ala Ser Gly Val Tyr Thr Thr Ser Phe
        50                  55                  60
Gly Asn Thr Leu Thr Cys Tyr Leu Lys Ala Ser Ala Ala Ile Arg Ala
65                  70                  75                  80
Ser Gly Leu Arg Asp Cys Thr Met Leu Val Tyr Gly Asp Asp Leu Val
                85                  90                  95
Val Ile Ala Glu Ser Asp Gly Val Glu Glu Asp Lys Arg Ala Leu Gly
            100                 105                 110
```

Val

<210> SEQ ID NO 112
<211> LENGTH: 340
<212> TYPE: DNA
<213> ORGANISM: hepatitis C virus

<400> SEQUENCE: 112

```
ctccactgta accgaaaagg acatcagggt cgaggaggag gtgtatcagt gttgtgacct      60
ggagcccgag gcccgcaagg caattactgc cctaacagag agactctatg tgggcggtcc     120
catgcataac agcaagggag acctgtgtgg gtatcgcaga tgccgcgcaa gcggcgtcta     180
caccaccagc ttcgggaaca cactgacgtg ctacctcaaa gcctcagccg ctatcagagc     240 ggcgggctg agagactgca ccatgttggt ctgtggtgat gacctggtcg tcatcgctga     300
gagcgatggc gttgaggagg acaaacgagc cctcggagcc                          340
```

<210> SEQ ID NO 113
<211> LENGTH: 113
<212> TYPE: PRT
<213> ORGANISM: hepatitis C virus

<400> SEQUENCE: 113

```
Ser Thr Val Thr Glu Lys Asp Ile Arg Val Glu Glu Val Tyr Gln
1               5                   10                  15

Cys Cys Asp Leu Glu Pro Glu Ala Arg Lys Ala Ile Thr Ala Leu Thr
                20                  25                  30

Glu Arg Leu Tyr Val Gly Gly Pro Met His Asn Ser Lys Gly Asp Leu
            35                  40                  45

Cys Gly Tyr Arg Arg Cys Arg Ala Ser Gly Val Tyr Thr Thr Ser Phe
50                  55                  60

Gly Asn Thr Leu Thr Cys Tyr Leu Lys Ala Ser Ala Ala Ile Arg Ala
65                  70                  75                  80

Ala Gly Leu Arg Asp Cys Thr Met Leu Val Cys Gly Asp Asp Leu Val
                85                  90                  95

Val Ile Ala Glu Ser Asp Gly Val Glu Glu Asp Lys Arg Ala Leu Gly
            100                 105                 110

Ala
```

<210> SEQ ID NO 114
<211> LENGTH: 340
<212> TYPE: DNA
<213> ORGANISM: hepatitis C virus

<400> SEQUENCE: 114

```
ctccacggtg accgaaaggg atatcaggac cgaggaagag atctaccagt gctgcgacct      60
ggagcccgaa gcccgcaagg tgatatccgc cctaacggaa agactctacg tgggcggtcc     120
catgtacaac tccaagggg acctatgcgg gcaacggagg tgccgcgcaa gcggggtcta     180
caccaccagc ttcgggaaca ctgtaacgtg ttatctcaag gccgttgcgg ctactagggc     240
cgcaggtctg aaaggttgca gcatgctggt ttgtggagac gacttagtcg tcatctgcga     300
gagcggcggc gtagaggagg atgcaagagc cctccgagcc                          340
```

<210> SEQ ID NO 115
<211> LENGTH: 113
<212> TYPE: PRT
<213> ORGANISM: hepatitis C virus -continued

```
<400> SEQUENCE: 115

Ser Thr Val Thr Glu Arg Asp Ile Arg Thr Glu Glu Ile Tyr Gln
1               5                   10                  15

Cys Cys Asp Leu Glu Pro Glu Ala Arg Lys Val Ile Ser Ala Leu Thr
            20                  25                  30

Glu Arg Leu Tyr Val Gly Gly Pro Met Tyr Asn Ser Lys Gly Asp Leu
        35                  40                  45

Cys Gly Gln Arg Arg Cys Arg Ala Ser Gly Val Tyr Thr Thr Ser Phe
    50                  55                  60

Gly Asn Thr Val Thr Cys Tyr Leu Lys Ala Val Ala Ala Thr Arg Ala
65                  70                  75                  80

Ala Gly Leu Lys Gly Cys Ser Met Leu Val Cys Gly Asp Asp Leu Val
                85                  90                  95

Val Ile Cys Glu Ser Gly Gly Val Glu Glu Asp Ala Arg Ala Leu Arg
            100                 105                 110

Ala

<210> SEQ ID NO 116
<211> LENGTH: 340
<212> TYPE: DNA
<213> ORGANISM: hepatitis C virus

<400> SEQUENCE: 116
ctccactgtg actgagagag acatcaaggt cgaagaagaa gtctatcagt gttgtgatct      60
ggagcccgag gcccgcaagg taatagccgc cctcacggag agactctacg tgggcggccc    120
catgcataac agcaagggag acctttgcgg gtatcgtaga tgccgcgcga gcggcgtata    180
caccaccagc ttcgggaaca caatgacgtg ctaccttaag gcctcagcag ccatcagggc    240 tgcgggcta aaggattgca ccatgctggt ttgcggtgac gacctagtcg tgatcgccga     300
gagcggtggc gttgaggagg acaaacgagc cctcggagct                           340

<210> SEQ ID NO 117
<211> LENGTH: 113
<212> TYPE: PRT
<213> ORGANISM: hepatitis C virus

<400> SEQUENCE: 117

Ser Thr Val Thr Glu Arg Asp Ile Lys Val Glu Glu Val Tyr Gln
1               5                   10                  15

Cys Cys Asp Leu Glu Pro Glu Ala Arg Lys Val Ile Ala Ala Leu Thr
            20                  25                  30

Glu Arg Leu Tyr Val Gly Gly Pro Met His Asn Ser Lys Gly Asp Leu
        35                  40                  45

Cys Gly Tyr Arg Arg Cys Arg Ala Ser Gly Val Tyr Thr Thr Ser Phe
    50                  55                  60

Gly Asn Thr Met Thr Cys Tyr Leu Lys Ala Ser Ala Ala Ile Arg Ala
65                  70                  75                  80

Ala Gly Leu Lys Asp Cys Thr Met Leu Val Cys Gly Asp Asp Leu Val
                85                  90                  95

Val Ile Ala Glu Ser Gly Gly Val Glu Glu Asp Lys Arg Ala Leu Gly
            100                 105                 110

Ala

<210> SEQ ID NO 118
<211> LENGTH: 574
```

```
<212> TYPE: DNA
<213> ORGANISM: hepatitis C virus

<400> SEQUENCE: 118
acttgcggct tgccgacct catgggatac atcccgctcg taggcgcccc tgtgggtggc      60
gtcgccaggg ccctggcaca cggtgttagg gctgtggagg acgggatcaa ttatgcgaca     120
gggaatcttc ccggttgctc tttctctatc ttcctcttgg cacttctttc gtgcctgact     180
gttcccacct cggccgtcaa ctatcgcaat gcctcgggca tctatcacat caccaatgac     240
tgcccgaact cgagcatagt gtacgagacc gagcaccaca tcctacacct cccagggtgt     300
ttaccctgcg tgagggttgg gaatcagtca cgctgctggg tggccctcac tcccaccgtg     360
gcggcgcctt acatcggcgc tccgcttgaa tccctccgga gtcatgtgga tctgatggta     420
ggtgccgcta ctgcgtgctc cgctctttac atcggagacc tgtgcggtgg cgtattcttg     480
gttggtcaga tgttctcttt ccagccgcgg cgccactgga ctacgcagga ctgcaattgt     540
tccatctacg cggggcacgt tacgggccac agga                                 574

<210> SEQ ID NO 119
<211> LENGTH: 191
<212> TYPE: PRT
<213> ORGANISM: hepatitis C virus

<400> SEQUENCE: 119

Thr Cys Gly Phe Ala Asp Leu Met Gly Tyr Ile Pro Leu Val Gly Ala
1               5                  10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Thr Ser
    50                  55                  60

Ala Val Asn Tyr Arg Asn Ala Ser Gly Ile Tyr His Ile Thr Asn Asp
65                  70                  75                  80

Cys Pro Asn Ser Ser Ile Val Tyr Glu Thr Glu His His Ile Leu His
                85                  90                  95

Leu Pro Gly Cys Leu Pro Cys Val Arg Val Gly Asn Gln Ser Arg Cys
            100                 105                 110

Trp Val Ala Leu Thr Pro Thr Val Ala Ala Pro Tyr Ile Gly Ala Pro
        115                 120                 125

Leu Glu Ser Leu Arg Ser His Val Asp Leu Met Val Gly Ala Ala Thr
    130                 135                 140

Ala Cys Ser Ala Leu Tyr Ile Gly Asp Leu Cys Gly Gly Val Phe Leu
145                 150                 155                 160

Val Gly Gln Met Phe Ser Phe Gln Pro Arg Arg His Trp Thr Thr Gln
                165                 170                 175

Asp Cys Asn Cys Ser Ile Tyr Ala Gly His Val Thr Gly His Arg
            180                 185                 190

<210> SEQ ID NO 120
<211> LENGTH: 574
<212> TYPE: DNA
<213> ORGANISM: hepatitis C virus

<400> SEQUENCE: 120
acgtgcggct tgccgacct catgggatac atcccgctcg tgggcgcccc tgtgggtggc       60
```

```
gtcgccaggg ccttggcaca tggtgtcagg gccgtggagg acgggattaa ctatgcaaca    120
gggaatcttc ccggttgctc cttttctatc ttccttctag cacttctctc gtgcttgact    180
gtcccggcct cggcgcagca ctaccggaac atctcgggca tttatcacgt caccaatgac    240
tgcccgaact ctagtatagt gtatgaagct gaccatcata tcatgcatct accagggtgt    300
gtgccttgcg tgagaaccgg gaacacctcg cgctgctggg ttcctttaac acccactgtg    360
gctgccccct atgttggcgc gccgctcgaa tccatgcggc ggcacgtgga cttaatggtg    420
ggtgccgcca ccgtctgctc ggccctgtac atcggagacc tttgcggagg tgtcttcctg    480
gtcgggcaga tgttcacctt ccggccgcgc cgccattgga ctacccagga ctgcaactgc    540
tctatctatg atggccacat caccggccat agaa                                574
```

<210> SEQ ID NO 121
<211> LENGTH: 191
<212> TYPE: PRT
<213> ORGANISM: hepatitis C virus

<400> SEQUENCE: 121

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Ala Ser
    50                  55                  60

Ala Gln His Tyr Arg Asn Ile Ser Gly Ile Tyr Val Thr Asn Asp
65                  70                  75                  80

Cys Pro Asn Ser Ser Ile Val Tyr Glu Ala Asp His His Ile Met His
                85                  90                  95

Leu Pro Gly Cys Val Pro Cys Val Arg Thr Gly Asn Thr Ser Arg Cys
            100                 105                 110

Trp Val Pro Leu Thr Pro Thr Val Ala Ala Pro Tyr Val Gly Ala Pro
        115                 120                 125

Leu Glu Ser Met Arg Arg His Val Asp Leu Met Val Gly Ala Ala Thr
    130                 135                 140

Val Cys Ser Ala Leu Tyr Ile Gly Asp Leu Cys Gly Gly Val Phe Leu
145                 150                 155                 160

Val Gly Gln Met Phe Thr Phe Arg Pro Arg Arg His Trp Thr Thr Gln
                165                 170                 175

Asp Cys Asn Cys Ser Ile Tyr Asp Gly His Ile Thr Gly His Arg
            180                 185                 190

<210> SEQ ID NO 122
<211> LENGTH: 574
<212> TYPE: DNA
<213> ORGANISM: hepatitis C virus

<400> SEQUENCE: 122

```
acgtgcggct cgccgacct catgggatac atcccgctcg tgggcgcccc cgttgggggc     60
gtcgccaggg ccctggcgca tggcgtcagg gctgtggagg acgggattaa ctatgcgaca   120
gggaatcttc ccggttgctc tttctctatc ttcctcctgg cacttctttc gtgcctcact   180
gtcccagcgt cagctgagca ctaccggaat gcttcgggca tctatcacat caccaatgac   240
tgtccgaatt ccagcgtagt ctatgaaact gaccaccata tattgcactt gccggggtgc   300
```

```
gtaccctgcg tgagggccgg gaacgtgtct cgttgctgga cgccggtaac acctacggtg    360
gctgccgtat ccatggacgc tccgctcgag tccttccggc ggcatgtgga cctaatggta    420
ggtgcggcca ccgtgtgttc tgtcctctat gttggagacc tctgtggagg tgctttccta    480
gtggggcaga tgttcacctt ccagccgcgt cgccactgga ccacgcagga ttgtaattgc    540
tccatctata ctggccatat caccggccac agga                                574
```

```
<210> SEQ ID NO 123
<211> LENGTH: 191
<212> TYPE: PRT
<213> ORGANISM: hepatitis C virus

<400> SEQUENCE: 123
```

```
Thr Cys Gly Phe Ala Asp Leu Met Gly Tyr Ile Pro Leu Val Gly Ala
  1               5                  10                  15

Pro Val Gly Gly Val Ala Arg Ala Leu Ala His Gly Val Arg Ala Val
                 20                  25                  30

Glu Asp Gly Ile Asn Tyr Ala Thr Gly Asn Leu Pro Gly Cys Ser Phe
             35                  40                  45

Ser Ile Phe Leu Leu Ala Leu Leu Ser Cys Leu Thr Val Pro Ala Ser
 50                  55                  60

Ala Glu His Tyr Arg Asn Ala Ser Gly Ile Tyr His Ile Thr Asn Asp
 65                  70                  75                  80

Cys Pro Asn Ser Ser Val Val Tyr Glu Thr Asp His His Ile Leu His
                 85                  90                  95

Leu Pro Gly Cys Val Pro Cys Val Arg Ala Gly Asn Val Ser Arg Cys
            100                 105                 110

Trp Thr Pro Val Thr Pro Thr Val Ala Val Ser Met Asp Ala Pro
            115                 120                 125

Leu Glu Ser Phe Arg Arg His Val Asp Leu Met Val Gly Ala Ala Thr
        130                 135                 140

Val Cys Ser Val Leu Tyr Val Gly Asp Leu Cys Gly Gly Ala Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg
            180                 185                 190
```

```
<210> SEQ ID NO 124
<211> LENGTH: 31
<212> TYPE: DNA
<213> ORGANISM: artificial
<220> FEATURE:
<221> NAME/KEY: misc_feature
<223> OTHER INFORMATION: HCPr206

<400> SEQUENCE: 124
tggggatccc gtatgatacc cgctgctttg a                                    31
```

```
<210> SEQ ID NO 125
<211> LENGTH: 30
<212> TYPE: DNA
<213> ORGANISM: artificial
<220> FEATURE:
<221> NAME/KEY: misc_feature
<223> OTHER INFORMATION: HCPr207

<400> SEQUENCE: 125
```

-continued ggcggaattc ctggtcatag cctccgtgaa           30

<210> SEQ ID NO 126
<211> LENGTH: 12
<212> TYPE: PRT
<213> ORGANISM: hepatitis C virus

<400> SEQUENCE: 126

Val Asn Tyr Arg Asn Ala Ser Gly Ile Tyr His Ile
1               5                   10

<210> SEQ ID NO 127
<211> LENGTH: 12
<212> TYPE: PRT
<213> ORGANISM: hepatitis C virus

<400> SEQUENCE: 127

Gln His Tyr Arg Asn Ile Ser Gly Ile Tyr His Val
1               5                   10

<210> SEQ ID NO 128
<211> LENGTH: 12
<212> TYPE: PRT
<213> ORGANISM: hepatitis C virus

<400> SEQUENCE: 128

Glu His Tyr Arg Asn Ala Ser Gly Ile Tyr His Ile
1               5                   10

<210> SEQ ID NO 129
<211> LENGTH: 11
<212> TYPE: PRT
<213> ORGANISM: hepatitis C virus

<400> SEQUENCE: 129

Val Tyr Glu Thr Glu His His Ile Leu His Leu
1               5                   10

<210> SEQ ID NO 130
<211> LENGTH: 11
<212> TYPE: PRT
<213> ORGANISM: hepatitis C virus

<400> SEQUENCE: 130

Val Tyr Glu Ala Asp His His Ile Met His Leu
1               5                   10

<210> SEQ ID NO 131
<211> LENGTH: 11
<212> TYPE: PRT
<213> ORGANISM: hepatitis C virus

<400> SEQUENCE: 131

Val Tyr Glu Thr Asp His His Ile Leu His Leu
1               5                   10

<210> SEQ ID NO 132
<211> LENGTH: 13
<212> TYPE: PRT
<213> ORGANISM: hepatitis C virus

<400> SEQUENCE: 132

Val Arg Val Gly Asn Gln Ser Arg Cys Trp Val Ala Leu
1               5                   10

```
<210> SEQ ID NO 133
<211> LENGTH: 13
<212> TYPE: PRT
<213> ORGANISM: hepatitis C virus

<400> SEQUENCE: 133

Val Arg Thr Gly Asn Thr Ser Arg Cys Trp Val Pro Leu
1               5                   10

<210> SEQ ID NO 134
<211> LENGTH: 13
<212> TYPE: PRT
<213> ORGANISM: hepatitis C virus

<400> SEQUENCE: 134

Val Arg Ala Gly Asn Val Ser Arg Cys Trp Thr Pro Val
1               5                   10

<210> SEQ ID NO 135
<211> LENGTH: 10
<212> TYPE: PRT
<213> ORGANISM: hepatitis C virus

<400> SEQUENCE: 135

Ala Pro Tyr Ile Gly Ala Pro Leu Glu Ser
1               5                   10

<210> SEQ ID NO 136
<211> LENGTH: 10
<212> TYPE: PRT
<213> ORGANISM: hepatitis C virus

<400> SEQUENCE: 136

Ala Pro Tyr Val Gly Ala Pro Leu Glu Ser
1               5                   10

<210> SEQ ID NO 137
<211> LENGTH: 10
<212> TYPE: PRT
<213> ORGANISM: hepatitis C virus

<400> SEQUENCE: 137

Ala Val Ser Met Asp Ala Pro Leu Glu Ser
1               5                   10

<210> SEQ ID NO 138
<211> LENGTH: 10
<212> TYPE: PRT
<213> ORGANISM: hepatitis C virus

<400> SEQUENCE: 138

Gln Pro Arg Arg His Trp Thr Thr Gln Asp
1               5                   10

<210> SEQ ID NO 139
<211> LENGTH: 10
<212> TYPE: PRT
<213> ORGANISM: hepatitis C virus

<400> SEQUENCE: 139

Arg Pro Arg Arg His Trp Thr Thr Gln Asp
1               5                   10

<210> SEQ ID NO 140
```

```
<211> LENGTH: 10
<212> TYPE: PRT
<213> ORGANISM: hepatitis C virus

<400> SEQUENCE: 140

Arg Pro Arg Arg His Trp Thr Thr Gln Asp
1               5                   10

<210> SEQ ID NO 141
<211> LENGTH: 23
<212> TYPE: DNA
<213> ORGANISM: artificial
<220> FEATURE:
<221> NAME/KEY: misc_feature
<223> OTHER INFORMATION: HCPr109

<400> SEQUENCE: 141
tgggatatga tgatgaactg gtc                                          23

<210> SEQ ID NO 142
<211> LENGTH: 24
<212> TYPE: DNA
<213> ORGANISM: artificial
<220> FEATURE:
<221> NAME/KEY: misc_feature
<223> OTHER INFORMATION: HCPr14

<400> SEQUENCE: 142
ccaggtacaa ccgaaccaat tgcc                                         24

<210> SEQ ID NO 143
<211> LENGTH: 957
<212> TYPE: DNA
<213> ORGANISM: hepatitis C virus

<400> SEQUENCE: 143
atgagcacaa atcctaaacc tcaaagaaaa accaaaagaa acactaaccg ccgcccacag    60
gacgtcaagt tcccgggcgg tggccagatc gttggtggag tatacttgtt gccgcgcagg   120
ggcccccggt tgggtgtgcg cgcgacgagg aaaacttccg agcggtccca gccacgtggg   180
aggcgccagc ccatccccaa agatcggcgc cccactggca agtcctgggg aaaaccagga   240
taccctttggc ccctgtacgg gaatgagggc ctcggctggg cagggtggct cctgtccccc   300
cgagggtctc gcccgtcatg gggcccaact gaccccggc acaggtcacg caacttgggt   360
aaggtcatcg ataccttac gtgtggcttt gccgacctca tggggtacat ccctgtcgtc   420
ggcgccccag ttggtggtgt cgccagagct ctcgcgcatg gcgtgagagt tctggaagac   480
gggataaact atgcaacagg gaacttgccc ggttgctcct ttctctatct cttattggcc   540
ctgctatctt gtatcactgt gccggtctcc ggcttgcagg tcaagaacac cagcagctct   600
tacatggtaa ccaatgactg ccagaacagt agcatcgtct ggcagctcag ggatgctgtt   660
cttcacgtcc ccgggtgtgt cccttgtgag gagaagggca catatcccg ctgttggata   720
ccggtttcgc ccaatatagc tgtgagccaa cctggtgcgc ttaccaaggg cctgcggacg   780
catattgata ccatcattgc atccgctacg ttttgctctg ccctgtacat aggagacctg   840
tgtggcgcgg tgatgttggc ttctcaagtc ttcatcatct cgccccagca tcataagttt   900
gtccaggact gcaactgttc catatacca ggccacatca ctggacatcg gatggcg     957

<210> SEQ ID NO 144
<211> LENGTH: 319
<212> TYPE: PRT
```

<213> ORGANISM: hepatitis C virus

<400> SEQUENCE: 144

```
Met Ser Thr Asn Pro Lys Pro Gln Arg Lys Thr Lys Arg Asn Thr Asn
1               5                   10                  15
Arg Arg Pro Gln Asp Val Lys Phe Pro Gly Gly Gly Gln Ile Val Gly
            20                  25                  30
Gly Val Tyr Leu Leu Pro Arg Arg Gly Pro Arg Leu Gly Val Arg Ala
        35                  40                  45
Thr Arg Lys Thr Ser Glu Arg Ser Gln Pro Arg Gly Arg Arg Gln Pro
    50                  55                  60
Ile Pro Lys Asp Arg Arg Pro Thr Gly Lys Ser Trp Gly Lys Pro Gly
65                  70                  75                  80
Tyr Pro Trp Pro Leu Tyr Gly Asn Glu Gly Leu Gly Trp Ala Gly Trp
                85                  90                  95
Leu Leu Ser Pro Arg Gly Ser Arg Pro Ser Trp Gly Pro Thr Asp Pro
            100                 105                 110
Arg His Arg Ser Arg Asn Leu Gly Lys Val Ile Asp Thr Leu Thr Cys
        115                 120                 125
Gly Phe Ala Asp Leu Met Gly Tyr Ile Pro Val Val Gly Ala Pro Val
    130                 135                 140
Gly Gly Val Ala Arg Ala Leu Ala His Gly Val Arg Val Leu Glu Asp
145                 150                 155                 160
Gly Ile Asn Tyr Ala Thr Gly Asn Leu Pro Gly Cys Ser Phe Ser Ile
                165                 170                 175
Phe Leu Leu Ala Leu Leu Ser Cys Ile Thr Val Pro Val Ser Gly Leu
            180                 185                 190
Gln Val Lys Asn Thr Ser Ser Tyr Met Val Thr Asn Asp Cys Gln
        195                 200                 205
Asn Ser Ser Ile Val Trp Gln Leu Arg Asp Ala Val Leu His Val Pro
    210                 215                 220
Gly Cys Val Pro Cys Glu Glu Lys Gly Asn Ile Ser Arg Cys Trp Ile
225                 230                 235                 240
Pro Val Ser Pro Asn Ile Ala Val Ser Gln Pro Gly Ala Leu Thr Lys
                245                 250                 255
Gly Leu Arg Thr His Ile Asp Thr Ile Ile Ala Ser Ala Thr Phe Cys
            260                 265                 270
Ser Ala Leu Tyr Ile Gly Asp Leu Cys Gly Ala Val Met Leu Ala Ser
        275                 280                 285
Gln Val Phe Ile Ile Ser Pro Gln His His Lys Phe Val Gln Asp Cys
    290                 295                 300
Asn Cys Ser Ile Tyr Pro Gly His Ile Thr Gly His Arg Met Ala
305                 310                 315
```

<210> SEQ ID NO 145
<211> LENGTH: 340
<212> TYPE: DNA
<213> ORGANISM: hepatitis C virus

<400> SEQUENCE: 145

```
ctcaacggtc acgagagggg acatcagaac tgaggagtcc atataccttg cttgctcttt     60
acccgagcag gcacggactg ccatacactc actgactgag aggctttacg tgggagggcc    120
catgctaaac agcaagggc aaacctgcgg atacagacgc tgccgcgcca gcggagtgtt    180
caccactagc atgggaaata ccatcacgtg ctacgtgaag gcacaagcag cctgtaaggc    240
```

```
tgcgggcata attgccccca cgatgctggt gtgcggcgac gatctagttg tcatctcaga    300
gagtcagggg accgaggagg acgagcggaa cctacgagcc                          340
```

<210> SEQ ID NO 146
<211> LENGTH: 113
<212> TYPE: PRT
<213> ORGANISM: hepatitis C virus

<400> SEQUENCE: 146

```
Ser Thr Val Thr Glu Arg Asp Ile Arg Thr Glu Glu Ser Ile Tyr Leu
1               5                   10                  15

Ala Cys Ser Leu Pro Glu Gln Ala Arg Thr Ala Ile His Ser Leu Thr
            20                  25                  30

Glu Arg Leu Tyr Val Gly Gly Pro Met Leu Asn Ser Lys Gly Gln Thr
        35                  40                  45

Cys Gly Tyr Arg Arg Cys Arg Ala Ser Gly Val Phe Thr Thr Ser Met
    50                  55                  60

Gly Asn Thr Ile Thr Cys Tyr Val Lys Ala Gln Ala Ala Cys Lys Ala
65                  70                  75                  80

Ala Gly Ile Ile Ala Pro Thr Met Leu Val Cys Gly Asp Asp Leu Val
                85                  90                  95

Val Ile Ser Glu Ser Gln Gly Thr Glu Glu Asp Glu Arg Asn Leu Arg
            100                 105                 110

Ala
```

<210> SEQ ID NO 147
<211> LENGTH: 345
<212> TYPE: DNA
<213> ORGANISM: hepatitis C virus

<400> SEQUENCE: 147

```
atgagcacac ttcctaaacc acaaagaaaa accaaaagaa acaccaaccc cggccacagg    60
acgttaagtt cccaggcggc ggtcagatcg ttggtggagt ttacgtgcta ccacgcaggg   120 gccccccagtt gggtgtgcgt gcagtgcgca agacttccga gcggtcgcaa cctcgcagta   180
ggcgccaacc catccccagg gcgcgccgaa ccgagggcag gtcctgggct cagcccgggt   240
acccttggcc cctatatggg aatgagggct gcgggtgggc agggtggctc ctgtccccgc   300
gcggctctcg cccgtcgtgg ggcccaaatg accccggcg cagga                    345
```

<210> SEQ ID NO 148
<211> LENGTH: 115
<212> TYPE: PRT
<213> ORGANISM: hepatitis C virus

<400> SEQUENCE: 148

```
Met Ser Thr Leu Pro Lys Pro Gln Arg Lys Thr Lys Arg Asn Thr Asn
1               5                   10                  15

Pro Gly His Arg Thr Leu Ser Ser Gln Ala Ala Val Arg Ser Leu Val
            20                  25                  30

Glu Phe Thr Cys Tyr His Ala Gly Ala Pro Ser Trp Val Cys Val Gln
        35                  40                  45

Cys Ala Arg Leu Pro Ser Gly Arg Asn Leu Ala Val Gly Ala Asn Pro
    50                  55                  60

Ser Pro Gly Arg Ala Glu Pro Arg Ala Gly Pro Gly Leu Ser Pro Gly
65                  70                  75                  80
```

```
Thr Leu Gly Pro Tyr Met Gly Met Arg Ala Ala Gly Gly Gln Gly Gly
                85                  90                  95
Ser Cys Pro Arg Ala Ala Leu Ala Arg Arg Gly Ala Gln Met Thr Pro
            100                 105                 110
Gly Ala Gly
        115
```

<210> SEQ ID NO 149
<211> LENGTH: 280
<212> TYPE: DNA
<213> ORGANISM: hepatitis C virus

<400> SEQUENCE: 149

```
ggcctgtgac ctcaaggacg aggctaggag ggtgataact tcactcacgg agcggcttta      60
ctgtggtggt cctatgttca acagcaaggg acaacactgc ggttaccgcc gctgccgtgc     120
tagtggggtg ctaccacca gcttcgggaa cacaatcacc tgttacatca agcaaaggc      180
agctaccaaa gctgccggaa ttaaaaatcc atcattcctt gtctgcggag atgacttggt     240
cgtgattgct gagagtgcag ggatcgatga ggacagagcg                           280
```

<210> SEQ ID NO 150
<211> LENGTH: 93
<212> TYPE: PRT
<213> ORGANISM: hepatitis C virus

<400> SEQUENCE: 150

```
Ala Cys Asp Leu Lys Asp Glu Ala Arg Arg Val Ile Thr Ser Leu Thr
1               5                   10                  15
Glu Arg Leu Tyr Cys Gly Gly Pro Met Phe Asn Ser Lys Gly Gln His
            20                  25                  30
Cys Gly Tyr Arg Arg Cys Arg Ala Ser Gly Val Leu Pro Thr Ser Phe
        35                  40                  45
Gly Asn Thr Ile Thr Cys Tyr Ile Lys Ala Lys Ala Thr Lys Ala
    50                  55                  60
Ala Gly Ile Lys Asn Pro Ser Phe Leu Val Cys Gly Asp Asp Leu Val
65                  70                  75                  80
Val Ile Ala Glu Ser Ala Gly Ile Asp Glu Asp Arg Ala
                85                  90
```

<210> SEQ ID NO 151
<211> LENGTH: 499
<212> TYPE: DNA
<213> ORGANISM: hepatitis C virus

<400> SEQUENCE: 151

```
atgagcacga atcctaaacc tcaaagaaaa accaaaagaa acaccaaccg tcgcccacag      60
gacgtcaagt tcccgggcgg tggtcagatc gttggcggag tttacttgtt gccgcgcagg     120
ggccctagga tgggtgtgcg cgcgactcgg aagacttcgg aacggtcgca accccgtgga     180
cggcgtcagc ctattcccaa ggcgcgccag cccacgggcc ggtcctgggg tcaacccggg     240
taccctttggc cccttttacgc caatgagggc ctcgggtggg cagggtggct gctctcccct     300
cgaggctctc ggcctaattg ggcccccaat gaccccgggc gaaaatcgcg taatttgggt     360
aaggtcatcg ataccctaac gtgcggattc gccgatctca tggggtatat cccgctcgta     420
ggcggcccca ttgggggcgt cgcaagggct ctcgcacacg tgtgagggt ccttgaggac     480
ggggtaaact atgcaacag                                                  499
```

```
<210> SEQ ID NO 152
<211> LENGTH: 166
<212> TYPE: PRT
<213> ORGANISM: hepatitis C virus

<400> SEQUENCE: 152

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gln Ile Val Gly
                20                  25                  30

Gly Val Tyr Leu Leu Pro Arg Arg Gly Pro Arg Met Gly Val Arg Ala
                35                  40                  45

Thr Arg Lys Thr Ser Glu Arg Ser Gln Pro Arg Gly Arg Arg Gln Pro
        50                  55                  60

Ile Pro Lys Ala Arg Gln Pro Thr Gly Arg Ser Trp Gly Gln Pro Gly
65              70                  75                  80

Tyr Pro Trp Pro Leu Tyr Ala Asn Glu Gly Leu Gly Trp Ala Gly Trp
                85                  90                  95

Leu Leu Ser Pro Arg Gly Ser Arg Pro Asn Trp Gly Pro Asn Asp Pro
                100                 105                 110

Arg Arg Lys Ser Arg Asn Leu Gly Lys Val Ile Asp Thr Leu Thr Cys
            115                 120                 125

Gly Phe Ala Asp Leu Met Gly Tyr Ile Pro Leu Val Gly Gly Pro Ile
        130                 135                 140

Gly Gly Val Ala Arg Ala Leu Ala His Gly Val Arg Val Leu Glu Asp
145                 150                 155                 160

Gly Val Asn Tyr Ala Thr
                165

<210> SEQ ID NO 153
<211> LENGTH: 579
<212> TYPE: DNA
<213> ORGANISM: hepatitis C virus

<400> SEQUENCE: 153
acgtgcggat cgccgatct  catggggtac atcccgctcg taggcggccc cgttgggggc    60
gtcgcaaggg ctctcgcaca cggtgtgagg gtccttgagg acgggtaaa ctatccaaca   120 gggaatttac ccggttgctc tttctctatc tttattcttg ctcttctctc gtgtctgacc   180
gttccggcct ctgcagttcc ctaccgaaat gcctctggga tttatcatgt accaatgat   240 tgcccaaact cttccatagt ctatgaggca gataacctga tcctacacgc acctggttgc   300
gtgccttgtg tcatgacagg taatgtgagt agatgctggg tccaaattac ccctacactg   360
tcagccccga gcctcggagc agtcacggct cctcttcgga gagccgttga ctacctagcg   420 ggagggctg ccctctgctc cgcgttatac gtaggagacg cgtgtgggc actattcttg    480 gtaggccaaa tgttcaccta taggcctcgc cagcacgcta cggtgcagaa ctgcaactgt    540
tccatttaca gtggccatgt taccggccac cggatggcg                          579

<210> SEQ ID NO 154
<211> LENGTH: 193
<212> TYPE: PRT
<213> ORGANISM: hepatitis C virus

<400> SEQUENCE: 154

Thr Cys Gly Phe Ala Asp Leu Met Gly Tyr Ile Pro Leu Val Gly Gly
1               5                   10                  15
```

Pro Val Gly Gly Val Ala Arg Ala Leu Ala His Gly Val Arg Val Leu
            20                  25                  30

Glu Asp Gly Val Asn Tyr Pro Thr Gly Asn Leu Pro Gly Cys Ser Phe
        35                  40                  45

Ser Ile Phe Ile Leu Ala Leu Leu Ser Cys Leu Thr Val Pro Ala Ser
    50                  55                  60

Ala Val Pro Tyr Arg Asn Ala Ser Gly Ile Tyr His Val Thr Asn Asp
65                  70                  75                  80

Cys Pro Asn Ser Ser Ile Val Tyr Glu Ala Asp Asn Leu Ile Leu His
                85                  90                  95

Ala Pro Gly Cys Val Pro Cys Val Met Thr Gly Asn Val Ser Arg Cys
            100                 105                 110

Trp Val Gln Ile Thr Pro Thr Leu Ser Ala Pro Ser Leu Gly Ala Val
            115                 120                 125

Thr Ala Pro Leu Arg Arg Ala Val Asp Tyr Leu Ala Gly Gly Ala Ala
        130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asn Cys Asn Cys Ser Ile Tyr Ser Gly His Val Thr Gly His Arg Met
                180                 185                 190

Ala

<210> SEQ ID NO 155
<211> LENGTH: 579
<212> TYPE: DNA
<213> ORGANISM: hepatitis C virus

<400> SEQUENCE: 155
acgtgcggat tcgccgacct cgtggggtac atcccgctcg taggcggccc cgttgggggc     60
gtcgcaaggg ctctcgcaca tggtgtgagg gttcttgagg acggggtgaa ttatgcaaca    120
gggaatctgc ctggttgctc tttctctatc ttcattcttg cacttctctc gtgcctcact    180
gtcccggcct ctgcagttcc ctaccgaaat gcctctggga tctatcatgt caccaatgat    240
tgcccaaact cttccatagt ctatgaggca gatgatctga tcctacacgc acctggctgc    300
gtgccttgtg tcaggaaaga taatgtgagt aggtgctggg tccaaattac ccccacgctg    360
tcagccccga gcttcggagc agtcacggct ccccttcgga gagccgttga ttacttggtg    420
ggagggctg ccctctgctc cgcgttatac gttggagacg cgtgtggggc actattttg     480
gtaggccaaa tgttcaccta taggcctcgc cagcatgcta cggtgcagga ctgcaactgt    540
tccatctaca gtggccacgt caccggccat cagatggca                          579

<210> SEQ ID NO 156
<211> LENGTH: 193
<212> TYPE: PRT
<213> ORGANISM: hepatitis C virus

<400> SEQUENCE: 156

Thr Cys Gly Phe Ala Asp Leu Val Gly Tyr Ile Pro Leu Val Gly Gly
1               5                   10                  15

Pro Val Gly Gly Val Ala Arg Ala Leu Ala His Gly Val Arg Val Leu
            20                  25                  30

Glu Asp Gly Val Asn Tyr Ala Thr Gly Asn Leu Pro Gly Cys Ser Phe

-continued

```
                35                  40                  45
Ser Ile Phe Ile Leu Ala Leu Leu Ser Cys Leu Thr Val Pro Ala Ser
                50                  55                  60

Ala Val Pro Tyr Arg Asn Ala Ser Gly Ile Tyr His Val Thr Asn Asp
 65                  70                  75                  80

Cys Pro Asn Ser Ser Ile Val Tyr Glu Ala Asp Leu Ile Leu His
                    85                  90                  95

Ala Pro Gly Cys Val Pro Cys Val Arg Lys Asp Asn Val Ser Arg Cys
                100                 105                 110

Trp Val Gln Ile Thr Pro Thr Leu Ser Ala Pro Ser Phe Gly Ala Val
                115                 120                 125

Thr Ala Pro Leu Arg Arg Ala Val Asp Tyr Leu Val Gly Gly Ala Ala
                130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                    165                 170                 175

Asp Cys Asn Cys Ser Ile Tyr Ser Gly His Val Thr Gly His Gln Met
                180                 185                 190

Ala
```

<210> SEQ ID NO 157
<211> LENGTH: 530
<212> TYPE: DNA
<213> ORGANISM: hepatitis C virus

<400> SEQUENCE: 157

```
cacctacgac agctctgctg gtggcccagt tactgcggat ccccaagtg gtcattgaca      60
tcatcgcagg gagccactgg ggggtcttgt ttgccgccgc atactatgca tcggtggcta    120
actggaccaa ggtcgtgctg gtcttgtttc tgtttgcagg ggttgatgct actacccaga    180
tttcgggcgg ctccagcgcc caaacgacgt atggcatcgc ctcatttatc acccgcggcg    240
cgcagcagaa actgcagctc ataaatacca acggaagctg gcacatcaac aggaccgccc    300
ttaattgtaa tgacagcctc cagactgggt tcatagccgg cctcttctac taccataagt    360
tcaactcttc tggatgcccg gatcggatgg ctagctgtag ggcccttgcc acttttgacc    420
agggctgggg aactatcagc tatgccaaca tatcgggtcc cagtgatgac aaaccatatt    480
gctggcacta tccccacgg ccgtgcggag tggtgccagc ccaagaggtc                530
```

<210> SEQ ID NO 158
<211> LENGTH: 176
<212> TYPE: PRT
<213> ORGANISM: hepatitis C virus

<400> SEQUENCE: 158

```
Pro Thr Thr Ala Leu Leu Val Ala Gln Leu Leu Arg Ile Pro Gln Val
 1               5                  10                  15

Val Ile Asp Ile Ile Ala Gly Ser His Trp Gly Val Leu Phe Ala Ala
                20                  25                  30

Ala Tyr Tyr Ala Ser Val Ala Asn Trp Thr Lys Val Val Leu Val Leu
                35                  40                  45

Phe Leu Phe Ala Gly Val Asp Ala Thr Thr Gln Ile Ser Gly Gly Ser
                50                  55                  60

Ser Ala Gln Thr Thr Tyr Gly Ile Ala Ser Phe Ile Thr Arg Gly Ala
 65                  70                  75                  80
```

```
Gln Gln Lys Leu Gln Leu Ile Asn Thr Asn Gly Ser Trp His Ile Asn
                85                  90                  95

Arg Thr Ala Leu Asn Cys Asn Asp Ser Leu Gln Thr Gly Phe Ile Ala
            100                 105                 110

Gly Leu Phe Tyr Tyr His Lys Phe Asn Ser Ser Gly Cys Pro Asp Arg
            115                 120                 125

Met Ala Ser Cys Arg Ala Leu Ala Thr Phe Asp Gln Gly Trp Gly Thr
            130                 135                 140

Ile Ser Tyr Ala Asn Ile Ser Gly Pro Ser Asp Asp Lys Pro Tyr Cys
145                 150                 155                 160

Trp His Tyr Pro Pro Arg Pro Cys Gly Val Val Pro Ala Gln Glu Val
                165                 170                 175

<210> SEQ ID NO 159
<211> LENGTH: 340
<212> TYPE: DNA
<213> ORGANISM: hepatitis C virus

<400> SEQUENCE: 159
ctcgaccgtt accgaacatg acataatgac cgaagagtcc atttaccaat catgtgactt      60
gcagcccgag gcacgcgcag caatacggtc actcacccaa cgcctctact gtggaggccc     120
catgtacaac agcaaggggc aacagtgtgg ttatcgcaga tgccgcgcca gcggcgtttt     180
caccaccagt atgggcaaca ccatgacgtg ctacatcaag gctttagcct cctgtagagc     240
cgcaaggctc cgggactgca cgctcctggt gtgtggtgac gatcttgtgg ccatctgcga     300
gagccagggg acacacgagg atgaagcaag cctgagagcc                           340

<210> SEQ ID NO 160
<211> LENGTH: 113
<212> TYPE: PRT
<213> ORGANISM: hepatitis C virus

<400> SEQUENCE: 160

Ser Thr Val Thr Glu His Asp Ile Met Thr Glu Ser Ile Tyr Gln
1               5                   10                  15

Ser Cys Asp Leu Gln Pro Glu Ala Arg Ala Ala Ile Arg Ser Leu Thr
                20                  25                  30

Gln Arg Leu Tyr Cys Gly Gly Pro Met Tyr Asn Ser Lys Gly Gln Gln
            35                  40                  45

Cys Gly Tyr Arg Arg Cys Arg Ala Ser Gly Val Phe Thr Thr Ser Met
50                  55                  60

Gly Asn Thr Met Thr Cys Tyr Ile Lys Ala Leu Ala Ser Cys Arg Ala
65                  70                  75                  80

Ala Arg Leu Arg Asp Cys Thr Leu Leu Val Cys Gly Asp Asp Leu Val
                85                  90                  95

Ala Ile Cys Glu Ser Gln Gly Thr His Glu Asp Glu Ala Ser Leu Arg
            100                 105                 110

Ala

<210> SEQ ID NO 161
<211> LENGTH: 340
<212> TYPE: DNA
<213> ORGANISM: hepatitis C virus

<400> SEQUENCE: 161
ctcaaccgcc accgaacatg acatattgac tgaagagtcc ataccaat catgtgactc       60
```

-continued

```
gcagcccgac gcacgcgcag caatacggtc actcacccaa cgcttgttct gtggaggccc      120
catgtataac agcaaggggc aacaatgtgg ttatcgcaga tgccgcgcca gcggcgtctt      180
caccaccagt atgggcaaca ccatgacgtg ctacattaag gctttagcct cctgtagaac      240
cgctgggctc cggactaca cgctcctggt gtgtggtgac gatcatgtgg ccatctgcga       300
gagccagggg acacacgagg atgaagcgaa cctgagagcc                            340
```

<210> SEQ ID NO 162
<211> LENGTH: 113
<212> TYPE: PRT
<213> ORGANISM: hepatitis C virus

<400> SEQUENCE: 162

```
Ser Thr Ala Thr Glu His Asp Ile Leu Thr Glu Ser Ile Tyr Gln
1               5                   10                  15

Ser Cys Asp Ser Gln Pro Asp Ala Arg Ala Ile Arg Ser Leu Thr
            20                  25                  30

Gln Arg Leu Phe Cys Gly Gly Pro Met Tyr Asn Ser Lys Gly Gln Gln
        35                  40                  45

Cys Gly Tyr Arg Arg Cys Arg Ala Ser Gly Val Phe Thr Thr Ser Met
    50                  55                  60

Gly Asn Thr Met Thr Cys Tyr Ile Lys Ala Leu Ala Ser Cys Arg Thr
65                  70                  75                  80

Ala Gly Leu Arg Asp Tyr Thr Leu Leu Val Cys Gly Asp Asp His Val
                85                  90                  95

Ala Ile Cys Glu Ser Gln Gly Thr His Glu Asp Glu Ala Asn Leu Arg
            100                 105                 110

Ala
```

<210> SEQ ID NO 163
<211> LENGTH: 499
<212> TYPE: DNA
<213> ORGANISM: hepatitis C virus

<400> SEQUENCE: 163

```
atgagcacga atcctaaaact tcaaagaaaa accaaacgta acaccaaccg ccgcccatg       60 gacgttaagt tcccgggtgg tggccagatc gttggcggag tttacttgtt gccgcgcagg      120
ggccctaggt tgggtgtgcg cgcgactcgg aagacttcgg agcggtcgca acctcgtggg      180
aggcgccaac ctatccccaa ggcgcgccga tccgagggca gatcctgggc gcagcccggg      240
tatccttggc ccctttacgg caatgagggc tgtgggtggg caggtggct cctgtcccct       300 cgcgggtctc ggccgtcttg gggccctaat gatccccggc ggaggtcccg caacctgggt      360
aaggtcatcg ataccctaac atgcggcttc gccgacctca tgggatacat cccgcttgta      420 ggcgccccg tggtggcgt cgccagagcc ctggcacacg tgttagggc tgtggaagac        480 gggatcaact acgcaacag                                                   499
```

<210> SEQ ID NO 164
<211> LENGTH: 166
<212> TYPE: PRT
<213> ORGANISM: hepatitis C virus

<400> SEQUENCE: 164

```
Met Ser Thr Asn Pro Lys Leu Gln Arg Lys Thr Lys Arg Asn Thr Asn
1               5                   10                  15
```

```
Arg Arg Pro Met Asp Val Lys Phe Pro Gly Gly Gly Gln Ile Val Gly
            20                  25                  30

Gly Val Tyr Leu Leu Pro Arg Gly Pro Arg Leu Gly Val Arg Ala
        35                  40                  45

Thr Arg Lys Thr Ser Glu Arg Ser Gln Pro Arg Gly Arg Arg Gln Pro
 50                  55                  60

Ile Pro Lys Ala Arg Arg Ser Glu Gly Arg Ser Trp Ala Gln Pro Gly
 65                  70                  75                  80

Tyr Pro Trp Pro Leu Tyr Gly Asn Glu Gly Cys Gly Trp Ala Gly Trp
                 85                  90                  95

Leu Leu Ser Pro Arg Gly Ser Arg Pro Ser Trp Gly Pro Asn Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Val
    130                 135                 140

Gly Gly Val Ala Arg Ala Leu Ala His Gly Val Arg Ala Val Glu Asp
145                 150                 155                 160

Gly Ile Asn Tyr Ala Thr
                165

<210> SEQ ID NO 165
<211> LENGTH: 499
<212> TYPE: DNA
<213> ORGANISM: hepatitis C virus
<220> FEATURE:
<221> NAME/KEY: misc_feature
<222> LOCATION: (306)..(306)
<223> OTHER INFORMATION: "n" is any nucleotide
<220> FEATURE:
<221> NAME/KEY: misc_feature
<222> LOCATION: (313)..(313)
<223> OTHER INFORMATION: "n" is any nucleotide
<220> FEATURE:
<221> NAME/KEY: misc_feature
<222> LOCATION: (340)..(340)
<223> OTHER INFORMATION: "n" is any nucleotide

<400> SEQUENCE: 165
atgagcacga atcctaaacc tcaaagaaaa accaaacgta acaccaaccg ccgccctatg      60
gacgttaagt tcccaggcgg tggtcagatc gttggcggag tttacttgtt gccgcgcagg    120
ggccccaggt tgggtgtgcg cgcgactcgg aagacttcgg agcggtcgca acctcgtggg    180
aggcgccaac ctatccccaa ggcgcgccga accgaggca gatcctgggc gcagcccggg    240
tatccttggc ccctttacgg caatgagggc tgtgggtggg caggtgggct cctgtcccct    300
cgcggntctc ggncgtcttg gggccccaat gatccccggn ggagatcccg caacttgggt    360
aaggtcatcg ataccctaac atgcggcttc gccgacctca tggatacat cccgcttgta    420 ggcgcccccg tgggtggcgt cgccagggcc ctggcacatg gtgttagggc tgtggaagac    480
gggatcaatt atgcaacag                                                 499

<210> SEQ ID NO 166
<211> LENGTH: 126
<212> TYPE: PRT
<213> ORGANISM: hepatitis C virus
<220> FEATURE:
<221> NAME/KEY: MISC_FEATURE
<222> LOCATION: (102)..(102)
<223> OTHER INFORMATION: "Xaa" is any amino acid
<220> FEATURE:
<221> NAME/KEY: MISC_FEATURE
```

```
<222> LOCATION: (105)..(105)
<223> OTHER INFORMATION: "Xaa" is any amino acid
<220> FEATURE:
<221> NAME/KEY: MISC_FEATURE
<222> LOCATION: (114)..(114)
<223> OTHER INFORMATION: "Xaa" is any amino acid

<400> SEQUENCE: 166
```

Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Thr Glu Gly Arg Ser Trp Ala Gln Pro Gly
65              70                  75                  80

Tyr Pro Trp Pro Leu Tyr Gly Asn Glu Gly Cys Gly Trp Ala Gly Trp
                85                  90                  95

Leu Leu Ser Pro Arg Xaa Ser Arg Xaa Ser Trp Gly Pro Asn Asp Pro
            100                 105                 110

Arg Xaa Arg Ser Arg Asn Leu Gly Lys Val Ile Asp Thr Leu
        115                 120                 125

```
<210> SEQ ID NO 167
<211> LENGTH: 579
<212> TYPE: DNA
<213> ORGANISM: hepatitis C virus
<400> SEQUENCE: 167
acatgcggct cgccgacct catgggatac atcccgcttg taggcgcccc cgtgggtggc      60
gtcgccaggg ccctggcaca tggtgttagg gctgtggaag acgggatcaa ttatgcaaca    120
gggaacccttc ccggttgctc cttttctatc ttcctcttgg cgctcctctc gtgcctgact    180
gttcccacat cggccgttaa ctatcgcaat gcttcgggca tttatcacat caccaatgac    240
tgcccgaatg caagcatagt gtacgagacc gaaaatcaca tcttacacct cccagggtgc    300
gtaccctgtg tgaggactgg gaaccagtcg cggtgttggg tggccctcac tcccacagta    360
gcgtcgccat acgccggtgc tccgcttgag cccttgcggc gtcatgtgga cctgatggta    420
ggtgctgcca ccatgtgttc cgccctctac atcggcgact gtgcggtgg cttattcttg    480
gtgggccaaa tgttcacctt ccaaccgcga cgtcactgga ccactcagga ctgcaattgt    540
tccatctaca cgggccacat tacgggtcat cggatggca                            579

<210> SEQ ID NO 168
<211> LENGTH: 193
<212> TYPE: PRT
<213> ORGANISM: hepatitis C virus

<400> SEQUENCE: 168
```

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Thr Ser

-continued

```
                 50                   55                  60
Ala Val Asn Tyr Arg Asn Ala Ser Gly Ile Tyr His Ile Thr Asn Asp
 65                  70                  75                  80

Cys Pro Asn Ala Ser Ile Val Tyr Glu Thr Glu Asn His Ile Leu His
                 85                  90                  95

Leu Pro Gly Cys Val Pro Cys Val Arg Thr Gly Asn Gln Ser Arg Cys
            100                 105                 110

Trp Val Ala Leu Thr Pro Thr Val Ala Ser Pro Tyr Ala Gly Ala Pro
            115                 120                 125

Leu Glu Pro Leu Arg Arg His Val Asp Leu Met Val Gly Ala Ala Thr
130                 135                 140

Met Cys Ser Ala Leu Tyr Ile Gly Asp Leu Cys Gly Gly Leu Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg Met
                180                 185                 190

Ala
```

<210> SEQ ID NO 169
<211> LENGTH: 579
<212> TYPE: DNA
<213> ORGANISM: hepatitis C virus

<400> SEQUENCE: 169

```
acatgcggct tcgccgacct catgggatac atcccgcttg taggcgcccc cgtgggtggc      60
gtcgccagag ccctggcaca cggtgttagg gctgtggaag acgggatcaa ctacgcaaca     120
gggaatctcc ccggttgctc cttttctatc ttcctcttgg cacttctctc gtgcctcact     180
gttcccgcgt cgggcgttaa ctatcgcaat gcttcgggcg tttatcacat caccaacgac     240
tgcccgaatg cgagcatagt gtacgagacc gacaatcaca tcttacacct cccagggtgc     300
gtaccctgtg tgaagaccgg gaaccagtcg cggtgttggg tggccctcac tcccacagtg     360
gcgtcgcctt acgtcggtgc tccgctcgag cccttgcggc gccatgtgga cctgatggta     420
ggtgctgcca ccgtgtgctc cgccctctac gtcggcgacc tgtgcggtgg cttattcttg     480
gtaggccaaa tgttcacctt ccaaccgcga cgccactgga cgacccagga ctgtaattgt     540
tccatctacg cagggcatat tacgggccat cggatggct                            579
```

<210> SEQ ID NO 170
<211> LENGTH: 193
<212> TYPE: PRT
<213> ORGANISM: hepatitis C virus

<400> SEQUENCE: 170

```
Thr Cys Gly Phe Ala Asp Leu Met Gly Tyr Ile Pro Leu Val Gly Ala
 1               5                  10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Ala Ser
         50                  55                  60

Gly Val Asn Tyr Arg Asn Ala Ser Gly Val Tyr His Ile Thr Asn Asp
 65                  70                  75                  80
```

```
Cys Pro Asn Ala Ser Ile Val Tyr Glu Thr Asp Asn His Ile Leu His
                85                  90                  95

Leu Pro Gly Cys Val Pro Cys Val Lys Thr Gly Asn Gln Ser Arg Cys
            100                 105                 110

Trp Val Ala Leu Thr Pro Thr Val Ala Ser Pro Tyr Val Gly Ala Pro
        115                 120                 125

Leu Glu Pro Leu Arg Arg His Val Asp Leu Met Val Gly Ala Ala Thr
    130                 135                 140

Val Cys Ser Ala Leu Tyr Val Gly Asp Leu Cys Gly Gly Leu Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Ala Gly His Ile Thr Gly His Arg Met
            180                 185                 190

Ala
```

<210> SEQ ID NO 171
<211> LENGTH: 579
<212> TYPE: DNA
<213> ORGANISM: hepatitis C virus

<400> SEQUENCE: 171

```
acatgcggct tcgccgacct catgggatac atcccgcttg tgggcgcccc tgttggtggc      60
gtcgccagag cccttgcgca cggcgtcagg gctgtggaag acgggattaa ctatgcaaca     120
gggaaccttc ctggttgctc cttttctatc ttccttctgg cacttctctc gtgcctgact     180
gtccccgcct cggctgtgca ttatcacaac acctcgggca tctaccacct caccaatgac     240
tgccctaact ctagcatagt ctttgaggca gtccatcaca tcttgcacct tccaggatgc     300
gtcccttgtg taagaactgg gaaccagtct cggtgctggg tagccttgac ccccacgctg     360
gccgcgccat accttggcgc tccactcgag tccatgcggc gtcacgtgga tttgatggtg     420
ggcactgcta cattgtgctc agcactctac gttggggacc tgtgcggggg catattccta     480
gcgggccaga tgttcacctt ccggccccgc ctccattgga ccacccagga gtgcaattgt     540
tccacctatc cgggccacat cacgggtcat agaatggcg                            579
```

<210> SEQ ID NO 172
<211> LENGTH: 193
<212> TYPE: PRT
<213> ORGANISM: hepatitis C virus

<400> SEQUENCE: 172

```
Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
        35                  40                  45

Ser Ile Phe Leu Leu Ala Leu Leu Ser Cys Leu Thr Val Pro Ala Ser
    50                  55                  60

Ala Val His Tyr His Asn Thr Ser Gly Ile Tyr His Leu Thr Asn Asp
65                  70                  75                  80

Cys Pro Asn Ser Ser Ile Val Phe Glu Ala Val His Ile Leu His
                85                  90                  95

Leu Pro Gly Cys Val Pro Cys Val Arg Thr Gly Asn Gln Ser Arg Cys
            100                 105                 110
```

-continued

```
Trp Val Ala Leu Thr Pro Thr Leu Ala Ala Pro Tyr Leu Gly Ala Pro
        115                 120                 125

Leu Glu Ser Met Arg Arg His Val Asp Leu Met Val Gly Thr Ala Thr
    130                 135                 140

Leu Cys Ser Ala Leu Tyr Val Gly Asp Leu Cys Gly Gly Ile Phe Leu
145                 150                 155                 160

Ala Gly Gln Met Phe Thr Phe Arg Pro Arg Leu His Trp Thr Thr Gln
                165                 170                 175

Glu Cys Asn Cys Ser Thr Tyr Pro Gly His Ile Thr Gly His Arg Met
            180                 185                 190

Ala

<210> SEQ ID NO 173
<211> LENGTH: 579
<212> TYPE: DNA
<213> ORGANISM: hepatitis C virus

<400> SEQUENCE: 173
acgtgcggtt ccgccgacct catgggatac atcccgctcg taggcgcccc tgtgggtggc      60
gtcgccaggg ccttggcgca tggcgtcagg gctgtggagg acgggataaa ctatgcaaca     120
gggaaccttc ctggttgctc tttttctatc ttccttctgg cacttctctc gtgcctgact     180
gtccccgcct cagctgtgca ttatcacaac acctcgggca tctatcacat cactaatgac     240
tgccctaact ctagcatagt ctttgaggca gagcatcaca tcttgcatct tccaggatgc     300
gtccctgtg tgagaactgg gaaccagtca cgatgctgga tagccttgac ccctacgttg     360
gccgcgccac acattggcgc tccacttgag tccatgcgac gtcatgtgga tttgatggta     420
ggcactgcca cattgtgctc cgcactctac attggagatc tgtgcggagg catatttcta     480
gtgggccaga tgttcaactt caggccccgc ctgcactgga ccacccagga gtgcaattgt     540
tccatctatc caggccacat cacgggtcac agaatggcg                            579

<210> SEQ ID NO 174
<211> LENGTH: 193
<212> TYPE: PRT
<213> ORGANISM: hepatitis C virus

<400> SEQUENCE: 174

Thr Cys Gly Ser Ala Asp Leu Met Gly Tyr Ile Pro Leu Val Gly Ala
1               5                  10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Ala Ser
    50                  55                  60

Ala Val His Tyr His Asn Thr Ser Gly Ile Tyr His Ile Thr Asn Asp
65                  70                  75                  80

Cys Pro Asn Ser Ser Ile Val Phe Glu Ala Glu His His Ile Leu His
                85                  90                  95

Leu Pro Gly Cys Val Pro Cys Val Arg Thr Gly Asn Gln Ser Arg Cys
            100                 105                 110

Trp Ile Ala Leu Thr Pro Thr Leu Ala Ala Pro His Ile Gly Ala Pro
        115                 120                 125

Leu Glu Ser Met Arg Arg His Val Asp Leu Met Val Gly Thr Ala Thr
```

-continued

```
             130                 135                 140
Leu Cys Ser Ala Leu Tyr Ile Gly Asp Leu Cys Gly Gly Ile Phe Leu
145                 150                 155                 160

Val Gly Gln Met Phe Asn Phe Arg Pro Arg Leu His Trp Thr Thr Gln
                165                 170                 175

Glu Cys Asn Cys Ser Ile Tyr Pro Gly His Ile Thr Gly His Arg Met
            180                 185                 190

Ala
```

<210> SEQ ID NO 175
<211> LENGTH: 579
<212> TYPE: DNA
<213> ORGANISM: hepatitis C virus

<400> SEQUENCE: 175

```
acgtgcggct tgccgacct catgggatac atcccgctcg tgggcgcccc tgtgggtggc     60
gtcgccaggg ccttggcaca tggtgtcagg gccgtggagg acgggattaa ctatgcaaca   120
gggaatcttc ccggttgctc cttttctatc ttccttctag cacttctctc gtgcttgact   180
gtcccggcct cggcgcagca ctaccggaac atctcgggca tttatcacgt caccaatgac   240
tgcccgaact ctagtatagt gtatgaagct gaccatcata tcatgcatct accagggtgt   300
gtgccttgcg tgagaaccgg gaacacctcg cgctgctggg ttcctttaac acccactgtg   360
gctgccccct atgttggcgc gccgctcgaa tccatgcggc ggcacgtgga cttaatggtg   420
ggtgccgcca ccgtctgctc ggccctgtac atcggagacc tttgcggagg tgtcttcctg   480
gtcgggcaga tgttcacctt ccggccgcgc cgccattgga ctacccagga ctgcaactgc   540
tctatctatg atggccacat caccggccat agaatggct                          579
```

<210> SEQ ID NO 176
<211> LENGTH: 193
<212> TYPE: PRT
<213> ORGANISM: hepatitis C virus

<400> SEQUENCE: 176

```
Thr Cys Gly Phe Ala Asp Leu Met Gly Tyr Ile Pro Leu Val Gly Ala
1               5                  10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Ala Ser
        50                  55                  60

Ala Gln His Tyr Arg Asn Ile Ser Gly Ile Tyr His Val Thr Asn Asp
65                  70                  75                  80

Cys Pro Asn Ser Ser Ile Val Tyr Glu Ala Asp His His Ile Met His
                85                  90                  95

Leu Pro Gly Cys Val Pro Cys Val Arg Thr Gly Asn Thr Ser Arg Cys
            100                 105                 110

Trp Val Pro Leu Thr Pro Thr Val Ala Ala Pro Tyr Val Gly Ala Pro
        115                 120                 125

Leu Glu Ser Met Arg Arg His Val Asp Leu Met Val Gly Ala Ala Thr
    130                 135                 140

Val Cys Ser Ala Leu Tyr Ile Gly Asp Leu Cys Gly Gly Val Phe Leu
145                 150                 155                 160
```

-continued

Val Gly Gln Met Phe Thr Phe Arg Pro Arg Arg His Trp Thr Thr Gln
            165                 170                 175

Asp Cys Asn Cys Ser Ile Tyr Asp Gly His Ile Thr Gly His Arg Met
            180                 185                 190

Ala

<210> SEQ ID NO 177
<211> LENGTH: 579
<212> TYPE: DNA
<213> ORGANISM: hepatitis C virus

<400> SEQUENCE: 177

```
acgtgcgggt tcgccgacct catgggatac atcccgctcg tgggcgctcc agtaggaggc    60
gtcgccagag ccttggcgca tggcgtcagg gctgtgaggg acgggatcaa ttacgcaaca   120
gggaaccttc ccggctgctc ctttctatc ttcctcttgg tacttctctc gcgcctaact   180
gtcccagcgt ctgctcagca ctaccggaat gcatcgggca tctaccatgt caccaacgac   240
tgcccgaact ccagtattgt gtatgaagcc gaccatcaca tcatgcacct acccgggtgt   300
gtgccctgtg taagaactgg gaatgtctcg cgttgctgga ttcctttaac acccactgta   360
gccgtcccct acctcggggc tccacttacg tctgtacggc agcatgtgga cctgatggtg   420
ggggcggcca cctatgctct tgccctctac atcggagacc attgcggagg tgtcttcttg   480
gcagggcaga tggtcagttt ccaaccccgg cgtcattgga ctacccagga ttgcaactgt   540
tccatctatg tgggccacat caccggccac aggatggcc                         579
```

<210> SEQ ID NO 178
<211> LENGTH: 193
<212> TYPE: PRT
<213> ORGANISM: hepatitis C virus

<400> SEQUENCE: 178

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
            20                  25                  30

Glu Asp Gly Ile Asn Tyr Ala Thr Gly Asn Leu Pro Gly Cys Ser Phe
            35                  40                  45

Ser Ile Phe Leu Leu Val Leu Leu Ser Arg Leu Thr Val Pro Ala Ser
        50                  55                  60

Ala Gln His Tyr Arg Asn Ala Ser Gly Ile Tyr His Val Thr Asn Asp
65                  70                  75                  80

Cys Pro Asn Ser Ser Ile Val Tyr Glu Ala Asp His His Ile Met His
                85                  90                  95

Leu Pro Gly Cys Val Pro Cys Val Arg Thr Gly Asn Val Ser Arg Cys
            100                 105                 110

Trp Ile Pro Leu Thr Pro Thr Val Ala Val Pro Tyr Leu Gly Ala Pro
        115                 120                 125

Leu Thr Ser Val Arg Gln His Val Asp Leu Met Val Gly Ala Ala Thr
    130                 135                 140

Leu Cys Ser Ala Leu Tyr Ile Gly Asp His Cys Gly Gly Val Phe Leu
145                 150                 155                 160

Ala Gly Gln Met Val Ser Phe Gln Pro Arg Arg His Trp Thr Thr Gln
                165                 170                 175

Asp Cys Asn Cys Ser Ile Tyr Val Gly His Ile Thr Gly His Arg Met
            180                 185                 190

Ala

<210> SEQ ID NO 179
<211> LENGTH: 579
<212> TYPE: DNA
<213> ORGANISM: hepatitis C virus
<220> FEATURE:
<221> NAME/KEY: misc_feature
<222> LOCATION: (568)..(579)
<223> OTHER INFORMATION: "n" is any nucleotide

<400> SEQUENCE: 179

```
acctgcggct tcgccgacct catgggatac atcccgctcg taggcgcccc cgtgggaggc     60
gtcgccagar ctctggcgca tggcgtcagg gctctggaag acgggatcaa ttatgcaaca    120
gggaatcttc ctggttgctc tttctctatc tcccttcttg aacttctctc gtgcctgact    180
gttcccgcct cagccatcca ctatcgcaat gcttcggacg gttattatat caccaatgat    240
tgcccgaact ctagcatagt gtatgaagcc gagaaccaca tcttgcacct tccggggtgt    300
ataccctgtg tgaagaccgg gaatcagtcg cggtgctggg tggctctcac ccccacgctg    360
gcggccccac acctacgtgc tccgctttcg tccttacggg cgcatgtgga cctaatggtg    420
ggggccgcca cggcatgctc cgcttttac attggagatc tgtgcggggg tgtgtttttg    480
gcgggccaac tgttcactat ccggccacgc attcatgaaa ccactcagga ctgcaattgc    540
tccatctact cagggcacat cacgggtnnn nnnnnnnnn                           579
```

<210> SEQ ID NO 180
<211> LENGTH: 193
<212> TYPE: PRT
<213> ORGANISM: hepatitis C virus
<220> FEATURE:
<221> NAME/KEY: MISC_FEATURE
<222> LOCATION: (24)..(24)
<223> OTHER INFORMATION: "Xaa" is any amino acid
<220> FEATURE:
<221> NAME/KEY: MISC_FEATURE
<222> LOCATION: (190)..(193)
<223> OTHER INFORMATION: "Xaa" is any amino acid

<400> SEQUENCE: 180

```
Thr Cys Gly Phe Ala Asp Leu Met Gly Tyr Ile Pro Leu Val Gly Ala
  1               5                  10                  15

Pro Val Gly Gly Val Ala Arg Xaa Leu Ala His Gly Val Arg Ala Leu
             20                  25                  30

Glu Asp Gly Ile Asn Tyr Ala Thr Gly Asn Leu Pro Gly Cys Ser Phe
         35                  40                  45

Ser Ile Ser Leu Leu Glu Leu Leu Ser Cys Leu Thr Val Pro Ala Ser
     50                  55                  60

Ala Ile His Tyr Arg Asn Ala Ser Asp Gly Tyr Tyr Ile Thr Asn Asp
 65                  70                  75                  80

Cys Pro Asn Ser Ser Ile Val Tyr Glu Ala Glu Asn His Ile Leu His
                 85                  90                  95

Leu Pro Gly Cys Ile Pro Cys Val Lys Thr Gly Asn Gln Ser Arg Cys
            100                 105                 110

Trp Val Ala Leu Thr Pro Thr Leu Ala Ala Pro His Leu Arg Ala Pro
        115                 120                 125

Leu Ser Ser Leu Arg Ala His Val Asp Leu Met Val Gly Ala Ala Thr
    130                 135                 140

Ala Cys Ser Ala Phe Tyr Ile Gly Asp Leu Cys Gly Gly Val Phe Leu
```

```
                    145                 150                 155                 160
Ala Gly Gln Leu Phe Thr Ile Arg Pro Arg Ile His Glu Thr Thr Gln
                165                 170                 175

Asp Cys Asn Cys Ser Ile Tyr Ser Gly His Ile Thr Gly Xaa Xaa Xaa
            180                 185                 190

Xaa

<210> SEQ ID NO 181
<211> LENGTH: 579
<212> TYPE: DNA
<213> ORGANISM: hepatitis C virus
<220> FEATURE:
<221> NAME/KEY: misc_feature
<222> LOCATION: (152)..(152)
<223> OTHER INFORMATION: "n" is any nucleotide

<400> SEQUENCE: 181
gcgtgcggct cgccgatct catgggatac atcccgctcg taggcgcccc cgtgggtggc     60
gtcgccagag ccctggcgca cggtgttagg gctgtggagg acgggattaa ctacgcaaca   120
gggaatcttc ctggttgctc tttctctatc tnccttctgg cacttctctc gtgcctgact   180
gtcccggcct cggctcagca ctaccggaat gtctcgggca tctaccacgt caccaatgat   240
tgcccgaatt ccagcatagt gtatgaagcc gatcaccaca tcatgcactt accagggtgc   300
ataccctgcg tgaggaccgg gaacgtttcg cgctgctggg tatctctgac acctactgtg   360
gctgctccct acctcggggc tccgcttacg tcgctacggc ggcatgtgga tttgatggtg   420
ggtgcagcca ccctttgctc tgccctctac gtcggagacc tctgtggagg tgtcttccta   480
gtgggacaga tgttcacctt ccagccgcgc cgccactgga ccactcagga ctgcaactgc   540
tccatttacg tcggccacat acaggccac agaatggct                          579

<210> SEQ ID NO 182
<211> LENGTH: 193
<212> TYPE: PRT
<213> ORGANISM: hepatitis C virus
<220> FEATURE:
<221> NAME/KEY: MISC_FEATURE
<222> LOCATION: (51)..(51)
<223> OTHER INFORMATION: "Xaa" is any amino acid

<400> SEQUENCE: 182

Ala Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Xaa Leu Leu Ala Leu Leu Ser Cys Leu Thr Val Pro Ala Ser
        50                  55                  60

Ala Gln His Tyr Arg Asn Val Ser Gly Ile Tyr His Val Thr Asn Asp
65                  70                  75                  80

Cys Pro Asn Ser Ser Ile Val Tyr Glu Ala Asp His His Ile Met His
                85                  90                  95

Leu Pro Gly Cys Ile Pro Cys Val Arg Thr Gly Asn Val Ser Arg Cys
            100                 105                 110

Trp Val Ser Leu Thr Pro Thr Val Ala Ala Pro Tyr Leu Gly Ala Pro
        115                 120                 125

Leu Thr Ser Leu Arg Arg His Val Asp Leu Met Val Gly Ala Ala Thr
```

-continued

```
        130                 135                 140
Leu Cys Ser Ala Leu Tyr Val Gly Asp Leu Cys Gly Gly Val Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Val Gly His Ile Thr Gly His Arg Met
                180                 185                 190

Ala

<210> SEQ ID NO 183
<211> LENGTH: 579
<212> TYPE: DNA
<213> ORGANISM: hepatitis C virus

<400> SEQUENCE: 183
acctgcggct tgccgacct catgggatac atcccgctcg taggcgcccc tgtgggtggc      60
gtcgccaggg ccctagaaca cggtgttagg gctgtggagg acggtattaa ttatgcaaca    120
gggaatctcc ccggttgctc ttttctatc tccctcttgg cacttctttc gtgcctgact    180
gttcccacct cagccgtcaa ctatcgcaac gcctcgggcg tctatcatat caccaatgac    240
tgcccgaatt cgagcatagt gtacgaggct gactaccaca tcctacacct ccctgggtgc    300
ttaccctgcg tgagggttgg gaatcagtca cgctgctggg tggcccttac tcccaccgtg    360
gcggcgcctt acgttggtgc tccgctagaa tccctccgga gtcatgtgga tctgatggta    420
ggtgctgcta ctgtgtgctc cgctctttac atcgggacc tgtgcggtgg cgtattttg    480 gttggtcaga tgtttctttt ccagccgcga cgccactgga ccacgcagga ctgcaattgt    540
tctatctacg cggggcacgt tacgggccac aggatggca                           579

<210> SEQ ID NO 184
<211> LENGTH: 193
<212> TYPE: PRT
<213> ORGANISM: hepatitis C virus

<400> SEQUENCE: 184

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Thr Ser
        50                  55                  60

Ala Val Asn Tyr Arg Asn Ala Ser Gly Ile Tyr His Ile Thr Asn Asp
65                  70                  75                  80

Cys Pro Asn Ala Ser Ile Val Tyr Glu Thr Glu Asn His Ile Leu His
                85                  90                  95

Leu Pro Gly Cys Val Pro Cys Val Arg Thr Gly Asn Gln Ser Arg Cys
            100                 105                 110

Trp Val Ala Leu Thr Pro Thr Val Ala Ser Pro Tyr Ala Gly Ala Pro
        115                 120                 125

Leu Glu Pro Leu Arg Arg His Val Asp Leu Met Val Gly Ala Ala Thr
    130                 135                 140

Met Cys Ser Ala Leu Tyr Ile Gly Asp Leu Cys Gly Gly Leu Phe Leu
145                 150                 155                 160
```

```
Val Gly Gln Met Phe Thr Phe Gln Pro Arg Arg His Trp Thr Thr Gln
            165                 170                 175
Asp Cys Asn Cys Ser Ile Tyr Thr Gly His Ile Thr Gly His Arg Met
            180                 185                 190
Ala
```

<210> SEQ ID NO 185
<211> LENGTH: 579
<212> TYPE: DNA
<213> ORGANISM: hepatitis C virus

<400> SEQUENCE: 185

```
acttgcggct tgccgacct catgggatac atcccgctcg taggcgcccc cgtgggtggc      60
gtcgccagag ccctggaaca tggtgttagg gctgtgagg acggcatcaa ttatgcaaca    120
gggaatctcc ccggttgctc tttctctatc tacctcttgg cacttctctc gtgcctgact    180
gttcccacct cggccatcca ctatcgcaat gcctcgggcg tctaccacgt caccaatgac    240
tgcccgaact cgagcatagt gtacgaggcc gaccaccaca tcctacacct tccagggtgc    300
ttaccctgtg tgagggttgg gaatcagtca cgttgttggg tggccctctc tcccaccgtg    360
gcggcgcctt acatcggtgc tccagttgaa tccttccgga gacacgtgga catgatggtg    420
ggcgctgcta ctgtgtgctc cgctctctat attggggact gtgtggtgg cgtattcttg    480
gttggtcaga tgtttctttt ccggccacga cgccactgga ctacgcagga ctgcaattgt    540
tccatctacg cggggcacat cactggccac ggaatggca                           579
```

<210> SEQ ID NO 186
<211> LENGTH: 193
<212> TYPE: PRT
<213> ORGANISM: hepatitis C virus

<400> SEQUENCE: 186

```
Thr Cys Gly Phe Ala Asp Leu Met Gly Tyr Ile Pro Leu Val Gly Ala
1               5                   10                  15
Pro Val Gly Gly Val Ala Arg Ala Leu Glu His Gly Val Arg Ala Val
            20                  25                  30
Glu Asp Gly Ile Asn Tyr Ala Thr Gly Asn Leu Pro Gly Cys Ser Phe
        35                  40                  45
Ser Ile Tyr Leu Leu Ala Leu Leu Ser Cys Leu Thr Val Pro Thr Ser
    50                  55                  60
Ala Ile His Tyr Arg Asn Ala Ser Gly Val Tyr His Val Thr Asn Asp
65                  70                  75                  80
Cys Pro Asn Ser Ser Ile Val Tyr Glu Ala Asp His His Ile Leu His
                85                  90                  95
Leu Pro Gly Cys Leu Pro Cys Val Arg Val Gly Asn Gln Ser Arg Cys
            100                 105                 110
Trp Val Ala Leu Ser Pro Thr Val Ala Ala Pro Tyr Ile Gly Ala Pro
        115                 120                 125
Val Glu Ser Phe Arg Arg His Val Asp Met Met Val Gly Ala Ala Thr
    130                 135                 140
Val Cys Ser Ala Leu Tyr Ile Gly Asp Leu Cys Gly Gly Val Phe Leu
145                 150                 155                 160
Val Gly Gln Met Phe Ser Phe Arg Pro Arg Arg His Trp Thr Thr Gln
                165                 170                 175
Asp Cys Asn Cys Ser Ile Tyr Ala Gly His Ile Thr Gly His Gly Met
            180                 185                 190
```

Ala

<210> SEQ ID NO 187
<211> LENGTH: 579
<212> TYPE: DNA
<213> ORGANISM: hepatitis C virus

<400> SEQUENCE: 187

```
acttgcggct tgccgacct catgggatac atcccgctcg taggcgcccc tgtgggtggc      60
gtcgccaggg ccctggcaca cggtgttagg gctgtggagg acgggatcaa ttatgcgaca     120
gggaatcttc ccggttgctc tttctctatc ttcctcttgg cacttctttc gtgcctgact    180
gttcccacct cggccgtcaa ctatcgcaat gcctcgggca tctatcacat caccaatgac    240
tgcccgaact cgagcatagt gtacgagacc gagcaccaca tcctacacct cccagggtgt    300
ttacccctgcg tgagggttgg gaatcagtca cgctgctggg tggccctcac tcccaccgtg   360
gcggcgcctt acatcggcgc tccgcttgaa tccctccgga gtcatgtgga tctgatggta    420
ggtgccgcta ctgcgtgctc cgctctttac atcggagacc tgtgcggtgg cgtattttg    480
gttggtcaga tgttctcttt ccagccgcgg cgccactgga ctacgcagga ctgcaattgt    540
tccatctacg cggggcacgt tacgggccac aggatggca                            579
```

<210> SEQ ID NO 188
<211> LENGTH: 193
<212> TYPE: PRT
<213> ORGANISM: hepatitis C virus

<400> SEQUENCE: 188

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Thr Ser
        50                  55                  60

Ala Val Asn Tyr Arg Asn Ala Ser Gly Ile Tyr His Ile Thr Asn Asp
65                  70                  75                  80

Cys Pro Asn Ser Ser Ile Val Tyr Glu Thr Glu His His Ile Leu His
                85                  90                  95

Leu Pro Gly Cys Leu Pro Cys Val Arg Val Gly Asn Gln Ser Arg Cys
            100                 105                 110

Trp Val Ala Leu Thr Pro Thr Val Ala Ala Pro Tyr Ile Gly Ala Pro
        115                 120                 125

Leu Glu Ser Leu Arg Ser His Val Asp Leu Met Val Gly Ala Ala Thr
    130                 135                 140

Ala Cys Ser Ala Leu Tyr Ile Gly Asp Leu Cys Gly Gly Val Phe Leu
145                 150                 155                 160

Val Gly Gln Met Phe Ser Phe Gln Pro Arg Arg His Trp Thr Thr Gln
                165                 170                 175

Asp Cys Asn Cys Ser Ile Tyr Ala Gly His Val Thr Gly His Arg Met
            180                 185                 190

Ala

<210> SEQ ID NO 189

-continued

```
<211> LENGTH: 579
<212> TYPE: DNA
<213> ORGANISM: hepatitis C virus

<400> SEQUENCE: 189
acgtgcggct cgccgacct catgggatac atcccgctcg tgggcgcccc cgttggggc      60 gtcgccaggg ccctggcgca tggcgtcagg gctgtggagg acgggattaa ctatgcgaca    120
gggaatcttc ccggttgctc tttctctatc ttcctcctgg cacttctttc gtgcctcact    180
gtcccagcgt cagctgagca ctaccggaat gcttcgggca tctatcacat caccaatgac    240
tgtccgaatt ccagcgtagt ctatgaaact gaccaccata tattgcactt gccggggtgc    300
gtaccctgcg tgagggccgg gaacgtgtct cgttgctgga cgccggtaac acctacggtg    360
gctgccgtat ccatggacgc tccgctcgag tccttccggc ggcatgtgga cctaatggta    420
ggtgcggcca ccgtgtgttc tgtcctctat gttggagacc tctgtggagg tgctttccta    480
gtggggcaga tgttcacctt ccagccgcgt cgccactgga ccacgcagga ttgtaattgc    540
tccatctata ctggccatat caccggccac aggatggcg                          579

<210> SEQ ID NO 190
<211> LENGTH: 193
<212> TYPE: PRT
<213> ORGANISM: hepatitis C virus

<400> SEQUENCE: 190

Thr Cys Gly Phe Ala Asp Leu Met Gly Tyr Ile Pro Leu Val Gly Ala
1               5                   10                  15

Pro Val Gly Gly Val Ala Arg Ala Leu Ala His Gly Val Arg Ala Val
                20                  25                  30

Glu Asp Gly Ile Asn Tyr Ala Thr Gly Asn Leu Pro Gly Cys Ser Phe
            35                  40                  45

Ser Ile Phe Leu Leu Ala Leu Leu Ser Cys Leu Thr Val Pro Ala Ser
    50                  55                  60

Ala Glu His Tyr Arg Asn Ala Ser Gly Ile Tyr His Ile Thr Asn Asp
65                  70                  75                  80

Cys Pro Asn Ser Ser Val Val Tyr Glu Thr Asp His His Ile Leu His
                85                  90                  95

Leu Pro Gly Cys Val Pro Cys Val Arg Ala Gly Asn Val Ser Arg Cys
            100                 105                 110

Trp Thr Pro Val Thr Pro Thr Val Ala Val Ser Met Asp Ala Pro
        115                 120                 125

Leu Glu Ser Phe Arg Arg His Val Asp Leu Met Val Gly Ala Ala Thr
    130                 135                 140

Val Cys Ser Val Leu Tyr Val Gly Asp Leu Cys Gly Gly Ala Phe Leu
145                 150                 155                 160

Val Gly Gln Met Phe Thr Phe Gln Pro Arg Arg His Trp Thr Thr Gln
                165                 170                 175

Asp Cys Asn Cys Ser Ile Tyr Thr Gly His Ile Thr Gly His Arg Met
            180                 185                 190

Ala

<210> SEQ ID NO 191
<211> LENGTH: 289
<212> TYPE: DNA
<213> ORGANISM: hepatitis C virus

<400> SEQUENCE: 191
```

-continued

```
atgagcacga atcctaaacc tcaaagaaaa accaaacgta acaccaaccg ccgcccatg      60 gacgttaagt tcccgggcgg tggccagatc gttggtggag tttacttgtt gccgcgcagg    120
ggccccaggt tgggtgtgcg cgcgactagg aagacttcgg agcggtcgca acctcgtggg    180
agacgtcagc ctatccccaa ggcacgtcga tctgagggaa ggtcctgggc tcagcccggg    240
tacccatggc ctctttacgg taatgagggt tgtgggtggg caggatggg                289
```

<210> SEQ ID NO 192
<211> LENGTH: 96
<212> TYPE: PRT
<213> ORGANISM: hepatitis C virus

<400> SEQUENCE: 192

```
Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Ser Glu Gly Arg Ser Trp Ala Gln Pro Gly
65                  70                  75                  80

Tyr Pro Trp Pro Leu Tyr Gly Asn Glu Gly Cys Gly Trp Ala Gly Trp
                85                  90                  95
```

<210> SEQ ID NO 193
<211> LENGTH: 498
<212> TYPE: DNA
<213> ORGANISM: hepatitis C virus

<400> SEQUENCE: 193

```
atgagcacga atcctaaacc tcaaagaaaa accaaacgta acaccaaccg ccgccctatg     60
gacgtaaagt tcccgggcgg tggacagatc gttggcggag tttacttgtt gccgcgcagg   120 ggccccggt tgggtgtgcg cgcgactcgg aagacttcgg agcggtcgca acctcgtggc    180
aggcgtcaac ctatccccaa ggcgcgccgg tccgagggca ggtcctgggc gcaagccggg   240 taccctggc ccctctatgg caatgagggc tgtgggtggg cagggtggct cctgtctcct    300
cgcggctctc ggccatcttg ggcccaaat gatccccgc ggagatcgcg caatctgggt     360
aaggtcatcg atacctgac gtgcggcttc gccgacctca tgggatacat cccgctcgtg    420 ggcgccccg tcggggcgt cgccagggcc ctggcgcatg gcgtcagggc tgtggaggac    480
gggattaact atcgacag                                                  498
```

<210> SEQ ID NO 194
<211> LENGTH: 166
<212> TYPE: PRT
<213> ORGANISM: hepatitis C virus

<400> SEQUENCE: 194

```
Met Ser Thr Asn Pro Lys Pro Gln Arg Lys Thr Lys Arg Asn Thr Asn
1               5                   10                  15

Arg Arg Pro Met Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45
```

-continued

```
Thr Arg Lys Thr Ser Glu Arg Ser Gln Pro Arg Gly Arg Arg Gln Pro
 50                  55                  60
Ile Pro Lys Ala Arg Arg Ser Glu Gly Arg Ser Trp Ala Gln Ala Gly
 65                  70                  75                  80
Tyr Pro Trp Pro Leu Tyr Gly Asn Glu Gly Cys Gly Trp Ala Gly Trp
                 85                  90                  95
Leu Leu Ser Pro Arg Gly Ser Arg Pro Ser Trp Gly Pro Asn Asp Pro
                100                 105                 110
Arg Arg Arg Ser Arg Asn Leu Gly Lys Val Ile Asp Thr Leu Thr Cys
                115                 120                 125
Gly Phe Ala Asp Leu Met Gly Tyr Ile Pro Leu Val Gly Ala Pro Val
                130                 135                 140
Gly Gly Val Ala Arg Ala Leu Ala His Gly Val Arg Ala Val Glu Asp
145                 150                 155                 160
Gly Ile Asn Tyr Arg Gln
                165
```

<210> SEQ ID NO 195
<211> LENGTH: 579
<212> TYPE: DNA
<213> ORGANISM: hepatitis C virus

<400> SEQUENCE: 195

```
acgtgcggat cgccgacctc gtggggtac atcccgctcg taggcggccc cgttggggc     60
gtcgcaaggg ctctcgcaca tggtgtgagg gttcttgagg acgggtgaa ttatgcaaca   120
gggaatctgc ctggttgctc tttctctatc ttcattcttg cacttctctc gtgcctcact   180
gtcccggcct ctgcagttcc ctaccgaaat gcctctggga tctatcatgt caccaatgat   240
tgcccaaact cttccatagt ctatgaggca gatgatctga tcctacacgc acctggctgc   300
gtgccttgtg tcaggaaaga taatgtgagt aggtgctggg tccaaattac ccccacgctg   360
tcagccccga gcttcggagc agtcacggct ccccttcgga gagccgttga ttacttggtg   420
ggagggctg ccctctgctc cgcgttatac gttggagacg cgtgtgggc actatttttg    480
gtaggccaaa tgttcaccta taggcctcgc cagcatgcta cggtgcagga ctgcaactgt   540
tccatctaca gtggccacgt caccggccat cagatggca                          579
```

<210> SEQ ID NO 196
<211> LENGTH: 193
<212> TYPE: PRT
<213> ORGANISM: hepatitis C virus

<400> SEQUENCE: 196

```
Thr Cys Gly Phe Ala Asp Leu Val Gly Tyr Ile Pro Leu Val Gly Gly
  1               5                  10                  15
Pro Val Gly Gly Val Ala Arg Ala Leu Ala His Gly Val Arg Val Leu
                 20                  25                  30
Glu Asp Gly Val Asn Tyr Ala Thr Gly Asn Leu Pro Gly Cys Ser Phe
                 35                  40                  45
Ser Ile Phe Ile Leu Ala Leu Leu Ser Cys Leu Thr Val Pro Ala Ser
 50                  55                  60
Ala Val Pro Tyr Arg Asn Ala Ser Gly Ile Tyr His Val Thr Asn Asp
 65                  70                  75                  80
Cys Pro Asn Ser Ser Ile Val Tyr Glu Ala Asp Asp Leu Ile Leu His
                 85                  90                  95
```

```
Ala Pro Gly Cys Val Pro Cys Val Arg Lys Asp Asn Val Ser Arg Cys
            100                 105                 110

Trp Val Gln Ile Thr Pro Thr Leu Ser Ala Pro Ser Phe Gly Ala Val
            115                 120                 125

Thr Ala Pro Leu Arg Arg Ala Val Asp Tyr Leu Val Gly Gly Ala Ala
        130                 135                 140

Leu Cys Ser Ala Leu Tyr Val Gly Asp Ala Cys Gly Ala Leu Phe Leu
145                 150                 155                 160

Val Gly Gln Met Phe Thr Tyr Arg Pro Arg Gln His Ala Thr Val Gln
                165                 170                 175

Asp Cys Asn Cys Ser Ile Tyr Ser Gly His Val Thr Gly His Gln Met
            180                 185                 190

Ala

<210> SEQ ID NO 197
<211> LENGTH: 1485
<212> TYPE: DNA
<213> ORGANISM: hepatitis C virus
<220> FEATURE:
<221> NAME/KEY: misc_feature
<222> LOCATION: (787)..(787)
<223> OTHER INFORMATION: "n" is any nucleotide
<220> FEATURE:
<221> NAME/KEY: misc_feature
<222> LOCATION: (1011)..(1011)
<223> OTHER INFORMATION: "n" is any nucleotide
<220> FEATURE:
<221> NAME/KEY: misc_feature
<222> LOCATION: (1444)..(1444)
<223> OTHER INFORMATION: "n" is any nucleotide

<400> SEQUENCE: 197
tgtgccagga ccatcaccac cggagcttct atcacatact ccacttacgg caagttcctt      60
gctgatggag ggtgttcagg cggcgcgcat gacgtgatca tatgcgacga gtgccattcc     120
caggacgcca ccaccattct tgggataggc actgtccttg accaggcaga gacggctgga     180
gctaggctcg tcgtcttggc cacggccacc cctcccggca gtgtgacaac gccccacccc     240
aacatcgagg aagtggccct gcctcaggag ggggaggttc ccttctacgg cagagccatt     300
cccctcgctt ttataaaggg tggtaggcat ctcatcttct gccattccaa gaaaaaatgt     360
gatgaactcg ccaagcaact gaccagcctg gcgtgaacg ccgtggcata ttatagaggt      420
ctagacgtcg ccgtcatacc cacaacagga gacgtggtcg tgtgcagcac cgacgcgctc     480
atgacgggat tcaccggcga ctttgattct gtcatagact gcaactccgc cgtcactcag     540
acggtggact tcagtctgga tcccactttt accattgaga ctaccacagt gccccaggac     600
gcagtgtcca gaagccagcg ttggggccgc acggggagag gtaggcacgg catataccgg     660
tatgtctcgg ctggagagag accgtctggc atgttcgact ccgtggtgct ctgtgagtgc     720
tacgatgccg gatgtgcatg gtacgatctg actcctgccg agactaccgt gaggttgcgc     780
gcttacntaa acacccccgg gctccctgtc tgtcaggacc atttggaatt ctgggagggg     840
gtgttcacgg ggctcactaa catcgacgct cacatgctgt cacagaccaa acagggtggg     900
gagaatttcc cataccttgt agcgtaccaa gcaacagtct gtgttcgcgc gaaagcgccc     960
ccccccagct gggacacaat gtggaaatgc atgctccgtc tcaaaccgac nttaactggc    1020
cctactcccc tcttgtacag gctggggccc gtccagaatg agatcacact gacgcacccc    1080
atcaccaagt acattatggc ttgcatgtct gcggacttgg aggtcattac cagcacttgg    1140
gttctggtgg ggggcgttgt ggcggccctg gcggcctact gcttgacggt gggttcggta    1200
```

-continued

```
gccatagtcg gtaggatcat cctctctggg aaacctgcca tcattcccga tagggaggta    1260
ttataccagc aatttgatga gatggaggag tgctcggcct cgttgcccta tatggacgaa    1320
acacgtgcca ttgccggaca attcaaagag aaagtgctcg gcttcatcag cacgaccggc    1380
cagaaggctg aaactctgaa gccggcagcc acgtctgtgt ggaacaaggc tgagcagttc    1440
tggnccacat acatgtggaa cttcatcagt gggatacaat aatag                    1485
```

<210> SEQ ID NO 198
<211> LENGTH: 484
<212> TYPE: PRT
<213> ORGANISM: hepatitis C virus
<220> FEATURE:
<221> NAME/KEY: MISC_FEATURE
<222> LOCATION: (263)..(263)
<223> OTHER INFORMATION: "Xaa" is any amino acid
<220> FEATURE:
<221> NAME/KEY: MISC_FEATURE
<222> LOCATION: (337)..(337)
<223> OTHER INFORMATION: "Xaa" is any amino acid
<220> FEATURE:
<221> NAME/KEY: MISC_FEATURE
<222> LOCATION: (482)..(482)
<223> OTHER INFORMATION: "Xaa" is any amino acid

<400> SEQUENCE: 198

```
Cys Ala Arg Thr Ile Thr Thr Gly Ala Ser Ile Thr Tyr Ser Thr Tyr
  1               5                  10                  15

Gly Lys Phe Leu Ala Asp Gly Gly Cys Ser Gly Gly Ala His Asp Val
             20                  25                  30

Ile Ile Cys Asp Glu Cys His Ser Gln Asp Ala Thr Thr Ile Leu Gly
         35                  40                  45

Ile Gly Thr Val Leu Asp Gln Ala Glu Thr Ala Gly Ala Arg Leu Val
     50                  55                  60

Val Leu Ala Thr Ala Thr Pro Pro Gly Ser Val Thr Thr Pro His Pro
 65                  70                  75                  80

Asn Ile Glu Glu Val Ala Leu Pro Gln Glu Gly Glu Val Pro Phe Tyr
                 85                  90                  95

Gly Arg Ala Ile Pro Leu Ala Phe Ile Lys Gly Gly Arg His Leu Ile
            100                 105                 110

Phe Cys His Ser Lys Lys Cys Asp Glu Leu Ala Lys Gln Leu Thr
            115                 120                 125

Ser Leu Gly Val Asn Ala Val Ala Tyr Tyr Arg Gly Leu Asp Val Ala
        130                 135                 140

Val Ile Pro Thr Thr Gly Asp Val Val Cys Ser Thr Asp Ala Leu
145                 150                 155                 160

Met Thr Gly Phe Thr Gly Asp Phe Asp Ser Val Ile Asp Cys Asn Ser
                165                 170                 175

Ala Val Thr Gln Thr Val Asp Phe Ser Leu Asp Pro Thr Phe Thr Ile
            180                 185                 190

Glu Thr Thr Thr Val Pro Gln Asp Ala Val Ser Arg Ser Gln Arg Trp
        195                 200                 205

Gly Arg Thr Gly Arg Gly Arg His Gly Ile Tyr Arg Tyr Val Ser Ala
    210                 215                 220

Gly Glu Arg Pro Ser Gly Met Phe Asp Ser Val Val Leu Cys Glu Cys
225                 230                 235                 240

Tyr Asp Ala Gly Cys Ala Trp Tyr Asp Leu Thr Pro Ala Glu Thr Thr
                245                 250                 255
```

-continued

```
Val Arg Leu Arg Ala Tyr Xaa Asn Thr Pro Gly Leu Pro Val Cys Gln
            260                 265                 270

Asp His Leu Glu Phe Trp Glu Gly Val Phe Thr Gly Leu Thr Asn Ile
            275                 280                 285

Asp Ala His Met Leu Ser Gln Thr Lys Gln Gly Gly Glu Asn Phe Pro
            290                 295                 300

Tyr Leu Val Ala Tyr Gln Ala Thr Val Cys Val Arg Ala Lys Ala Pro
305                 310                 315                 320

Pro Pro Ser Trp Asp Thr Met Trp Lys Cys Met Leu Arg Leu Lys Pro
                325                 330                 335

Xaa Leu Thr Gly Pro Thr Pro Leu Leu Tyr Arg Leu Gly Pro Val Gln
            340                 345                 350

Asn Glu Ile Thr Leu Thr His Pro Ile Thr Lys Tyr Ile Met Ala Cys
            355                 360                 365

Met Ser Ala Asp Leu Glu Val Ile Thr Ser Thr Trp Val Leu Val Gly
            370                 375                 380

Gly Val Val Ala Ala Leu Ala Ala Tyr Cys Leu Thr Val Gly Ser Val
385                 390                 395                 400

Ala Ile Val Gly Arg Ile Ile Leu Ser Gly Lys Pro Ala Ile Ile Pro
                405                 410                 415

Asp Arg Glu Val Leu Tyr Gln Gln Phe Asp Glu Met Glu Glu Cys Ser
            420                 425                 430

Ala Ser Leu Pro Tyr Met Asp Glu Thr Arg Ala Ile Ala Gly Gln Phe
            435                 440                 445

Lys Glu Lys Val Leu Gly Phe Ile Ser Thr Thr Gly Gln Lys Ala Glu
            450                 455                 460

Thr Leu Lys Pro Ala Ala Thr Ser Val Trp Asn Lys Ala Glu Gln Phe
465                 470                 475                 480

Trp Xaa Thr Tyr
```

<210> SEQ ID NO 199
<211> LENGTH: 1485
<212> TYPE: DNA
<213> ORGANISM: hepatitis C virus
<220> FEATURE:
<221> NAME/KEY: misc_feature
<222> LOCATION: (684)..(684)
<223> OTHER INFORMATION: "n" is any nucleotide
<220> FEATURE:
<221> NAME/KEY: misc_feature
<222> LOCATION: (909)..(909)
<223> OTHER INFORMATION: "n" is any nucleotide
<220> FEATURE:
<221> NAME/KEY: misc_feature
<222> LOCATION: (1058)..(1058)
<223> OTHER INFORMATION: "n" is any nucleotide
<220> FEATURE:
<221> NAME/KEY: misc_feature
<222> LOCATION: (1133)..(1133)
<223> OTHER INFORMATION: "n" is any nucleotide

<400> SEQUENCE: 199

```
tgtgccagga ccatcaccac cggagcttct atcacatact ccacttacgg caagttcctt      60
gctgatggag ggtgttcagg cggcgcgtat gacgtgatca tatgcgacga gtgccattcc     120
caggacgcca ccaccattct tgggataggc actgtccttg accaggcaga cgcggctgga     180
gctaggctcg tcgtcttggc cacggccacc ctcccggca gtgtgacaac gccccacccc      240
aacatcgagg aagtggccct gcctcaggag ggggaggttc ccttctacgg cagagccatt     300 cccctttgctt ttataaaggg tggtaggcat ctcatcttct gccattccaa gaaaaaatgt    360
```

```
gatgaactcg ccaagcaact gaccagcctg ggcgtgaacg ccgtggcata ttatagaggt      420
ctagacgtcg ccgtcatccc cacagcagga gacgtggtcg tgtgcagcac cgacgcgctc      480
atgacgggat tcaccggcga ctttgattct gtcatagact gcaactccgc cgtcactcag      540
acggtggact tcagtctgga tcccactttt accattgaga ctaccacagt gccccaggac      600
gcagtgtcca gaagccagcg taggggccga acggggagag gtaggcacgg catataccgg      660
tatgtctcgg ctggagagag accntctgac atgttcgact ccgtggtgct ctgtgagtgc      720
tacgatgccg gatgtgcgtg gtatgatctg actcctgccg agactaccgt gaggttgcgc      780
gcttacataa acaccccggg gctccctgtc tgtcaggacc atttggaatt ctgggagggg      840
gtgttcacgg ggctcactaa catcgacgct cacatgctgt cacagaccaa acagggtggg      900
gagaatttnc catccttgt agcgtaccaa gcaacagtct gtgttcgcgc gaaagcgccc      960
ccccccagct gggacacaat gtggaaatgc atgctccgtc tcaaaccgac tttaactggc     1020
cctactcccc tcttgtacag gctggggccc gtccagantg agatcacact gacgcacccc     1080
atcaccaagt acattatggc ttgcatgtct gcggacttgg aggtcattac cancacttgg     1140
gttctggtgg ggggcgttgt ggcggccctg gcggcctact gcttgacggt gggttcggta     1200
gccatagtcg gtaggatcat cctctctggg aaacctgcca tcattcccga tagggaggca     1260
ttataccagc aatttgatga gatggaggag tgctcggcct cgttgcccta tatggacgag     1320
acacgtgcca ttgccggaca attcaaagag aaagtgctcg gcttcatcag cacgaccggc     1380
cagaaggctg aaactctgaa gccggcagcc acgtctgtgt ggaacaaggc tgagcagttc     1440
tgggccacat acatgtggaa cttcatcagc gggatacaat aatag                     1485
```

<210> SEQ ID NO 200
<211> LENGTH: 484
<212> TYPE: PRT
<213> ORGANISM: hepatitis C virus
<220> FEATURE:
<221> NAME/KEY: MISC_FEATURE
<222> LOCATION: (228)..(228)
<223> OTHER INFORMATION: "Xaa" is any amino acid
<220> FEATURE:
<221> NAME/KEY: MISC_FEATURE
<222> LOCATION: (303)..(303)
<223> OTHER INFORMATION: "Xaa" is any amino acid
<220> FEATURE:
<221> NAME/KEY: MISC_FEATURE
<222> LOCATION: (353)..(353)
<223> OTHER INFORMATION: "Xaa" is any amino acid
<220> FEATURE:
<221> NAME/KEY: MISC_FEATURE
<222> LOCATION: (378)..(378)
<223> OTHER INFORMATION: "Xaa" is any amino acid

<400> SEQUENCE: 200

```
Cys Ala Arg Thr Ile Thr Thr Gly Ala Ser Ile Thr Tyr Ser Thr Tyr
1               5                   10                  15

Gly Lys Phe Leu Ala Asp Gly Gly Cys Ser Gly Gly Ala Tyr Asp Val
            20                  25                  30

Ile Ile Cys Asp Glu Cys His Ser Gln Asp Ala Thr Thr Ile Leu Gly
        35                  40                  45

Ile Gly Thr Val Leu Asp Gln Ala Glu Thr Ala Gly Ala Arg Leu Val
    50                  55                  60

Val Leu Ala Thr Ala Thr Pro Pro Gly Ser Val Thr Thr Pro His Pro
65                  70                  75                  80

Asn Ile Glu Glu Val Ala Leu Pro Gln Glu Gly Glu Val Pro Phe Tyr
```

```
                85                  90                  95
Gly Arg Ala Ile Pro Leu Ala Phe Ile Lys Gly Arg His Leu Ile
            100                 105                 110
Phe Cys His Ser Lys Lys Lys Cys Asp Glu Leu Ala Lys Gln Leu Thr
            115                 120                 125
Ser Leu Gly Val Asn Ala Val Ala Tyr Tyr Arg Gly Leu Asp Val Ala
130                 135                 140
Val Ile Pro Thr Ala Gly Asp Val Val Cys Ser Thr Asp Ala Leu
145                 150                 155                 160
Met Thr Gly Phe Thr Gly Asp Phe Asp Ser Val Ile Asp Cys Asn Ser
                165                 170                 175
Ala Val Thr Gln Thr Val Asp Phe Ser Leu Asp Pro Thr Phe Thr Ile
                180                 185                 190
Glu Thr Thr Thr Val Pro Gln Asp Ala Val Ser Arg Ser Gln Arg Arg
                195                 200                 205
Gly Arg Thr Gly Arg Gly Arg His Gly Ile Tyr Arg Tyr Val Ser Ala
            210                 215                 220
Gly Glu Arg Xaa Ser Asp Met Phe Asp Ser Val Val Leu Cys Glu Cys
225                 230                 235                 240
Tyr Asp Ala Gly Cys Ala Trp Tyr Asp Leu Thr Pro Ala Glu Thr Thr
                245                 250                 255
Val Arg Leu Arg Ala Tyr Ile Asn Thr Pro Gly Leu Pro Val Cys Gln
                260                 265                 270
Asp His Leu Glu Phe Trp Glu Gly Val Phe Thr Gly Leu Thr Asn Ile
            275                 280                 285
Asp Ala His Met Leu Ser Gln Thr Lys Gln Gly Gly Glu Asn Xaa Pro
            290                 295                 300
Tyr Leu Val Ala Tyr Gln Ala Thr Val Cys Val Arg Ala Lys Ala Pro
305                 310                 315                 320
Pro Pro Ser Trp Asp Thr Met Trp Lys Cys Met Leu Arg Leu Lys Pro
                325                 330                 335
Thr Leu Thr Gly Pro Thr Pro Leu Leu Tyr Arg Leu Gly Pro Val Gln
                340                 345                 350
Xaa Glu Ile Thr Leu Thr His Pro Ile Thr Lys Tyr Ile Met Ala Cys
            355                 360                 365
Met Ser Ala Asp Leu Glu Val Ile Thr Xaa Thr Trp Val Leu Val Gly
            370                 375                 380
Gly Val Val Ala Ala Leu Ala Ala Tyr Cys Leu Thr Val Gly Ser Val
385                 390                 395                 400
Ala Ile Val Gly Arg Ile Ile Leu Ser Gly Lys Pro Ala Ile Ile Pro
                405                 410                 415
Asp Arg Glu Ala Leu Tyr Gln Gln Phe Asp Glu Met Glu Glu Cys Ser
            420                 425                 430
Ala Ser Leu Pro Tyr Met Asp Glu Thr Arg Ala Ile Ala Gly Gln Phe
            435                 440                 445
Lys Glu Lys Val Leu Gly Phe Ile Ser Thr Thr Gly Gln Lys Ala Glu
            450                 455                 460
Thr Leu Lys Pro Ala Ala Thr Ser Val Trp Asn Lys Ala Glu Gln Phe
465                 470                 475                 480
Trp Ala Thr Tyr

<210> SEQ ID NO 201
<211> LENGTH: 340
```

<212> TYPE: DNA
<213> ORGANISM: hepatitis C virus

<400> SEQUENCE: 201

```
ctccactgtg actgagagag acatcagggt cgaagaagaa gtctatcagt gttgtgatct    60
ggagcccgag gcccgcaagg taataaccgc cctcacggag agactctacg tgggcggccc   120
tatgtacaat agcaagggag acctttgcgg gtatcgcagg tgccgcgcaa gcggcgtata   180
taccaccagc ttcgggaaca cactgacgtg ctaccttaaa gcctcagcag ccatcagggc   240
tgcgggctg aaggactgca ccatgctggt ttgcggtgac gacttagtcg tgatcgctga    300
aagcggtggc gtcgaggagg acaagcgagc cctcggagct                         340
```

<210> SEQ ID NO 202
<211> LENGTH: 113
<212> TYPE: PRT
<213> ORGANISM: hepatitis C virus

<400> SEQUENCE: 202

```
Ser Thr Val Thr Glu Arg Asp Ile Arg Val Glu Glu Val Tyr Gln
1               5                  10                  15

Cys Cys Asp Leu Glu Pro Glu Ala Arg Lys Val Ile Thr Ala Leu Thr
            20                  25                  30

Glu Arg Leu Tyr Val Gly Gly Pro Met Tyr Asn Ser Lys Gly Asp Leu
        35                  40                  45

Cys Gly Tyr Arg Arg Cys Arg Ala Ser Gly Val Tyr Thr Thr Ser Phe
50                  55                  60

Gly Asn Thr Leu Thr Cys Tyr Leu Lys Ala Ser Ala Ala Ile Arg Ala
65                  70                  75                  80

Ala Gly Leu Lys Asp Cys Thr Met Leu Val Cys Gly Asp Asp Leu Val
                85                  90                  95

Val Ile Ala Glu Ser Gly Gly Val Glu Glu Asp Lys Arg Ala Leu Gly
            100                 105                 110

Ala
```

<210> SEQ ID NO 203
<211> LENGTH: 340
<212> TYPE: DNA
<213> ORGANISM: hepatitis C virus

<400> SEQUENCE: 203

```
ctccacagtg actgaaagag acatcagggt cgaggaagag gtctaccagt gttgtgacct    60
ggagcctgaa acccgcaagg taatatctgc cctcactgaa agactctatg tgggcggtcc   120
catgcacaac agcaggggag acctatgcgg gtaccgtaga tgccgcgcga gcggcgtata   180
caccacaagc ttcgggaaca ctctgacgtg cttcctcaag gccacagcgg ccaccaaagc   240
cgctggccta aggactgca ccatgttggt gtgtggtgac gacttagtcg ttatcgccga     300
aagcgatggt gtcgaagagg accgccgagc cctcggagct                         340
```

<210> SEQ ID NO 204
<211> LENGTH: 113
<212> TYPE: PRT
<213> ORGANISM: hepatitis C virus

<400> SEQUENCE: 204

```
Ser Thr Val Thr Glu Arg Asp Ile Arg Val Glu Glu Val Tyr Gln
1               5                  10                  15
```

```
Cys Cys Asp Leu Glu Pro Glu Thr Arg Lys Val Ile Ser Ala Leu Thr
                20                  25                  30
Glu Arg Leu Tyr Val Gly Gly Pro Met His Asn Ser Arg Gly Asp Leu
            35                  40                  45
Cys Gly Tyr Arg Arg Cys Arg Ala Ser Gly Val Tyr Thr Thr Ser Phe
        50                  55                  60
Gly Asn Thr Leu Thr Cys Phe Leu Lys Ala Thr Ala Ala Thr Lys Ala
65                  70                  75                  80
Ala Gly Leu Lys Asp Cys Thr Met Leu Val Cys Gly Asp Asp Leu Val
                85                  90                  95
Val Ile Ala Glu Ser Asp Gly Val Glu Glu Asp Arg Arg Ala Leu Gly
            100                 105                 110
Ala
```

<210> SEQ ID NO 205
<211> LENGTH: 340
<212> TYPE: DNA
<213> ORGANISM: hepatitis C virus

<400> SEQUENCE: 205

```
ctccacggtg accgaaaggg atatcaggac cgaggaagag atctaccagt gctgcgacct    60
ggagcccgaa gcccgcaagg tgatatccgc cctaacggaa agactctacg tgggcggtcc   120
catgtacaac tccaagggg g acctatgcgg gcaacggagg tgccgcgcaa gcgggtctac   180
caccaccagc ttcgggaaca ctgtaacgtg ttatctcaag gccgttgcgg ctactagggc   240
cgcaggtctg aaaggttgca gcatgctggt tgtggagac gacttagtcg tcatctgcga   300
gagcggcggc gtagaggagg atgcaagagc cctccgagcc                         340
```

<210> SEQ ID NO 206
<211> LENGTH: 113
<212> TYPE: PRT
<213> ORGANISM: hepatitis C virus

<400> SEQUENCE: 206

```
Ser Thr Val Thr Glu Arg Asp Ile Arg Thr Glu Glu Ile Tyr Gln
1               5                   10                  15
Cys Cys Asp Leu Glu Pro Glu Ala Arg Lys Val Ile Ser Ala Leu Thr
                20                  25                  30
Glu Arg Leu Tyr Val Gly Gly Pro Met Tyr Asn Ser Lys Gly Asp Leu
            35                  40                  45
Cys Gly Gln Arg Arg Cys Arg Ala Ser Gly Val Tyr Thr Thr Ser Phe
        50                  55                  60
Gly Asn Thr Val Thr Cys Tyr Leu Lys Ala Val Ala Ala Thr Arg Ala
65                  70                  75                  80
Ala Gly Leu Lys Gly Cys Ser Met Leu Val Cys Gly Asp Asp Leu Val
                85                  90                  95
Val Ile Cys Glu Ser Gly Gly Val Glu Glu Asp Ala Arg Ala Leu Arg
            100                 105                 110
Ala
```

<210> SEQ ID NO 207
<211> LENGTH: 340
<212> TYPE: DNA
<213> ORGANISM: hepatitis C virus

<400> SEQUENCE: 207

```
ctccacggtg actgaaaggg acattagggt cgaggaagag atctaccagt gctgtgacct      60
ggagcccgag gcacgcaagg tgatatccgc tctcacagaa agactctaca agggcggccc     120
catgtataac agcaagggg acctatgcgg gcttcggagg tgccgcgcaa gcggggtata     180
caccacaagc ttcgggaaca cggtgacatg ctaccttaaa gccacagcag ccaccagggc     240
tgcagggctg aaagattgca ctatgctggt atgcggtgac gacttagtcg ttattgccga     300
aagcggtggc gtggaggagg acgcccgagc cctccgagcc                           340
```

<210> SEQ ID NO 208
<211> LENGTH: 113
<212> TYPE: PRT
<213> ORGANISM: hepatitis C virus

<400> SEQUENCE: 208

```
Ser Thr Val Thr Glu Arg Asp Ile Arg Val Glu Glu Ile Tyr Gln
1               5                   10                  15

Cys Cys Asp Leu Glu Pro Glu Ala Arg Lys Val Ile Ser Ala Leu Thr
                20                  25                  30

Glu Arg Leu Tyr Lys Gly Gly Pro Met Tyr Asn Ser Lys Gly Asp Leu
            35                  40                  45

Cys Gly Leu Arg Arg Cys Arg Ala Ser Gly Val Tyr Thr Thr Ser Phe
        50                  55                  60

Gly Asn Thr Val Thr Cys Tyr Leu Lys Ala Thr Ala Ala Thr Arg Ala
65                  70                  75                  80

Ala Gly Leu Lys Asp Cys Thr Met Leu Val Cys Gly Asp Asp Leu Val
                85                  90                  95

Val Ile Ala Glu Ser Gly Gly Val Glu Glu Asp Ala Arg Ala Leu Arg
            100                 105                 110

Ala
```

<210> SEQ ID NO 209
<211> LENGTH: 340
<212> TYPE: DNA
<213> ORGANISM: hepatitis C virus
<220> FEATURE:
<221> NAME/KEY: misc_feature
<222> LOCATION: (13)..(13)
<223> OTHER INFORMATION: "n" is any nucleotide
<220> FEATURE:
<221> NAME/KEY: misc_feature
<222> LOCATION: (23)..(23)
<223> OTHER INFORMATION: "n" is any nucleotide
<220> FEATURE:
<221> NAME/KEY: misc_feature
<222> LOCATION: (65)..(65)
<223> OTHER INFORMATION: "n" is any nucleotide
<220> FEATURE:
<221> NAME/KEY: misc_feature
<222> LOCATION: (72)..(72)
<223> OTHER INFORMATION: "n" is any nucleotide
<220> FEATURE:
<221> NAME/KEY: misc_feature
<222> LOCATION: (277)..(277)
<223> OTHER INFORMATION: "n" is any nucleotide
<220> FEATURE:
<221> NAME/KEY: misc_feature
<222> LOCATION: (337)..(337)
<223> OTHER INFORMATION: "n" is any nucleotide

<400> SEQUENCE: 209

```
ccccaccgtg acngagaggg acntcagggt cgaggaagag gtctatcagt gctgtaatct      60
ggagnccgat gnccgcaagg tcatcaacgc cctcacagag agactctacg tgggcggccc     120
```

```
tatgcacaac agcaagggag acctgtgtgg catccgtaga tgccgcgcga gcggcgttta      180
caccacgagc ttcggaaaca cgctgacttg ctacctcaaa gccacagcgg ccaccagggc      240
cgcgggcttg aaggattgca ccatgctggt ctgcggngac gacctggttg tcattgctga      300
gagcattggc atagacgagg acaagcaagc cctccgnact                            340
```

<210> SEQ ID NO 210
<211> LENGTH: 113
<212> TYPE: PRT
<213> ORGANISM: hepatitis C virus
<220> FEATURE:
<221> NAME/KEY: MISC_FEATURE
<222> LOCATION: (8)..(8)
<223> OTHER INFORMATION: "Xaa" is any amino acid
<220> FEATURE:
<221> NAME/KEY: MISC_FEATURE
<222> LOCATION: (22)..(22)
<223> OTHER INFORMATION: "Xaa" is any amino acid
<220> FEATURE:
<221> NAME/KEY: MISC_FEATURE
<222> LOCATION: (24)..(24)
<223> OTHER INFORMATION: "Xaa" is any amino acid

<400> SEQUENCE: 210

```
Pro Thr Val Thr Glu Arg Asp Xaa Arg Val Glu Glu Glu Val Tyr Gln
1               5                   10                  15

Cys Cys Asn Leu Glu Xaa Asp Xaa Arg Lys Val Ile Asn Ala Leu Thr
            20                  25                  30

Glu Arg Leu Tyr Val Gly Gly Pro Met His Asn Ser Lys Gly Asp Leu
        35                  40                  45

Cys Gly Ile Arg Arg Cys Arg Ala Ser Gly Val Tyr Thr Thr Ser Phe
    50                  55                  60

Gly Asn Thr Leu Thr Cys Tyr Leu Lys Ala Thr Ala Ala Thr Arg Ala
65                  70                  75                  80

Ala Gly Leu Lys Asp Cys Thr Met Leu Val Cys Gly Asp Asp Leu Val
                85                  90                  95

Val Ile Ala Glu Ser Ile Gly Ile Asp Glu Asp Lys Gln Ala Leu Arg
            100                 105                 110

Thr
```

<210> SEQ ID NO 211
<211> LENGTH: 340
<212> TYPE: DNA
<213> ORGANISM: hepatitis C virus
<220> FEATURE:
<221> NAME/KEY: misc_feature
<222> LOCATION: (11)..(11)
<223> OTHER INFORMATION: "n" is any nucleotide
<220> FEATURE:
<221> NAME/KEY: misc_feature
<222> LOCATION: (327)..(327)
<223> OTHER INFORMATION: "n" is any nucleotide
<220> FEATURE:
<221> NAME/KEY: misc_feature
<222> LOCATION: (333)..(334)
<223> OTHER INFORMATION: "n" is any nucleotide
<220> FEATURE:
<221> NAME/KEY: misc_feature
<222> LOCATION: (340)..(340)
<223> OTHER INFORMATION: "n" is any nucleotide

<400> SEQUENCE: 211

```
ctcgactgtg nccgagaggg acatcaggac agagggagag gtctatcagt gttgcgacct      60
ggaaccggaa gcccgcaagg taatcaccgc cctcactgag agactctatg tgggcggacc     120
```

```
catgttcaac agcaagggag acctgtgcgg acaacgccgg tgccgcgcaa gcggcgtgtt    180
caccaccagc ttcgggaaca cactgacgtg ctaccttaaa gccacagctg ctactagagc    240
agccggctta aaagattgca ccatgctggt ctgcggtgac gacttagtcg ttatttccga    300
gagcgccggt gtggaggagg atcccanaac ccnncgaccn                          340
```

<210> SEQ ID NO 212
<211> LENGTH: 113
<212> TYPE: PRT
<213> ORGANISM: hepatitis C virus
<220> FEATURE:
<221> NAME/KEY: MISC_FEATURE
<222> LOCATION: (4)..(4)
<223> OTHER INFORMATION: "Xaa" is any amino acid
<220> FEATURE:
<221> NAME/KEY: MISC_FEATURE
<222> LOCATION: (109)..(109)
<223> OTHER INFORMATION: "Xaa" is any amino acid
<220> FEATURE:
<221> NAME/KEY: MISC_FEATURE
<222> LOCATION: (111)..(111)
<223> OTHER INFORMATION: "Xaa" is any amino acid

<400> SEQUENCE: 212

```
Ser Thr Val Xaa Glu Arg Asp Ile Arg Thr Glu Gly Glu Val Tyr Gln
1               5                   10                  15

Cys Cys Asp Leu Glu Pro Glu Ala Arg Lys Val Ile Thr Ala Leu Thr
            20                  25                  30

Glu Arg Leu Tyr Val Gly Gly Pro Met Phe Asn Ser Lys Gly Asp Leu
        35                  40                  45

Cys Gly Gln Arg Arg Cys Arg Ala Ser Gly Val Phe Thr Thr Ser Phe
    50                  55                  60

Gly Asn Thr Leu Thr Cys Tyr Leu Lys Ala Thr Ala Ala Thr Arg Ala
65                  70                  75                  80

Ala Gly Leu Lys Asp Cys Thr Met Leu Val Cys Gly Asp Asp Leu Val
                85                  90                  95

Val Ile Ser Glu Ser Ala Gly Val Glu Glu Asp Pro Xaa Thr Xaa Arg
            100                 105                 110

Pro
```

<210> SEQ ID NO 213
<211> LENGTH: 340
<212> TYPE: DNA
<213> ORGANISM: hepatitis C virus

<400> SEQUENCE: 213

```
ctcaacagtc accgagaacg acatccgtgt tgaggagtca atttaccaat gttgtgactt    60
ggcccccgag gccagacagg ccataaagtc gctcacagag cggctttata tcggggtcc    120 cctgactaat tcaaaggggc agaactgtgg ctatcgccga tgccgcgcaa gcggcgtgct    180
gacgaccagc tgcggtaata cccttacatg ttacctaaag gcctctgcag cctgtcgagc    240
tgcgaagctc caggactgca cgatgctcgt gtgcggggac gaccttgtcg ttatctgtga    300
aagcgcggga acccaagagg acgcggcgag cctacgagtc                         340
```

<210> SEQ ID NO 214
<211> LENGTH: 113
<212> TYPE: PRT
<213> ORGANISM: hepatitis C virus

<400> SEQUENCE: 214

```
Ser Thr Val Thr Glu Asn Asp Ile Arg Val Glu Ser Ile Tyr Gln
1               5                   10                  15

Cys Cys Asp Leu Ala Pro Glu Ala Arg Gln Ala Ile Lys Ser Leu Thr
                20                  25                  30

Glu Arg Leu Tyr Ile Gly Gly Pro Leu Thr Asn Ser Lys Gly Gln Asn
            35                  40                  45

Cys Gly Tyr Arg Arg Cys Arg Ala Ser Gly Val Leu Thr Thr Ser Cys
    50                  55                  60

Gly Asn Thr Leu Thr Cys Tyr Leu Lys Ala Ser Ala Ala Cys Arg Ala
65                  70                  75                  80

Ala Lys Leu Gln Asp Cys Thr Met Leu Val Cys Gly Asp Asp Leu Val
                85                  90                  95

Val Ile Cys Glu Ser Ala Gly Thr Gln Glu Asp Ala Ala Ser Leu Arg
            100                 105                 110

Val

<210> SEQ ID NO 215
<211> LENGTH: 340
<212> TYPE: DNA
<213> ORGANISM: hepatitis C virus

<400> SEQUENCE: 215
ctcaaccgtc acggagaggg atataagaac agaagaatcc atatatcaag cttgttccct      60
gccccaagag gccagaactg tcatacactc gctcaccgag agactctacg tgggagggcc     120
catgataaac agcaaagggc aatcctgcgg ttacaggcgt tgccgcgcaa gcggtgtttt     180
caccaccagc atgggaata ccatgacgtg ttacatcaaa gcccttgcag cgtgtaaagc     240
cgcagggatc gtggaccccg tcatgctggt gtgtggagac gacctggtcg tcatctcgga     300
gagccagggt aacgaggagg acgagcgaaa cctgagagct                            340

<210> SEQ ID NO 216
<211> LENGTH: 113
<212> TYPE: PRT
<213> ORGANISM: hepatitis C virus

<400> SEQUENCE: 216

Ser Thr Val Thr Glu Arg Asp Ile Arg Thr Glu Glu Ser Ile Tyr Gln
1               5                   10                  15

Ala Cys Ser Leu Pro Gln Glu Ala Arg Thr Val Ile His Ser Leu Thr
                20                  25                  30

Glu Arg Leu Tyr Val Gly Gly Pro Met Ile Asn Ser Lys Gly Gln Ser
            35                  40                  45

Cys Gly Tyr Arg Arg Cys Arg Ala Ser Gly Val Phe Thr Thr Ser Met
    50                  55                  60

Gly Asn Thr Met Thr Cys Tyr Ile Lys Ala Leu Ala Ala Cys Lys Ala
65                  70                  75                  80

Ala Gly Ile Val Asp Pro Val Met Leu Val Cys Gly Asp Asp Leu Val
                85                  90                  95

Val Ile Ser Glu Ser Gln Gly Asn Glu Glu Asp Glu Arg Asn Leu Arg
            100                 105                 110

Ala

<210> SEQ ID NO 217
<211> LENGTH: 340
<212> TYPE: DNA
<213> ORGANISM: hepatitis C virus
```

-continued

```
<400> SEQUENCE: 217
ctcgactgtc actgaacagg acatcagggt ggaagaggag atatatcaat gctgcaacct      60
tgaaccggag gccaggaaag tgatctcctc cctcacggag cggctttact gcggaggccc     120
tatgtttaac agcaaggggg cccagtgtgg ttatcgccgt tgccgtgcca gtggagttct     180
gcctaccagc tttggcaaca caatcacttg ttacatcaag gccacaacgg ccgcgaaggc     240
cgcaggcctc cggaacccgg actttcttgt ctgcggagat gatctggtcg tggtggctga     300
gagtgatggc gtcgacgagg atagagcagc cctgagagcc                           340

<210> SEQ ID NO 218
<211> LENGTH: 113
<212> TYPE: PRT
<213> ORGANISM: hepatitis C virus

<400> SEQUENCE: 218

Ser Thr Val Thr Glu Gln Asp Ile Arg Val Glu Glu Ile Tyr Gln
1               5                   10                  15

Cys Cys Asn Leu Glu Pro Glu Ala Arg Lys Val Ile Ser Ser Leu Thr
            20                  25                  30

Glu Arg Leu Tyr Cys Gly Gly Pro Met Phe Asn Ser Lys Gly Ala Gln
        35                  40                  45

Cys Gly Tyr Arg Arg Cys Arg Ala Ser Gly Val Leu Pro Thr Ser Phe
    50                  55                  60

Gly Asn Thr Ile Thr Cys Tyr Ile Lys Ala Thr Thr Ala Ala Lys Ala
65                  70                  75                  80

Ala Gly Leu Arg Asn Pro Asp Phe Leu Val Cys Gly Asp Asp Leu Val
                85                  90                  95

Val Val Ala Glu Ser Asp Gly Val Asp Glu Asp Arg Ala Ala Leu Arg
                100                 105                 110

Ala

<210> SEQ ID NO 219
<211> LENGTH: 10
<212> TYPE: PRT
<213> ORGANISM: hepatitis C virus

<400> SEQUENCE: 219

Arg Ser Glu Gly Arg Thr Ser Trp Ala Gln
1               5                   10

<210> SEQ ID NO 220
<211> LENGTH: 10
<212> TYPE: PRT
<213> ORGANISM: hepatitis C virus

<400> SEQUENCE: 220

Arg Ser Glu Gly Arg Thr Ser Trp Ala Gln
1               5                   10

<210> SEQ ID NO 221
<211> LENGTH: 10
<212> TYPE: PRT
<213> ORGANISM: hepatitis C virus

<400> SEQUENCE: 221

Arg Thr Glu Gly Arg Thr Ser Trp Ala Gln
1               5                   10
```

<210> SEQ ID NO 222
<211> LENGTH: 629
<212> TYPE: DNA
<213> ORGANISM: hepatitis C virus

<400> SEQUENCE: 222

```
tagactttg ggagagcgtc ttcactggac taactcacat agatgcccac tttctgtcac      60
agactaagca gcagggactc aacttctcgt tcctgactgc ctaccaagcc actgtgtgcg    120
ctcgcgcgca ggctcctccc ccaagttggg acgagatgtg gaagtgtctc gtacggctta    180
agccaacact acatggacct acgcctcttc tatatcggtt ggggcctgtc caaaatgaaa    240
tctgcttgac acccccatc acaaaataca tcatggcatg catgtcagct gatctggaag     300
taaccaccag cacctgggtt tgcttggag gggtcctcgc ggccctagcg gcctactgct     360
tgtcagtcgg ttgtgttgtg attgtgggtc atatcgagct gggggcaag ccggcaatcg     420
ttccagacaa agaggtgttg tatcaacaat acgatgagat ggaagagtgc tcacaagctg    480
ccccatatat cgaacaagct caggtaatag ctcaccagtt caaggaaaaa gtccttggat    540
tgctgcagcg agccacccaa caacaagctg tcattgagcc catagtaact accaactggc    600
aaaagcttga ggccttttgg cacaagcat                                       629
```

<210> SEQ ID NO 223
<211> LENGTH: 209
<212> TYPE: PRT
<213> ORGANISM: hepatitis C virus

<400> SEQUENCE: 223

```
Asp Phe Trp Glu Ser Val Phe Thr Gly Leu Thr His Ile Asp Ala His
 1               5                  10                  15

Phe Leu Ser Gln Thr Lys Gln Gln Gly Leu Asn Phe Ser Phe Leu Thr
             20                  25                  30

Ala Tyr Gln Ala Thr Val Cys Ala Arg Ala Gln Ala Pro Pro Pro Ser
         35                  40                  45

Trp Asp Glu Met Trp Lys Cys Leu Val Arg Leu Lys Pro Thr Leu His
     50                  55                  60

Gly Pro Thr Pro Leu Leu Tyr Arg Leu Gly Pro Val Gln Asn Glu Ile
 65                  70                  75                  80

Cys Leu Thr His Pro Ile Thr Lys Tyr Ile Met Ala Cys Met Ser Ala
                 85                  90                  95

Asp Leu Glu Val Thr Thr Ser Thr Trp Val Leu Leu Gly Gly Val Leu
            100                 105                 110

Ala Ala Leu Ala Ala Tyr Cys Leu Ser Val Gly Cys Val Val Ile Val
        115                 120                 125

Gly His Ile Glu Leu Gly Gly Lys Pro Ala Ile Val Pro Asp Lys Glu
    130                 135                 140

Val Leu Tyr Gln Gln Tyr Asp Glu Met Glu Glu Cys Ser Gln Ala Ala
145                 150                 155                 160

Pro Tyr Ile Glu Gln Ala Gln Val Ile Ala His Gln Phe Lys Glu Lys
                165                 170                 175

Val Leu Gly Leu Leu Gln Arg Ala Thr Gln Gln Ala Val Ile Glu
            180                 185                 190

Pro Ile Val Thr Thr Asn Trp Gln Lys Leu Glu Ala Phe Trp His Lys
        195                 200                 205

His
```

```
<210> SEQ ID NO 224
<211> LENGTH: 12
<212> TYPE: PRT
<213> ORGANISM: hepatitis C virus

<400> SEQUENCE: 224

Ile His Tyr Arg Asn Ala Ser Gly Ile Tyr His Ile
1               5                   10

<210> SEQ ID NO 225
<211> LENGTH: 12
<212> TYPE: PRT
<213> ORGANISM: hepatitis C virus

<400> SEQUENCE: 225

Val Asn Tyr Arg Asn Ala Ser Gly Ile Tyr His Ile
1               5                   10

<210> SEQ ID NO 226
<211> LENGTH: 12
<212> TYPE: PRT
<213> ORGANISM: hepatitis C virus

<400> SEQUENCE: 226

Val Asn Tyr Arg Asn Ala Ser Gly Val Tyr His Ile
1               5                   10

<210> SEQ ID NO 227
<211> LENGTH: 12
<212> TYPE: PRT
<213> ORGANISM: hepatitis C virus

<400> SEQUENCE: 227

Val Asn Tyr His Asn Thr Ser Gly Ile Tyr His Leu
1               5                   10

<210> SEQ ID NO 228
<211> LENGTH: 12
<212> TYPE: PRT
<213> ORGANISM: hepatitis C virus

<400> SEQUENCE: 228

Gln His Tyr Arg Asn Ala Ser Gly Ile Tyr His Val
1               5                   10

<210> SEQ ID NO 229
<211> LENGTH: 12
<212> TYPE: PRT
<213> ORGANISM: hepatitis C virus

<400> SEQUENCE: 229

Gln His Tyr Arg Asn Val Ser Gly Ile Tyr His Val
1               5                   10

<210> SEQ ID NO 230
<211> LENGTH: 12
<212> TYPE: PRT
<213> ORGANISM: hepatitis C virus

<400> SEQUENCE: 230

Ile His Tyr Arg Asn Ala Ser Asp Gly Tyr Tyr Ile
1               5                   10

<210> SEQ ID NO 231
```

```
<211> LENGTH: 12
<212> TYPE: PRT
<213> ORGANISM: hepatitis C virus

<400> SEQUENCE: 231

Leu Gln Val Lys Asn Thr Ser Ser Ser Tyr Met Val
1               5                   10

<210> SEQ ID NO 232
<211> LENGTH: 11
<212> TYPE: PRT
<213> ORGANISM: hepatitis C virus

<400> SEQUENCE: 232

Val Trp Gln Leu Arg Ala Ile Val Leu His Val
1               5                   10

<210> SEQ ID NO 233
<211> LENGTH: 11
<212> TYPE: PRT
<213> ORGANISM: hepatitis C virus

<400> SEQUENCE: 233

Val Tyr Glu Ala Asp Tyr His Ile Leu His Leu
1               5                   10

<210> SEQ ID NO 234
<211> LENGTH: 11
<212> TYPE: PRT
<213> ORGANISM: hepatitis C virus

<400> SEQUENCE: 234

Val Tyr Glu Thr Asp Asn His Ile Leu His Leu
1               5                   10

<210> SEQ ID NO 235
<211> LENGTH: 11
<212> TYPE: PRT
<213> ORGANISM: hepatitis C virus

<400> SEQUENCE: 235

Val Tyr Glu Thr Glu Asn His Ile Leu His Leu
1               5                   10

<210> SEQ ID NO 236
<211> LENGTH: 11
<212> TYPE: PRT
<213> ORGANISM: hepatitis C virus

<400> SEQUENCE: 236

Val Phe Glu Thr Val His His Ile Leu His Leu
1               5                   10

<210> SEQ ID NO 237
<211> LENGTH: 11
<212> TYPE: PRT
<213> ORGANISM: hepatitis C virus

<400> SEQUENCE: 237

Val Phe Glu Thr Glu His His Ile Leu His Leu
1               5                   10

<210> SEQ ID NO 238
<211> LENGTH: 11
<212> TYPE: PRT
```

-continued

<213> ORGANISM: hepatitis C virus

<400> SEQUENCE: 238

Val Phe Glu Thr Asp His His Ile Met His Leu
1 5 10

<210> SEQ ID NO 239
<211> LENGTH: 11
<212> TYPE: PRT
<213> ORGANISM: hepatitis C virus

<400> SEQUENCE: 239

Val Tyr Glu Thr Glu Asn His Ile Leu His Leu
1 5 10

<210> SEQ ID NO 240
<211> LENGTH: 11
<212> TYPE: PRT
<213> ORGANISM: hepatitis C virus

<400> SEQUENCE: 240

Val Tyr Glu Ala Asp Ala Leu Ile Leu His Ala
1 5 10

<210> SEQ ID NO 241
<211> LENGTH: 13
<212> TYPE: PRT
<213> ORGANISM: hepatitis C virus

<400> SEQUENCE: 241

Val Gln Asp Gly Asn Thr Ser Ala Cys Trp Thr Pro Val
1 5 10

<210> SEQ ID NO 242
<211> LENGTH: 13
<212> TYPE: PRT
<213> ORGANISM: hepatitis C virus

<400> SEQUENCE: 242

Val Lys Thr Gly Asn Gln Ser Arg Cys Trp Val Ala Leu
1 5 10

<210> SEQ ID NO 243
<211> LENGTH: 13
<212> TYPE: PRT
<213> ORGANISM: hepatitis C virus

<400> SEQUENCE: 243

Val Lys Thr Gly Asn Gln Ser Arg Cys Trp Val Ala Leu
1 5 10

<210> SEQ ID NO 244
<211> LENGTH: 13
<212> TYPE: PRT
<213> ORGANISM: hepatitis C virus

<400> SEQUENCE: 244

Val Arg Thr Gly Asn Gln Ser Arg Cys Trp Val Ala Leu
1 5 10

<210> SEQ ID NO 245
<211> LENGTH: 13
<212> TYPE: PRT
<213> ORGANISM: hepatitis C virus

```
<400> SEQUENCE: 245

Val Lys Thr Gly Asn Gln Ser Arg Cys Trp Ile Ala Leu
1               5                   10

<210> SEQ ID NO 246
<211> LENGTH: 13
<212> TYPE: PRT
<213> ORGANISM: hepatitis C virus

<400> SEQUENCE: 246

Val Lys Thr Gly Asn Gln Ser Arg Cys Trp Ile Ala Leu
1               5                   10

<210> SEQ ID NO 247
<211> LENGTH: 13
<212> TYPE: PRT
<213> ORGANISM: hepatitis C virus

<400> SEQUENCE: 247

Val Lys Thr Gly Asn Ser Val Arg Cys Trp Ile Pro Leu
1               5                   10

<210> SEQ ID NO 248
<211> LENGTH: 13
<212> TYPE: PRT
<213> ORGANISM: hepatitis C virus

<400> SEQUENCE: 248

Val Lys Thr Gly Asn Val Ser Arg Cys Trp Ile Ser Leu
1               5                   10

<210> SEQ ID NO 249
<211> LENGTH: 13
<212> TYPE: PRT
<213> ORGANISM: hepatitis C virus

<400> SEQUENCE: 249

Val Arg Lys Asp Asn Val Ser Arg Cys Trp Val Gln Ile
1               5                   10

<210> SEQ ID NO 250
<211> LENGTH: 10
<212> TYPE: PRT
<213> ORGANISM: hepatitis C virus

<400> SEQUENCE: 250

Ala Pro Ser Phe Gly Ala Val Thr Ala Pro
1               5                   10

<210> SEQ ID NO 251
<211> LENGTH: 10
<212> TYPE: PRT
<213> ORGANISM: hepatitis C virus

<400> SEQUENCE: 251

Val Ser Gln Pro Gly Ala Leu Thr Lys Gly
1               5                   10

<210> SEQ ID NO 252
<211> LENGTH: 10
<212> TYPE: PRT
<213> ORGANISM: hepatitis C virus

<400> SEQUENCE: 252
```

Val Lys Tyr Val Gly Ala Thr Thr Ala Ser
1               5                   10

<210> SEQ ID NO 253
<211> LENGTH: 10
<212> TYPE: PRT
<213> ORGANISM: hepatitis C virus

<400> SEQUENCE: 253

Ala Pro Tyr Ile Gly Ala Pro Val Glu Ser
1               5                   10

<210> SEQ ID NO 254
<211> LENGTH: 10
<212> TYPE: PRT
<213> ORGANISM: hepatitis C virus

<400> SEQUENCE: 254

Ala Gln His Leu Asn Ala Pro Leu Glu Ser
1               5                   10

<210> SEQ ID NO 255
<211> LENGTH: 10
<212> TYPE: PRT
<213> ORGANISM: hepatitis C virus

<400> SEQUENCE: 255

Ser Pro Tyr Val Gly Ala Pro Leu Glu Pro
1               5                   10

<210> SEQ ID NO 256
<211> LENGTH: 10
<212> TYPE: PRT
<213> ORGANISM: hepatitis C virus

<400> SEQUENCE: 256

Ser Pro Tyr Ala Gly Ala Pro Leu Glu Pro
1               5                   10

<210> SEQ ID NO 257
<211> LENGTH: 10
<212> TYPE: PRT
<213> ORGANISM: hepatitis C virus

<400> SEQUENCE: 257

Ala Pro Tyr Leu Gly Ala Pro Leu Glu Ser
1               5                   10

<210> SEQ ID NO 258
<211> LENGTH: 10
<212> TYPE: PRT
<213> ORGANISM: hepatitis C virus

<400> SEQUENCE: 258

Ala Pro Tyr Leu Gly Ala Pro Leu Glu Ser
1               5                   10

<210> SEQ ID NO 259
<211> LENGTH: 10
<212> TYPE: PRT
<213> ORGANISM: hepatitis C virus

<400> SEQUENCE: 259

Ala Pro Tyr Val Gly Ala Pro Leu Glu Ser
1               5                   10

```
<210> SEQ ID NO 260
<211> LENGTH: 11
<212> TYPE: PRT
<213> ORGANISM: hepatitis C virus

<400> SEQUENCE: 260

Asn Val Pro Tyr Leu Gly Ala Pro Leu Thr Ser
1               5                   10

<210> SEQ ID NO 261
<211> LENGTH: 10
<212> TYPE: PRT
<213> ORGANISM: hepatitis C virus

<400> SEQUENCE: 261

Ala Pro His Leu Arg Ala Pro Leu Ser Ser
1               5                   10

<210> SEQ ID NO 262
<211> LENGTH: 10
<212> TYPE: PRT
<213> ORGANISM: hepatitis C virus

<400> SEQUENCE: 262

Ala Pro Tyr Leu Gly Ala Pro Leu Thr Ser
1               5                   10

<210> SEQ ID NO 263
<211> LENGTH: 10
<212> TYPE: PRT
<213> ORGANISM: hepatitis C virus

<400> SEQUENCE: 263

Arg Pro Arg Gln His Ala Thr Val Gln Asp
1               5                   10

<210> SEQ ID NO 264
<211> LENGTH: 10
<212> TYPE: PRT
<213> ORGANISM: hepatitis C virus

<400> SEQUENCE: 264

Ser Pro Gln His His Lys Phe Val Gln Asp
1               5                   10

<210> SEQ ID NO 265
<211> LENGTH: 10
<212> TYPE: PRT
<213> ORGANISM: hepatitis C virus

<400> SEQUENCE: 265

Arg Pro Arg Arg Leu Trp Thr Thr Gln Glu
1               5                   10

<210> SEQ ID NO 266
<211> LENGTH: 10
<212> TYPE: PRT
<213> ORGANISM: hepatitis C virus

<400> SEQUENCE: 266

Pro Pro Arg Ile His Glu Thr Thr Gln Asp
1               5                   10
```

<210> SEQ ID NO 267
<211> LENGTH: 14
<212> TYPE: PRT
<213> ORGANISM: hepatitis C virus

<400> SEQUENCE: 267

Thr Ile Ser Tyr Ala Asn Gly Ser Gly Pro Ser Asp Asp Lys
1               5                   10

<210> SEQ ID NO 268
<211> LENGTH: 19
<212> TYPE: PRT
<213> ORGANISM: hepatitis C virus

<400> SEQUENCE: 268

Ser Arg Arg Gln Pro Ile Pro Arg Ala Arg Thr Glu Gly Arg Ser
1               5                   10                  15

Trp Ala Gln

<210> SEQ ID NO 269
<211> LENGTH: 1443
<212> TYPE: DNA
<213> ORGANISM: hepatitis C virus

<400> SEQUENCE: 269

| accatcacca | ccggagcttc | tatcacatac | tccacttacg | gcaagttcct | tgctgatgga | 60 |
| gggtgttcag | gcggcgcgta | tgacgtgatc | atatgcgacg | agtgccattc | ccaggacgcc | 120 |
| accaccattc | ttgggatagg | cactgtcctt | gaccaggcag | agacggctgg | agctaggctc | 180 |
| gtcgtcttgg | ccacggccac | ccctcccggc | agtgtgacaa | cgccccaccc | caacatcgag | 240 |
| gaagtggccc | tgcctcagga | gggggaggtt | cccttctacg | gcagagccat | tccccttgct | 300 |
| tttataaagg | gtggtaggca | tctcatcttc | tgccattcca | agaaaaaatg | tgatgaactc | 360 |
| gccaagcaac | tgaccagcct | gggcgtgaac | gccgtggcat | attatagagg | tctagacgtc | 420 |
| gccgtcatcc | ccacagcagg | agacgtggtc | gtgtgcagca | ccgacgcgct | catgacggga | 480 |
| ttcaccggcg | actttgattc | tgtcatagac | tgcaactccg | ccgtcactca | gacggtggac | 540 |
| ttcagtctgg | atcccacttt | taccattgag | actaccacag | tgccccagga | cgcagtgtcc | 600 |
| agaagccagc | gtaggggccg | cacggggaga | ggtaggcacg | gcatataccg | gtatgtctcg | 660 |
| gctggagaga | gaccgtctga | catgttcgac | tccgtggtgc | tctgtgagtg | ctacgatgcc | 720 |
| ggatgtgcgt | ggtatgatct | gactcctgcc | gagactaccg | tgaggttgcg | cgcttacata | 780 |
| aacaccccccg | gctccctgt | ctgtcaggac | catttggaat | ctgggagggg | gtgttcacg | 840 |
| gggctcacta | acatcgacgc | tcacatgctg | tcacagacca | aacagggtgg | ggagaatttc | 900 |
| ccataccttg | tagcgtacca | agcaacagtc | tgtgttcgcg | cgaaagcgcc | cccccccagc | 960 |
| tgggacacaa | tgtggaaatg | catgctccgt | ctcaaaccga | cttttaactgg | ccctactccc | 1020 |
| ctccttgtaca | ggctggggcc | cgtccagaat | gagatcacac | tgacgcaccc | catcaccaag | 1080 |
| tacattatgg | cttgcatgtc | tgcggacttg | gaggtcatta | ccagcacttg | ggttctggtg | 1140 |
| gggggcgttg | tggcggccct | gcggcctac | tgcttgacgg | tgggttcggt | agccatagtc | 1200 |
| ggtaggatca | tcctctctgg | gaaacctgcc | atcattcccg | ataggaggc | attataccag | 1260 |
| caatttgatg | agatggagga | gtgctcggcc | tcgttgccct | atatgacga | acacgtgcc | 1320 |
| attgccggac | aattcaaaga | gaaagtgctg | ggcttcatca | gcacgaccgg | ccagaaggct | 1380 |
| gaaactctga | agccggcagc | cacgtctgtg | tggaacaagg | ctgagcagtt | ctgggccaca | 1440 |

```
                                                                      1443
tac
```

<210> SEQ ID NO 270
<211> LENGTH: 481
<212> TYPE: PRT
<213> ORGANISM: hepatitis C virus

<400> SEQUENCE: 270

```
Thr Ile Thr Thr Gly Ala Ser Ile Thr Tyr Ser Thr Tyr Gly Lys Phe
 1               5                  10                  15

Leu Ala Asp Gly Gly Cys Ser Gly Gly Ala Tyr Asp Val Ile Ile Cys
             20                  25                  30

Asp Glu Cys His Ser Gln Asp Ala Thr Thr Ile Leu Gly Ile Gly Thr
         35                  40                  45

Val Leu Asp Gln Ala Glu Thr Ala Gly Ala Arg Leu Val Val Leu Ala
     50                  55                  60

Thr Ala Thr Pro Pro Gly Ser Val Thr Thr Pro His Pro Asn Ile Glu
 65                  70                  75                  80

Glu Val Ala Leu Pro Gln Glu Gly Val Pro Phe Tyr Gly Arg Ala
                 85                  90                  95

Ile Pro Leu Ala Phe Ile Lys Gly Gly Arg His Leu Ile Phe Cys His
                100                 105                 110

Ser Lys Lys Lys Cys Asp Glu Leu Ala Lys Gln Leu Thr Ser Leu Gly
            115                 120                 125

Val Asn Ala Val Ala Tyr Tyr Arg Gly Leu Asp Val Ala Val Ile Pro
        130                 135                 140

Thr Ala Gly Asp Val Val Cys Ser Thr Asp Ala Leu Met Thr Gly
145                 150                 155                 160

Phe Thr Gly Asp Phe Asp Ser Val Ile Asp Cys Asn Ser Ala Val Thr
                165                 170                 175

Gln Thr Val Asp Phe Ser Leu Asp Pro Thr Phe Thr Ile Glu Thr Thr
            180                 185                 190

Thr Val Pro Gln Asp Ala Val Ser Arg Ser Gln Arg Arg Gly Arg Thr
        195                 200                 205

Gly Arg Gly Arg His Gly Ile Tyr Arg Tyr Val Ser Ala Gly Glu Arg
    210                 215                 220

Pro Ser Asp Met Phe Asp Ser Val Val Leu Cys Glu Cys Tyr Asp Ala
225                 230                 235                 240

Gly Cys Ala Trp Tyr Asp Leu Thr Pro Ala Glu Thr Thr Val Arg Leu
                245                 250                 255

Arg Ala Tyr Ile Asn Thr Pro Gly Leu Pro Val Cys Gln Asp His Leu
            260                 265                 270

Glu Phe Trp Glu Gly Val Phe Thr Gly Leu Thr Asn Ile Asp Ala His
        275                 280                 285

Met Leu Ser Gln Thr Lys Gln Gly Gly Glu Asn Phe Pro Tyr Leu Val
    290                 295                 300

Ala Tyr Gln Ala Thr Val Cys Val Arg Ala Lys Ala Pro Pro Pro Ser
305                 310                 315                 320

Trp Asp Thr Met Trp Lys Cys Met Leu Arg Leu Lys Pro Thr Leu Thr
                325                 330                 335

Gly Pro Thr Pro Leu Leu Tyr Arg Leu Gly Pro Val Gln Asn Glu Ile
            340                 345                 350

Thr Leu Thr His Pro Ile Thr Lys Tyr Ile Met Ala Cys Met Ser Ala
        355                 360                 365
```

```
Asp Leu Glu Val Ile Thr Ser Thr Trp Val Leu Val Gly Val Val
    370                 375                 380

Ala Ala Leu Ala Ala Tyr Cys Leu Thr Val Gly Ser Val Ala Ile Val
385                 390                 395                 400

Gly Arg Ile Ile Leu Ser Gly Lys Pro Ala Ile Ile Pro Asp Arg Glu
                405                 410                 415

Ala Leu Tyr Gln Gln Phe Asp Glu Met Glu Glu Cys Ser Ala Ser Leu
            420                 425                 430

Pro Tyr Met Asp Glu Thr Arg Ala Ile Ala Gly Gln Phe Lys Glu Lys
        435                 440                 445

Val Leu Gly Phe Ile Ser Thr Thr Gly Gln Lys Ala Glu Thr Leu Lys
    450                 455                 460

Pro Ala Ala Thr Ser Val Trp Asn Lys Ala Glu Gln Phe Trp Ala Thr
465                 470                 475                 480

Tyr
```

```
<210> SEQ ID NO 271
<211> LENGTH: 5
<212> TYPE: PRT
<213> ORGANISM: hepatitis C virus

<400> SEQUENCE: 271

Leu Glu Trp Arg Asn
1               5
```

```
<210> SEQ ID NO 272
<211> LENGTH: 20
<212> TYPE: PRT
<213> ORGANISM: hepatitis C virus

<400> SEQUENCE: 272

Leu Ser Gly Lys Pro Ala Ile Ile Pro Asp Arg Glu Val Leu Tyr Arg
1               5                   10                  15

Glu Phe Asp Glu
            20
```

```
<210> SEQ ID NO 273
<211> LENGTH: 20
<212> TYPE: PRT
<213> ORGANISM: hepatitis C virus

<400> SEQUENCE: 273

Ser Gln His Leu Pro Tyr Ile Glu Gln Gly Met Met Leu Ala Glu Gln
1               5                   10                  15

Phe Lys Gln Lys
            20
```

```
<210> SEQ ID NO 274
<211> LENGTH: 20
<212> TYPE: PRT
<213> ORGANISM: hepatitis C virus

<400> SEQUENCE: 274

Leu Ala Glu Gln Phe Lys Gln Lys Ala Leu Gly Leu Leu Gln Thr Ala
1               5                   10                  15

Ser Arg Gln Ala
            20
```

```
<210> SEQ ID NO 275
<211> LENGTH: 20
```

```
<212> TYPE: PRT
<213> ORGANISM: hepatitis C virus

<400> SEQUENCE: 275

Leu Ser Gly Arg Pro Ala Val Ile Pro Asp Arg Glu Val Leu Tyr Gln
1               5                   10                  15

Glu Phe Asp Glu
            20

<210> SEQ ID NO 276
<211> LENGTH: 20
<212> TYPE: PRT
<213> ORGANISM: hepatitis C virus

<400> SEQUENCE: 276

Ala Ser His Leu Pro Tyr Ile Glu Gln Gly Met Gln Leu Ala Glu Gln
1               5                   10                  15

Phe Lys Gln Lys
            20

<210> SEQ ID NO 277
<211> LENGTH: 20
<212> TYPE: PRT
<213> ORGANISM: hepatitis C virus

<400> SEQUENCE: 277

Leu Ala Glu Gln Phe Lys Gln Lys Ala Leu Gly Leu Leu Gln Thr Ala
1               5                   10                  15

Thr Lys Gln Ala
            20

<210> SEQ ID NO 278
<211> LENGTH: 20
<212> TYPE: PRT
<213> ORGANISM: hepatitis C virus

<400> SEQUENCE: 278

Val Asn Gln Arg Ala Val Val Ala Pro Asp Lys Glu Val Leu Tyr Glu
1               5                   10                  15

Ala Phe Asp Glu
            20

<210> SEQ ID NO 279
<211> LENGTH: 20
<212> TYPE: PRT
<213> ORGANISM: hepatitis C virus

<400> SEQUENCE: 279

Ala Ser Arg Ala Ala Leu Ile Glu Glu Gly Gln Arg Ile Ala Glu Met
1               5                   10                  15

Leu Lys Ser Lys
            20

<210> SEQ ID NO 280
<211> LENGTH: 20
<212> TYPE: PRT
<213> ORGANISM: hepatitis C virus

<400> SEQUENCE: 280

Ile Ala Glu Met Leu Lys Ser Lys Ile Gln Gly Leu Leu Gln Gln Ala
1               5                   10                  15

Ser Lys Gln Ala
```

```
<210> SEQ ID NO 281
<211> LENGTH: 20
<212> TYPE: PRT
<213> ORGANISM: hepatitis C virus

<400> SEQUENCE: 281

Leu Asn Asp Arg Val Val Val Ala Pro Asp Lys Glu Ile Leu Tyr Glu
1               5                   10                  15

Ala Phe Asp Glu
            20

<210> SEQ ID NO 282
<211> LENGTH: 20
<212> TYPE: PRT
<213> ORGANISM: hepatitis C virus

<400> SEQUENCE: 282

Ala Ser Lys Ala Ala Leu Ile Glu Glu Gly Gln Arg Met Ala Glu Met
1               5                   10                  15

Leu Lys Ser Lys
            20

<210> SEQ ID NO 283
<211> LENGTH: 20
<212> TYPE: PRT
<213> ORGANISM: hepatitis C virus

<400> SEQUENCE: 283

Met Ala Glu Met Leu Lys Ser Lys Ile Gln Gly Leu Leu Gln Gln Ala
1               5                   10                  15

Thr Arg Gln Ala
            20

<210> SEQ ID NO 284
<211> LENGTH: 20
<212> TYPE: PRT
<213> ORGANISM: hepatitis C virus

<400> SEQUENCE: 284

Ala Ala Ser Leu Pro Tyr Met Asp Glu Thr Arg Ala Ile Ala Gly Gln
1               5                   10                  15

Phe Lys Glu Lys
            20
```